(12) United States Patent
Han et al.

(10) Patent No.: US 11,177,441 B2
(45) Date of Patent: *Nov. 16, 2021

(54) ORGANIC COMPOUND, COMPOSITION, ORGANIC OPTOELECTRONIC DEVICE, AND DISPLAY DEVICE

(71) Applicant: SAMSUNG SDI CO., LTD., Yongin-si (KR)

(72) Inventors: Su-Jin Han, Suwon-si (KR); Han-ILL Lee, Suwon-si (KR); Soo-Hyun Min, Suwon-si (KR); Eun-Sun Yu, Suwon-si (KR); Ho-Kuk Jung, Suwon-si (KR); Pyeong-Seok Cho, Suwon-si (KR)

(73) Assignee: Samsung SDI Co., Ltd., Yongin-si (KR)

( * ) Notice: Subject to any disclaimer, the term of this patent is extended or adjusted under 35 U.S.C. 154(b) by 57 days.

This patent is subject to a terminal disclaimer.

(21) Appl. No.: 15/037,419

(22) PCT Filed: Dec. 23, 2014

(86) PCT No.: PCT/KR2014/012749
§ 371 (c)(1),
(2) Date: May 18, 2016

(87) PCT Pub. No.: WO2015/111848
PCT Pub. Date: Jul. 30, 2015

(65) Prior Publication Data
US 2016/0301012 A1 Oct. 13, 2016

(30) Foreign Application Priority Data

Jan. 24, 2014 (KR) .................. 10-2014-0009230
Dec. 19, 2014 (KR) .................. 10-2014-0184653

(51) Int. Cl.
*H01L 51/00* (2006.01)
*C07D 251/24* (2006.01)
(Continued)

(52) U.S. Cl.
CPC ........ *H01L 51/0067* (2013.01); *C07D 209/86* (2013.01); *C07D 213/06* (2013.01);
(Continued)

(58) Field of Classification Search
CPC ............. H01L 51/0067; H01L 51/0052; H01L 51/5016; C07D 213/16; C07D 239/26;
(Continued)

(56) References Cited

U.S. PATENT DOCUMENTS 6,057,048 A    5/2000   Hu et al.
6,225,467 B1   5/2001   Esteghamatian et al.
(Continued)

FOREIGN PATENT DOCUMENTS

CN    1010510585 A    8/2009
CN    101656301 A    2/2010
(Continued)

OTHER PUBLICATIONS

Shi-Jian Su et al. Structure-Property Relationship of Pyridine-Containing Triphenyl Benzene Electron-Transport Materials for Highly Efficient Blue Phosphorescent Oleds, AFM Journal 2009, pp. 1260-1267.
(Continued)

*Primary Examiner* — Alexander C Kollias
(74) *Attorney, Agent, or Firm* — Lee IP Law, PC

(57) ABSTRACT

Provided are an organic compound represented by the following Chemical Formula 1 and having a molecular weight of greater than or equal to 538 and less than 750, a composition for an organic optoelectronic device including
(Continued)

the organic compound, an organic optoelectric device including the organic compound or the composition, and a display device including the organic optoelectronic device.

[Chemical Formula 1]

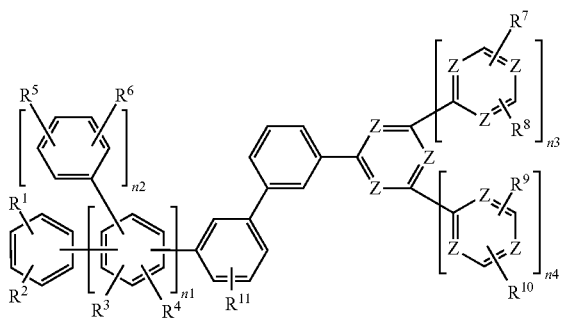

In Chemical Formula 1, Z, $R^1$ to $R^{11}$, n1 to n4 are the same as defined in the specification.

11 Claims, 1 Drawing Sheet

(51) Int. Cl.
| | | |
|---|---|---|
| C07D 213/16 | (2006.01) | |
| C07D 239/26 | (2006.01) | |
| C07D 213/06 | (2006.01) | |
| C09K 11/06 | (2006.01) | |
| C09K 11/02 | (2006.01) | |
| C07D 209/86 | (2006.01) | |
| C07D 401/14 | (2006.01) | |
| C07D 487/04 | (2006.01) | |
| H01L 51/50 | (2006.01) | |

(52) U.S. Cl.
CPC ......... *C07D 213/16* (2013.01); *C07D 239/26* (2013.01); *C07D 251/24* (2013.01); *C07D 401/14* (2013.01); *C07D 487/04* (2013.01); *C09K 11/025* (2013.01); *C09K 11/06* (2013.01); *H01L 51/0052* (2013.01); *C09K 2211/1007* (2013.01); *C09K 2211/1029* (2013.01); *C09K 2211/185* (2013.01); *H01L 51/5016* (2013.01); *Y02E 10/549* (2013.01)

(58) Field of Classification Search
CPC .. C07D 213/06; C07D 209/86; C07D 401/14; C07D 487/04; C07D 251/24; C09K 11/06; C09K 11/025; C09K 2211/1007; C09K 2211/1029; C09K 2211/185; Y02E 10/549
See application file for complete search history.

(56) References Cited

U.S. PATENT DOCUMENTS

| | | | |
|---|---|---|---|
| 6,821,643 B1 | 11/2004 | Hu et al. | |
| 10,193,081 B2 * | 1/2019 | Kim | H01L 51/0054 |
| 2003/0166920 A1 | 9/2003 | Lu et al. | |
| 2007/0190355 A1 * | 8/2007 | Ikeda | C07D 239/26 428/690 |
| 2010/0039026 A1 * | 2/2010 | Yang | C07D 239/26 313/504 |
| 2011/0278555 A1 * | 11/2011 | Inoue | C07D 209/82 257/40 |
| 2013/0241904 A1 * | 9/2013 | Lo | G09G 5/00 345/204 |
| 2014/0131665 A1 | 5/2014 | Xia et al. | |
| 2016/0301012 A1 | 10/2016 | Han et al. | |
| 2017/0098778 A1 | 4/2017 | Oh et al. | |
| 2018/0114918 A1 * | 4/2018 | Han | C07D 401/14 |

FOREIGN PATENT DOCUMENTS

| | | |
|---|---|---|
| CN | 10-2036957 A | 4/2011 |
| CN | 102272122 | 12/2011 |
| CN | 102439004 A | 5/2012 |
| CN | 103391922 A | 11/2013 |
| EP | 2091095 A2 | 8/2009 |
| JP | 2005-302657 | 10/2005 |
| JP | 2007-223929 | 9/2007 |
| JP | 2007-534722 A | 11/2007 |
| JP | 4106974 | 6/2008 |
| JP | 2008-280330 | 11/2008 |
| JP | 2009-224512 A | 10/2009 |
| JP | 4474493 B1 | 6/2010 |
| JP | 2012-149059 A | 9/2012 |
| JP | 5206907 B1 | 6/2013 |
| JP | 2013-183113 A | 9/2013 |
| JP | 5312824 B2 | 10/2013 |
| JP | 2015-027986 A | 2/2015 |
| KR | 10-2000-0052560 A | 8/2000 |
| KR | 10-2007-0009074 | 1/2007 |
| KR | 10-0721565 B1 | 5/2007 |
| KR | 20070090952 A | 9/2007 |
| KR | 2008-0039941 A | 5/2008 |
| KR | 2009-0047547 A | 5/2009 |
| KR | 10-2009-0101954 | 9/2009 |
| KR | 10-2009-0130008 A | 12/2009 |
| KR | 10-2010-0021908 | 2/2010 |
| KR | 10-0958641 B1 | 5/2010 |
| KR | 10-2011-0017392 A | 2/2011 |
| KR | 10-2011-0049012 | 5/2011 |
| KR | 10-2011-0049554 A | 5/2011 |
| KR | 10-2011-0106325 A | 9/2011 |
| KR | 10-2012-0025006 | 3/2012 |
| KR | 2012-0046778 A | 5/2012 |
| KR | 10-2012-0082938 A | 7/2012 |
| KR | 2013-0130788 A | 12/2013 |
| KR | 20140010133 A | 1/2014 |
| KR | 20140135524 A | 11/2014 |
| KR | 10-2014-0145000 A | 12/2014 |
| KR | 10-2015-0088712 A | 3/2015 |
| KR | 10-1502316 B1 | 3/2015 |
| KR | 2015-0036736 A | 4/2015 |
| KR | 10-2015-0117173 A | 10/2015 |
| KR | 10-2015-0120875 A | 10/2015 |
| KR | 10-2015-0129282 A | 11/2015 |
| KR | 10-2016-0049842 A | 5/2016 |
| KR | 10-2016-0051133 A | 5/2016 |
| KR | 10-2016-0051142 A | 5/2016 |
| KR | 10-1829745 B1 | 2/2018 |
| TW | 2010-33176 | 9/2010 |
| WO | WO 2005/003783 A1 | 1/2005 |
| WO | WO 2005/085387 A1 | 9/2005 |
| WO | WO 2006/067976 A | 6/2006 |
| WO | WO 2007/0231840 A1 | 3/2007 |
| WO | WO 2010/080471 A1 | 7/2010 |
| WO | WO 2012/059600 A1 | 5/2012 |
| WO | WO 2012/087960 A1 | 6/2012 |
| WO | WO 2012/137958 A1 | 10/2012 |
| WO | WO 2014/171541 A1 | 10/2014 |
| WO | WO 2015/111848 A1 | 7/2015 |

OTHER PUBLICATIONS

Shi-Jian Su et al., Pyridine-Containing Triphenylbenzene Derivatives With High Electron Mobility for Highly Efficient Phosphorescent OLEDS, AFM Journal, 2008, pp. 2125-2213.
Chinese Search Report dated Jun. 28, 2017.
Search Report dated Feb. 27, 2018, which was attached to the Office Action dated Mar. 7, 2018, of the corresponding Chinese Patent Application No. 201480073378.2.

(56) References Cited

OTHER PUBLICATIONS

Provisional double patenting rejection over claims of the above-identified application; USPTO Office action dated Dec. 17, 2018, in U.S. Appl. No. 15/316,720.
Provisional double patenting rejection of claims; USPTO Office action dated Jul. 9, 2019, in U.S. Appl. No. 15/567,491.
Su, Shi-Jian et al., Novel Four-Pyridylbenzene-Armed Biphenyls as Electron-Transport Materials for Phosphorescent OLEDs, Organic Letters, 2008, vol. 10, No. 5, p. 941-944.
Daisuke Yokoyama, et al., "Molecular stacking induced by intermolecular C—H—N hydrogen bonds leading to high carrier mobility in vacuum-deposited organic films", Advanced Functional Materials, 2011, vol. 21, No. 8, pp. 1375-1382.
International Search Report for PCT/KR2015/012412 filed on Nov. 18, 2015.
USPTO Rejection dated Dec. 3, 2018 for U.S. Appl. No. 15/567,491.
USPTO Rejection dated Jul. 9, 2019 for U.S. Appl. No. 15/567,491.
U.S. Appl. No. 15/567,491, filed Oct. 18, 2017.
Kimura et al. A Rigid 1,3,5,-phenylene-based metallodendrimer containing a ruthenium bis(terpyridyl) complex, Oct. 26, 1999, The Royal Society of Chemistry 2000.
Chinese Office Action dated Oct. 9, 2019.

\* cited by examiner

[FIG. 1]
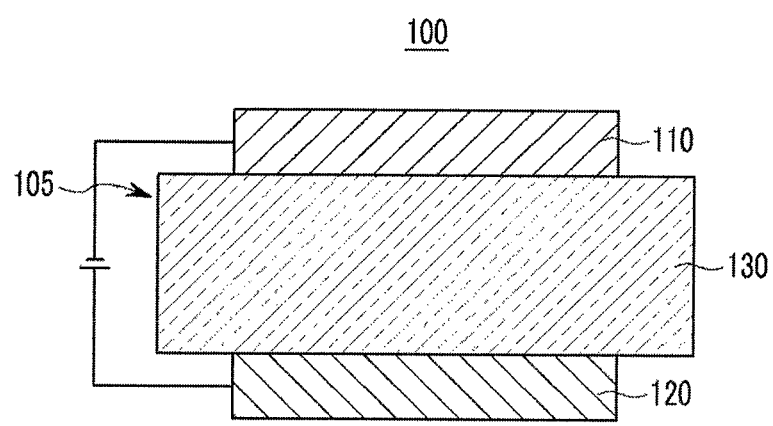
[FIG. 2]
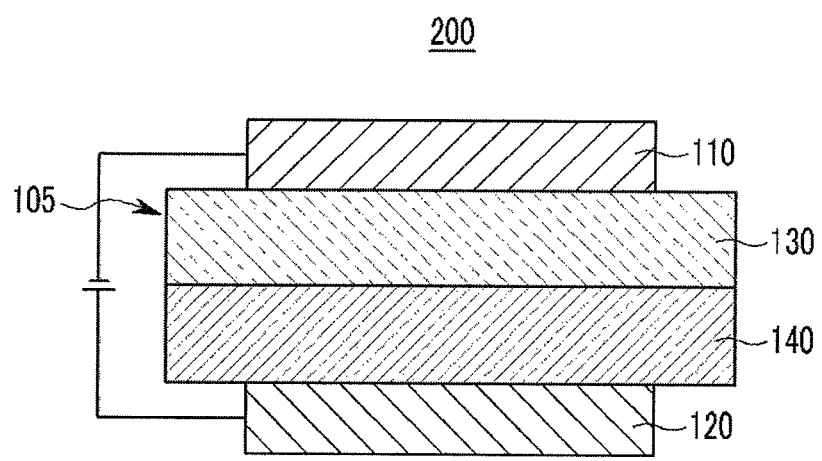

ORGANIC COMPOUND, COMPOSITION, ORGANIC OPTOELECTRONIC DEVICE, AND DISPLAY DEVICE

CROSS REFERENCE TO RELATED APPLICATIONS

This is the U.S. national phase application based on PCT Application No. PCT/KR2014/012749, filed Dec. 23, 2014, which is based on Korean Patent Application Nos. 10-2014-0009230, filed Jan. 24, 2014, and 10-2014-0184653, filed Dec. 19, 2014, the entire contents of all of which are hereby incorporated by reference.

TECHNICAL FIELD

An organic compound, a composition, an organic optoelectric device and a display device are disclosed.

BACKGROUND ART

An organic optoelectric device is a device that converts electrical energy into photoenergy, and vice versa.

An organic optoelectric device may be classified as follows in accordance with its driving principles. One is an optoelectric device where excitons are generated by photoenergy, separated into electrons and holes, and are transferred to different electrodes to generate electrical energy, and the other is a light emitting device where a voltage or a current is supplied to an electrode to generate photoenergy from electrical energy.

Examples of an organic optoelectric device may be an organic photoelectric device, an organic light emitting diode, an organic solar cell and an organic photo conductor drum.

Of these, an organic light emitting diode (OLED) has recently drawn attention due to an increase in demand for flat panel displays. Such an organic light emitting diode converts electrical energy into light by applying current to an organic light emitting material. It has a structure in which an organic layer is interposed between an anode and a cathode. Herein, an organic layer may include an emission layer and optionally an auxiliary layer, and the auxiliary layer may include, for example at least one selected from a hole injection layer, a hole transport layer, an electron blocking layer, an electron transport auxiliary layer, an electron injection layer and a hole blocking layer in order increase efficiency and stability of an organic light emitting diode.

Performance of an organic light emitting diode may be affected by characteristics of the organic layer, and among them, may be mainly affected by characteristics of an organic material of the organic layer.

Particularly, development for an organic material being capable of increasing hole and electron mobility and simultaneously increasing electrochemical stability is needed so that the organic light emitting diode may be applied to a large-size flat panel display.

DISCLOSURE

Technical Problem

One embodiment provides an organic compound being capable of realizing an organic optoelectric device having high efficiency and long life-span.

Another embodiment provides a composition for an organic optoelectric device including the organic compound.

Yet another embodiment provides an organic optoelectric device including the organic compound.

Still another embodiment provides a display device including the organic optoelectronic device.

Technical Solution

According to one embodiment, an organic compound represented by the following Chemical Formula 1 and having a molecular weight of greater than or equal to 538 and less than 750 is provided:

[Chemical Formula 1]

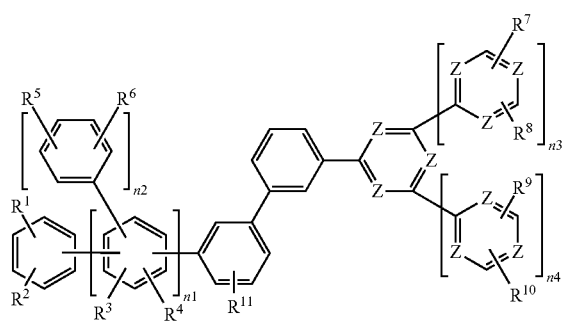

In Chemical Formula 1,

Z is each independently N, C or $CR^a$, at least one of Z is N, $R^1$ to $R^{11}$ and $R^a$ are each independently hydrogen, deuterium, a substituted or unsubstituted C1 to C10 alkyl group, a substituted or unsubstituted C6 to C12 aryl group, a substituted or unsubstituted C3 to C12 heteroaryl group, or a combination thereof, $R^1$ and $R^2$ are independently present or are linked to each other to form a ring, $R^5$ and $R^6$ are independently present or are linked to each other to form a ring, $R^7$ and $R^8$ are independently present or are linked to each other to form a ring, $R^9$ and $R^{10}$ are independently present or are linked to each other to form a ring, n1 is an integer ranging from 1 to 5, n2 is an integer ranging from 0 to 2, and n3 and n4 are each independently 0 or 1.

According to another embodiment, a composition for an organic optoelectric device including the organic compound as a first organic compound and at least one second organic compound having a carbazole moiety is provided.

According to yet another embodiment, provided is an organic optoelectric device that includes an anode and a cathode facing each other and at least one organic layer between the anode and the cathode, wherein the organic layer includes the organic compound or the composition for an organic optoelectronic device.

According to still another embodiment, a display device including the organic optoelectric device is provided. An organic optoelectric device having high efficiency long life-span may be realized.

Advantageous Effects

An organic optoelectronic device having high efficiency and long life-span may be realized.

DESCRIPTION OF DRAWINGS

FIGS. 1 and 2 are cross-sectional views showing organic light emitting diodes according to various embodiments.

BEST MODE

Hereinafter, embodiments of the present invention are described in detail. However, these embodiments are exemplary, and this disclosure is not limited thereto.

In the present specification, when a definition is not otherwise provided, the term "substituted" refers to one substituted with a substituent selected from deuterium, a halogen, a hydroxy group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C3 to C30 cycloalkyl group, a C3 to C30 heterocycloalkyl group, a C6 to C30 aryl group, a C6 to C30 heteroaryl group, a C1 to C20 alkoxy group, a fluoro group, a C1 to C10 trifluoroalkyl group such as a trifluoromethyl group and the like or a cyano group.

In addition, the adjacent two substituents selected from the substituted halogen, hydroxy group, an amino group, a substituted or unsubstituted C1 to C20 amine group, a nitro group, a substituted or unsubstituted C3 to C40 silyl group, C1 to C30 alkyl group, C1 to C10 alkylsilyl group, C3 to C30 cycloalkyl group, C3 to C30 heterocycloalkyl group, C6 to C30 aryl group, C6 to C30 heteroaryl group, C1 to C20 alkoxy group, fluoro group, C1 to C10 trifluoroalkyl group such as a trifluoromethyl group and the like, or cyano group may be fused to each other to form a ring. For example, the substituted C6 to C30 aryl group may be fused to another adjacent substituted C6 to C30 aryl group to form a substituted or unsubstituted fluorene ring.

In the present specification, when specific definition is not otherwise provided, "hetero" refers to one including 1 to 3 hetero atoms selected from N, O, S, P, and Si, and remaining carbons in one functional group.

In the present specification, when a definition is not otherwise provided, "alkyl group" refers to an aliphatic hydrocarbon group. The alkyl group may be "a saturated alkyl group" without any double bond or triple bond.

The alkyl group may be a C1 to C30 alkyl group. More specifically, the alkyl group may be a C1 to C20 alkyl group or a C1 to C10 alkyl group. For example, a C1 to C4 alkyl group may have 1 to 4 carbon atoms in an alkyl chain which may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

In the present specification, the term "aryl group" refers to a substituent including all element of the cycle having p-orbitals which form conjugation, and may be monocyclic, polycyclic or fused ring polycyclic (i.e., rings sharing adjacent pairs of carbon atoms) functional group.

In the present specification, the term "heteroaryl group" refers to aryl group including 1 to 3 heteroatoms selected from N, O, S, P and Si and remaining carbon. When the heteroaryl group is a fused ring, each ring may include 1 to 3 heteroatoms.

More specifically, a substituted or unsubstituted C6 to C30 aryl group and/or a substituted or unsubstituted C2 to C30 heteroaryl group may be a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted fluorenyl group, a substituted or unsubstituted dibenzofuranyl group, a substituted or unsubstituted dibenzothiophenyl group, a substituted or unsubstituted carbazole group, a combination thereof, or a combined fused ring of the foregoing groups, but is not limited thereto.

In the specification, hole characteristics refer to characteristics capable of donating an electron to form a hole when electric field is applied, and characteristics that hole formed in the anode is easily injected into the emission layer and transported in the emission layer due to conductive characteristics according to HOMO level.

In addition, electron characteristics refer to characteristics capable of accepting an electron when electric field is applied, and characteristics that electron formed in the cathode is easily injected into the emission layer and transported in the emission layer due to conductive characteristics according to LUMO level.

Hereinafter, an organic compound according to one embodiment is described.

An organic compound according to one embodiment is represented by the following Chemical Formula 1.

[Chemical Formula 1]

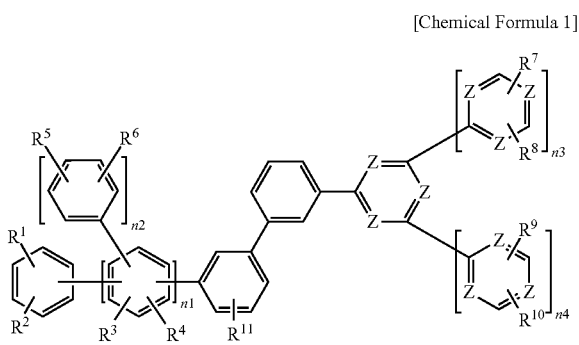

In Chemical Formula 1,

Z is each independently N, C or CR$^a$, at least one of Z is N,

R$^1$ to R$^{11}$ and R$^a$ are each independently hydrogen, deuterium, a substituted or unsubstituted C1 to C10 alkyl group, a substituted or unsubstituted C6 to C12 aryl group, a substituted or unsubstituted C3 to C12 heteroaryl group, or a combination thereof, R$^1$ and R$^2$ are independently present or are linked to each other to form a ring, R$^5$ and R$^6$ are independently present or are linked to each other to form a ring, R$^7$ and R$^8$ are independently present or are linked to each other to form a ring, R$^9$ and R$^{10}$ are independently present or are linked to each other to form a ring, n1 is an integer ranging from 1 to 5, n2 is an integer ranging from 0 to 2, and n3 and n4 are each independently 0 or 1.

The organic compound represented by the Chemical Formula 1 includes two or more substituted or unsubstituted aryl groups and a heteroaryl group having at least one nitrogen that are bound at each meta position relative to two phenylene groups.

The organic compound includes a ring containing at least one nitrogen and may have a structure of easily receiving electrons when an electric field is applied thereto, and thus, the driving voltage of an organic optoelectronic device manufactured by applying the organic compound may be decreased.

In addition, the organic compound has a bipolar structure including both of a plurality of substituted or unsubstituted aryl group moiety easily receiving holes and a nitrogen-containing ring moiety easily receiving electrons and may appropriately balance flows of holes and electrons, and thus, efficiency of an organic optoelectronic device manufactured by applying the organic compound may be improved.

In addition, the two phenylene groups bound at a meta position may appropriately localize a plurality of substituted or unsubstituted aryl group moiety easily receiving holes and a nitrogen-containing ring moiety easily receiving electrons in the compound having the above bipolar structure and control a flow in a conjugation system and thus, realize excellent bipolar characteristics. Herein, one or two out of the two phenylene groups may be an unsubstituted phenylene group. Accordingly, the life-span of an organic optoelectronic device manufactured by applying the organic compound may be improved.

In addition, the organic compound has a substantial linear structure and thus, is self-arranged during the deposition and thus, may increase process stability and thin film uniformity.

The organic compound has a molecular weight of greater than or equal to about 538 and less than 750. When the organic compound has a molecular weight within the range, the compound may be suppressed from being thermally decomposition at a high temperature during a deposit process and improve heat resistance. The organic compound may have a molecular weight of about 538 to 749, about 550 to 730, and about 600 to 700 within the range.

The organic compound may be, for example, represented by the following Chemical Formula 1-A.

[Chemical Formula 1-A]

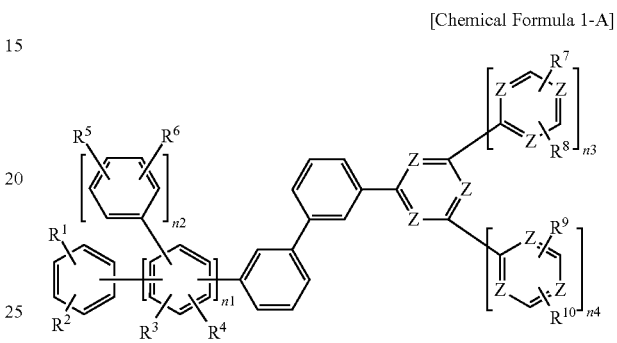

In Chemical Formula 1-A, Z, R$^1$ to R$^{10}$, R$^a$, and n1 to n4 are the same as described above.

In Chemical Formula 1-A, two phenylene groups bound at the meta positions may be unsubstituted phenylene groups.

The organic compound may be, for example, represented by one of the following Chemical Formulae 2 to 4.

[Chemical Formula 2]

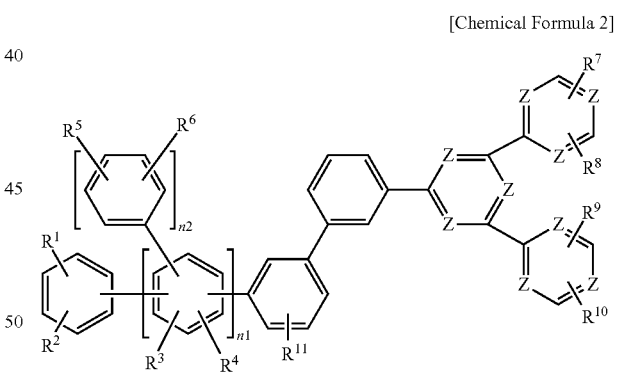

[Chemical Formula 3]

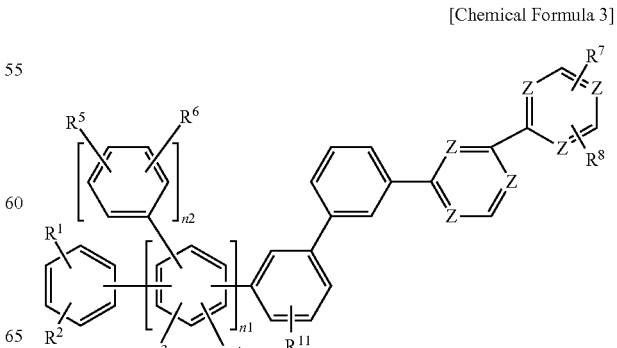

[Chemical Formula 4]

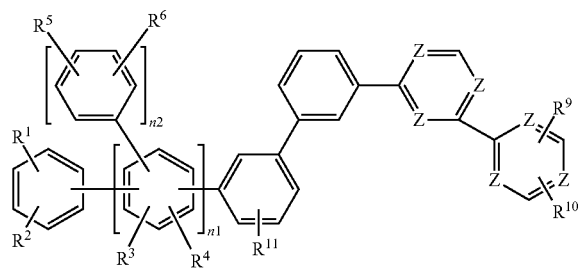

[Chemical Formula 5]

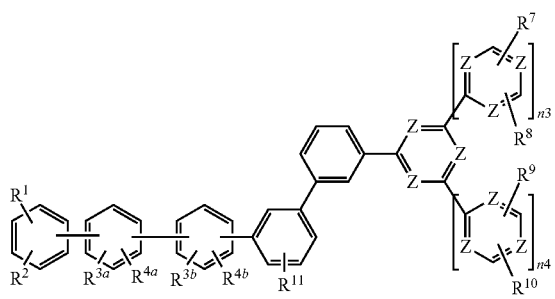

[Chemical Formula 6]

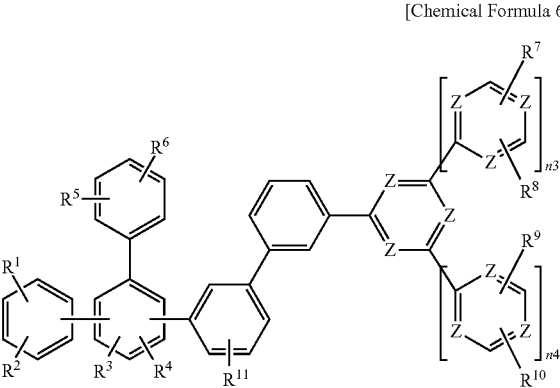

In Chemical Formulae 2 to 4, Z and $R^1$ to $R^{11}$ are the same as described above.

In Chemical Formula 2, n1 may be, for example integers of 1 to 3, and the sum of n1 and n2 satisfies $1<n1+n2<3$.

In the Chemical Formula 3 and Chemical Formula 4, n1 may be, for example integers of 1 to 4, and the sum of n1 and n2 satisfies $1<n1+n2<4$.

The organic compound may be, for example represented by the following Chemical Formula 5 or 6.

In Chemical Formula 5 or 6, Z, $R^1$ to $R^{11}$, n3 and n4 are the same as described above, $R^{3a}$ and $R^{3b}$ are the same as $R^3$, and $R^{4a}$ and $R^{4b}$ are the same as $R^4$.

The compound represented by the Chemical Formula 5 may be, for example represented by one of the following Chemical Formulae 5a to 5g.

[Chemical Formula 5a]

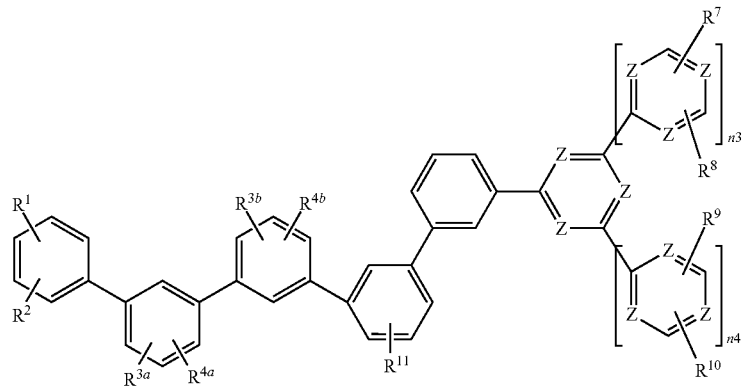

[Chemical Formula 5b]

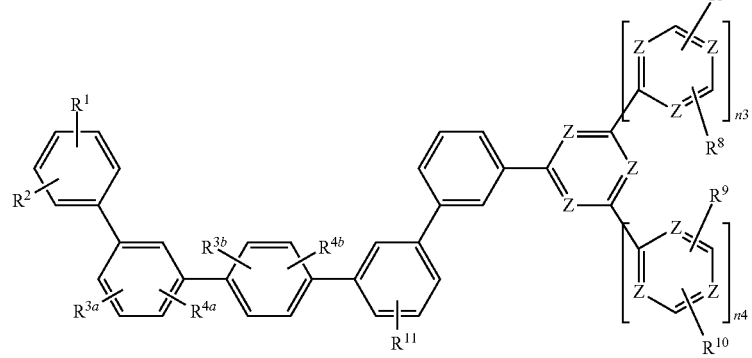

[Chemical Formula 5c]
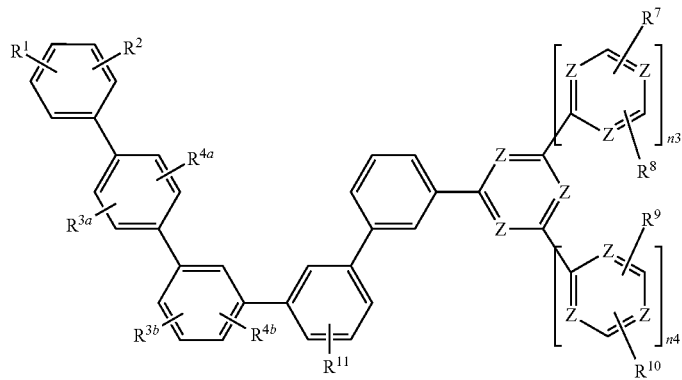
[Chemical Formula 5d]
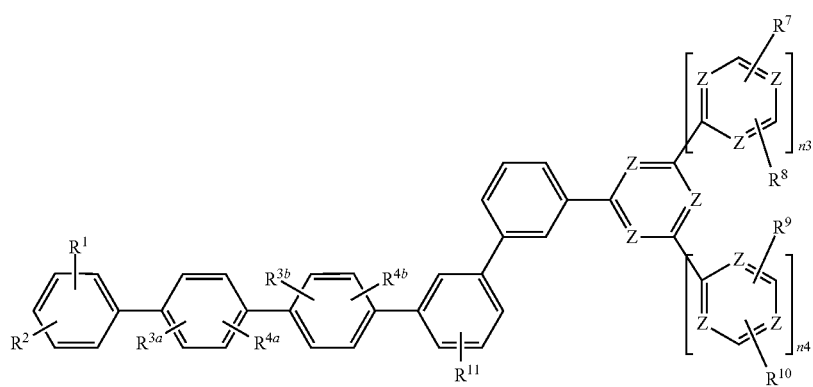
[Chemical Formula 5e]
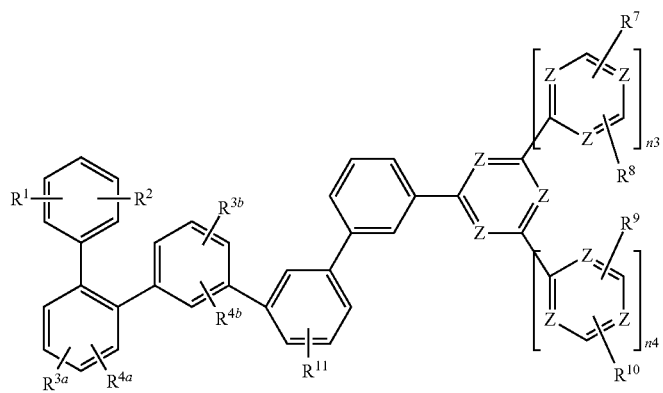

[Chemical Formula 5f]

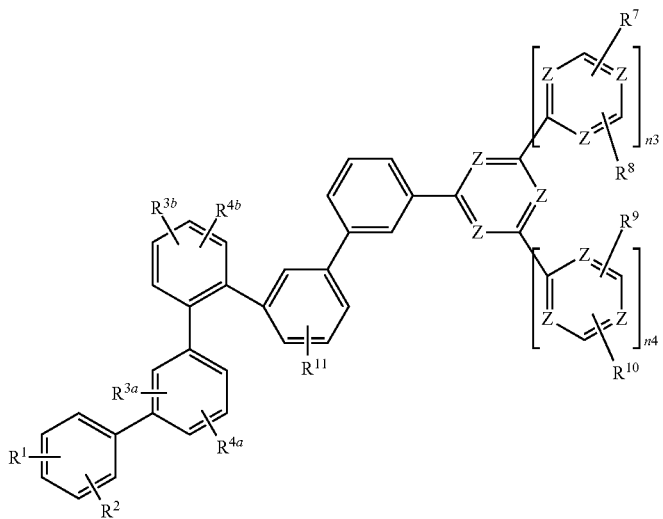

[Chemical Formula 5g]

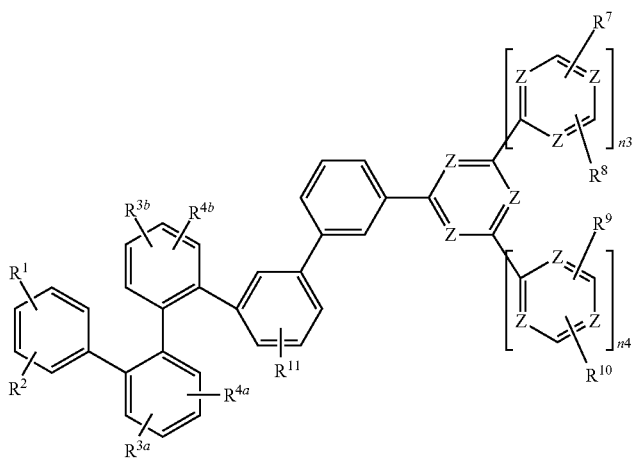

In the Chemical Formulae 5a to 5g, Z, $R^1$, $R^2$, $R^{3a}$, $R^{4a}$, $R^{3b}$, $R^{4b}$, $R^7$ to $R^{11}$, n3 and n4 are the same as described above.

At least one of the $R^1$, $R^2$, $R^{3a}$, $R^{4a}$, $R^{3b}$, $R^{4b}$ and $R^{11}$ of the Chemical Formula 5a to 5g may be a substituted or unsubstituted C6 to C12 aryl group. For example, at least one of $R^1$, $R^2$, $R^{3a}$, $R^{4a}$, $R^{3b}$, $R^{4b}$ and $R^{11}$ of above Chemical Formulae 5a to 5g may be a substituted or unsubstituted phenyl group or a substituted or unsubstituted naphthyl group.

The compound represented by the Chemical Formula 6 may be, for example represented by the following Chemical Formula 6a.

[Chemical Formula 6a]

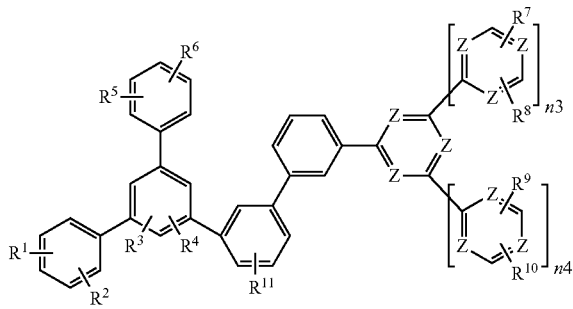

In Chemical Formula 6a, Z, $R^1$ to $R^{11}$, n3 and n4 are the same as described above.

At least one of $R^1$ to $R^6$ and $R^{11}$ of the Chemical Formula 6a may be a substituted or unsubstituted C6 to C12 aryl group. For example, at least one of the $R^1$ to $R^6$ and $R^{11}$ in the Chemical Formula 6a may be a substituted or unsubstituted phenyl group or a substituted or unsubstituted naphthyl group.

For example, in the Chemical Formulae 1 to 6, $R^7$ to $R^{10}$ are independently hydrogen or a substituted or unsubstituted C6 to C12 aryl group, and for example, $R^7$ to $R^{10}$ are independently hydrogen, a substituted or unsubstituted phenyl group, a substituted or unsubstituted naphthyl group or a substituted or unsubstituted biphenyl group.

For example, when at least one of $R^7$ to $R^{10}$ in the Chemical Formula 1 to 6 is a substituted or unsubstituted C6 to C12 aryl group, the substituted or unsubstituted C6 to C12 aryl group may not be bound at an ortho position.

For example, when at least one of $R^7$ to $R^{10}$ in the Chemical Formulae 1 to 6 is a substituted or unsubstituted phenyl group, the phenyl group may not be bound at ortho and para positions.

The organic compound may be, for example represented by the following Chemical Formula 7.

[Chemical Formula 7]

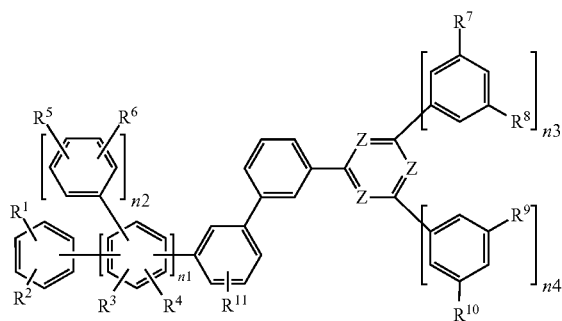

In Chemical Formula 7,

Z, $R^1$ to $R^6$, $R^a$ and n1 to n4 are the same as described above, and $R^7$ to $R^{10}$ may be independently hydrogen or a substituted or unsubstituted C6 to C12 aryl group.

The organic compound may be, for example compounds listed in the following Group 1, but are not limited thereto.

[Group 1]

[Group 1]

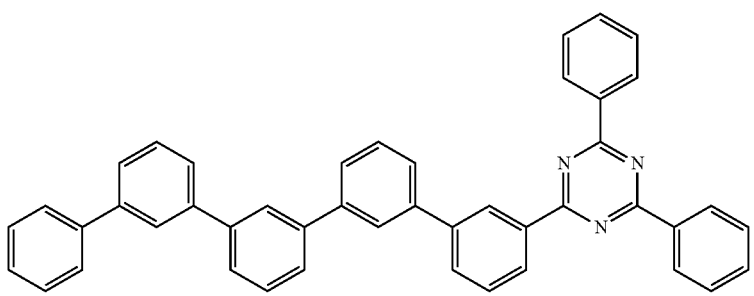

1

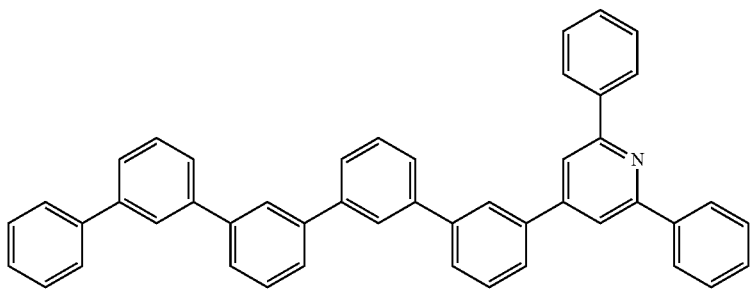

2

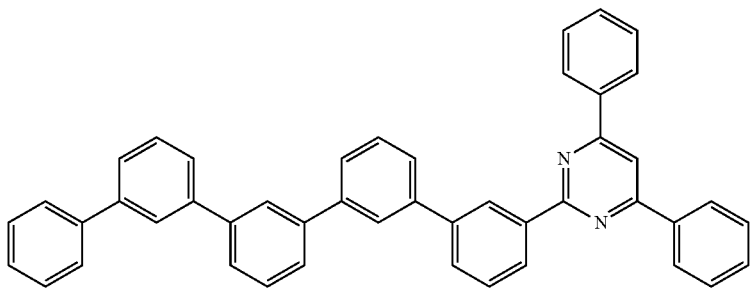

3

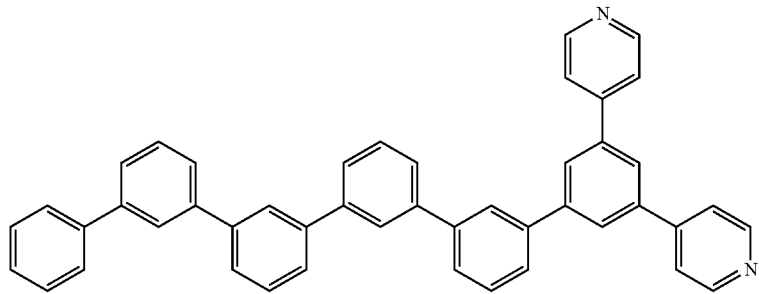
4
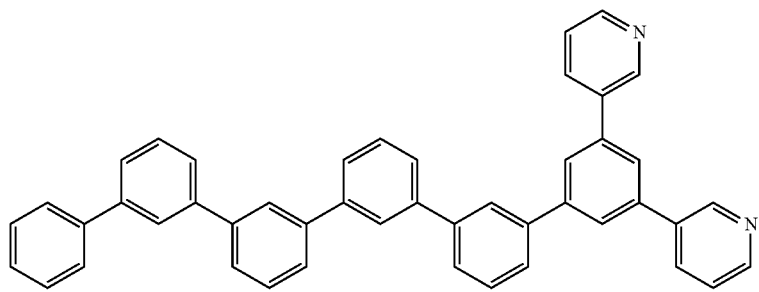
5
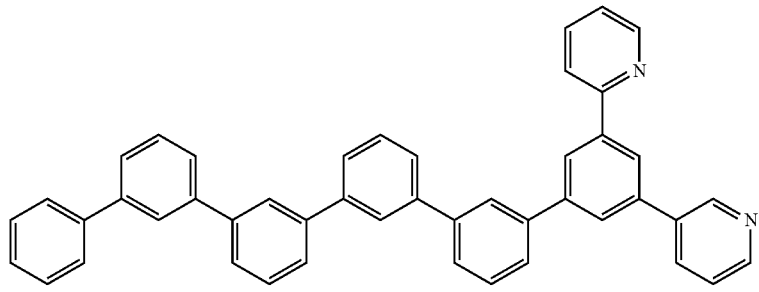
6
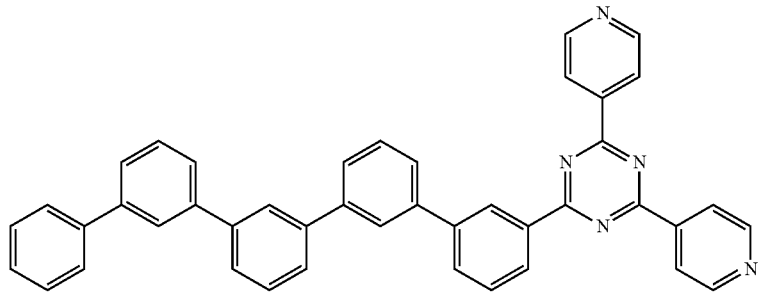
7
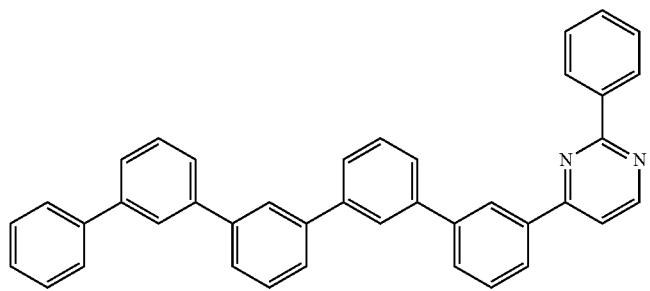
8

9
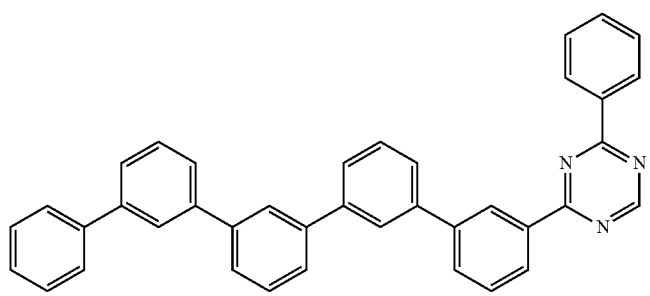
10
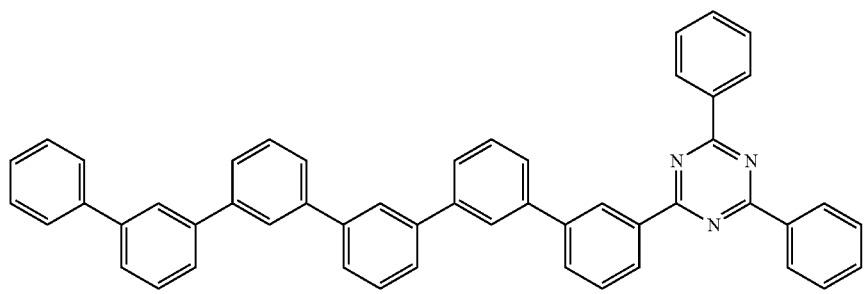
11
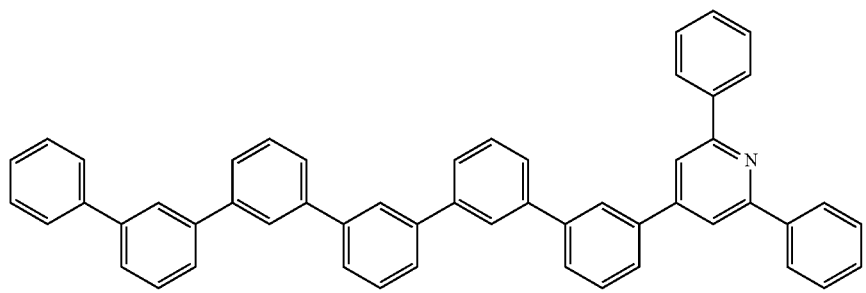
12
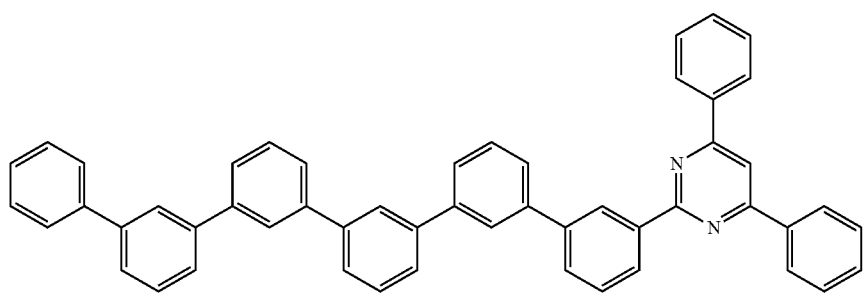
13
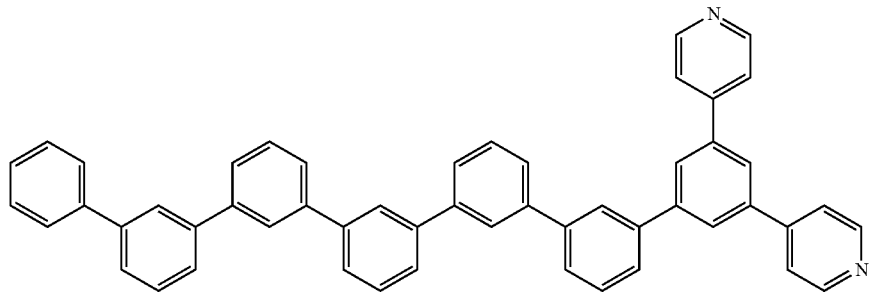

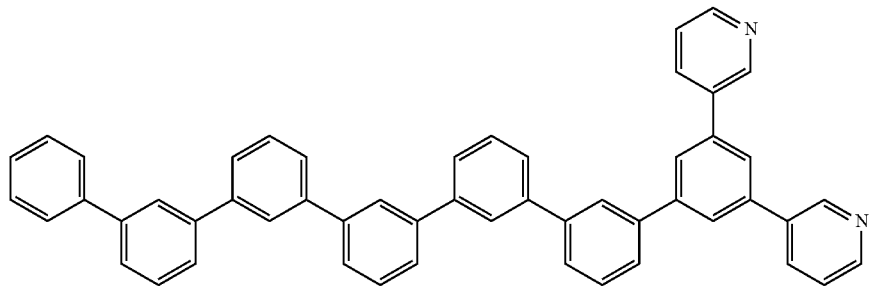
14
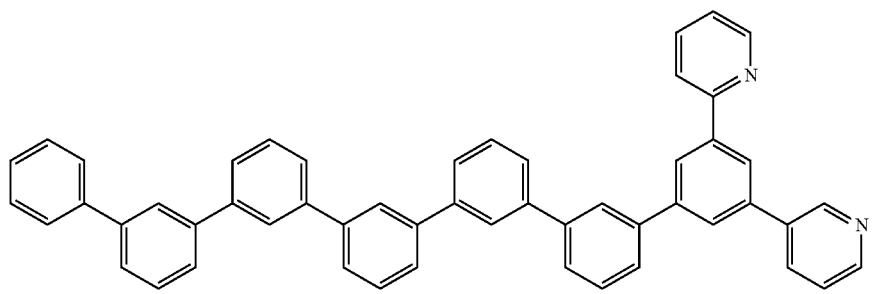
15
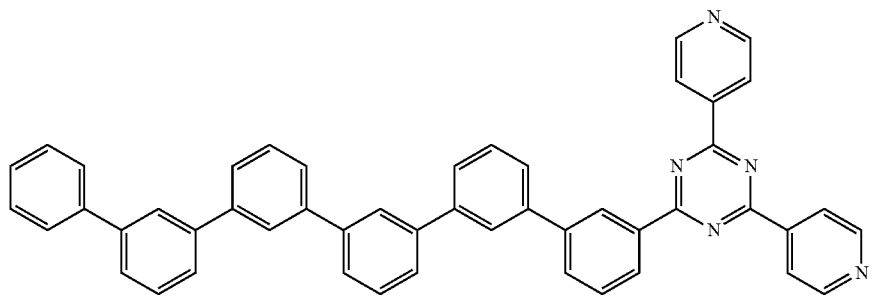
16
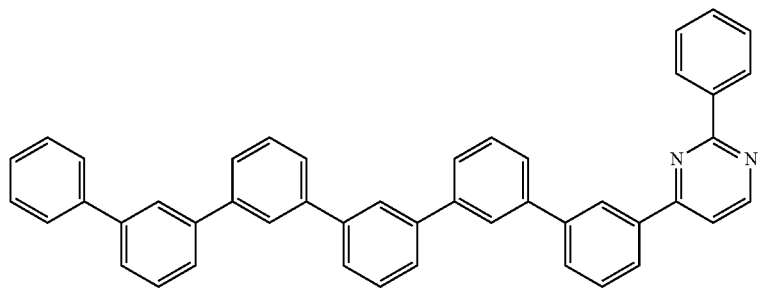
17
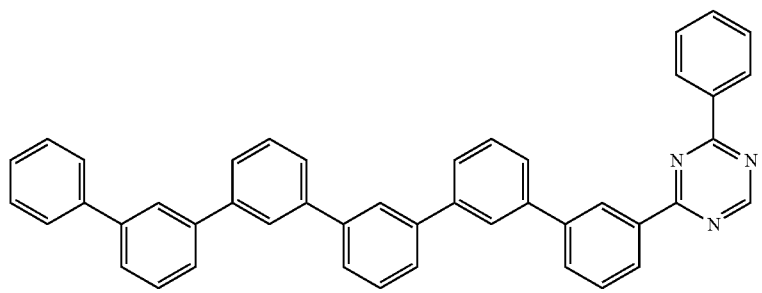
18

-continued
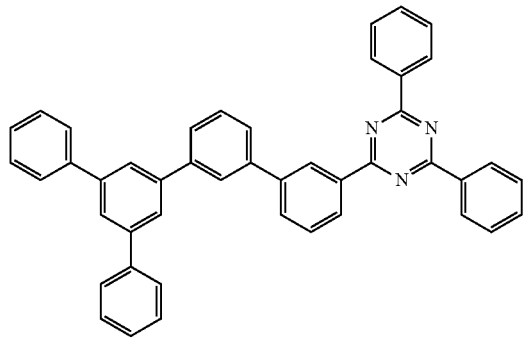
19
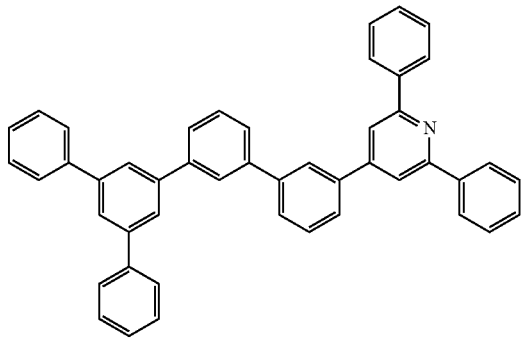
20
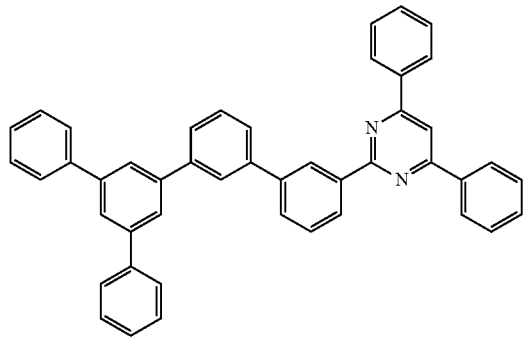
21
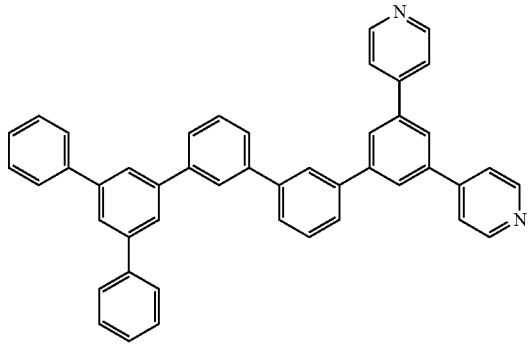
22
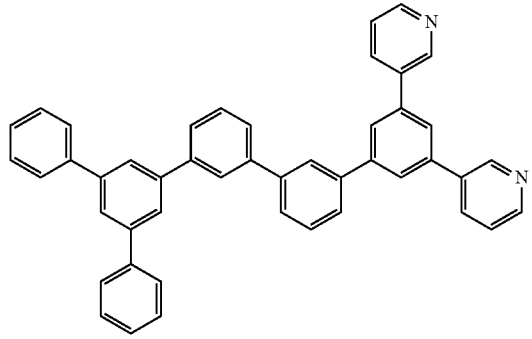
23
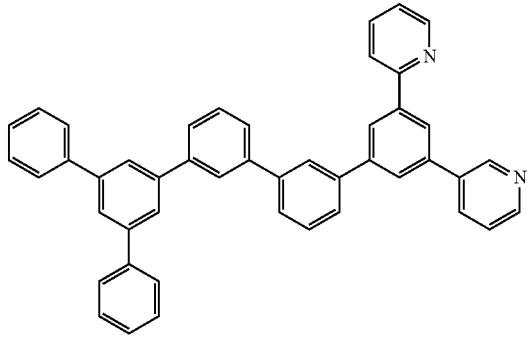
24
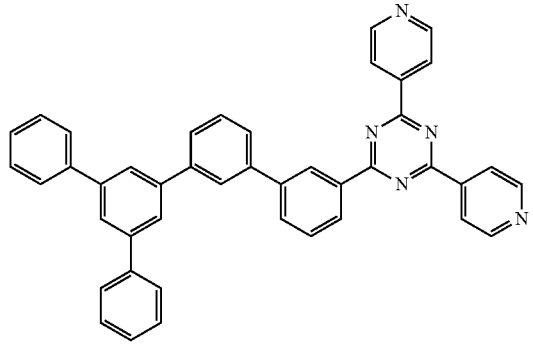
25
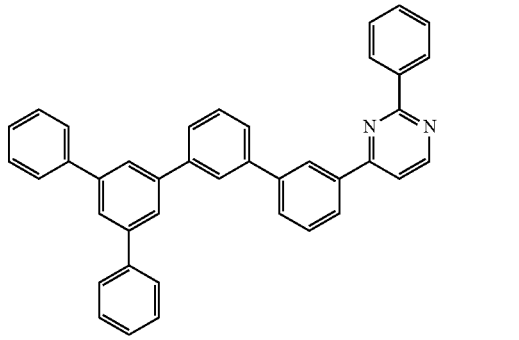
26

-continued
27
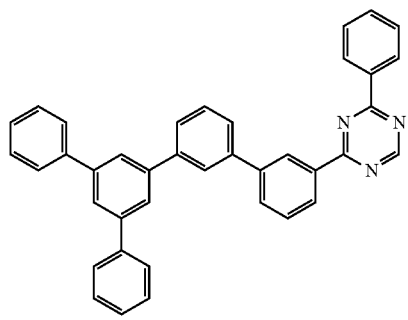
28
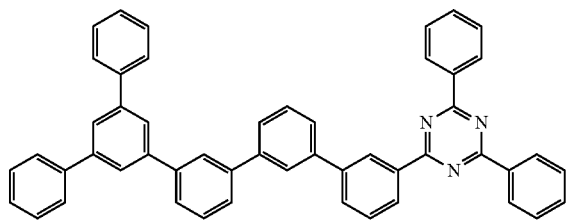
29
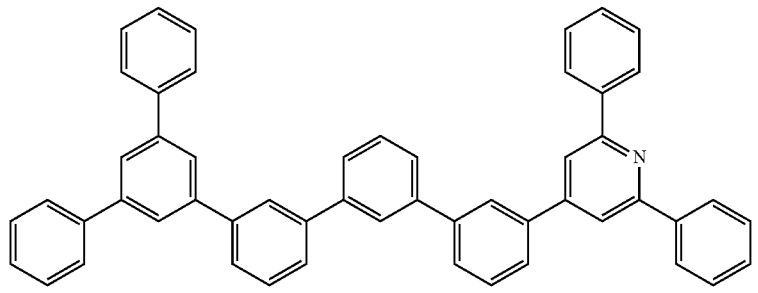
30
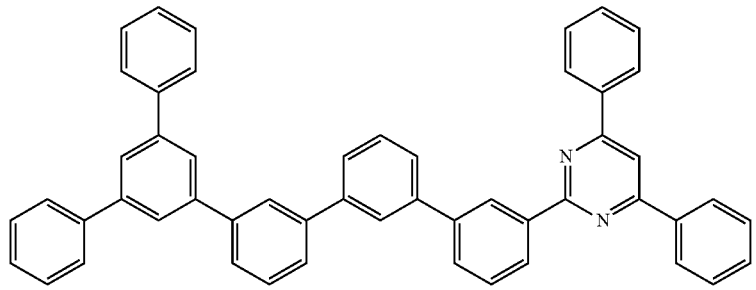
31
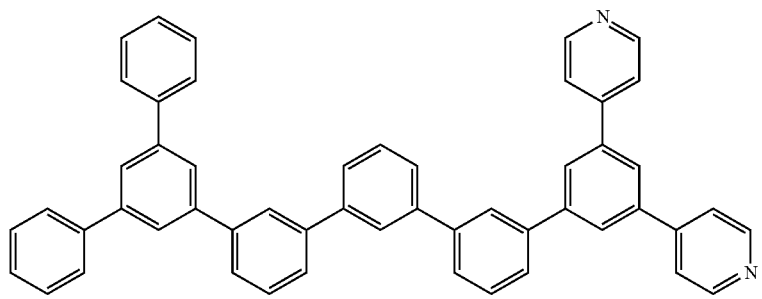
32
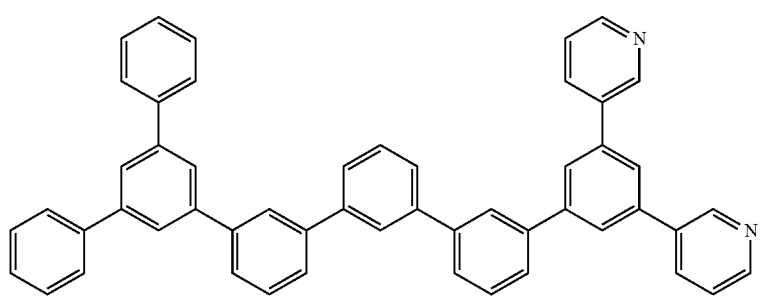

-continued
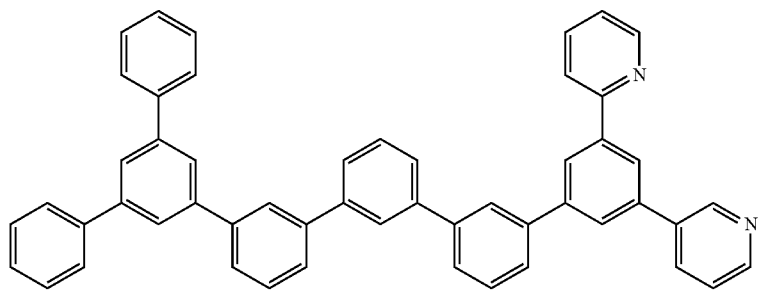
33
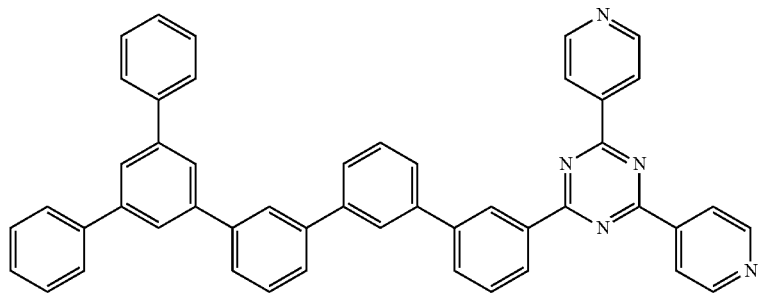
34
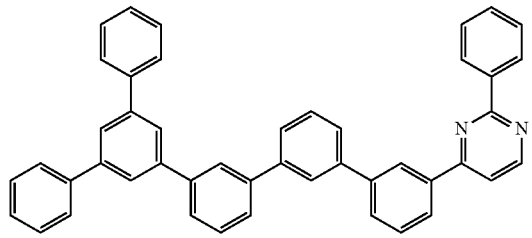
35
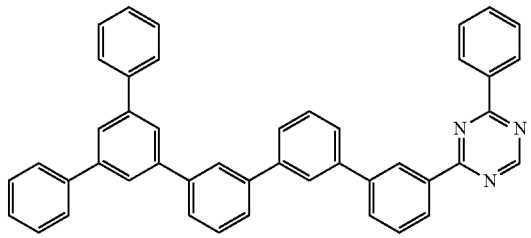
36
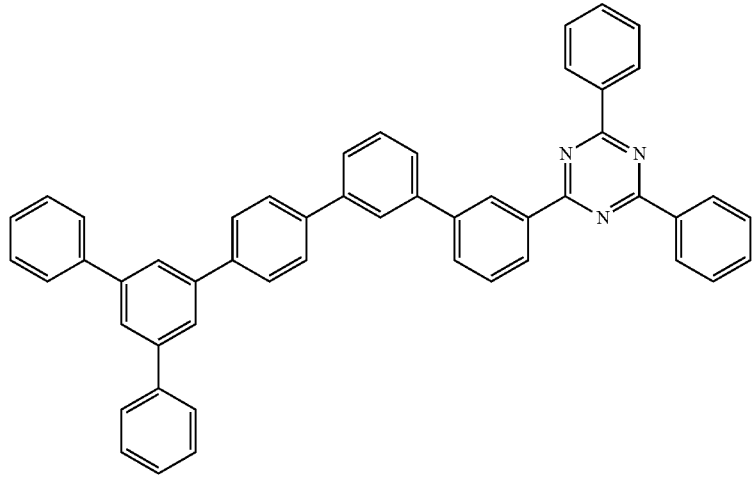
37

38
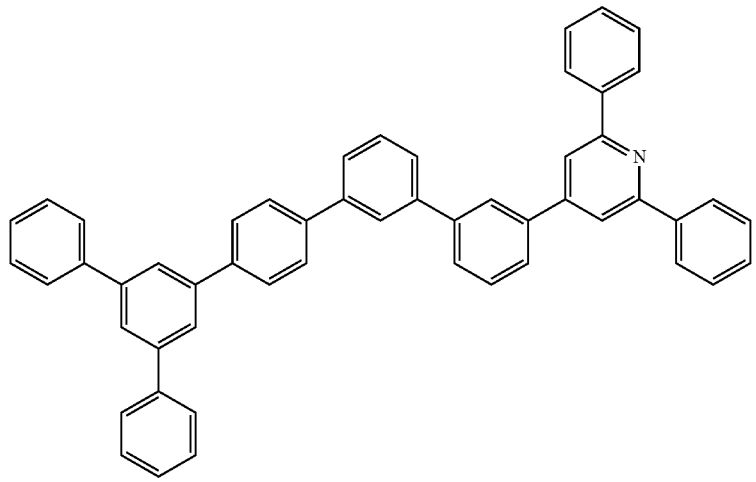
39
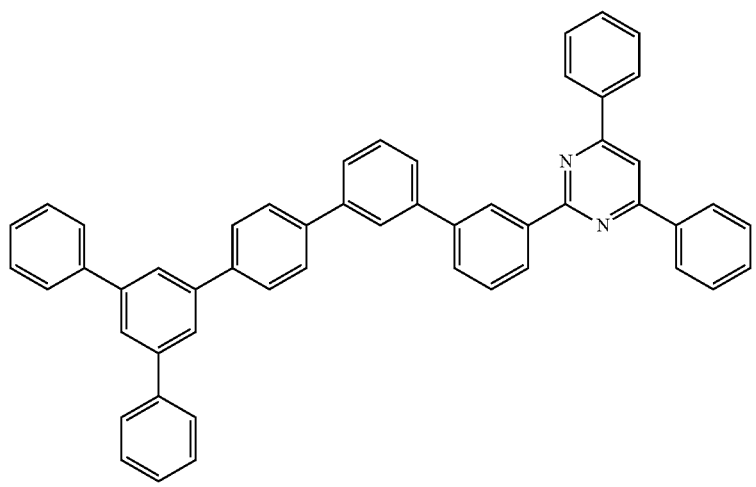
40
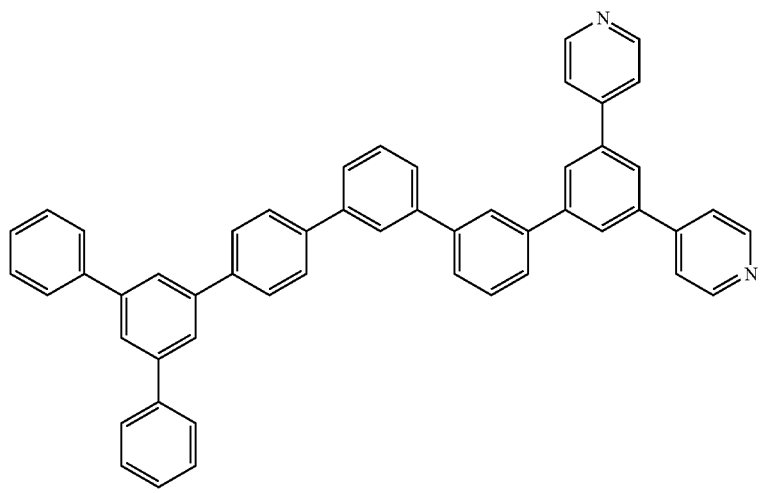

41
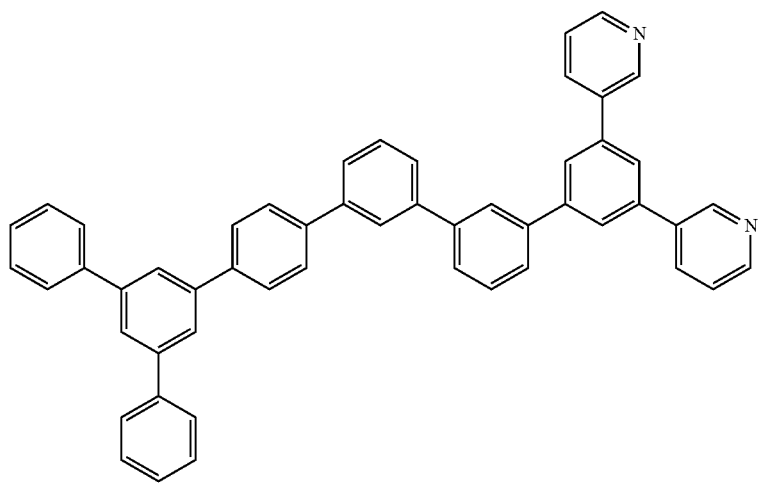
42
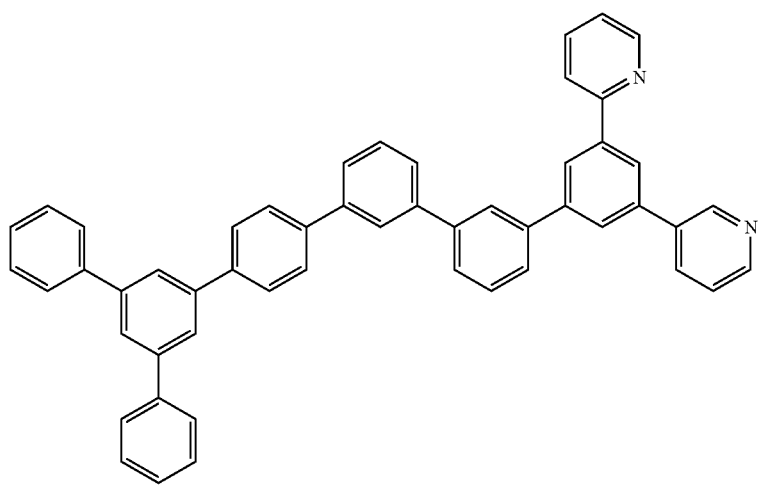
43
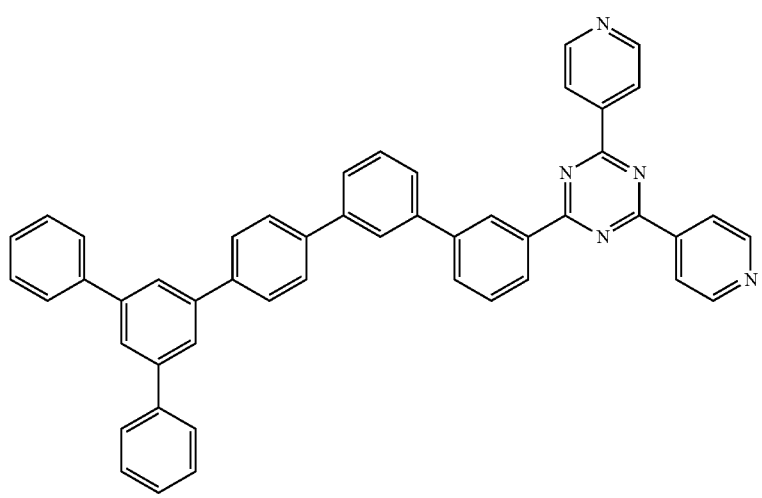

-continued
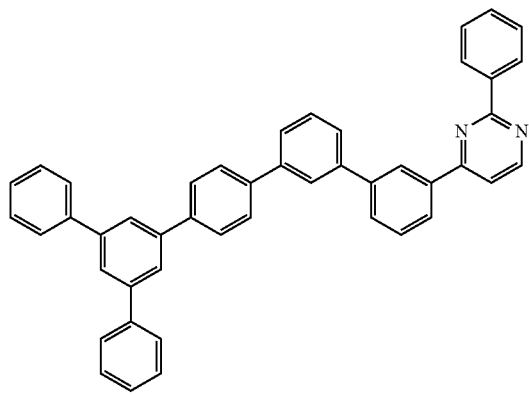
44
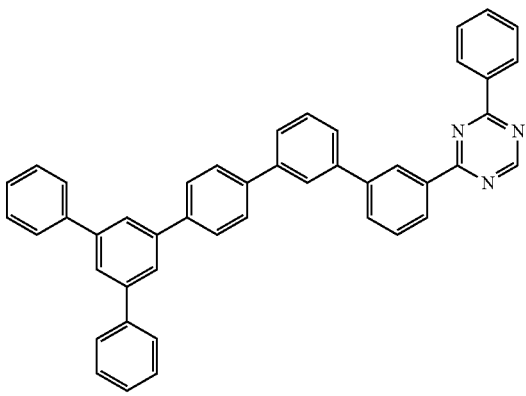
45
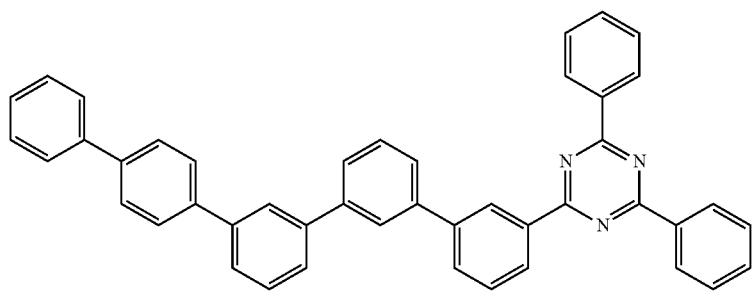
46
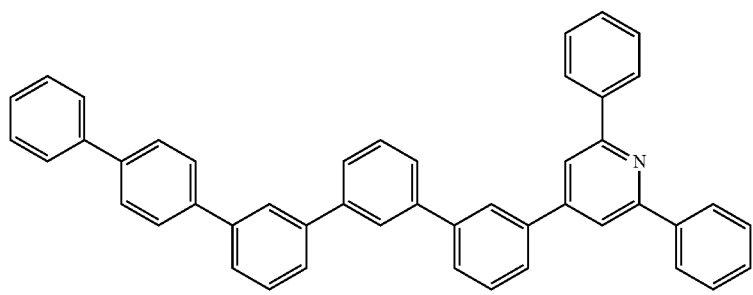
47
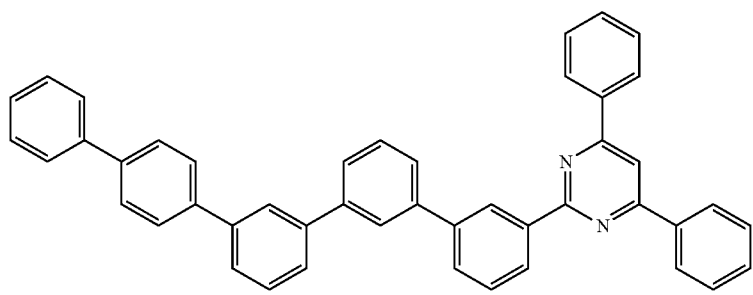
48
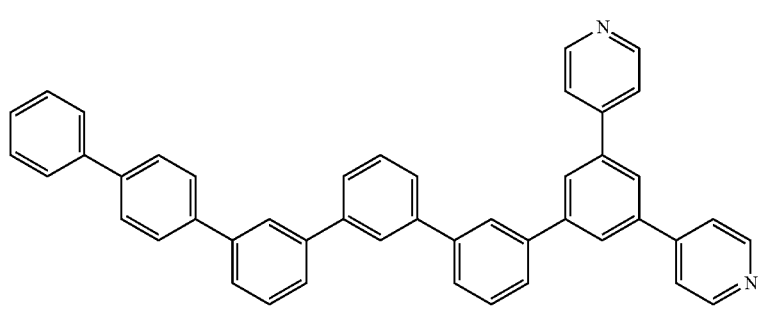
49

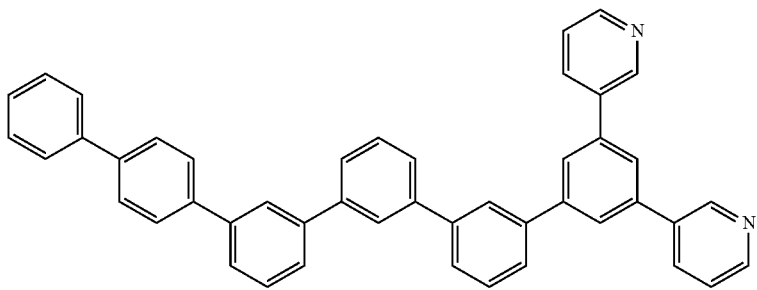
50
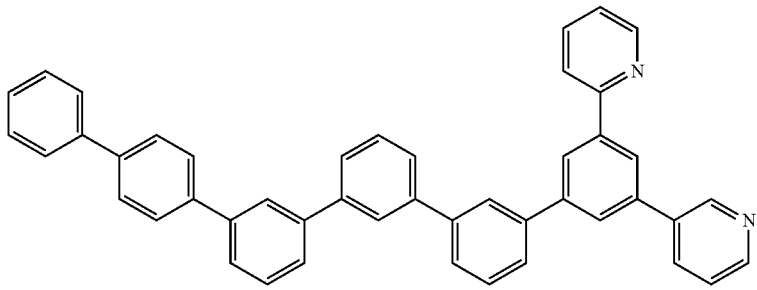
51
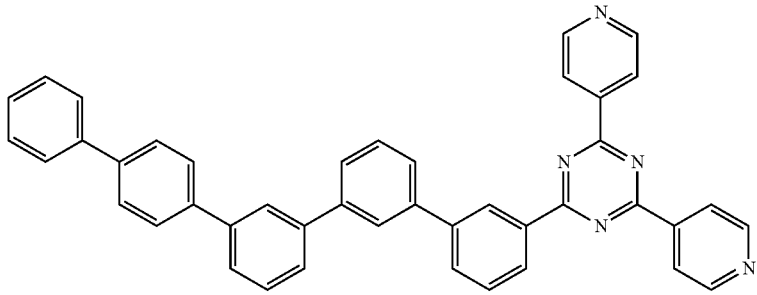
52
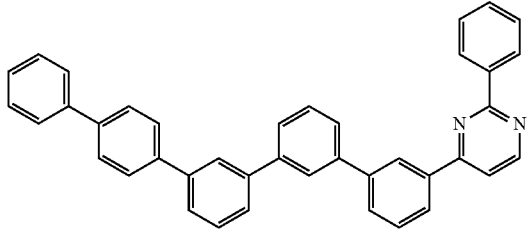
53
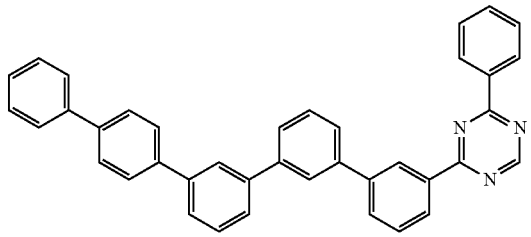
54
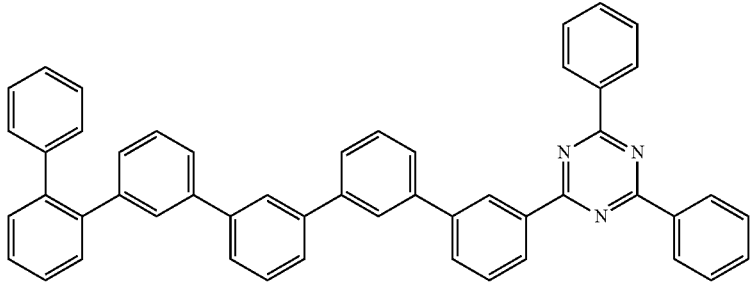
55

56
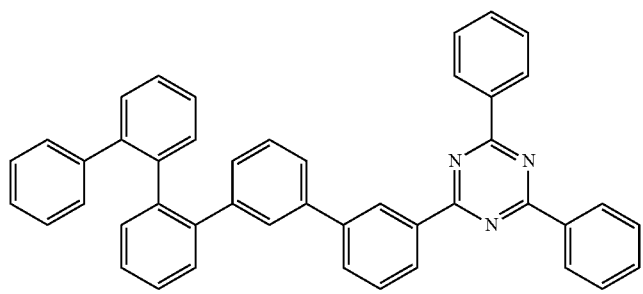
57
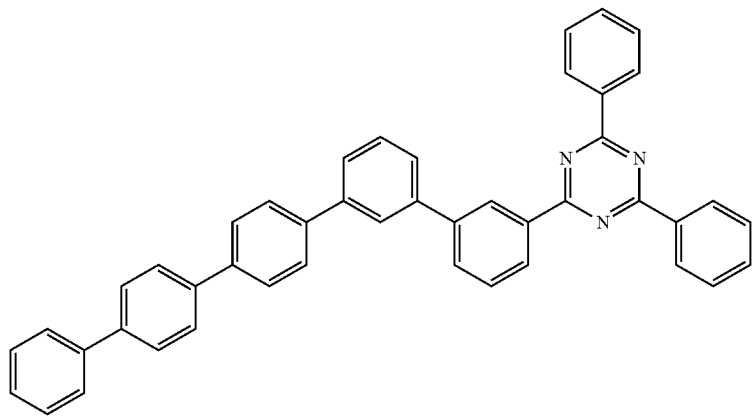
58
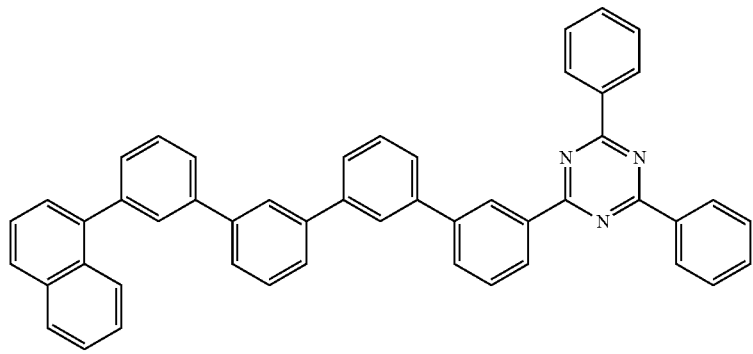
59
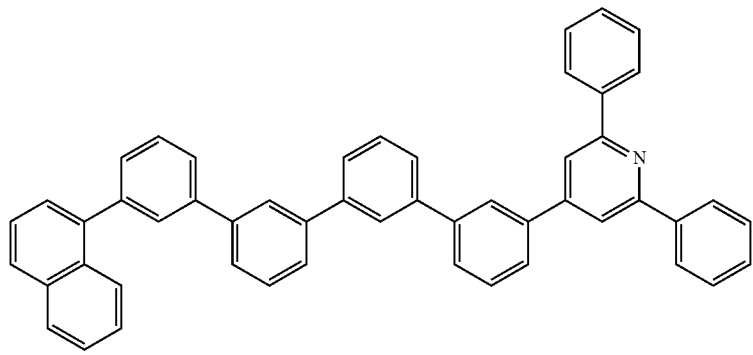

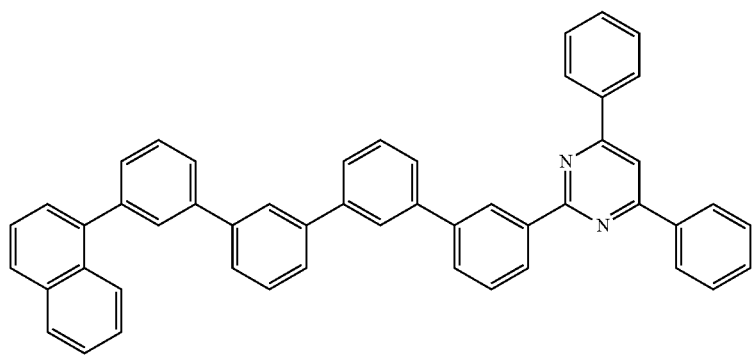
60
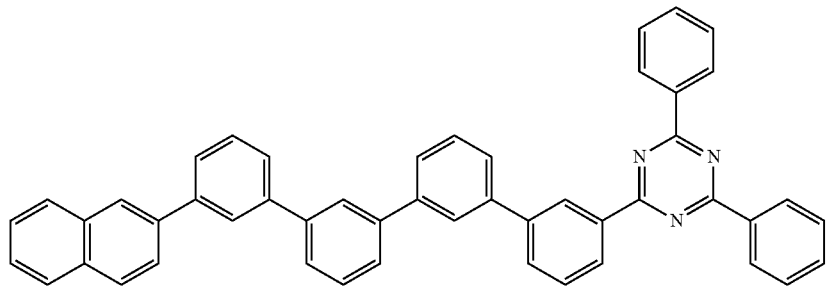
61
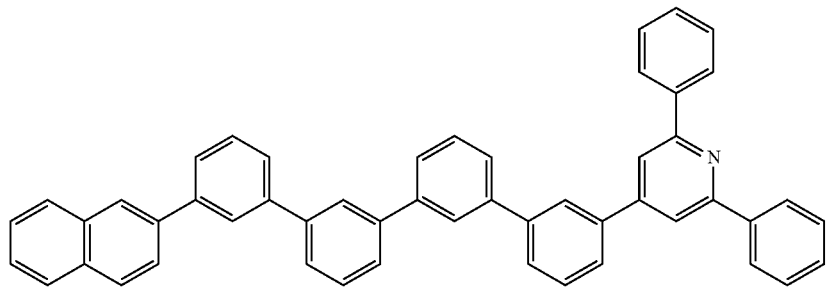
62
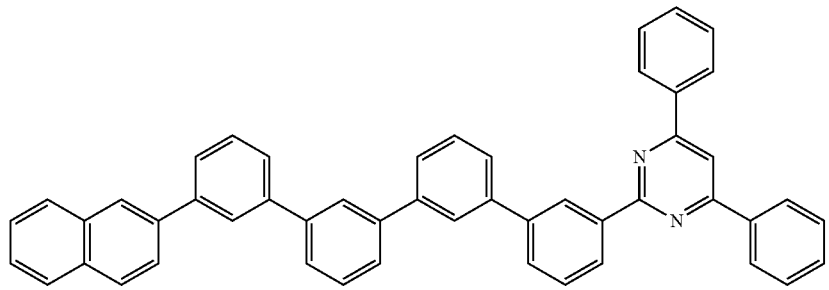
63
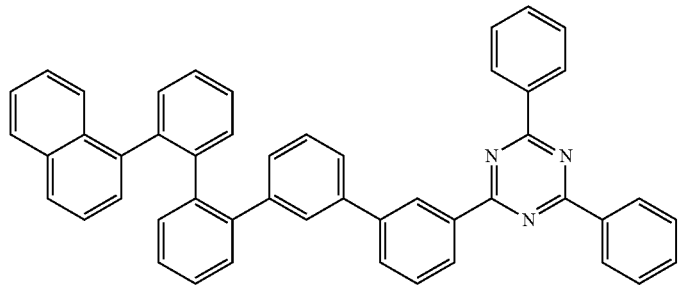
64

65
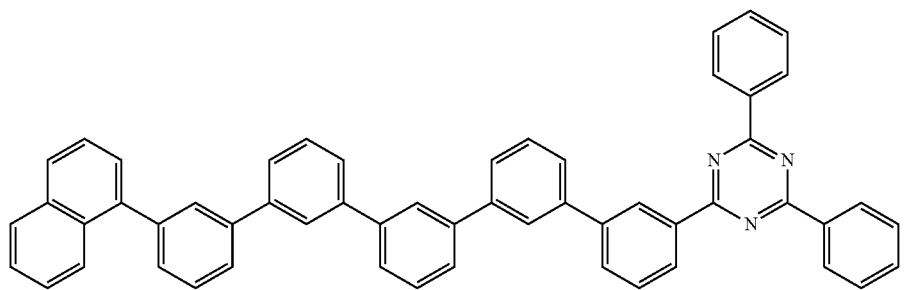
66
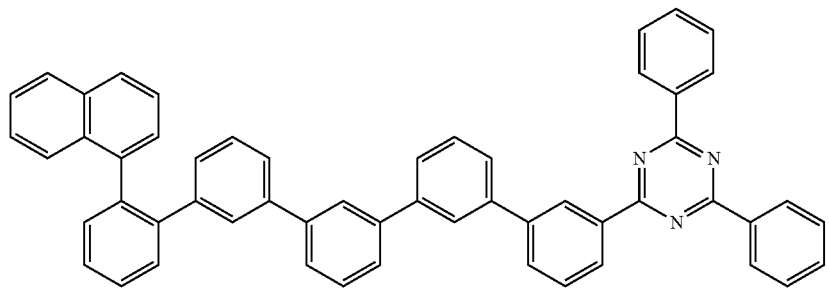
67
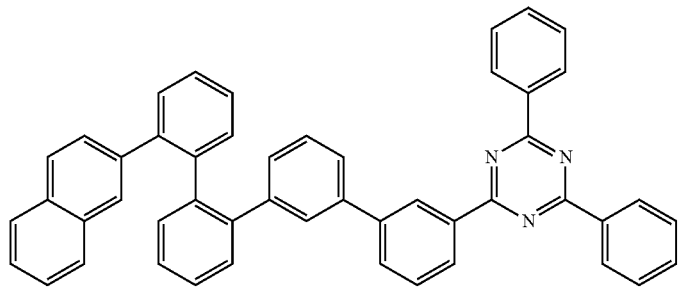
68
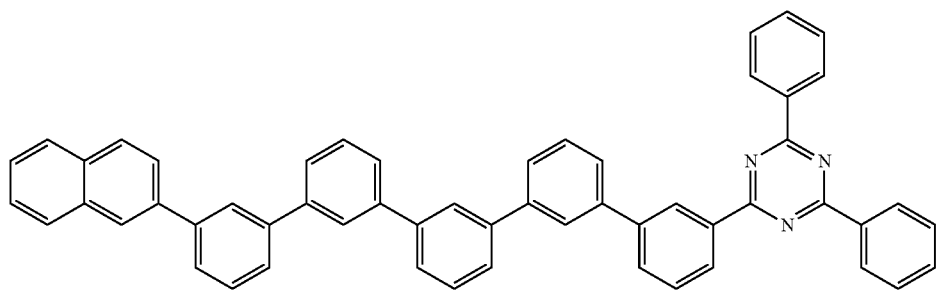
69
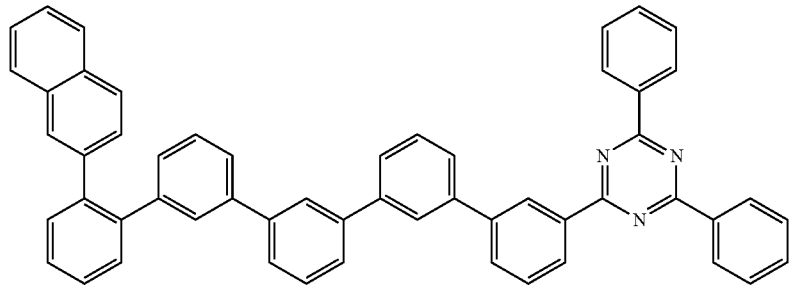

-continued
70
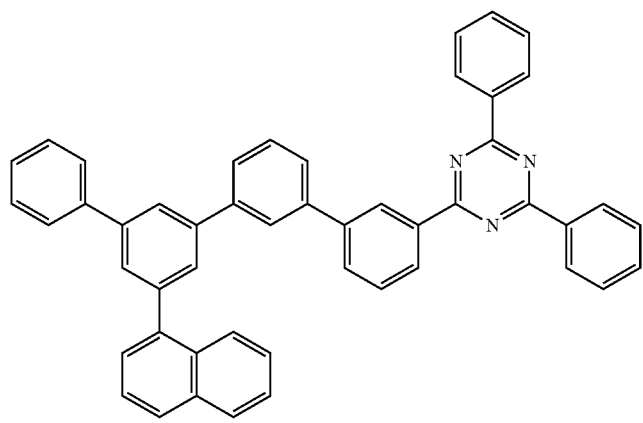
71
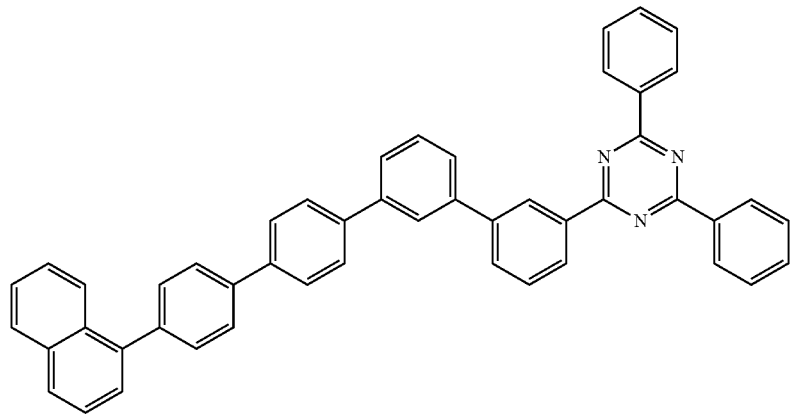
72
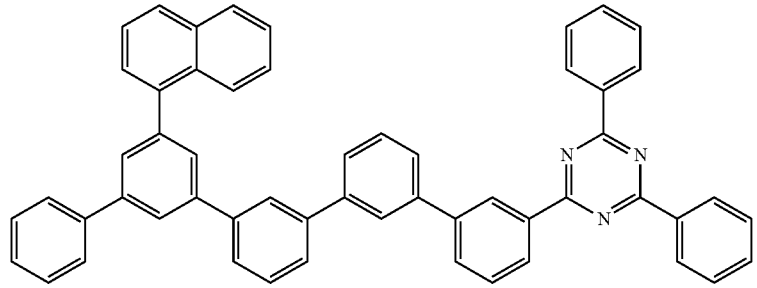
73
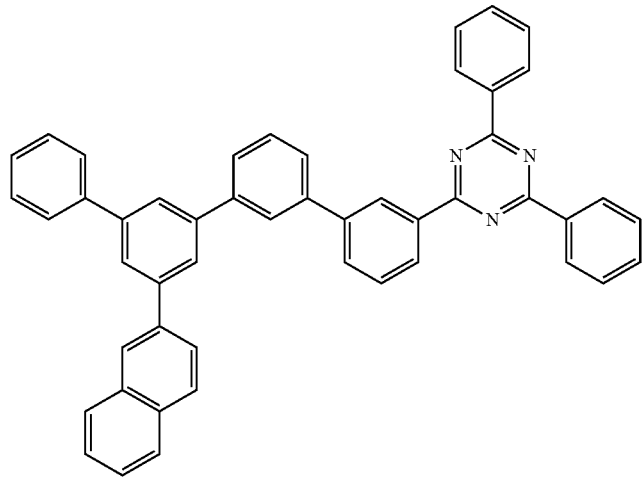

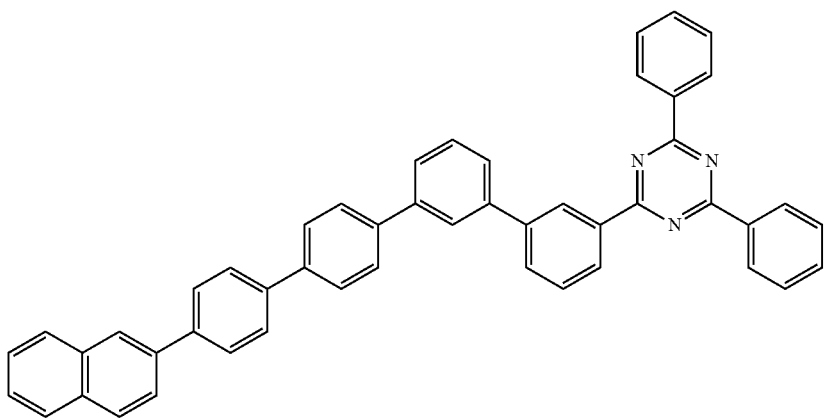
74
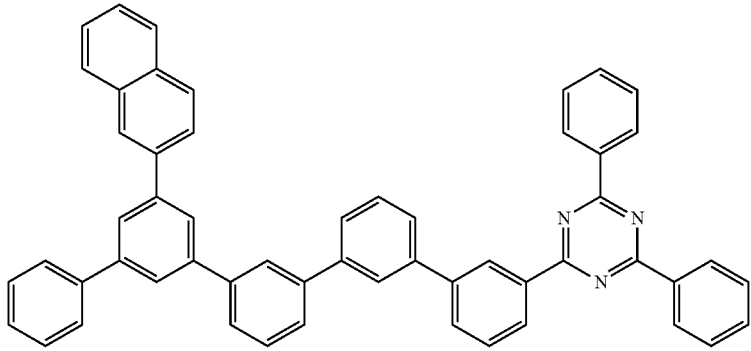
75
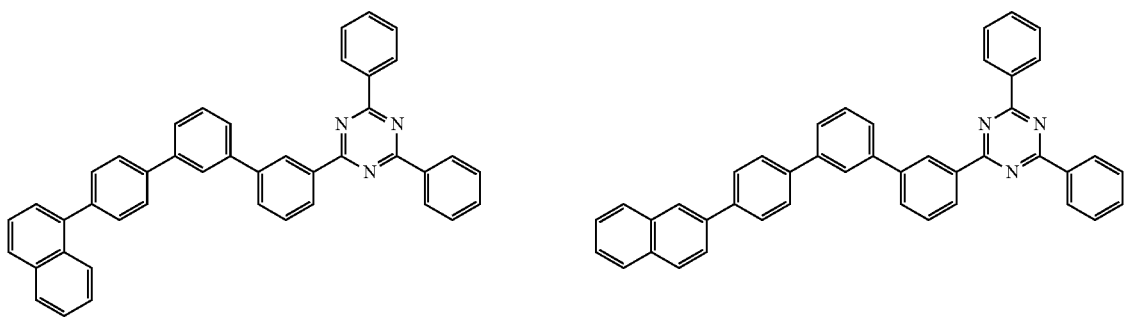
76  77
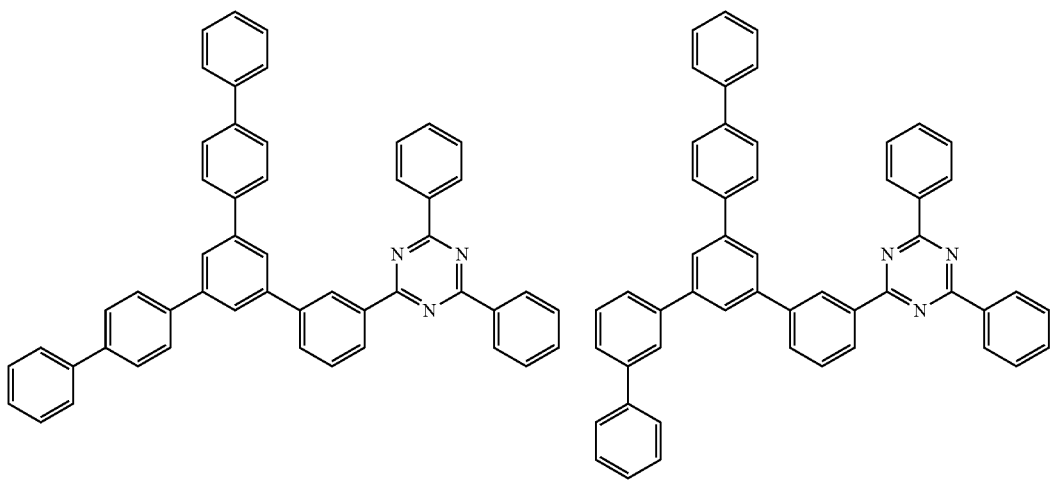
78  79

-continued
80
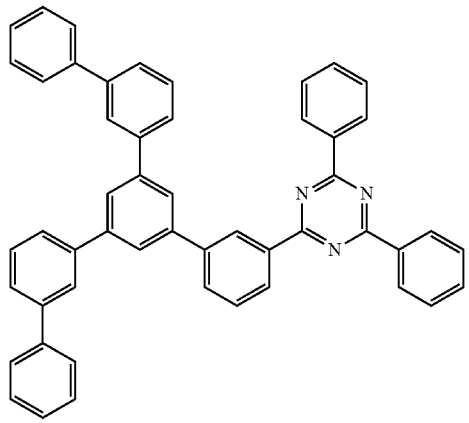
81
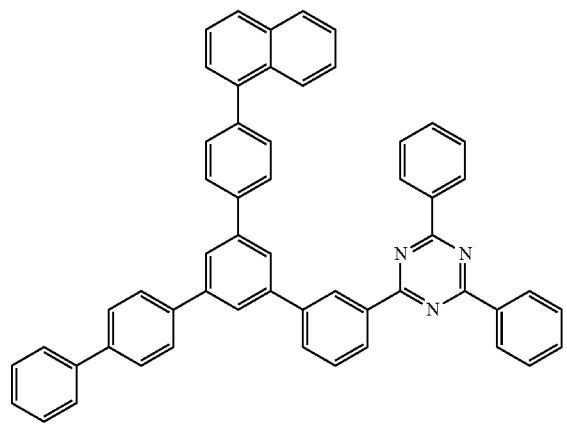
82
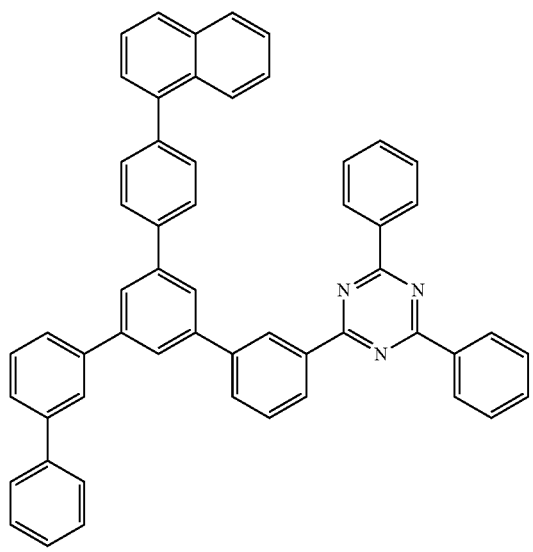
83
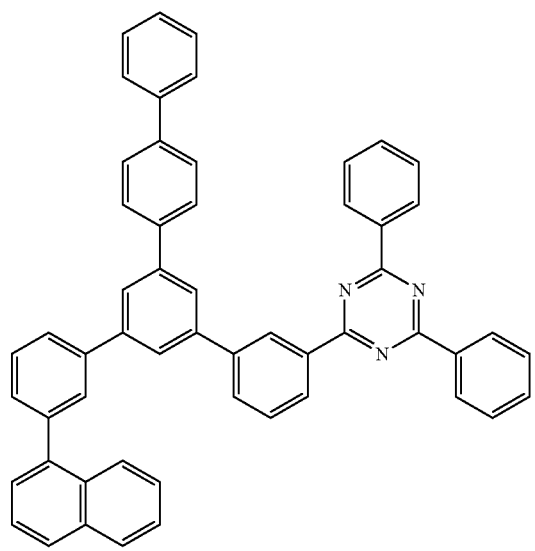
84
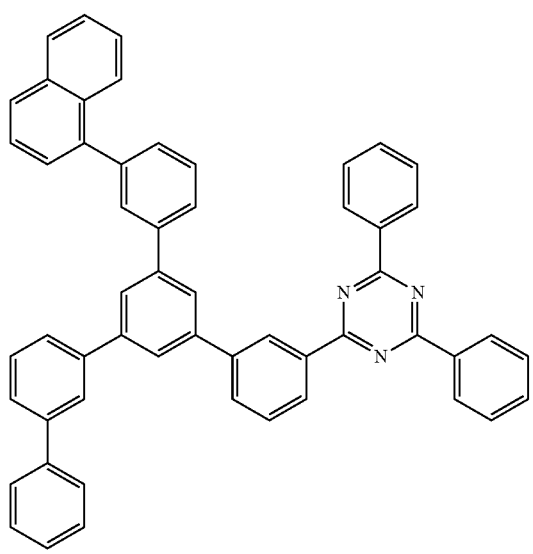

85
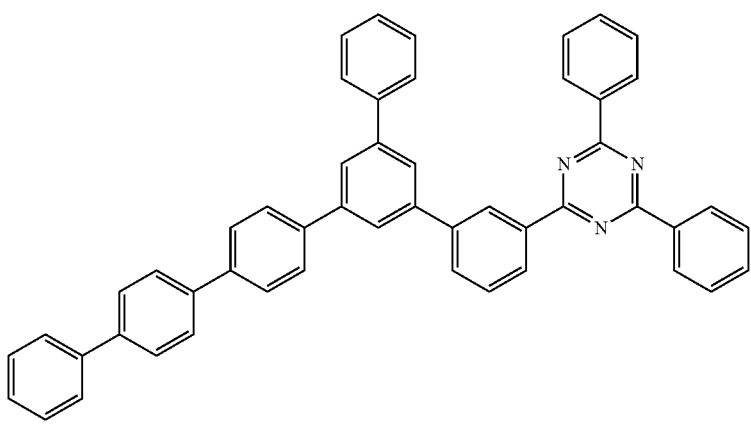
86
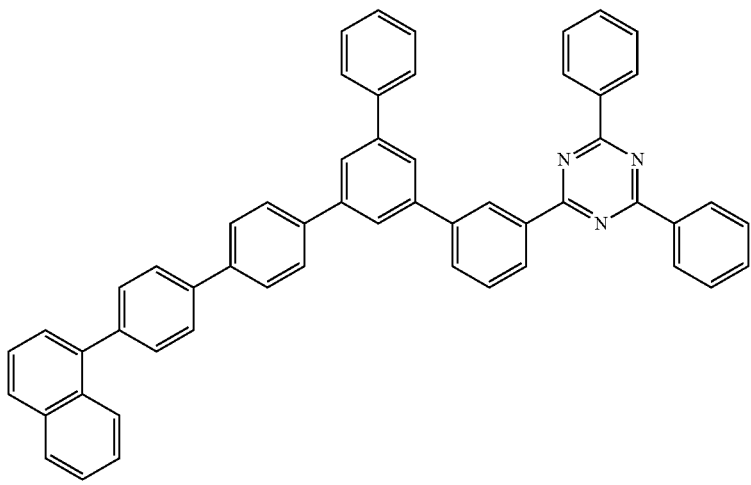
87
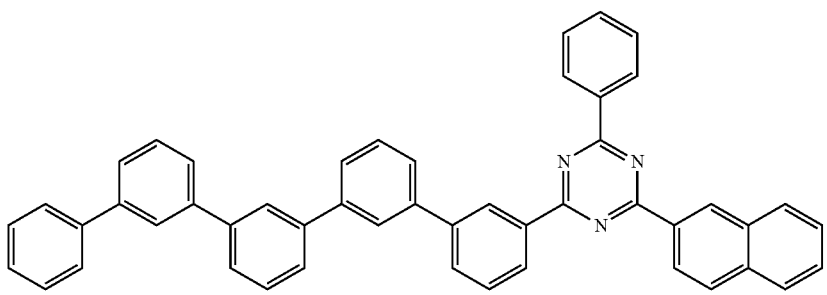
88
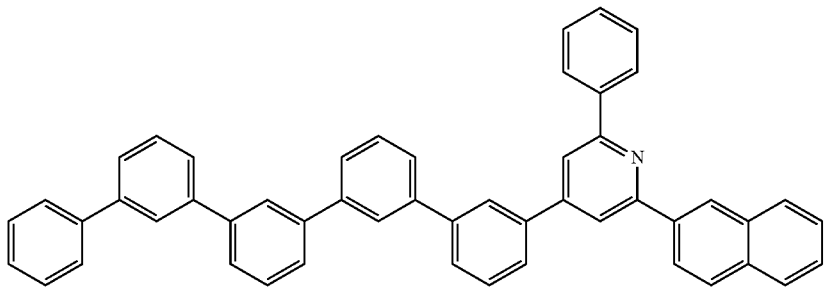

89
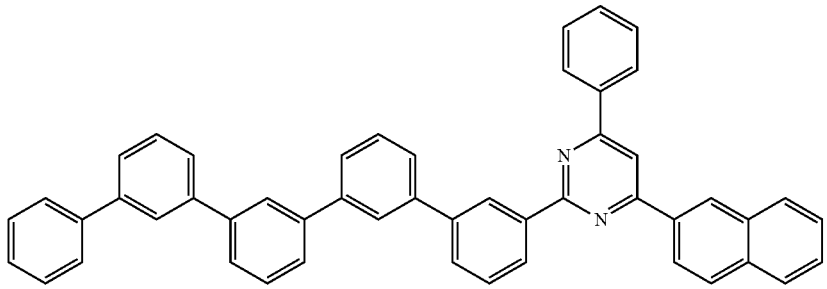
90
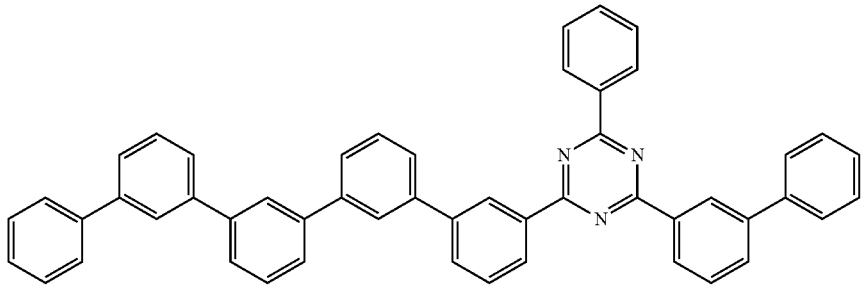
91
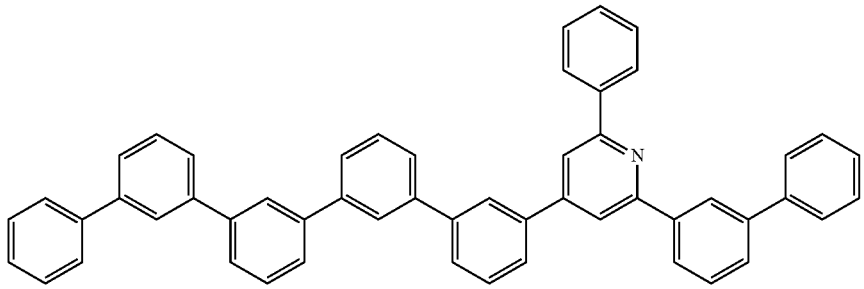
92
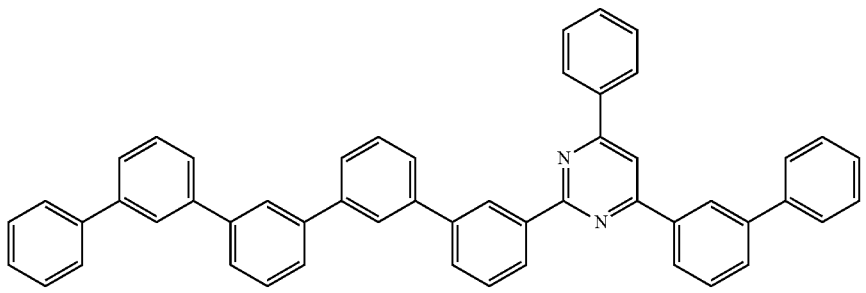
93
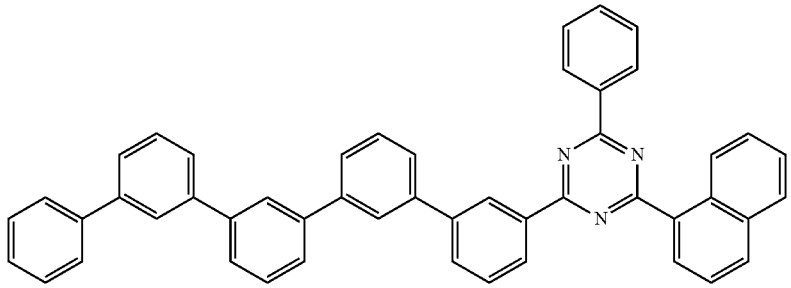

94
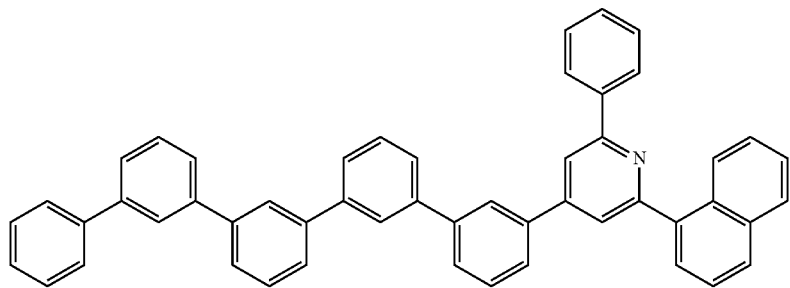
95
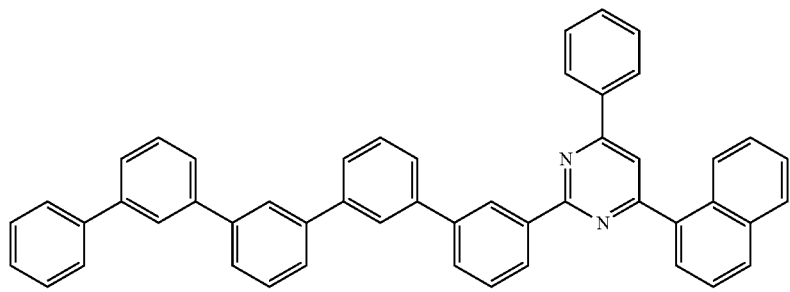
96
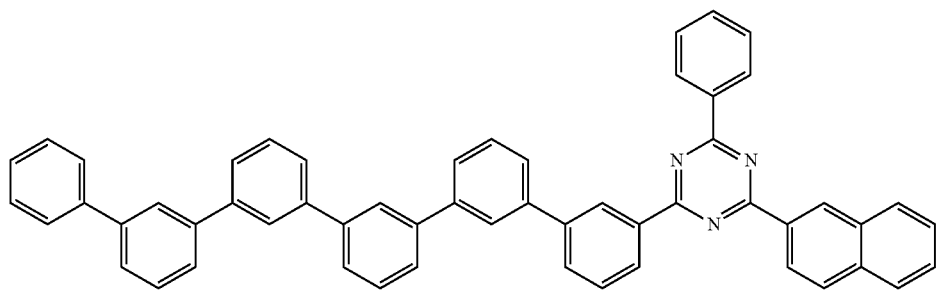
97
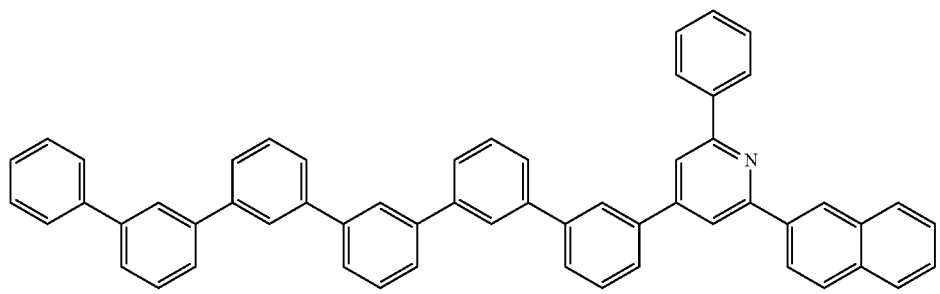
98
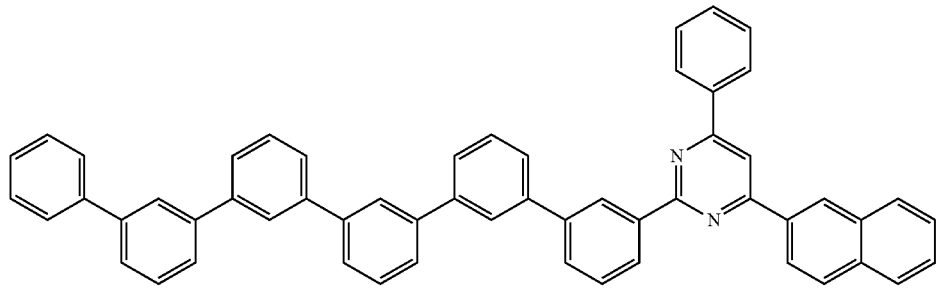

-continued
99
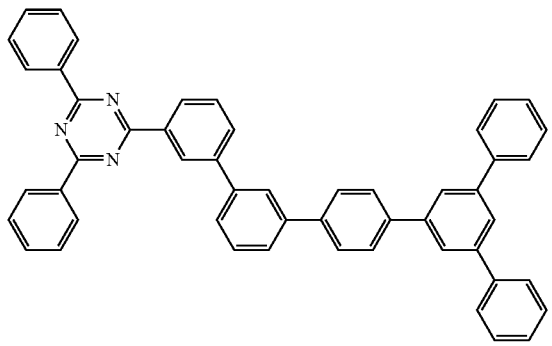
100
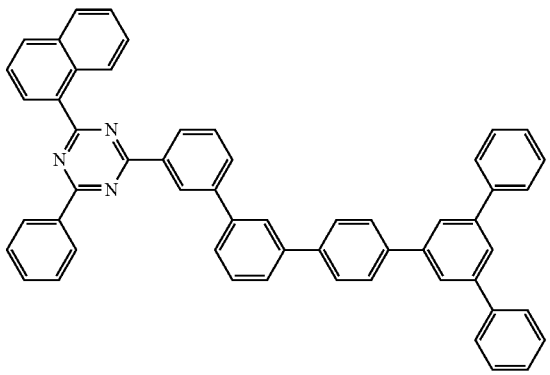
101
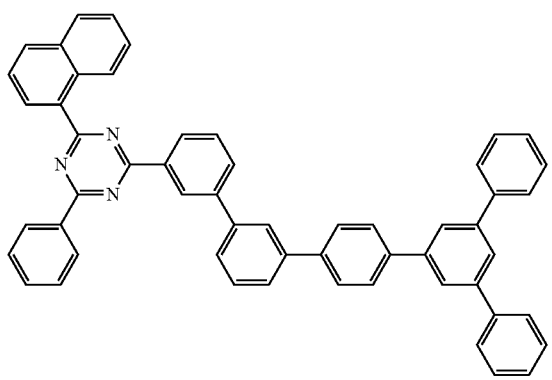
102
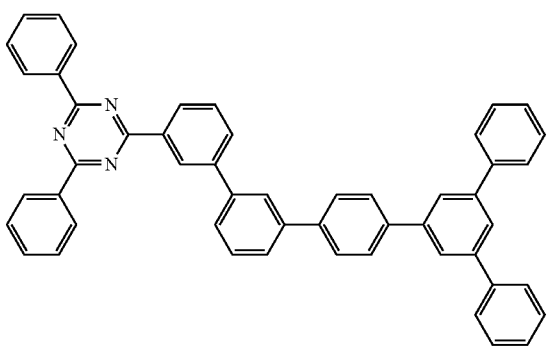
103
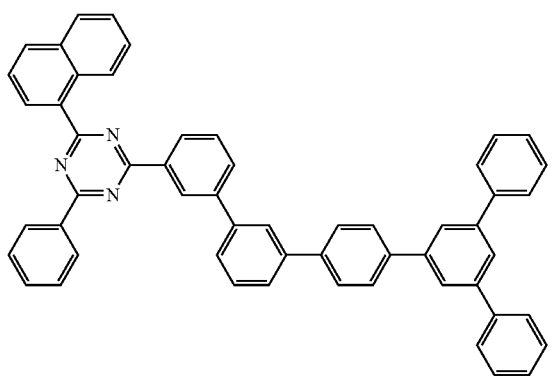
104
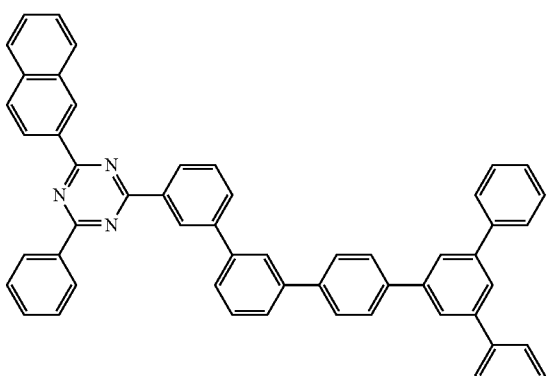
105
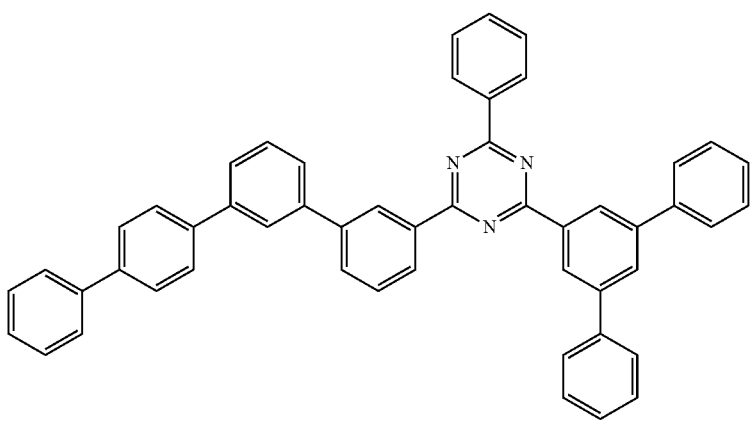

106
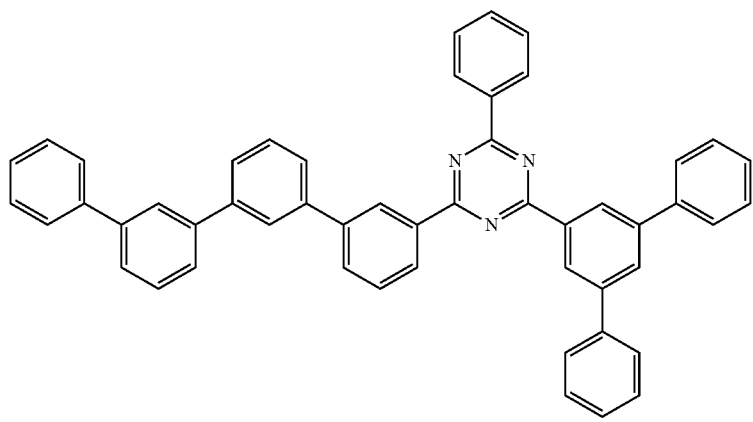
107
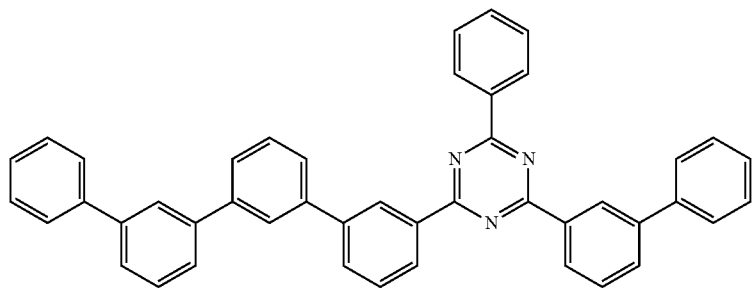
108
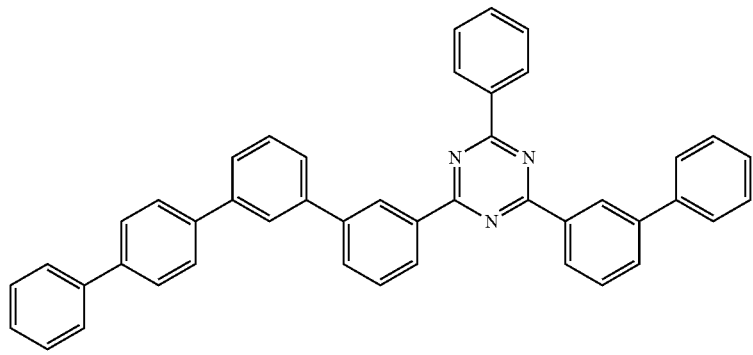
109
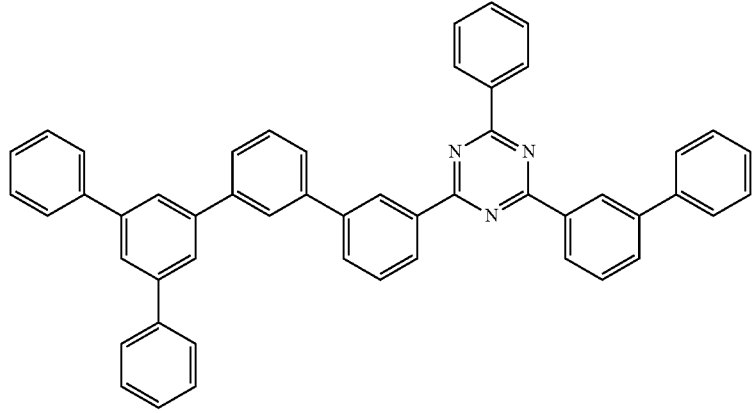

110
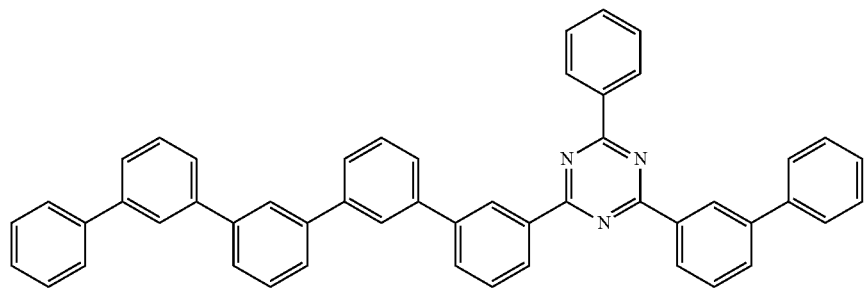
111
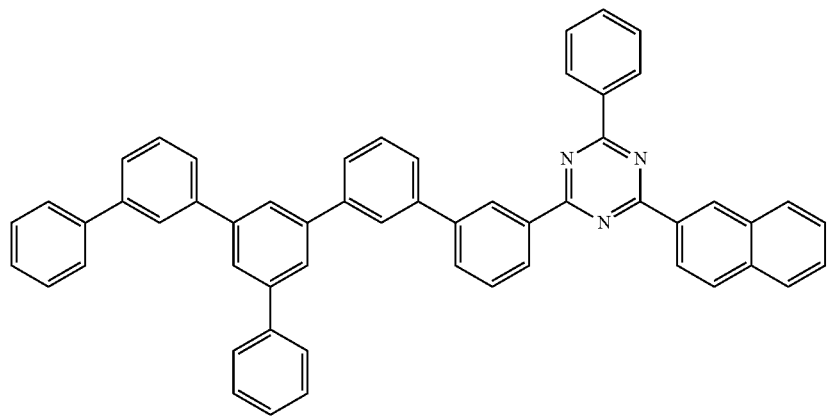
112
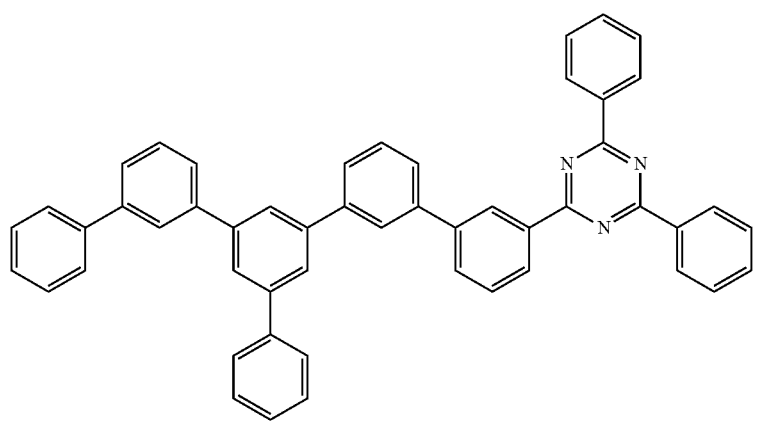
113
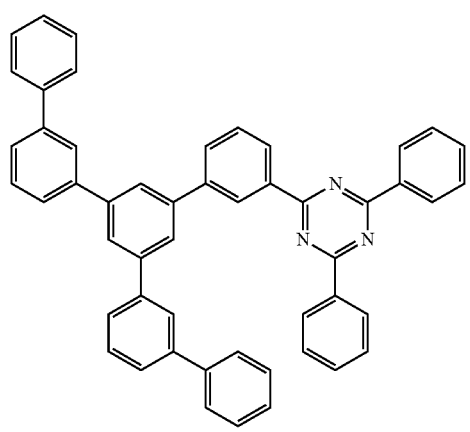
114
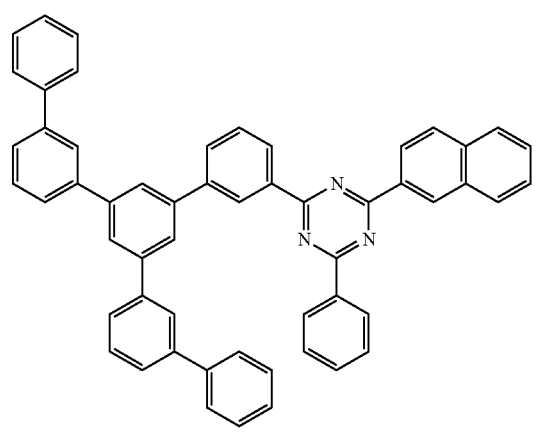

115
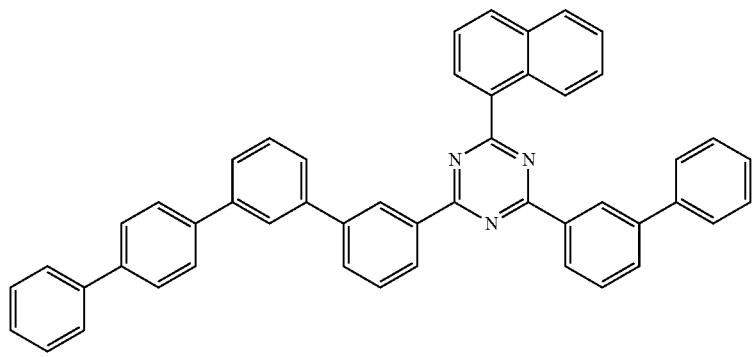
116
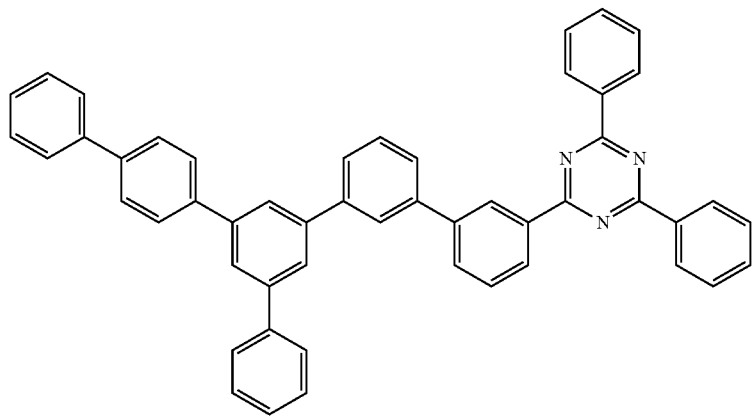
117
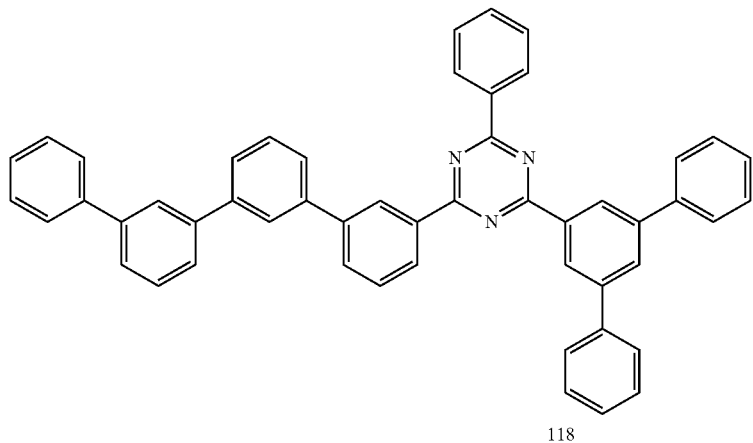
118  119
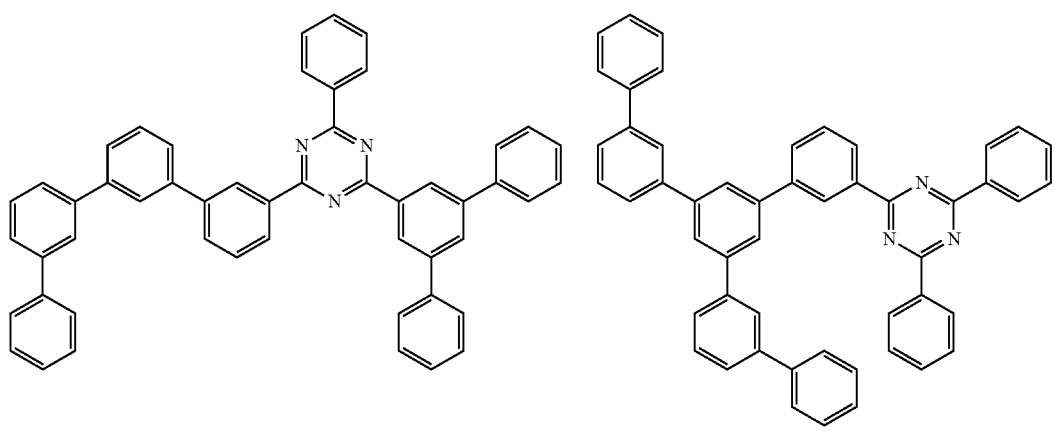

120
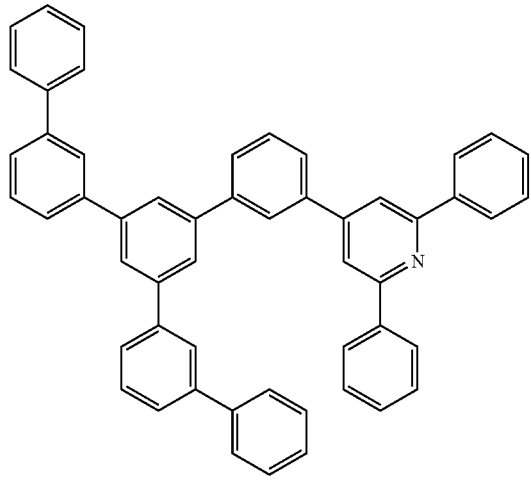
121
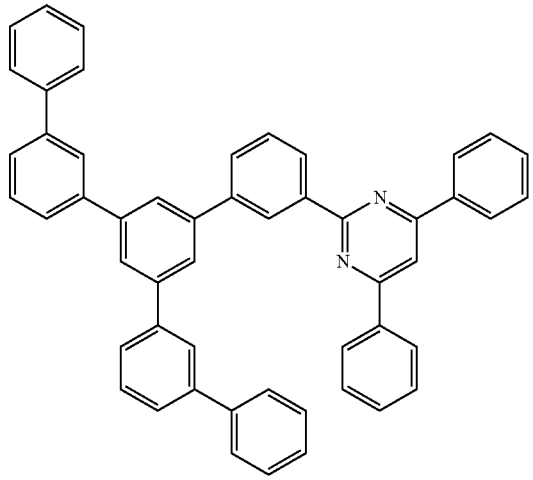
122
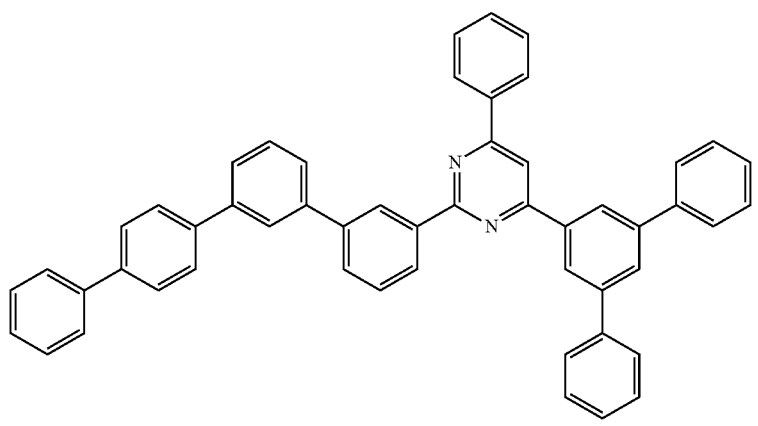
123
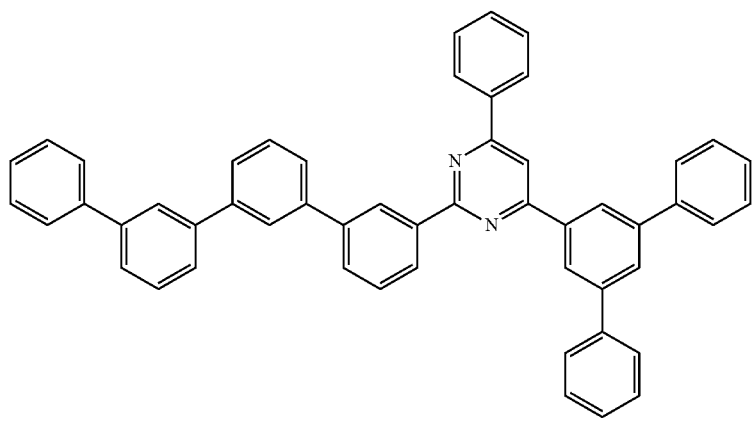

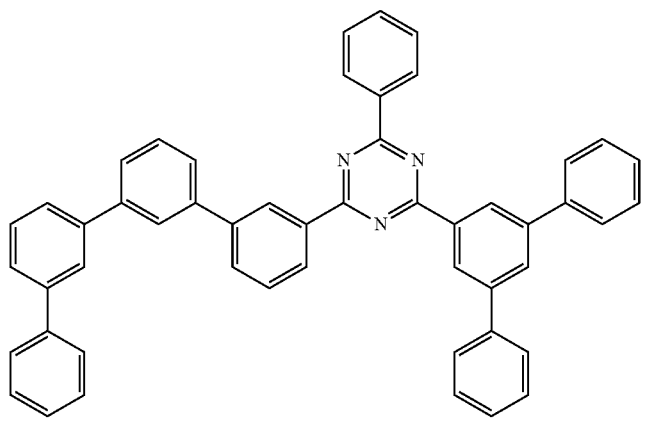
124
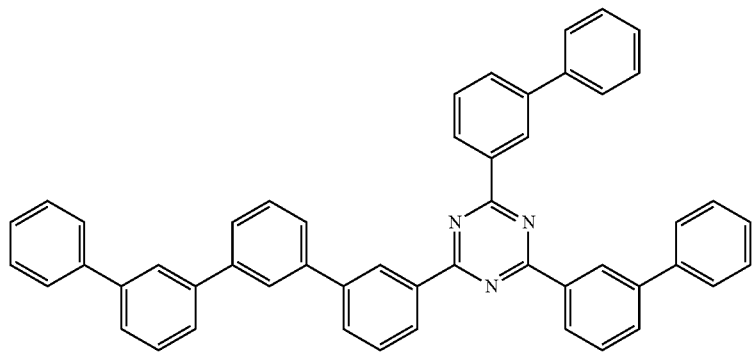
125
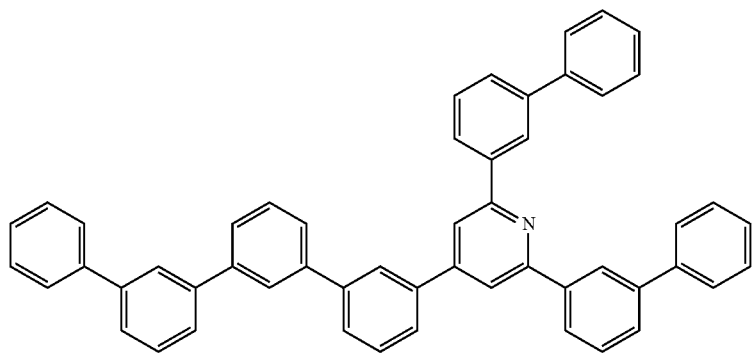
126
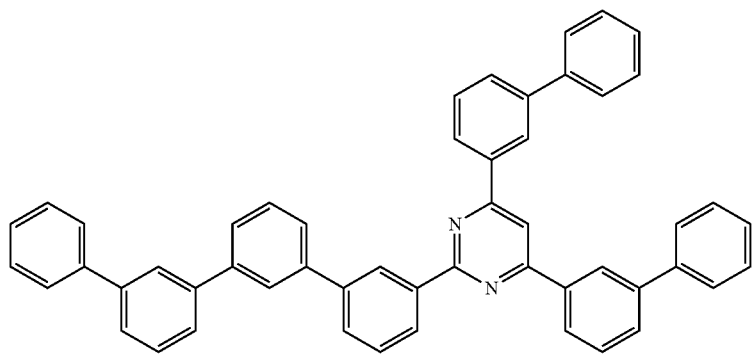
127

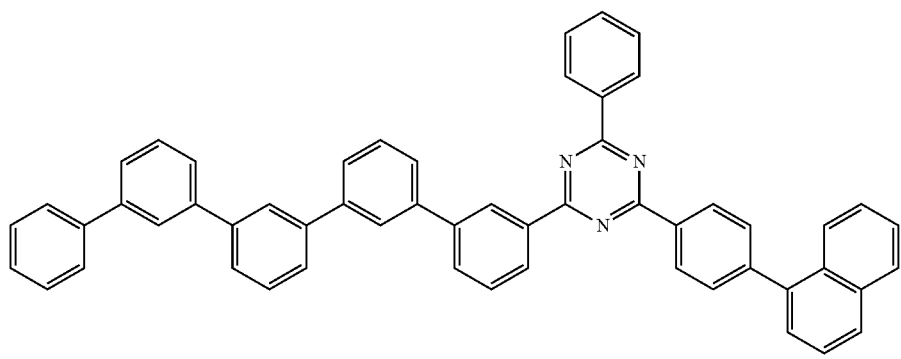
128
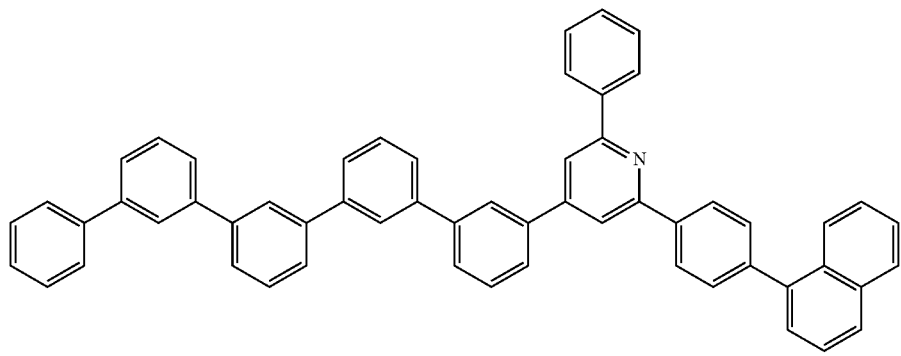
129
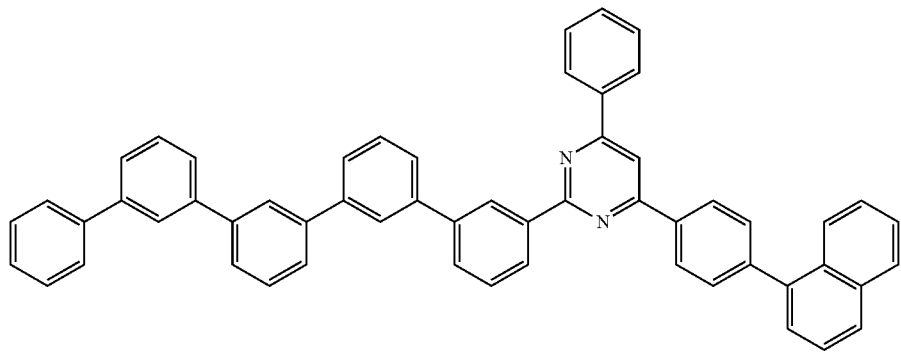
130
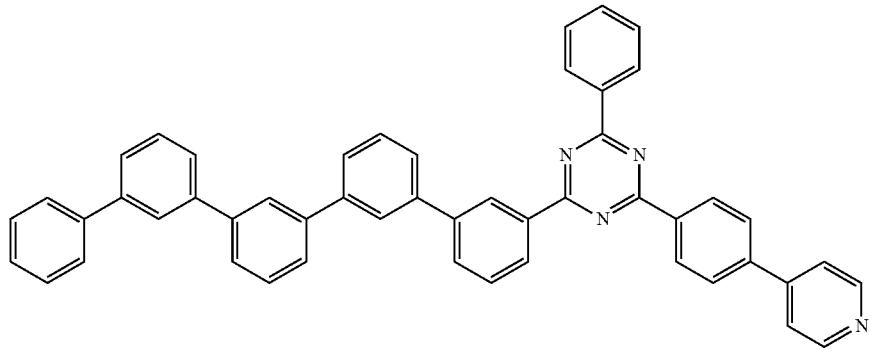
131

-continued
132
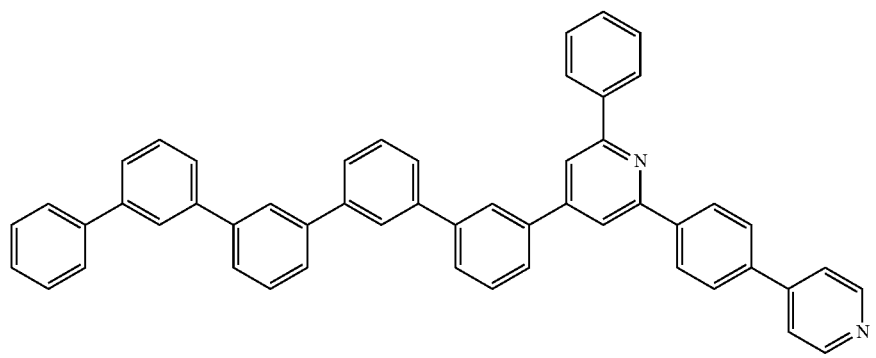
133
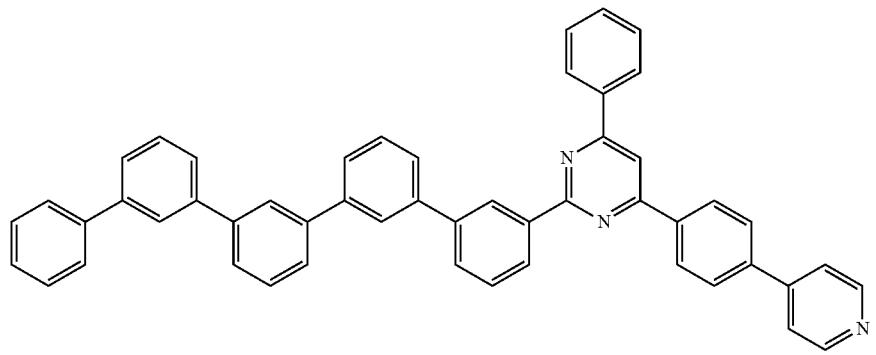
134
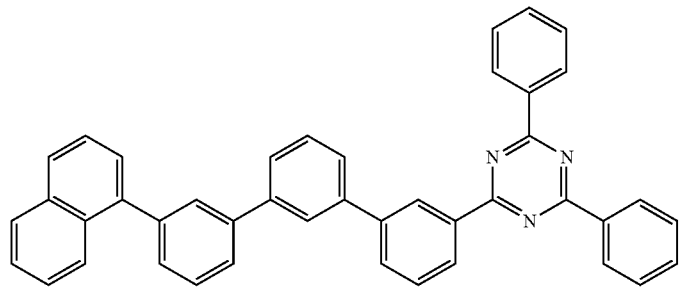
135
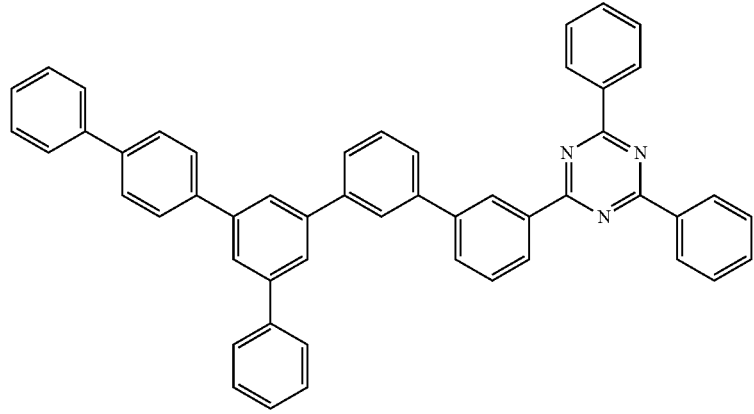

136
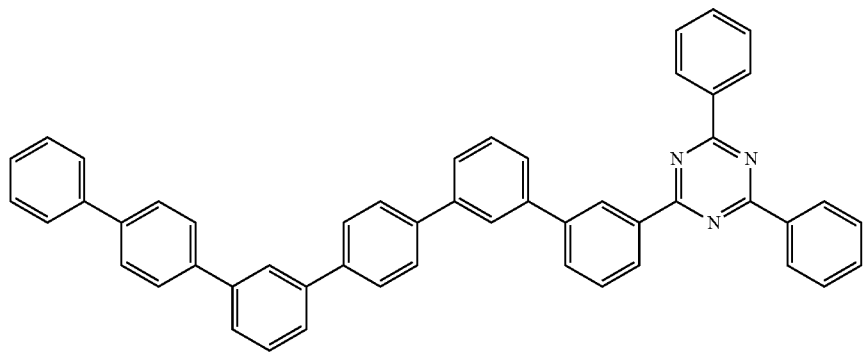
137
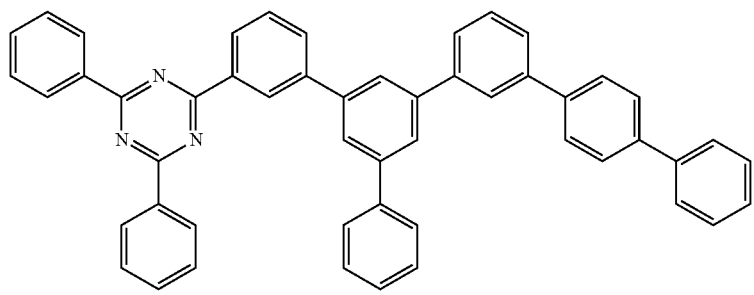
138
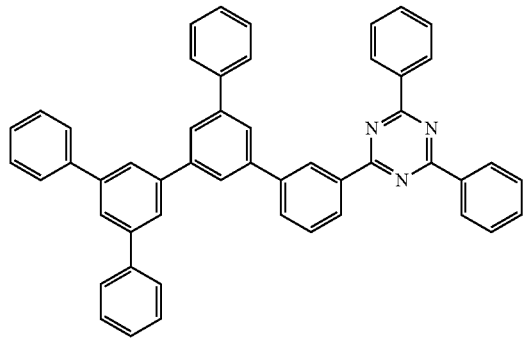
139
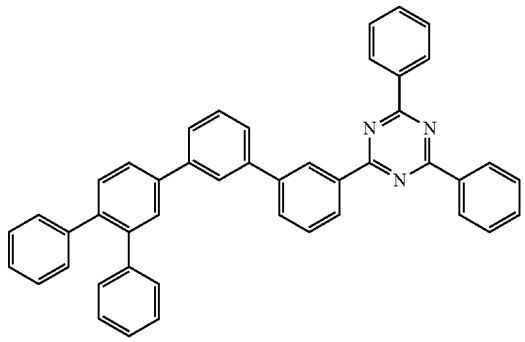
140
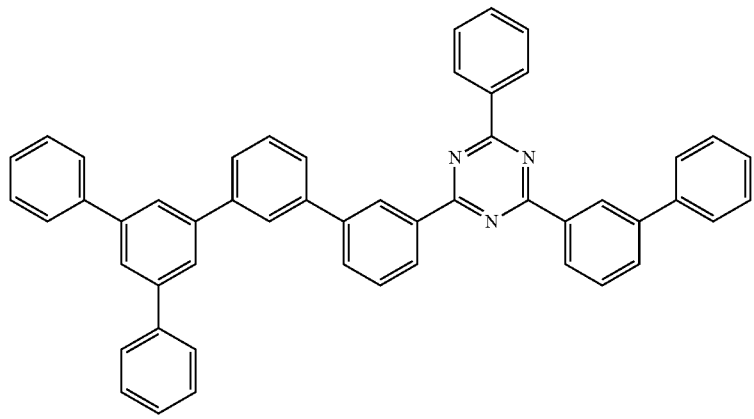

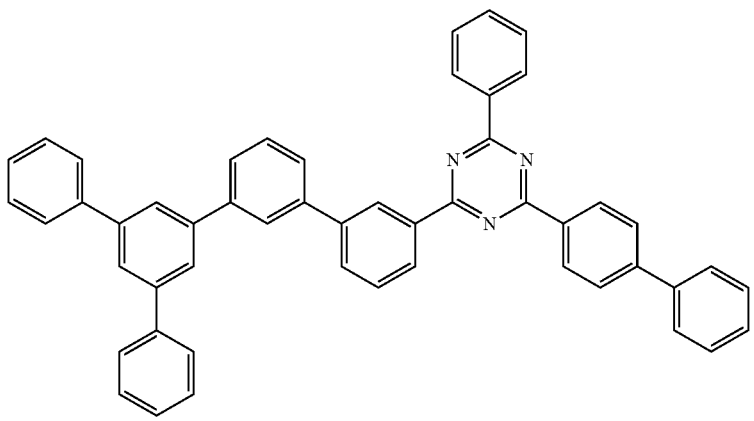

The organic compound may be used for an organic optoelectric device.

The organic compound may be applied to an organic optoelectronic device at alone or along with another organic compound. When the organic compound is used along with another organic compound, they may be applied in a form of a composition.

Hereinafter, one example of a composition for an organic optoelectronic device including the organic compound is described.

The composition for an organic optoelectronic device may be, for example a composition including the organic compound and at least one organic compound having a carbazole moiety. Hereinafter, the organic compound is referred to as a 'first organic compound' and the at least one organic compound having a carbazole moiety is referred to as a 'second organic compound'.

The second organic compound may be, for example a compound represented by the following Chemical Formula 8.

[Chemical Formula 8]

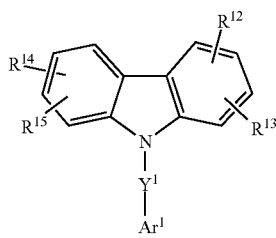

In Chemical Formula 8, $Y^1$ is a single bond, a substituted or unsubstituted C1 to C20 alkylene group, a substituted or unsubstituted C2 to C20 alkenylene group, a substituted or unsubstituted C6 to C30 arylene group, a substituted or unsubstituted C2 to C30 heteroarylene group, or a combination thereof, $Ar^1$ is a substituted or unsubstituted C6 to C30 aryl group, a substituted or unsubstituted C2 to C30 heteroaryl group, or a combination thereof, $R^{12}$ to $R^{15}$ are each independently hydrogen, deuterium, a substituted or unsubstituted C1 to C20 alkyl group, a substituted or unsubstituted C6 to C50 aryl group, a substituted or unsubstituted C2 to C50 heteroaryl group, or a combination thereof, and at least one of $R^{12}$ to $R^{15}$ and $Ar^1$ includes a substituted or unsubstituted triphenylene group or a substituted or unsubstituted carbazole group.

The second organic compound represented by the Chemical Formula 8 may be, for example represented by at least one of the following Chemical Formulae 8-I to 8-III:

[Chemical Formula 8-I]

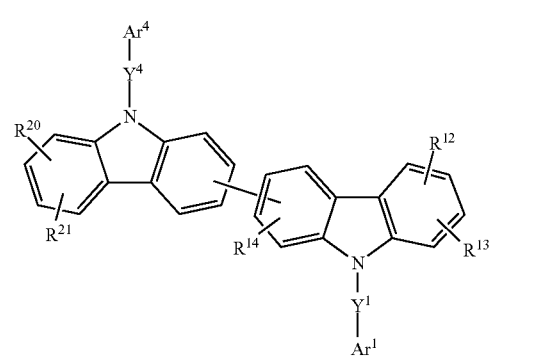

[Chemical Formula 8-II]

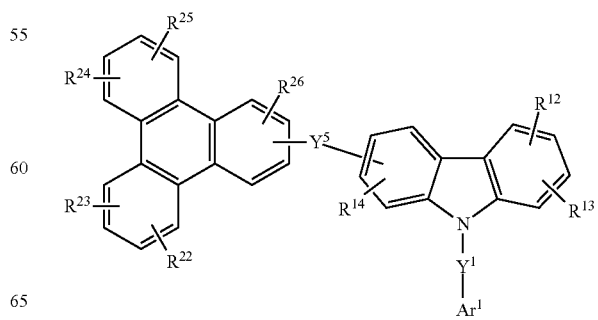

[Chemical Formula 8-III]

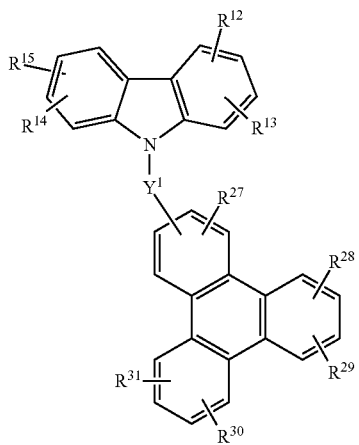

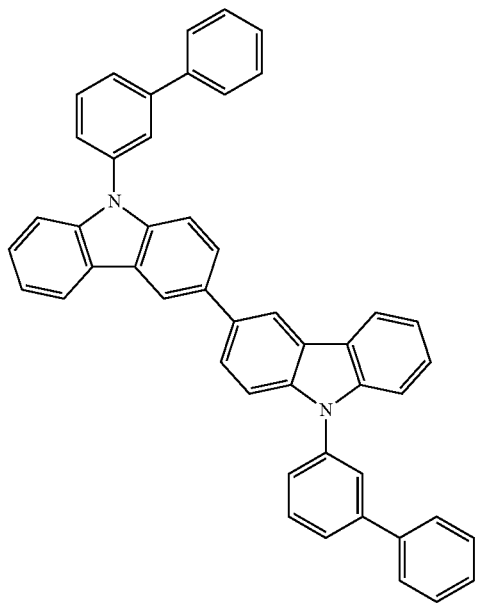

B-112

In Chemical Formulae 8-I to 8-III, $Y^1$, $Y^4$ and $Y^5$ are each independently a single bond, a substituted or unsubstituted C1 to C20 alkylene group, a substituted or unsubstituted C2 to C20 alkenylene group, a substituted or unsubstituted C6 to C30 arylene group, a substituted or unsubstituted C2 to C30 heteroarylene group, or a combination thereof, $Ar^1$ and $Ar^4$ are each independently substituted or unsubstituted C6 to C30 aryl group, a substituted or unsubstituted C2 to C30 heteroaryl group, or a combination thereof, and $R^{12}$ to $R^{15}$ and $R^{20}$ to $R^{31}$ are independently hydrogen, deuterium, a substituted or unsubstituted C1 to C20 alkyl group, a substituted or unsubstituted C6 to C50 aryl group, a substituted or unsubstituted C2 to C50 heteroaryl group, or a combination thereof.

The second organic compound represented by the Chemical Formula 8 may be, for example one of compounds listed in Group 2, but is not limited thereto.

B-111

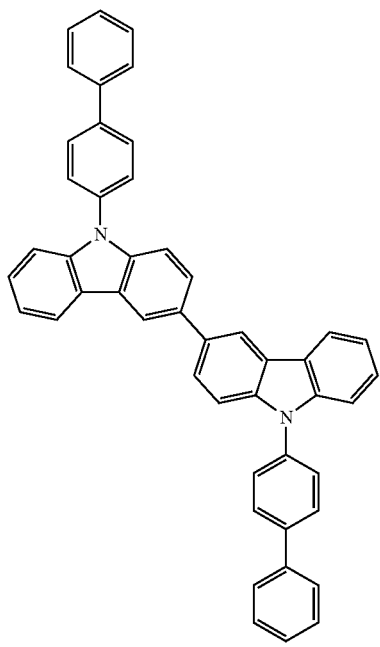

B-113

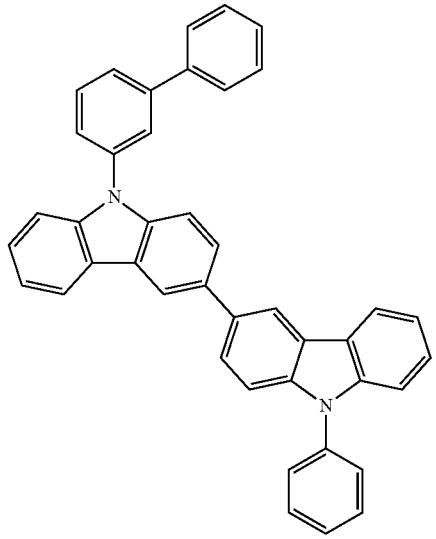

B-114
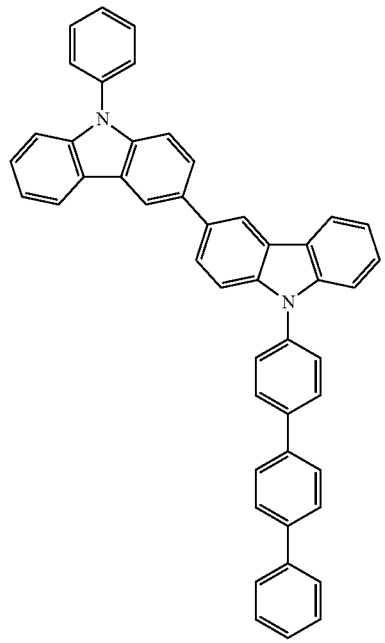
B-116
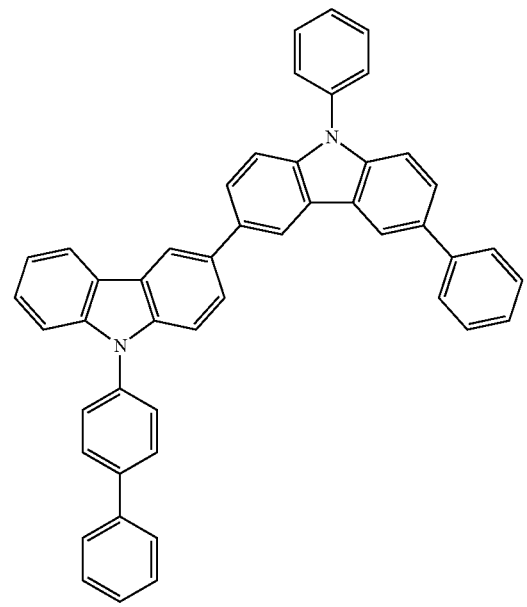
B-115
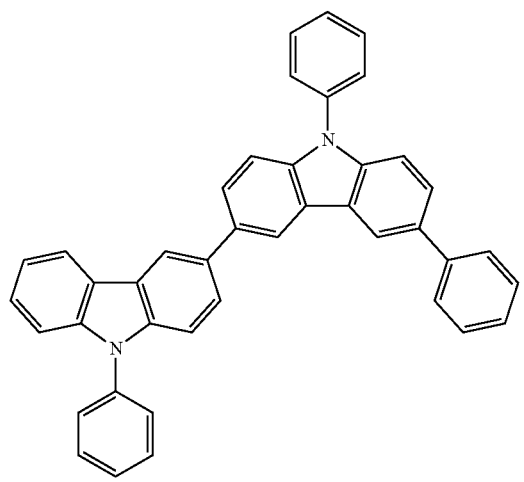
B-117
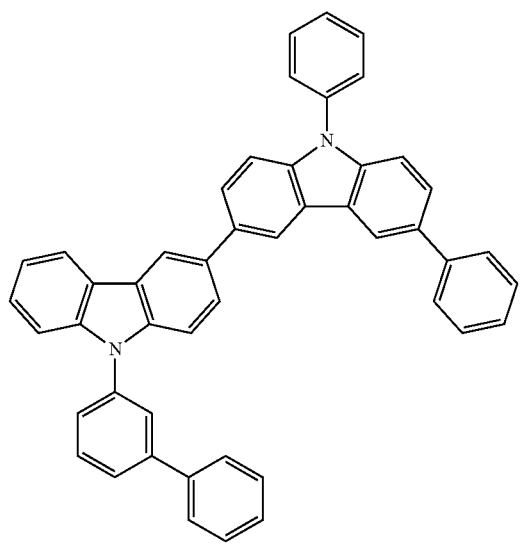

B-118
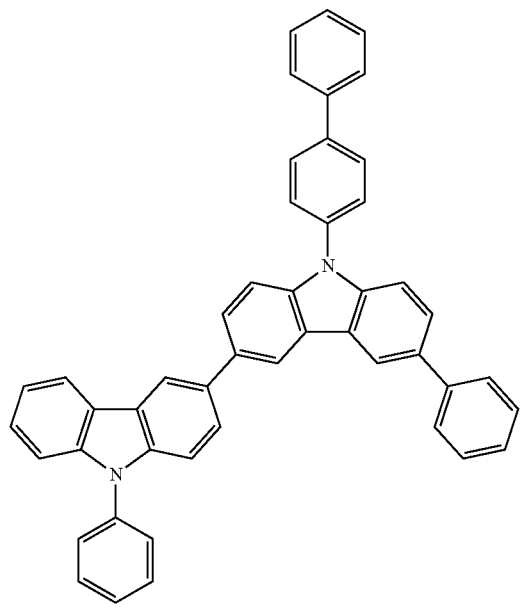
B-119
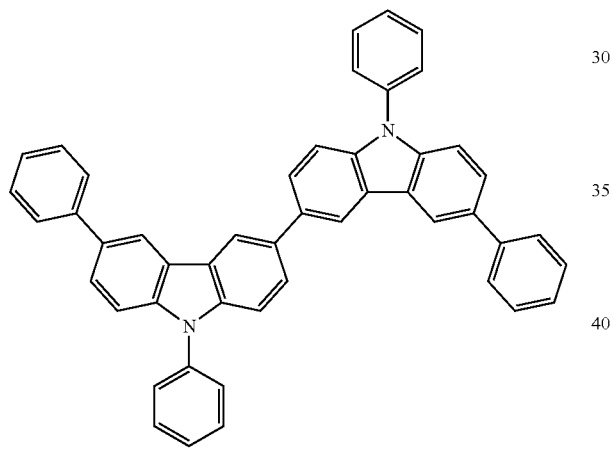
B-120
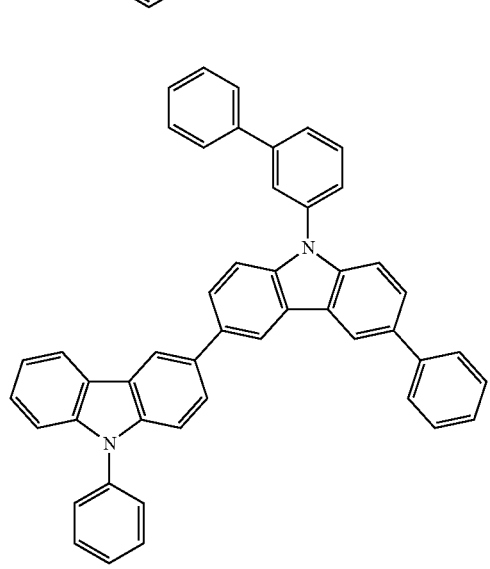
B-121
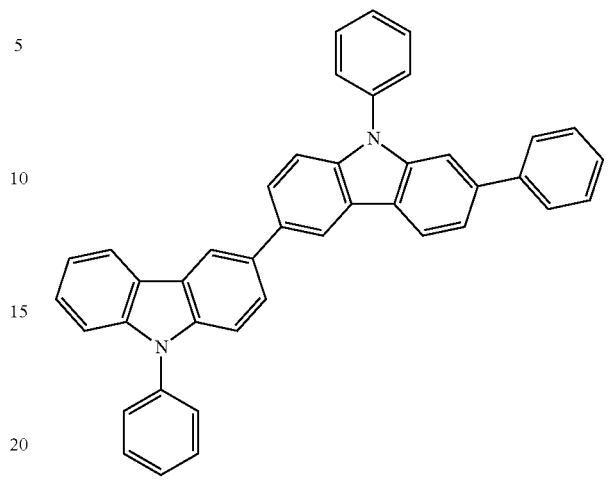
B-122
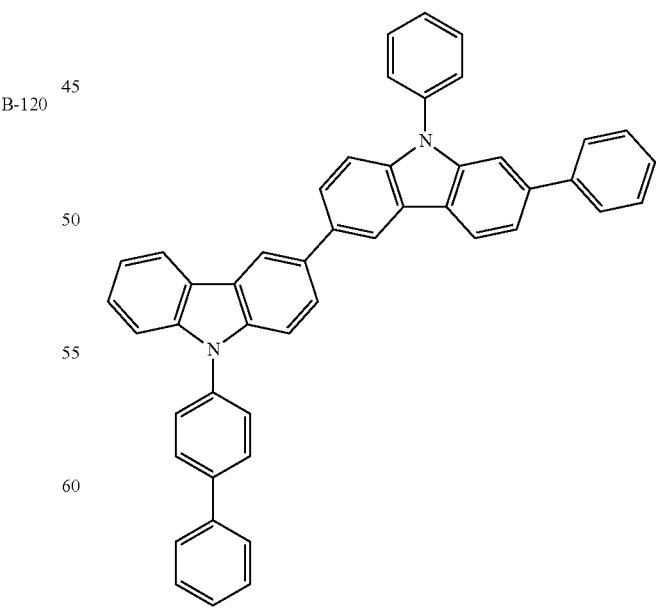

B-123
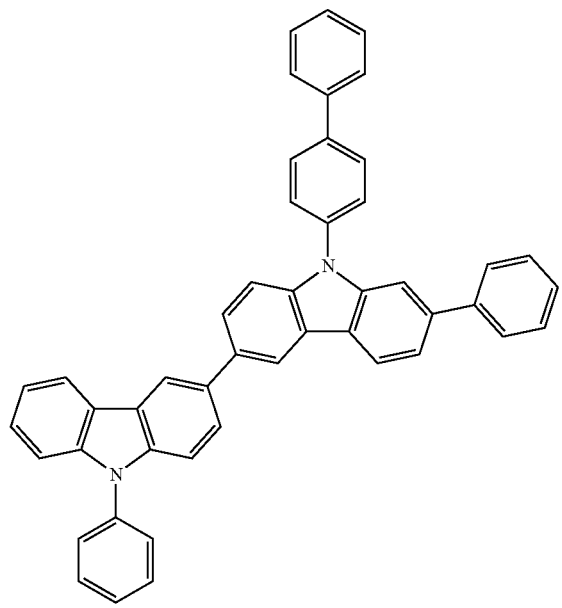
B-124
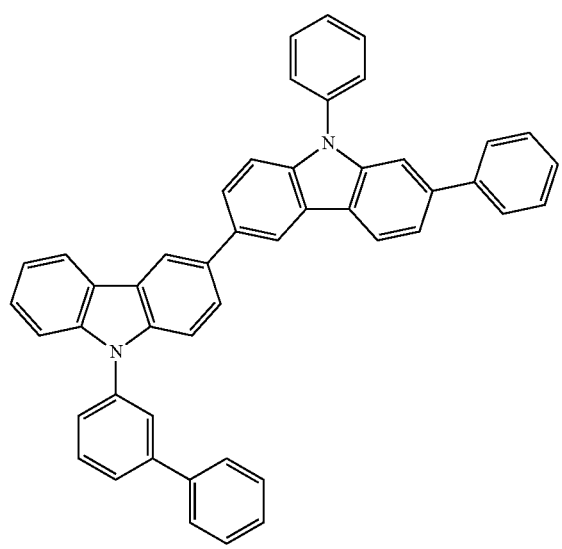
B-125
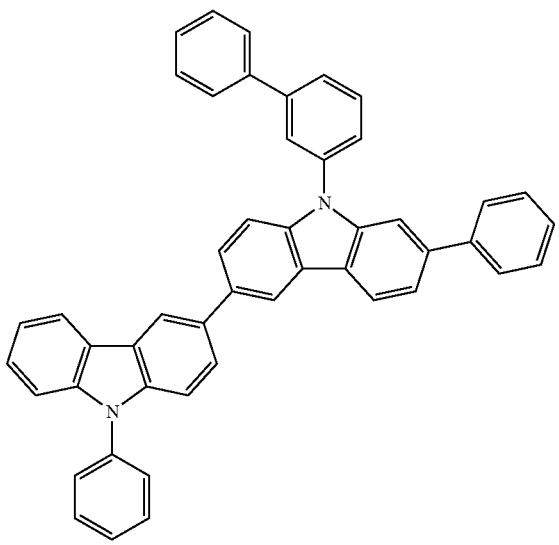
C-10
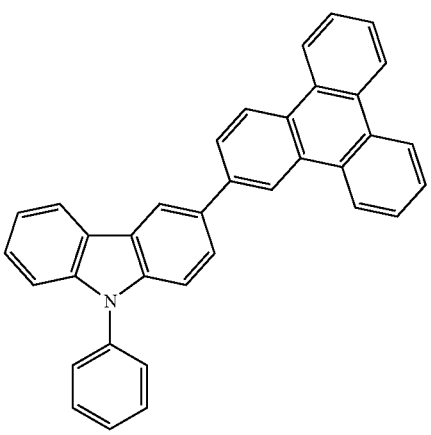
C-11
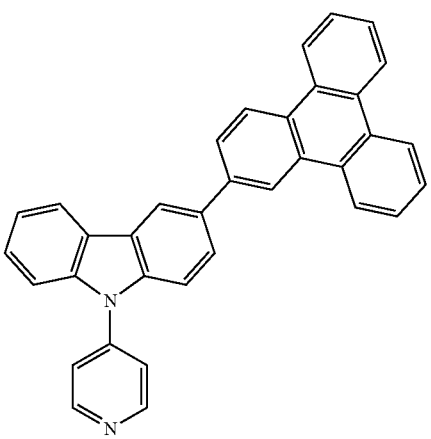

C-12
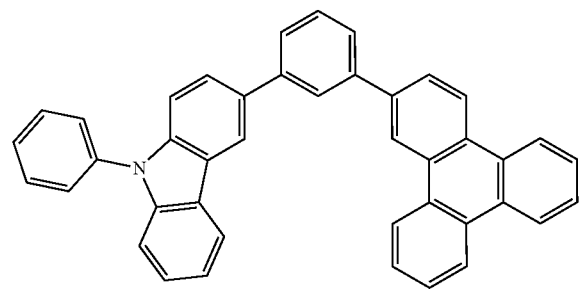
C-13
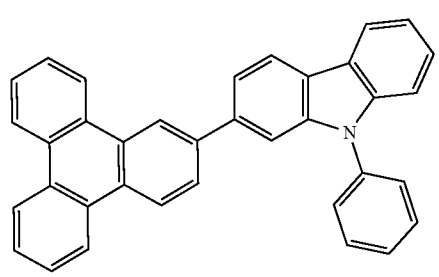
C-14
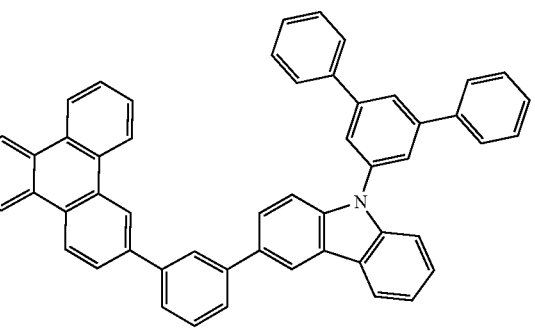
C-15
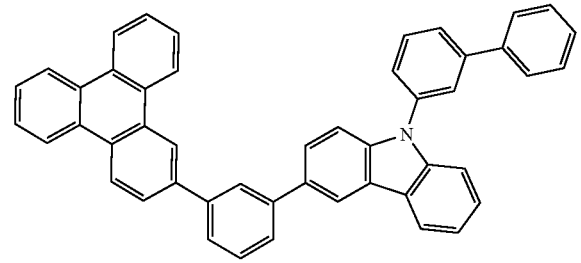
C-16
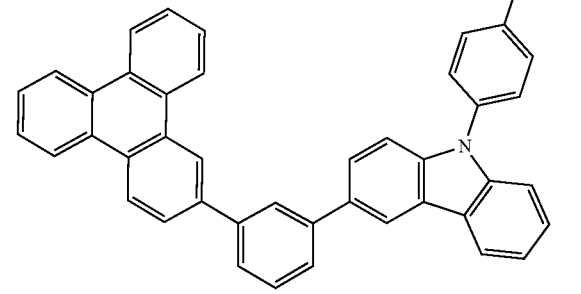
C-17
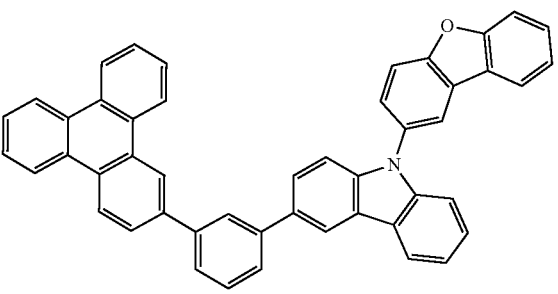
C-18
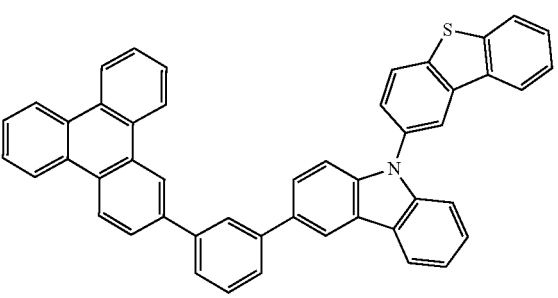
C-19
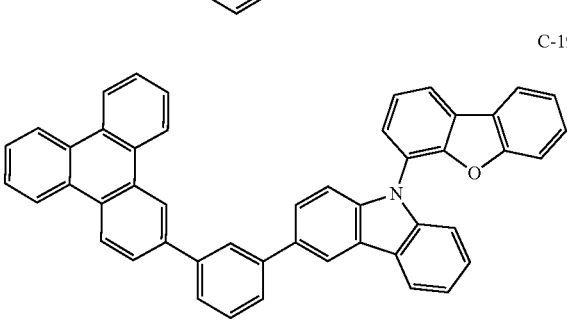
C-20
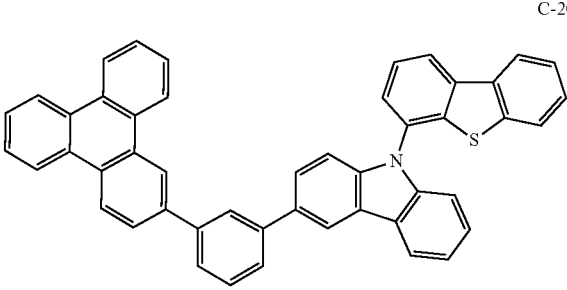
C-21
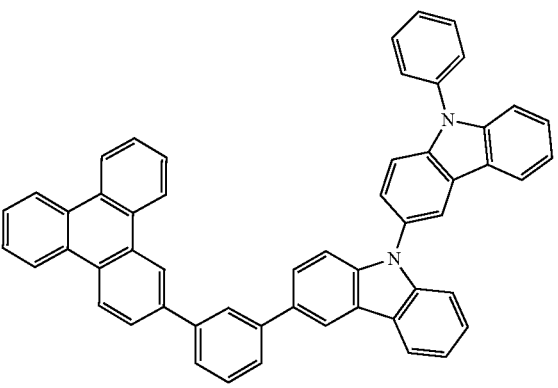

C-22
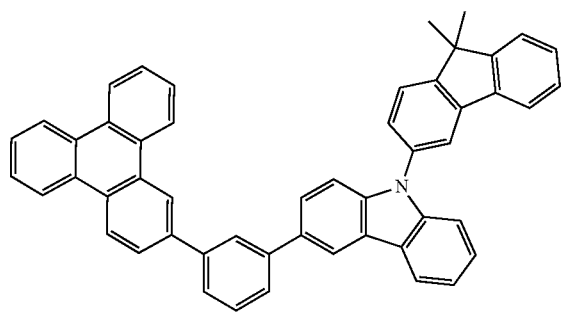
C-27
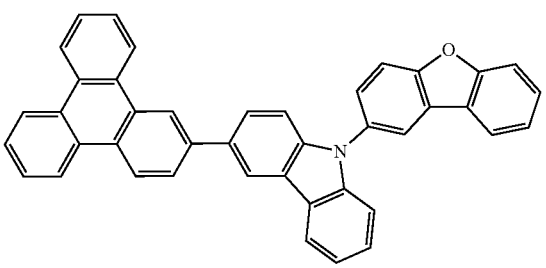
C-23
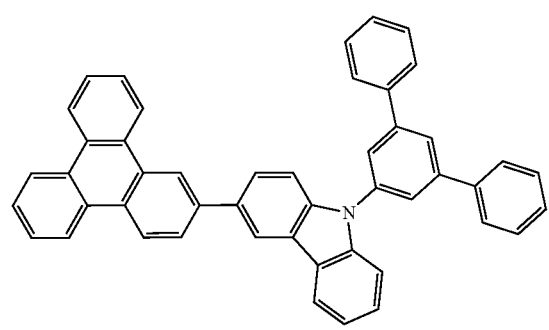
C-28
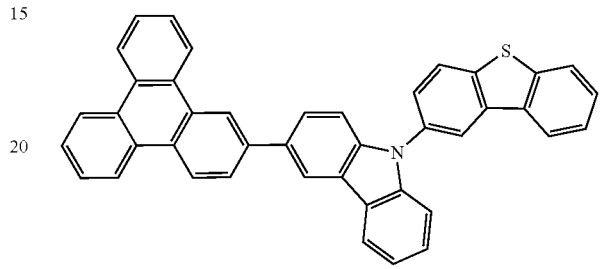
C-24
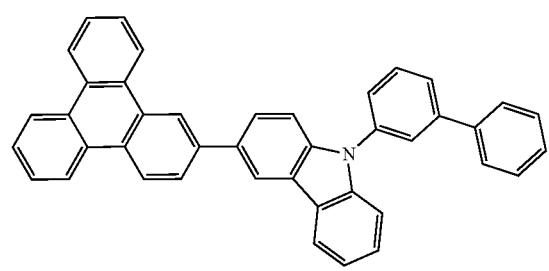
C-29
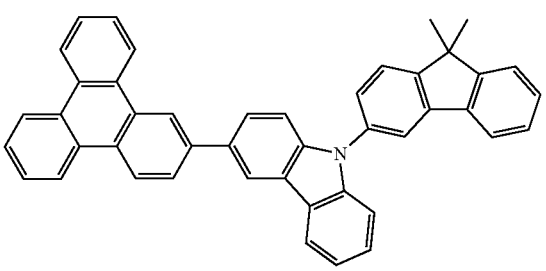
C-25
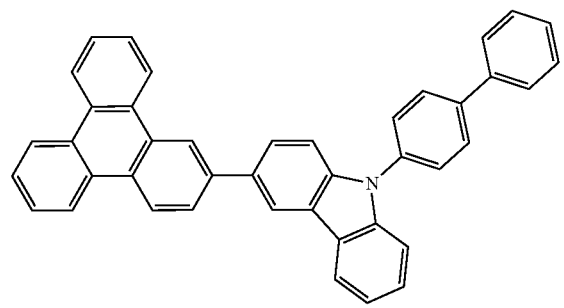
C-30
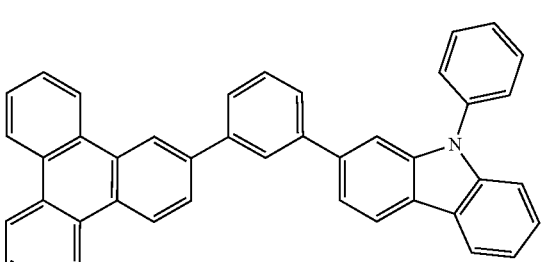
C-26
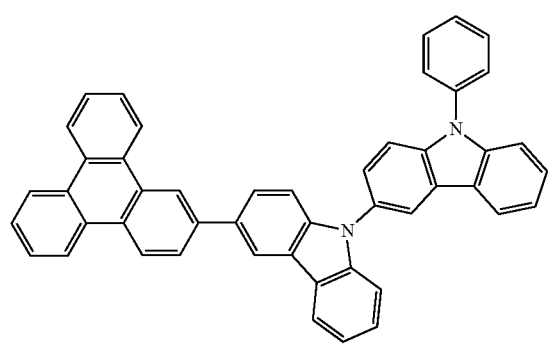
C-31
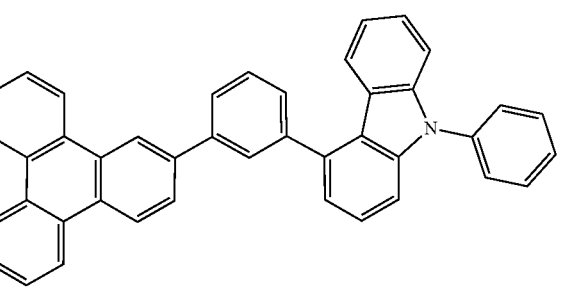

C-32
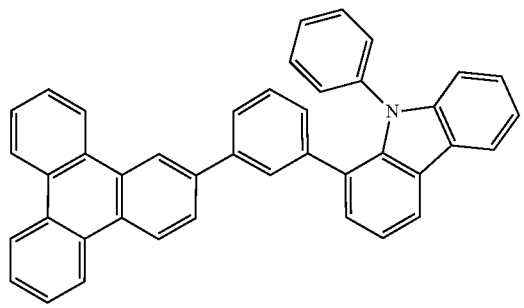
C-33
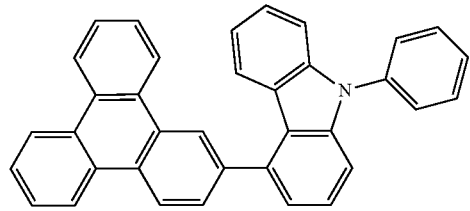
D-10
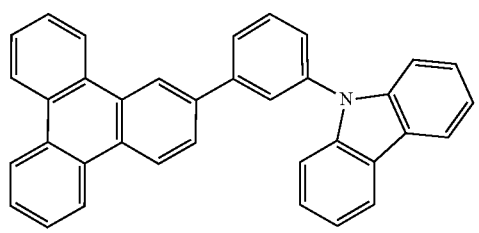
D-11
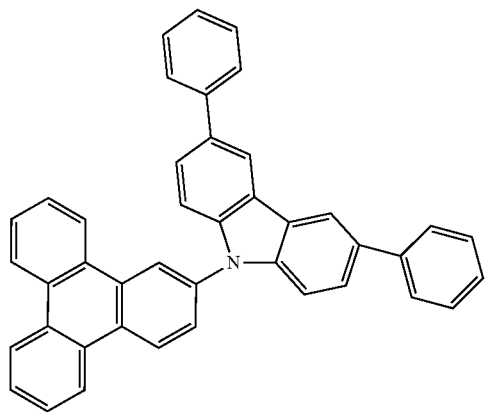
D-12
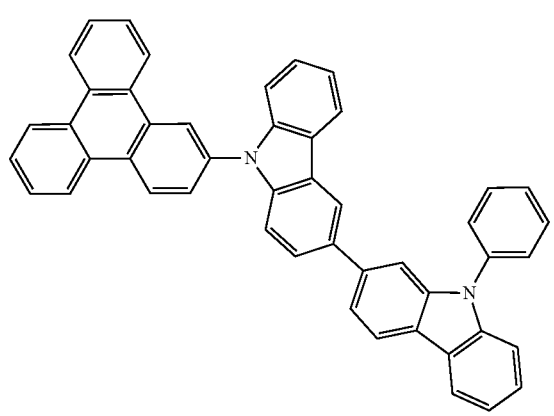
D-13
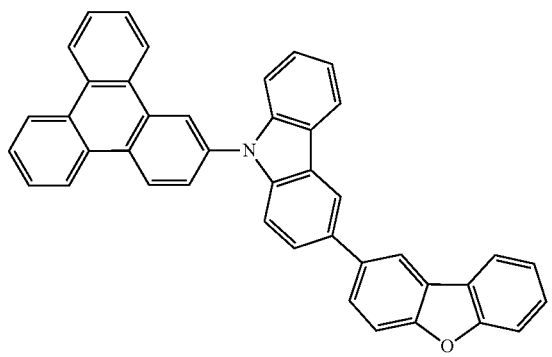
D-14
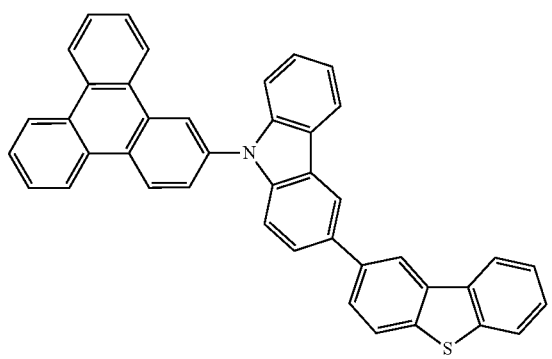
D-15
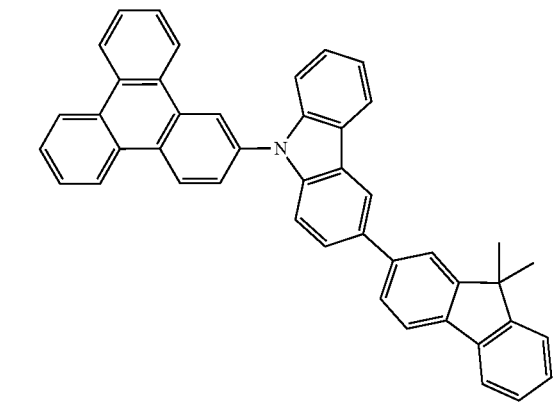
D-16
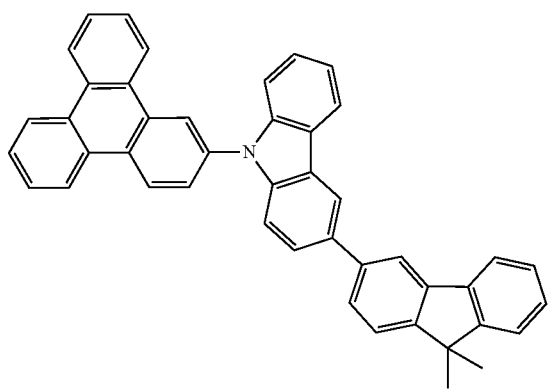

D-17
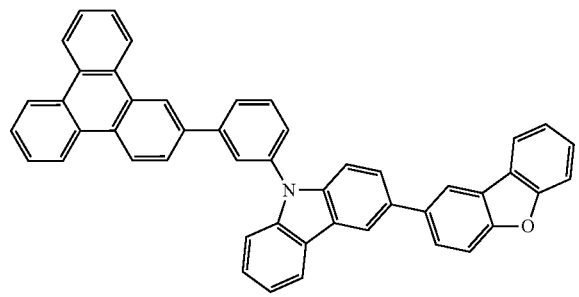
D-18
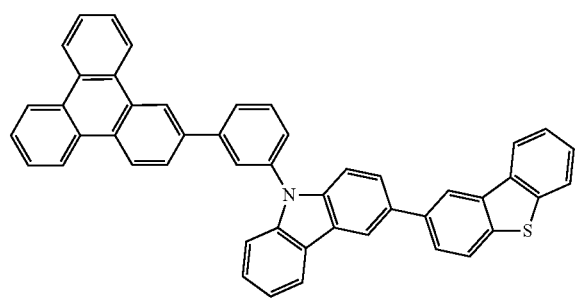
D-19
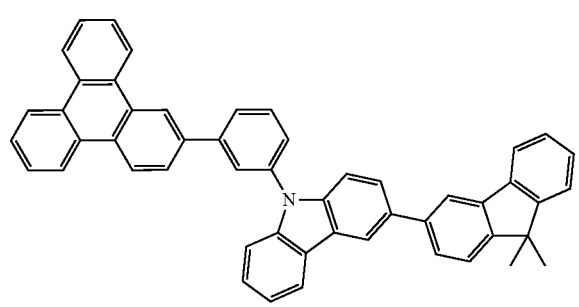
D-20
D-21
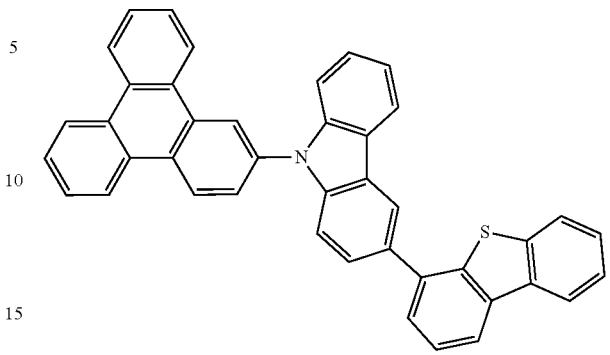
D-22
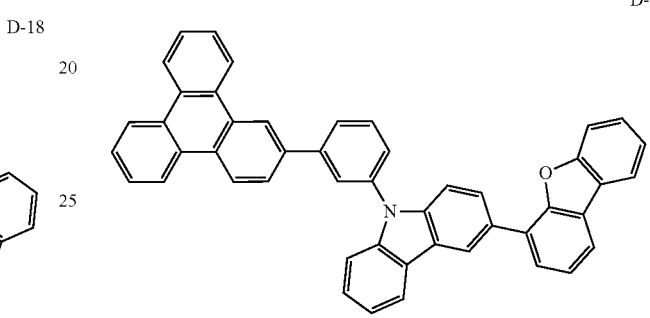
D-23
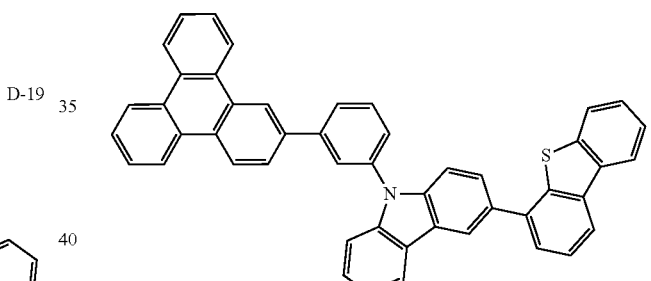
D-24
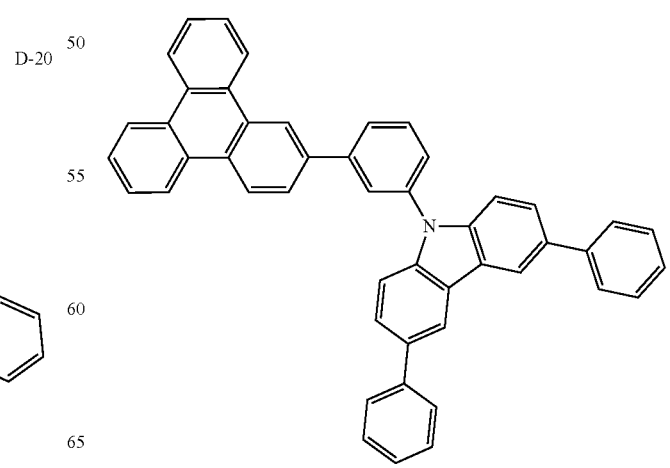

-continued

D-25
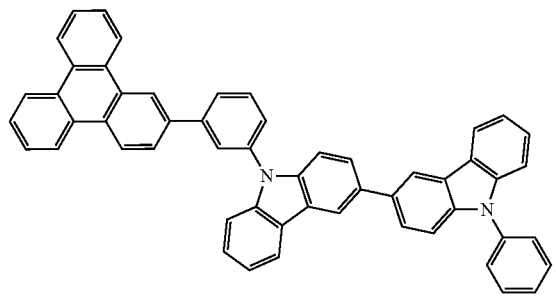

D-26
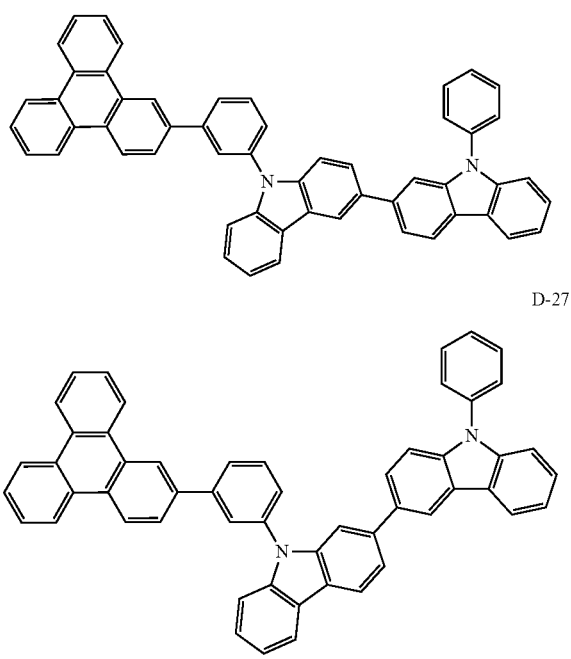

D-27

D-28
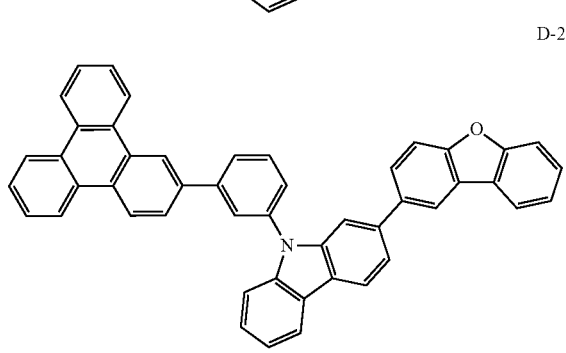

D-29
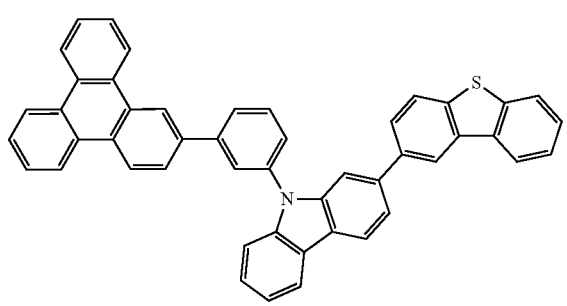

The second organic compound is a compound consisting of a combination of, for example a moiety represented by the following Chemical Formula 9 and a moiety represented by the following Chemical Formula 10.

[Chemical Formula 9]

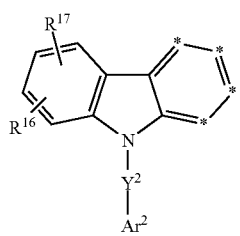

[Chemical Formula 10]

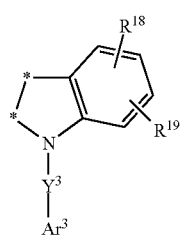

In Chemical Formulae 9 and 10, $Y^2$ and $Y^3$ are each independently a single bond, a substituted or unsubstituted C1 to C20 alkylene group, a substituted or unsubstituted C2 to C20 alkenylene group, a substituted or unsubstituted C6 to C30 arylene group, a substituted or unsubstituted C2 to C30 heteroarylene group, or a combination thereof, $Ar^2$ and $Ar^3$ are each independently substituted or unsubstituted C6 to C30 aryl group, a substituted or unsubstituted C2 to C30 heteroaryl group, or a combination thereof, $R^{16}$ to $R^{19}$ are each independently hydrogen, deuterium, a substituted or unsubstituted C1 to C20 alkyl group, a substituted or unsubstituted C6 to C50 aryl group, a substituted or unsubstituted C2 to C50 heteroaryl group, or a combination thereof, the adjacent two *'s of the Chemical Formula 9 are bound to two *'s of the Chemical Formula 10 to form a fused ring, and * that does not form the fused ring in the Chemical Formula 9 is each independently $CR^b$, and $R^b$ is hydrogen, deuterium, a substituted or unsubstituted C1 to C10 alkyl group, a substituted or unsubstituted C6 to C12 aryl group, a substituted or unsubstituted C3 to C12 heteroaryl group, or a combination thereof.

The organic compound consisting of the combination of the moiety represented by the Chemical Formula 9 and the moiety represented by the Chemical Formula 10 may be one of compounds listed in the following Group 3, but is not limited thereto.

[Group 3]
E-1
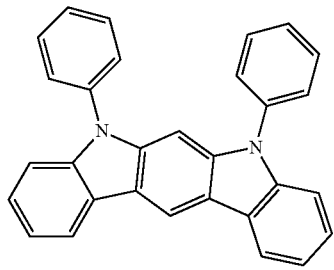
E-2
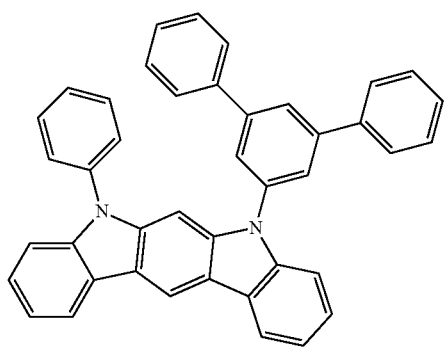
E-3
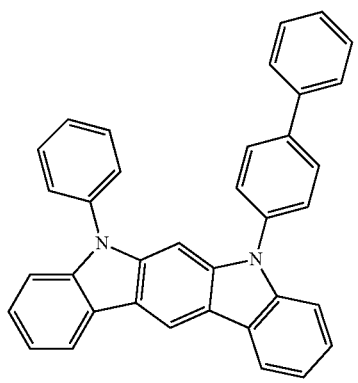
E-4
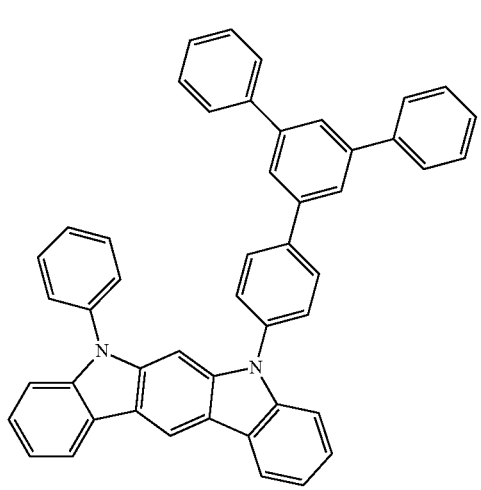
-continued
E-5
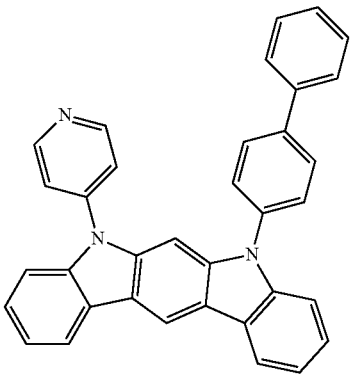
E-6
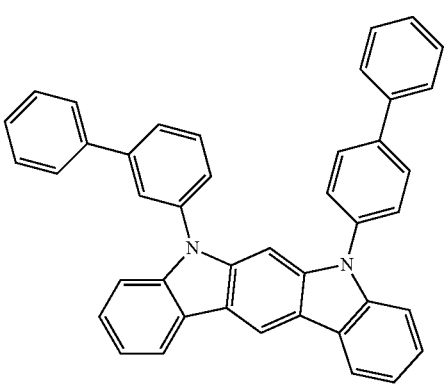
E-7
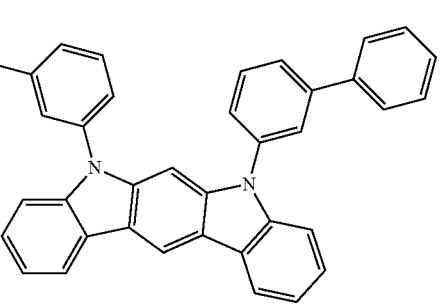
E-8
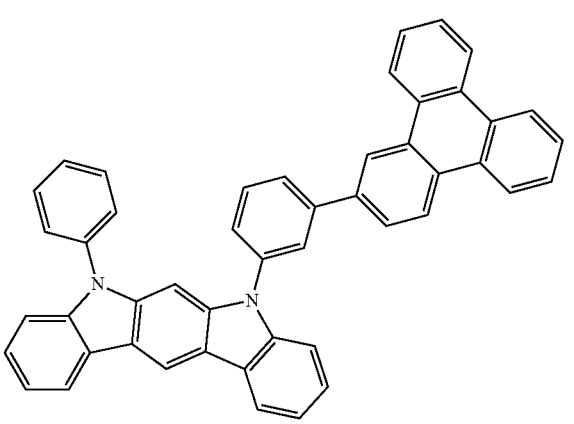

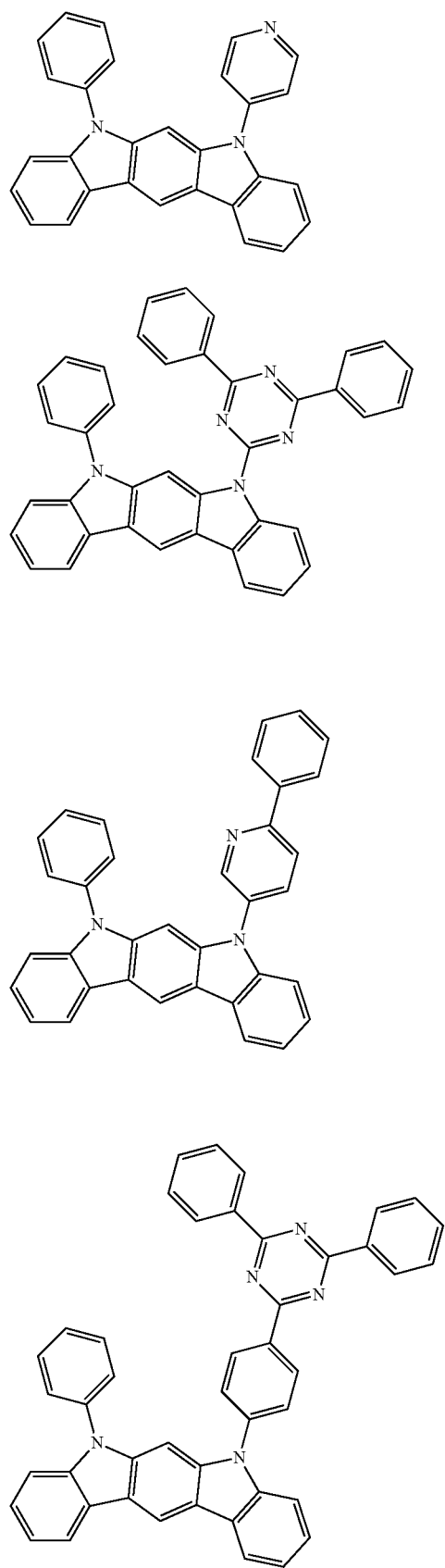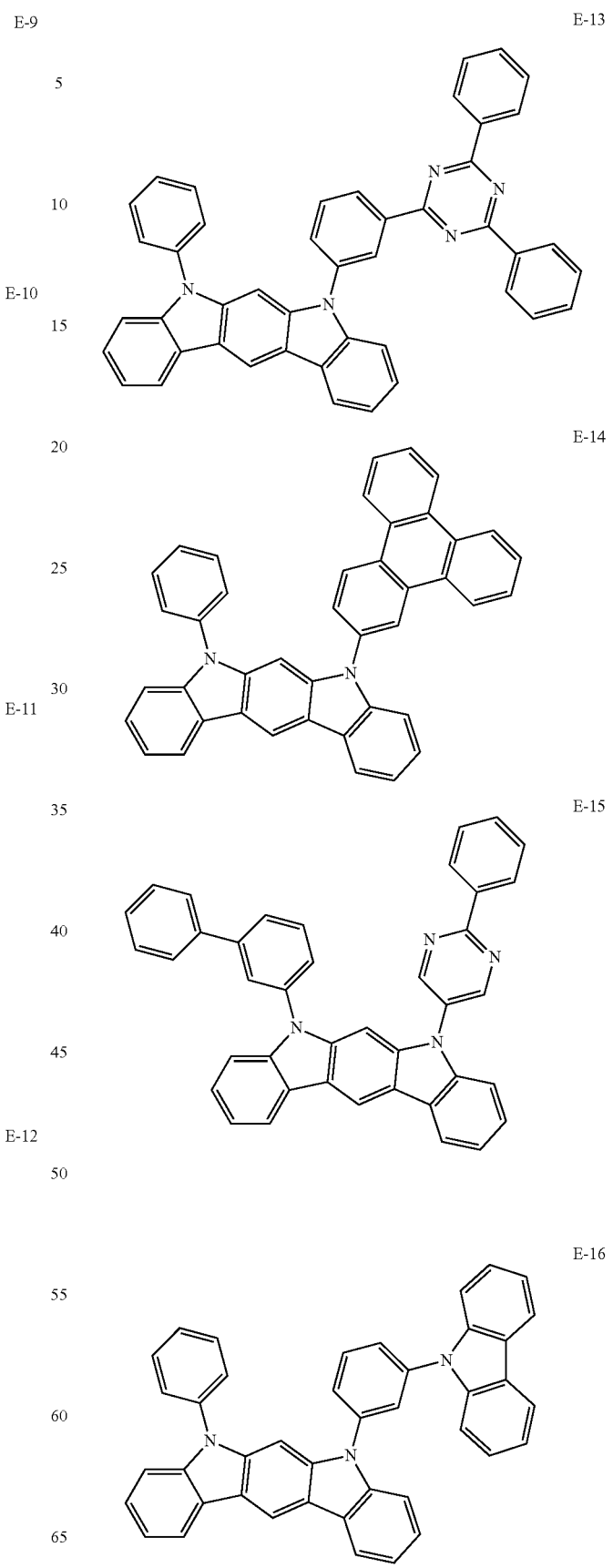

-continued
E-17
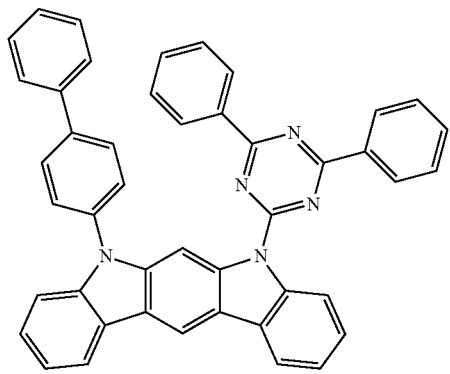
E-18
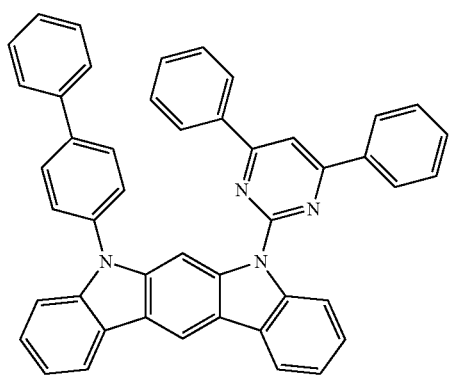
E-19
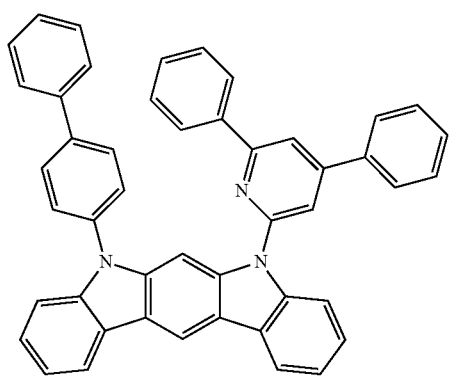
E-20
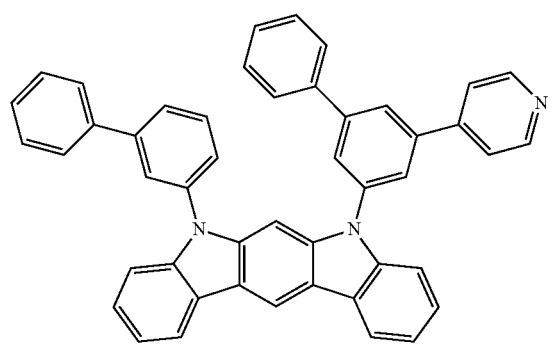
-continued
E-21
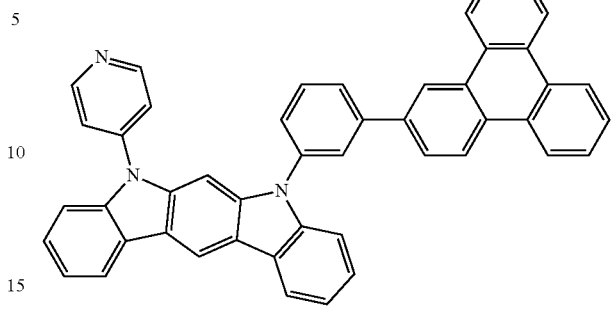
E-22
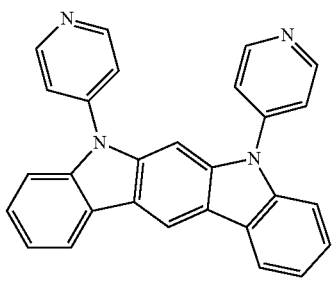
E-23
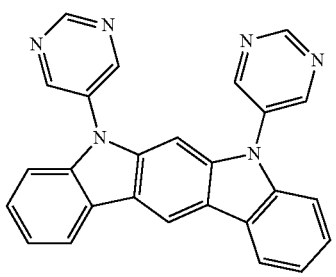
E-24
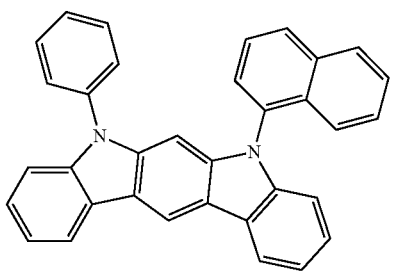
E-25
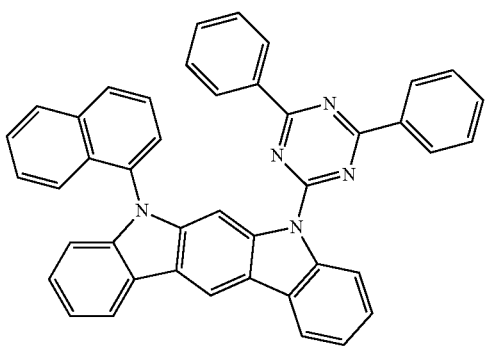

E-26
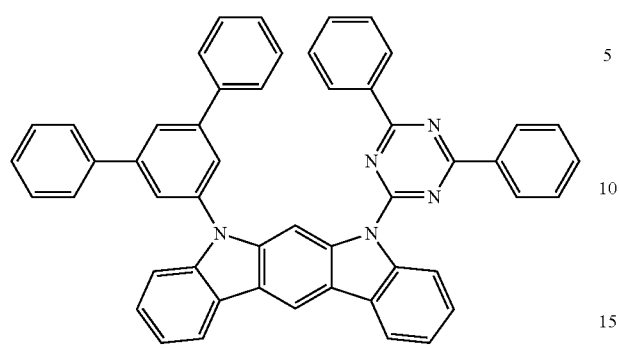
E-27
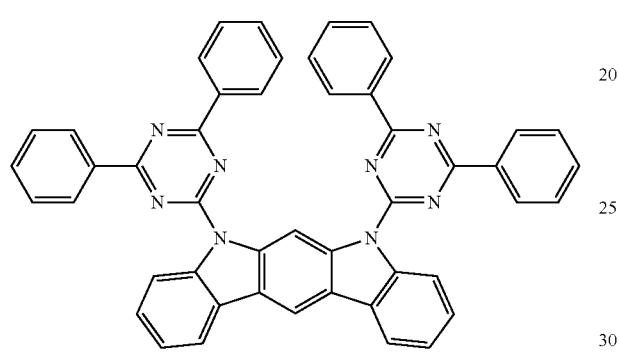
E-28
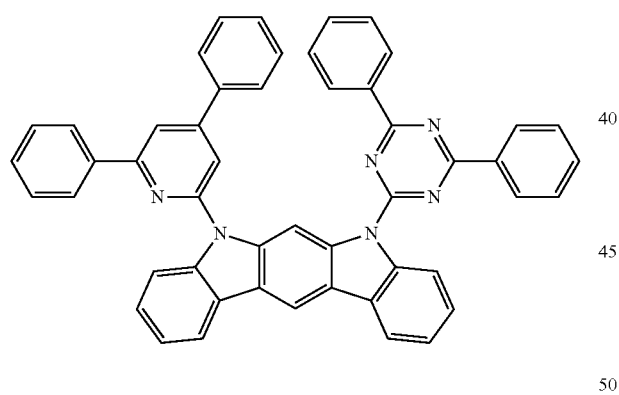
E-29
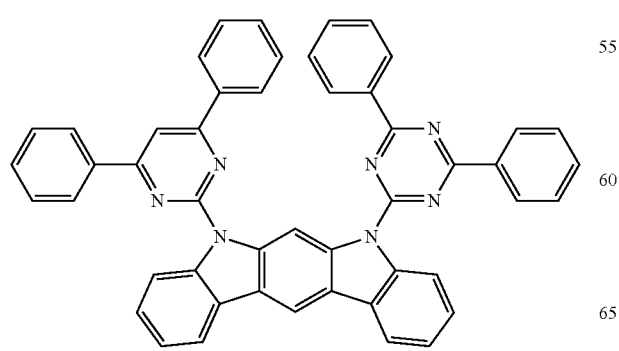
E-30
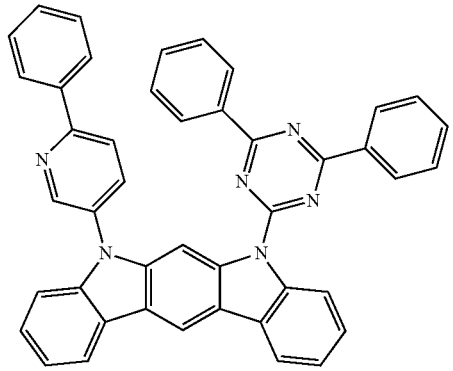
E-31
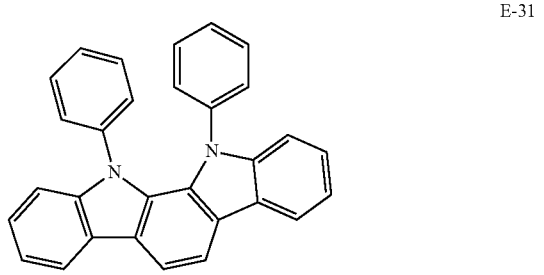
E-32
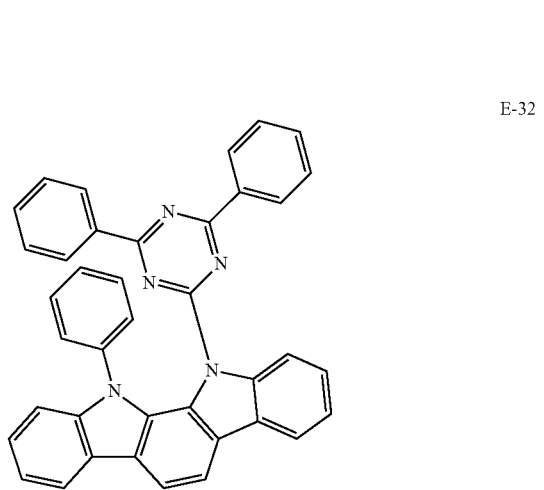
E-33
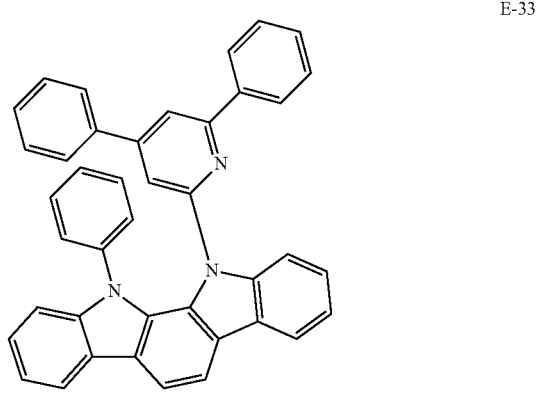

-continued
E-34
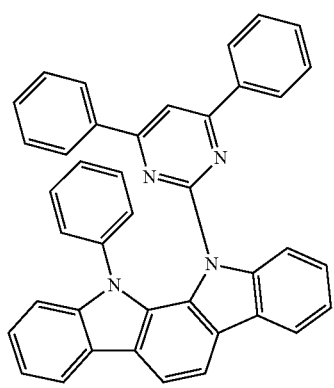
E-35
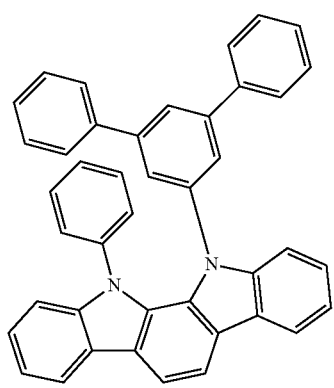
E-36
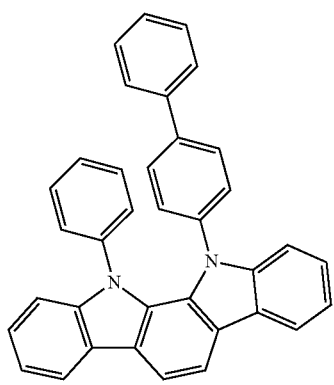
E-37
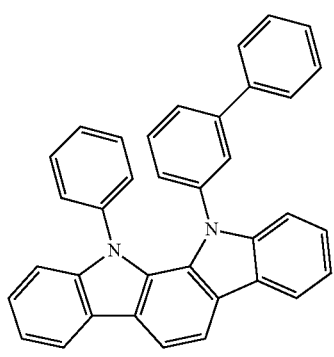
-continued
E-38
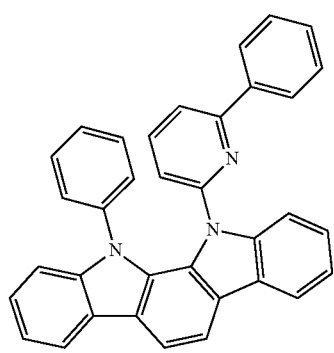
E-39
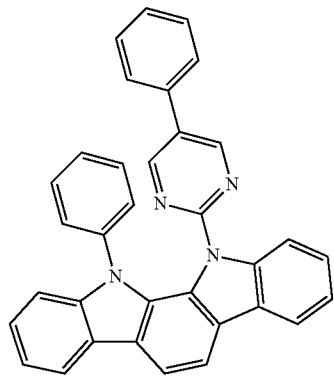
E-40
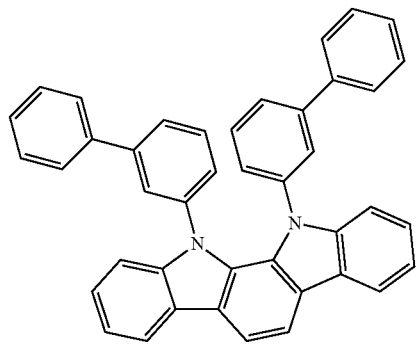
E-41
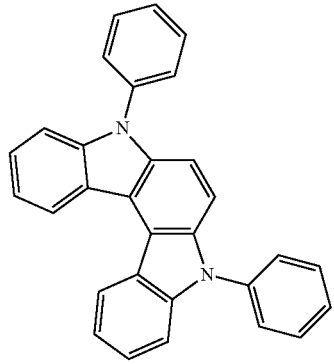

-continued
E-42
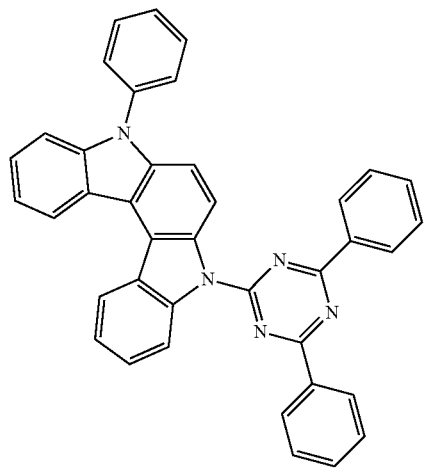
E-43
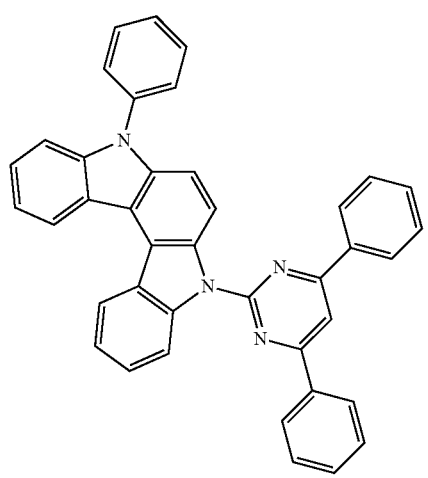
E-44
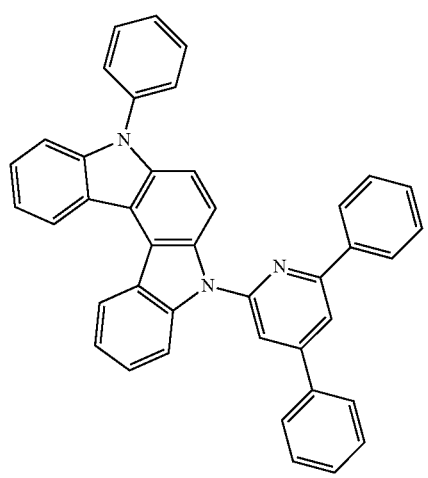
-continued
E-45
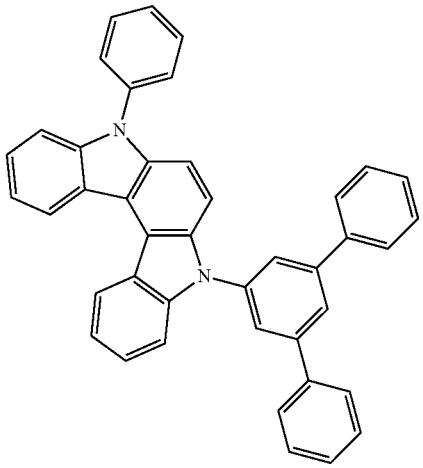
E-46
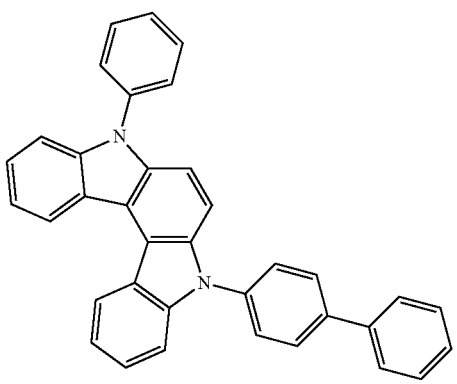
E-47
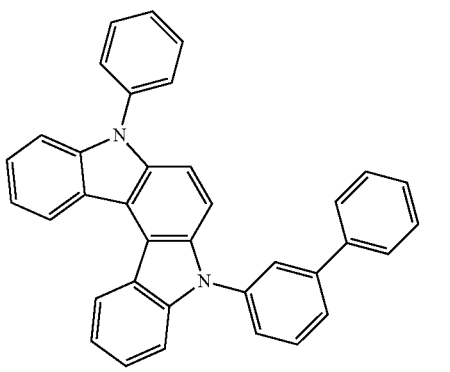
E-48
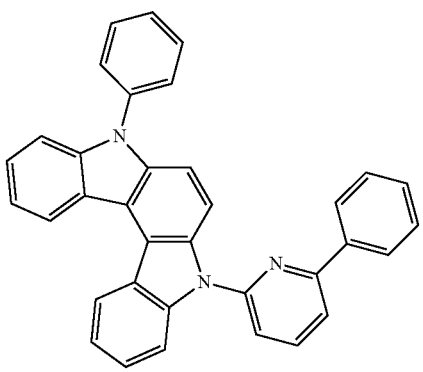

E-49
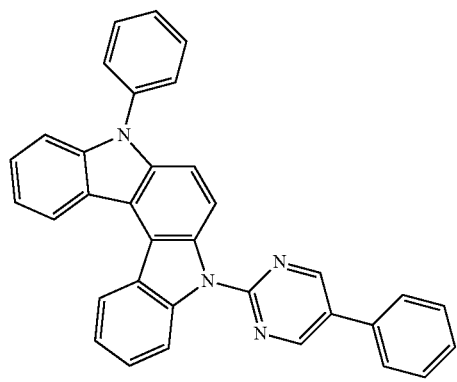
E-50
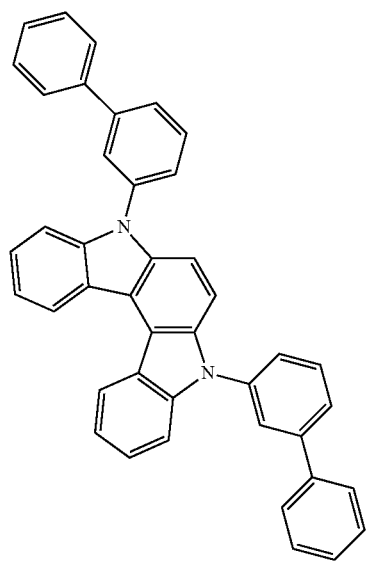
E-51
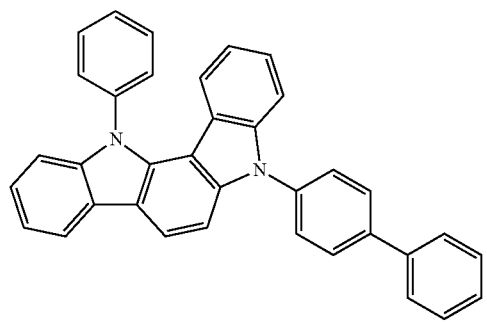
E-52
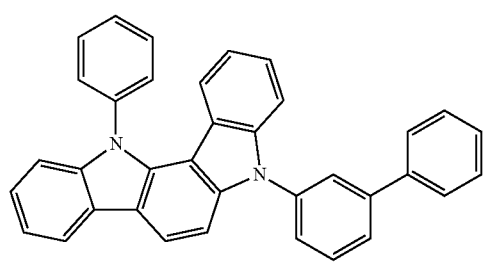
E-53
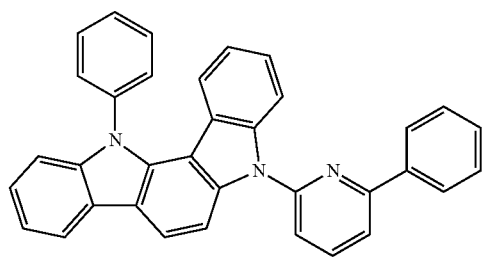
E-54
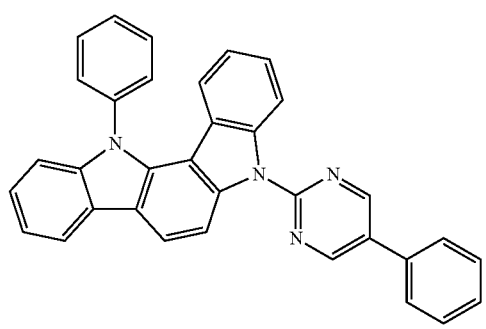
E-55
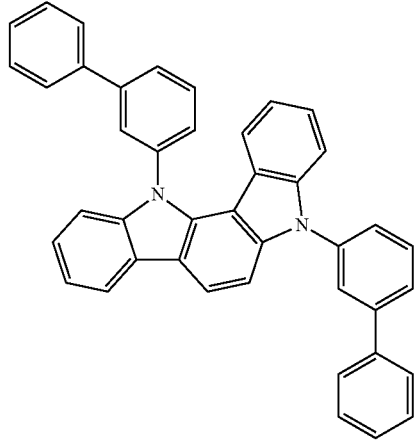
E-56
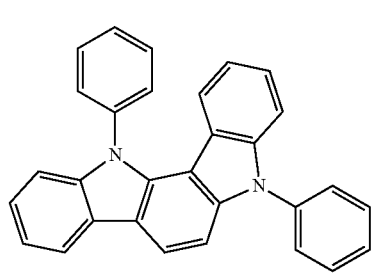

-continued
E-57
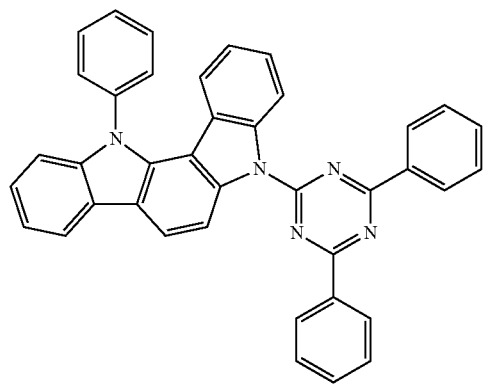
E-58
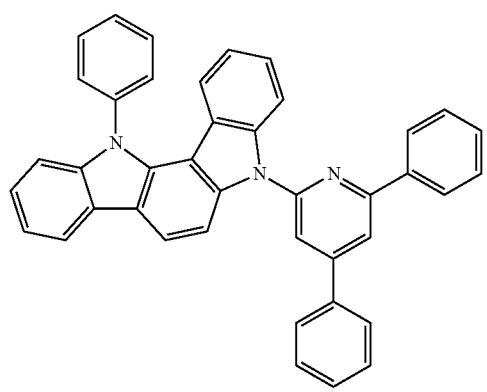
E-59
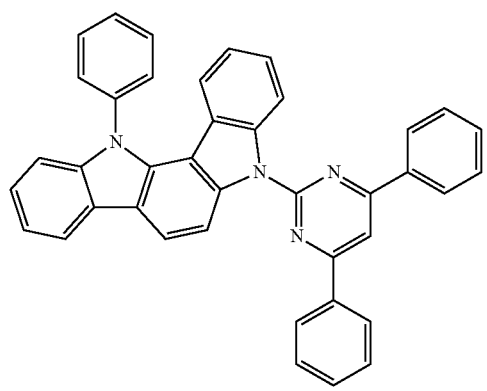
E-60
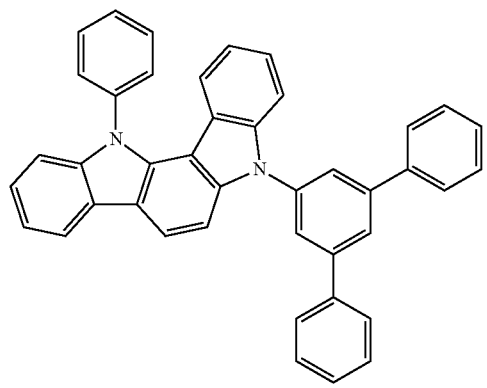
-continued
E-61
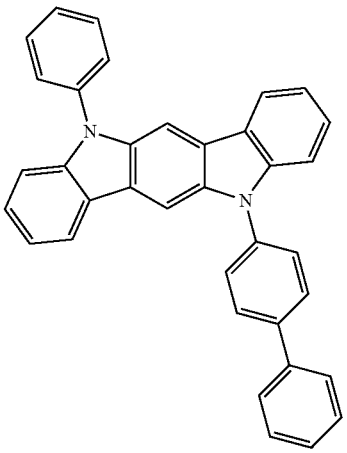
E-62
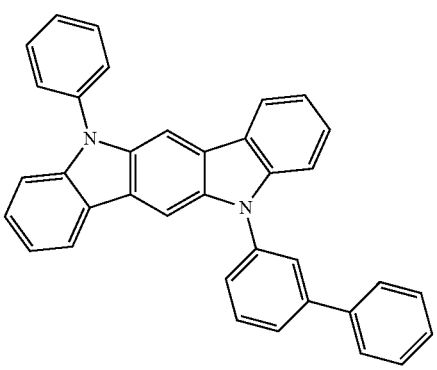
E-63
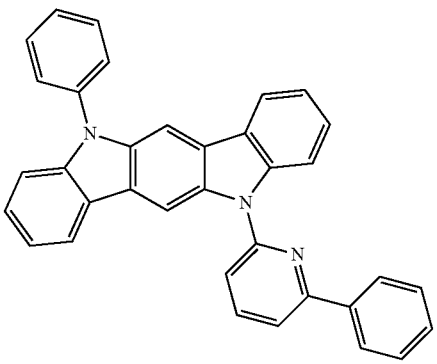
E-64
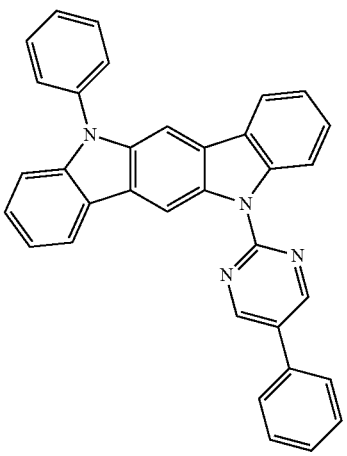

-continued

E-65

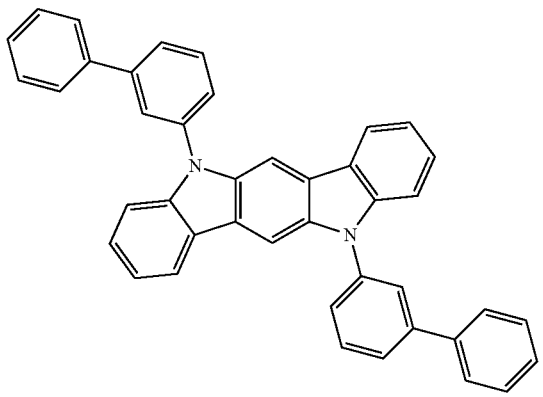

The second organic compound may include at least one of the compound represented by the Chemical Formula 8 and a compound consisting of a combination of a moiety represented by the Chemical Formula 9 and a moiety represented by the Chemical Formula 10.

The composition may include the first organic compound and the second organic compound in a weight ratio of about 1:10 to 10:1.

The composition may be applied in an organic layer of an organic optoelectronic device, and for example the first organic compound and the second organic compound may function as a host of an emission layer. Herein, the first organic compound may be a compound having bipolar characteristics in which electron characteristics are relatively strong and the second organic compound may be a compound having bipolar characteristics in which hole characteristics are relatively strong, and when it is used with the first organic compound, to increase charge mobility and stability and thus luminous efficiency and life-span characteristics.

The composition may further include one or more organic compound besides the first organic compound and the second organic compound.

The composition may further include a dopant. The dopant may be a red, green, or blue dopant, for example a phosphorescent dopant.

The dopant is mixed with the first host compound and the second host compound in a small amount to cause light emission, and may be generally a material such as a metal complex that emits light by multiple excitation into a triplet or more. The dopant may be, for example an inorganic, organic, or organic/inorganic compound, and one or more kinds thereof may be used.

The phosphorescent dopant may be an organic metal compound including Ir, Pt, Os, Ti, Zr, Hf, Eu, Tb, Tm, Fe, Co, Ni, Ru, Rh, Pd or a combination thereof. The phosphorescent dopant may be, for example a compound represented by the following Chemical Formula Z, but is not limited thereto.

$L_2MX$ [Chemical Formula Z]

In the Chemical Formula Z, M is a metal, and L and X are the same or different, and are a ligand to form a complex compound with M.

The M may be, for example Ir, Pt, Os, Ti, Zr, Hf, Eu, Tb, Tm, Fe, Co, Ni, Ru, Rh, Pd or a combination thereof, and the L and X may be, for example a bidentate ligand.

The composition may be applied to an organic layer of an organic optoelectronic device, and for example, the first organic compound and the second organic compound may be applied to an electron transport auxiliary layer interposed between an emission layer and an electron transport layer.

The first compound and the second compound are combined in various ratios and applied to an electron transport auxiliary layer, and thereby electron transport capability from an electron transport layer to an emission layer may be controlled, and electron transport capability with an emission layer may be balanced so that electrons may not be accumulated at the interface. In addition, the electron transport auxiliary layer converts holes from an anode to an emission layer and/or excitons produced in an emission layer into excitons having lower energy than the energy of the excitons of the emission layer, and thereby holes and/or excitons may be prohibited from being transported to the electron transport layer through the emission layer, effectively. Accordingly, efficiency and life-span of an organic optoelectronic device may be improved. The first compound and the second compound may be, for example included in a weight ratio of about 1:99 to 99:1.

The composition may be formed using a dry film formation method such as chemical vapor deposition or a solution process.

Hereinafter, an organic optoelectric device to which the organic compound or the composition is applied is described.

The organic optoelectric device may be any device to convert electrical energy into photoenergy and vice versa without particular limitation, and may be, for example an organic photoelectric device, an organic light emitting diode, an organic solar cell, and an organic photo-conductor drum.

The organic optoelectric device includes an anode and a cathode facing each other, and at least one organic layer interposed between the anode and the cathode, wherein the organic layer includes the organic compound or the composition.

Herein, an organic light emitting diode as one example of an organic optoelectric device is described referring to drawings.

FIGS. 1 and 2 are cross-sectional views of each organic light emitting diode according to one embodiment.

Referring to FIG. 1, an organic light emitting diode 100 according to one embodiment includes an anode 120 and a cathode 110 facing each other and an organic layer 105 interposed between the anode 120 and cathode 110.

The anode 120 may be made of a conductor having a high work function to help hole injection, and may be for example metal, metal oxide and/or a conductive polymer. The anode 120 may be, for example a metal nickel, platinum, vanadium, chromium, copper, zinc, gold, and the like or an alloy thereof; metal oxide such as zinc oxide, indium oxide, indium tin oxide (ITO), indium zinc oxide (IZO), and the like; a combination of metal and oxide such as ZnO and Al or SnO$_2$ and Sb; a conductive polymer such as poly(3-methylthiophene), poly(3,4-(ethylene-1,2-dioxy)thiophene) (PEDOT), polypyrrole, and polyaniline, but is not limited thereto.

The cathode 110 may be made of a conductor having a low work function to help electron injection, and may be for example metal, metal oxide and/or a conductive polymer. The cathode 110 may be for example a metal or an alloy thereof such as magnesium, calcium, sodium, potassium, titanium, indium, yttrium, lithium, gadolinium, aluminum silver, tin, lead, cesium, barium, and the like; a multi-layer structure material such as LiF/Al, LiO2/Al, LiF/Ca, LiF/Al and BaF2/Ca, but is not limited thereto.

The organic layer 105 includes an emission layer 130 including the organic compound or the composition.

The emission layer 130 may include, for example the organic compound at alone, a mixture of at least two kinds of the organic compound or the composition.

Referring to FIG. 2, the organic light emitting diode 200 further include a hole auxiliary layer 140 as well as an emission layer 130. The hole auxiliary layer 140 may increase hole injection and/or hole mobility between the anode 120 and the emission layer 130, and block electrons. The hole auxiliary layer 140 may be, for example a hole transport layer, a hole injection layer and/or an electron blocking layer, and may include at least one layer.

In addition, in one embodiment of the present invention, in FIG. 1 or FIG. 2, the organic light emitting diode may further include an electron transport layer, an electron transport auxiliary layer, an electron injection layer, and the like as the organic layer 105.

The organic light emitting diodes 100 and 200 may be manufactured by forming an anode or a cathode on a substrate, forming an organic layer in accordance with a dry coating method such as evaporation, sputtering, plasma plating, and ion plating, and forming a cathode or an anode thereon, and two or more compounds may be simultaneously used for formation of a thin film or a mixture of compounds having the same deposition temperature may be used for formation of a thin film. Then, a cathode or an anode may be formed thereon.

The organic light emitting diode may be applied to an organic light emitting diode display.

MODE FOR INVENTION

Hereinafter, the embodiments are illustrated in more detail with reference to examples. These examples, however, are not in any sense to be interpreted as limiting the scope of the invention.

Synthesis of Organic Compound

Representative Synthesis Method

A representative synthesis method is shown in the following Representative Reaction Scheme.

[Representative Reaction Scheme]

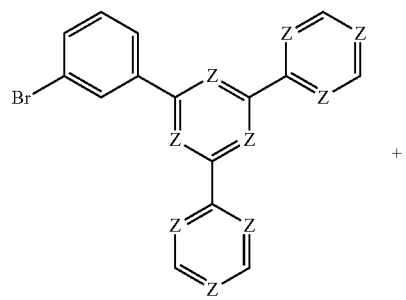
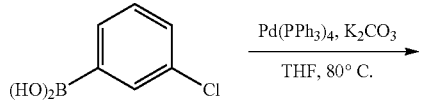
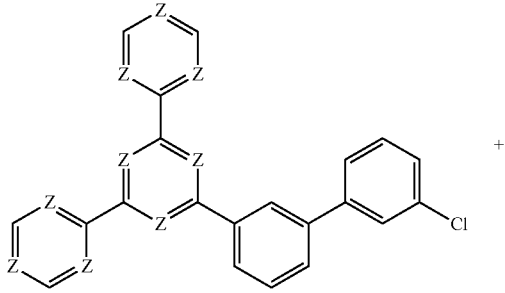
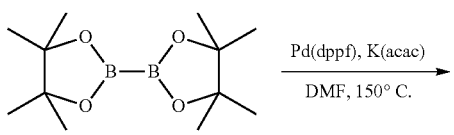
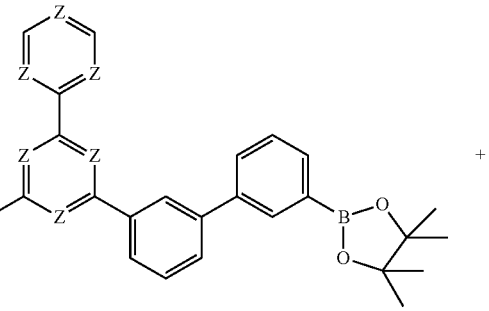
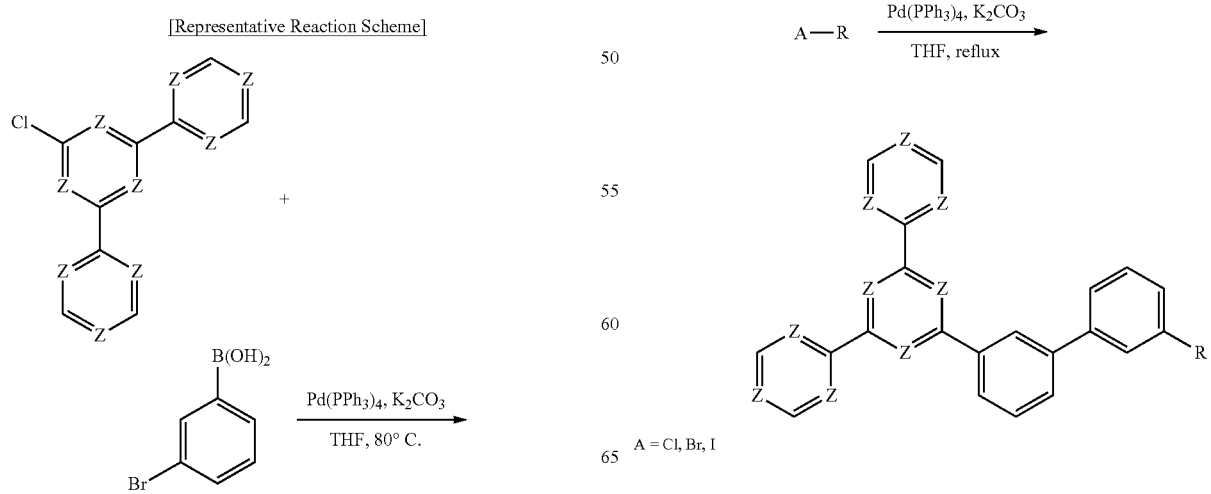

Synthesis of Intermediate

Synthesis Example 1: Synthesis of Intermediate I-1

[Reaction Scheme 1]

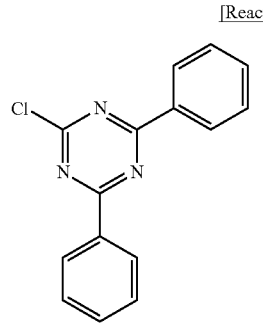

I-1

Synthesis Example 2: Synthesis of Intermediate I-2

[Reaction Scheme 2]

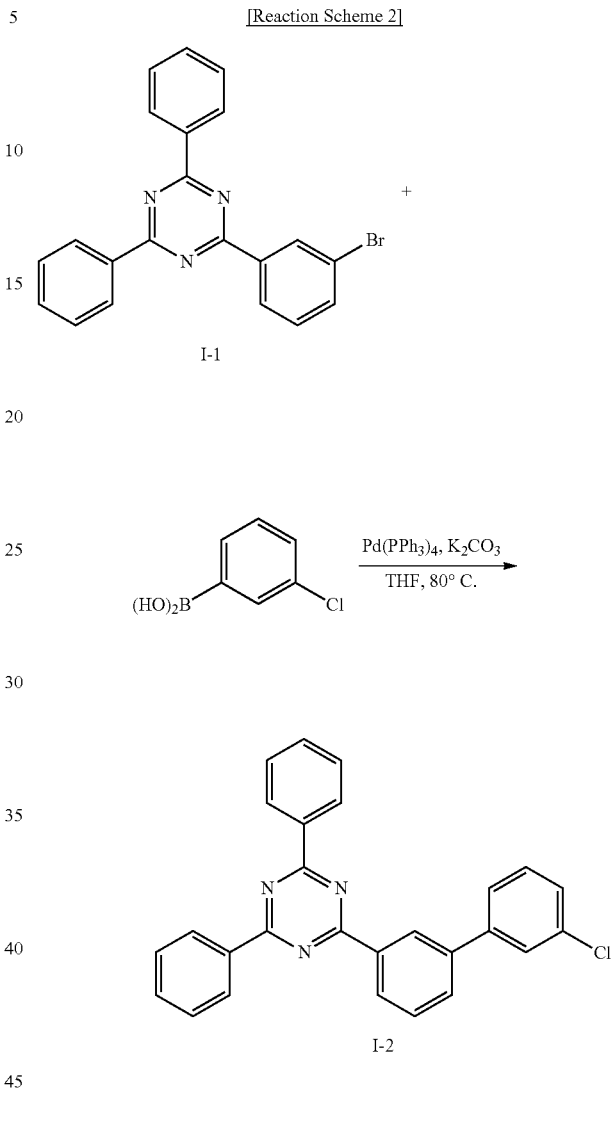

I-2

The compound of 2-chloro-4,6-diphenyl-1,3,5-triazine (50 g, 187 mmol) was dissolved in 1 L of THF (tetrahydrofuran) under a nitrogen atmosphere, (3-bromophenyl)boronic acid (45 g, 224.12 mmol) and tetrakis(triphenylphosphine)palladium (2.1 g, 1.87 mmol) were added thereto, and the mixture was agitated. Next, potassium carbonate saturated in water (64 g, 467 mmol) was added thereto, and the obtained mixture was heated and refluxed at 80° C. for 12 hours. When the reaction was terminated, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain the compound I-1 (69 g, 95%).

HRMS (70 eV, EI+): m/z calcd for C21H14BrN3: 387.0371, found: 387.

Elemental Analysis: C, 65%; H, 4%

The compound I-1 (50 g, 128 mmol) was dissolved in 1 L of THF under a nitrogen atmosphere, (3-chlorophenyl)boronic acid (24 g, 155 mmol) and tetrakis(triphenylphosphine)palladium (1.5 g, 1.3 mmol) were added thereto, and the mixture was agitated. Then, potassium carbonate saturated in water (44 g, 320 mmol) was added thereto, and the resultant was heated and refluxed at 80° C. for 12 hours. When the reaction was terminated, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain the compound I-2 (51 g, 95%).

HRMS (70 eV, EI+): m/z calcd for C27H18ClN3: 419.1189, found: 419.

Elemental Analysis: C, 77%; H, 4%

Synthesis Example 3: Synthesis of Intermediate I-3

[Reaction Scheme 3]

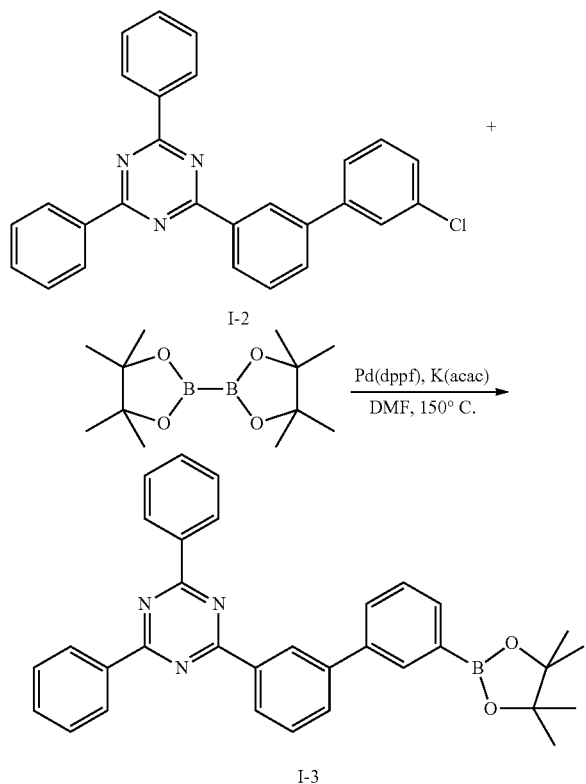

The compound I-2 (100 g, 238 mmol) was dissolved in 1 L of dimethylforamide (DMF) under a nitrogen atmosphere, bis(pinacolato)diboron (72.5 g, 285 mmol), (1,1-bis(diphenylphosphine)ferrocene)dichloropalladium (II) (2 g, 2.38 mmol) and potassium acetate (58 g, 595 mmol) were added thereto, and the mixture was heated and refluxed at 150° C. for 48 hours. When the reaction was terminated, water was added to the reaction solution, and the mixture was filtered and dried in a vacuum oven. The obtained residue was separated and purified through flash column chromatography to obtain the compound I-3 (107 g, 88%).

HRMS (70 eV, EI+): m/z calcd for C33H30BN3O2: 511.2431, found: 511

Elemental Analysis: C, 77%; H, 6%

Synthesis Example 4: Synthesis of Intermediate I-4

[Reaction Scheme 4]

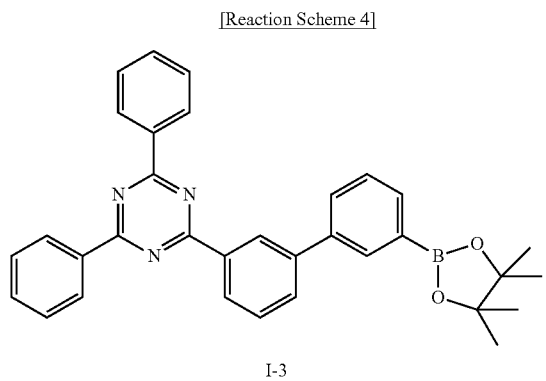

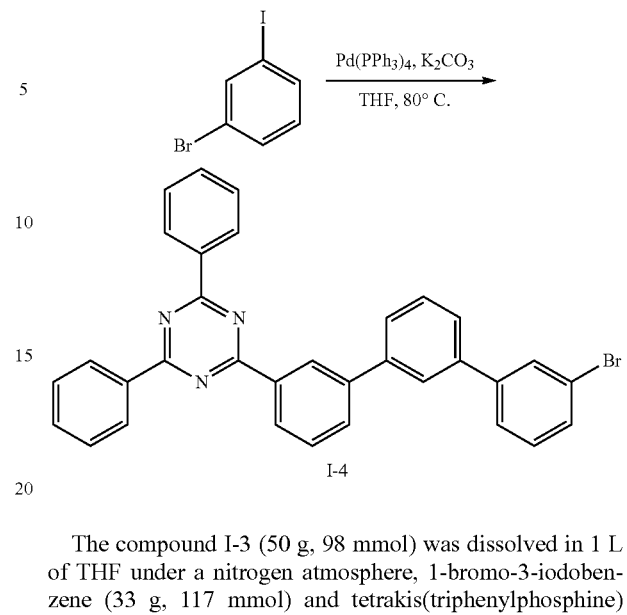

The compound I-3 (50 g, 98 mmol) was dissolved in 1 L of THF under a nitrogen atmosphere, 1-bromo-3-iodobenzene (33 g, 117 mmol) and tetrakis(triphenylphosphine) palladium (1 g, 0.98 mmol) were added thereto, and the mixture was agitated. Then, potassium carbonate saturated in water (34 g, 245 mmol) was added thereto, and the obtained mixture was heated and refluxed at 80° C. for 12 hours. When the reaction was terminated, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain the compound I-4 (50 g, 95%).

HRMS (70 eV, EI+): m/z calcd for C30H27BO2: 539.0997, found: 539.

Elemental Analysis: C, 73.34; H, 4.10

Synthesis Example 5: Synthesis of Intermediate I-5

[Reaction Scheme 5]

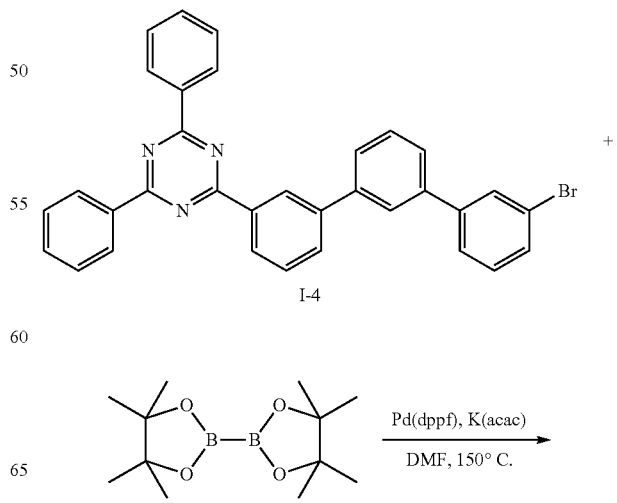

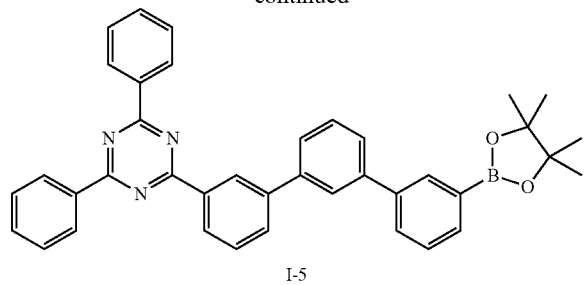

I-5

The compound I-4 (100 g, 185 mmol) was dissolved in 1 L of dimethylforamide (DMF) under a nitrogen atmosphere, bis(pinacolato)diboron (56 g, 222 mmol), (1,1-bis(diphenylphosphine)ferrocene)dichloropalladium (II) (1.5 g, 1.85 mmol) and potassium acetate (45 g, 595 mmol) were added thereto, and the mixture was heated and refluxed at 150° C. for 5 hours. When the reaction was terminated, water was added to the reaction solution, and the mixture was filtered and dried in a vacuum oven. The obtained residue was separated and purified through flash column chromatography to obtain the compound I-5 (95 g, 88%).

HRMS (70 eV, EI+): m/z calcd for C39H34BN3O2: 587.2744, found: 587

Elemental Analysis: C, 80%; H, 6%

Synthesis Example 6: Synthesis of Intermediate I-6

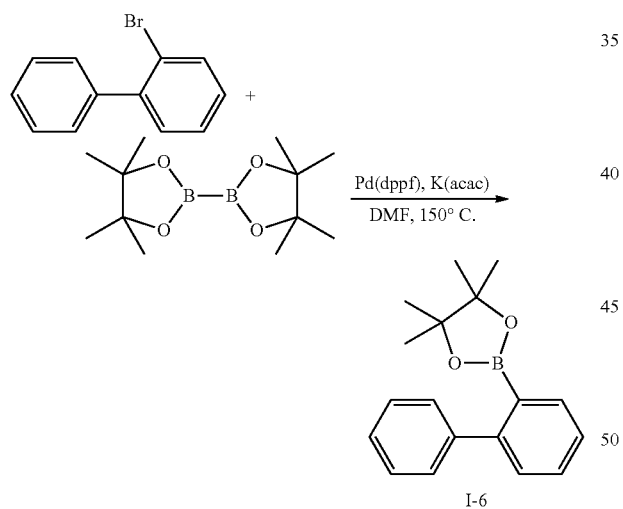

I-6

2-bromo-1,1'-biphenyl (20 g, 85.8 mmol) was dissolved in 1 L of dimethylforamide (DMF) under a nitrogen atmosphere, bis(pinacolato)diboron (26 g, 103 mmol), (1,1'-bis(diphenylphosphine)ferrocene)dichloropalladium (II) (0.7 g, 0.85 mmol) and potassium acetate (58 g, 595 mmol) were added thereto, and the mixture was heated and refluxed at 150° C. for 5 hours. When the reaction was terminated, water was added to the reaction solution, and the mixture was filtered and dried in a vacuum oven. The obtained residue was separated and purified through flash column chromatography to obtain the compound I-6 (19 g, 83%).

HRMS (70 eV, EI+): m/z calcd for C18H21BO2: 280.1635, found: 280

Elemental Analysis: C, 77%; H, 7%

Synthesis Example 7: Synthesis of Intermediate I-7

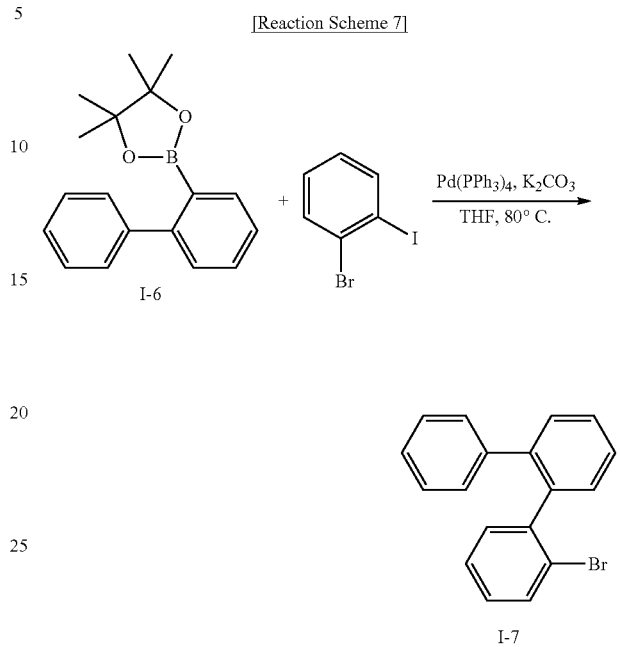

I-7

The compound I-6 (20 g, 71 mmol) was dissolved in 1 L of THF under a nitrogen atmosphere, 1-bromo-2-iodobenzene (22 g, 78 mmol) and tetrakis(triphenylphosphine) palladium (0.8 g, 0.71 mmol) were added thereto, and the mixture was agitated. Then, potassium carbonate saturated in water (25 g, 177 mmol) was added thereto, and the obtained mixture was heated and refluxed at 80° C. for 12 hours. When the reaction was terminated, water was added to the reaction solution, the mixture was extracted with dichloromethane (DCM), and the extract was treated with anhydrous MgSO4 to remove moisture therefrom, filtered, and concentrated under a reduced pressure. The obtained residue was separated and purified through flash column chromatography to obtain the compound I-7 (19 g, 87%).

HRMS (70 eV, EI+): m/z calcd for C18H13Br: 308.0201, found: 308 Elemental Analysis: C, 70%; H, 4%

Synthesis Example 8: Synthesis of Intermediate I-8

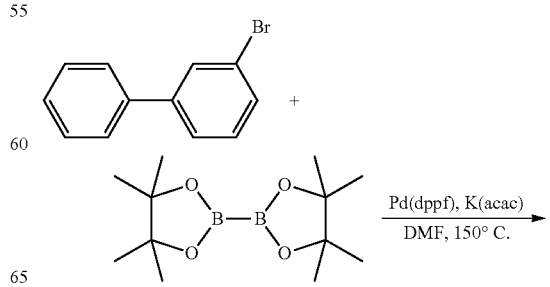

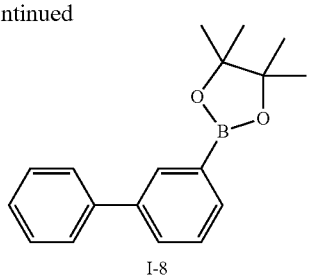

I-8

3-bromo-1,1'-biphenyl (20 g, 85.8 mmol) was dissolved in 1 L of dimethylforamide (DMF) under a nitrogen atmosphere, bis(pinacolato)diboron (26 g, 103 mmol), (1,1-bis(diphenylphosphine)ferrocene)dichloropalladium (II) (0.7 g, 0.85 mmol) and potassium acetate (58 g, 595 mmol) were added thereto, and the mixture was heated and refluxed at 150° C. for 5 hours. When the reaction was terminated, water was added to the reaction solution, and the mixture was filtered and dried in a vacuum oven. The obtained residue was separated and purified through flash column chromatography to obtain the compound I-8 (20 g, 85%).

HRMS (70 eV, EI+): m/z calcd for C18H21BO2: 280.1635, found: 280.

Elemental Analysis: C, 77%; H, 7%

Synthesis Example 9: Synthesis of Intermediate I-9

[Reaction Scheme 9]

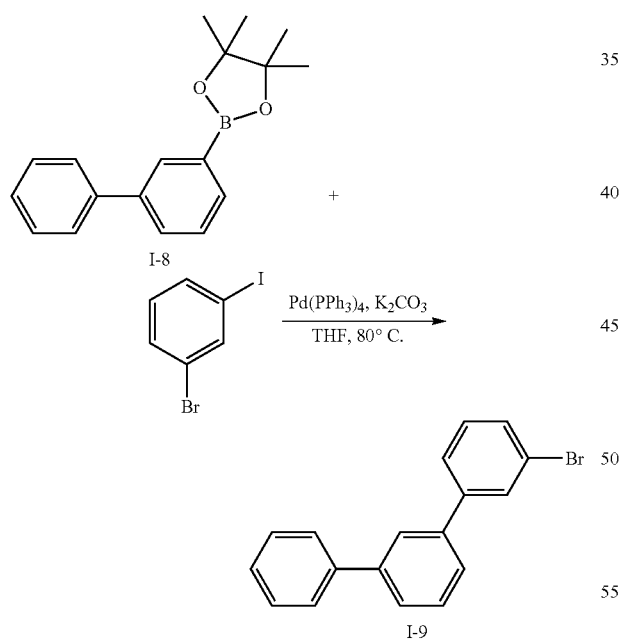

The compound I-8 (20 g, 71 mmol) was dissolved in 1 L of THF under a nitrogen atmosphere, 1-bromo-3-iodobenzene (22 g, 78 mmol) and tetrakis(triphenylphosphine) palladium (0.8 g, 0.71 mmol) were added thereto, and the mixture was agitated. Then, potassium carbonate saturated in water (25 g, 177 mmol) was added thereto, and the obtained mixture was heated and refluxed at 80° C. for 12 hours. When the reaction was terminated, water was added to the reaction solution, the mixture was extracted with dichloromethane (DCM), and the extract was treated with anhydrous MgSO4 to remove moisture therefrom, filtered, and concentrated under a reduced pressure. The obtained residue was separated and purified through flash column chromatography to obtain the compound I-9 (20 g, 91%).

HRMS (70 eV, EI+): m/z calcd for C18H13Br: 308.0201, found: 308 Elemental Analysis: C, 70%; H, 4%

Synthesis Example 10: Synthesis of Intermediate I-10

[Reaction Scheme 10]

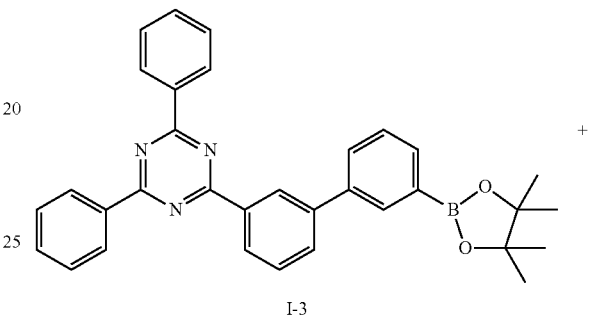

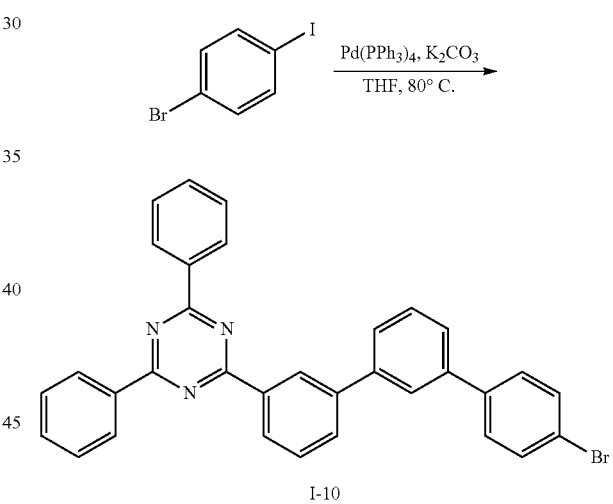

The compound I-3 (50 g, 98 mmol) was dissolved in 1 L of THF under a nitrogen atmosphere, 1-bromo-4-iodobenzene (33 g, 117 mmol) and tetrakis(triphenylphosphine) palladium (1 g, 0.98 mmol) were added thereto, and the mixture was agitated. Then, potassium carbonate saturated in water (34 g, 245 mmol) was added thereto, and the obtained mixture was heated and refluxed at 80° C. for 12 hours. When the reaction was terminated, water was added to the reaction solution, the mixture was extracted with dichloromethane (DCM), and the extract was treated with anhydrous MgSO4 to remove moisture therefrom, filtered, and concentrated under a reduced pressure. The obtained residue was separated and purified through flash column chromatography to obtain the compound I-10 (50 g, 95%).

HRMS (70 eV, EI+): m/z calcd for C30H27BO2: 539.0997, found: 539 540.

Elemental Analysis: C, 730.34; H, 4.10

Synthesis Example 11: Synthesis of Intermediate I-11

Synthesis Example 12: Synthesis of Intermediate I-12

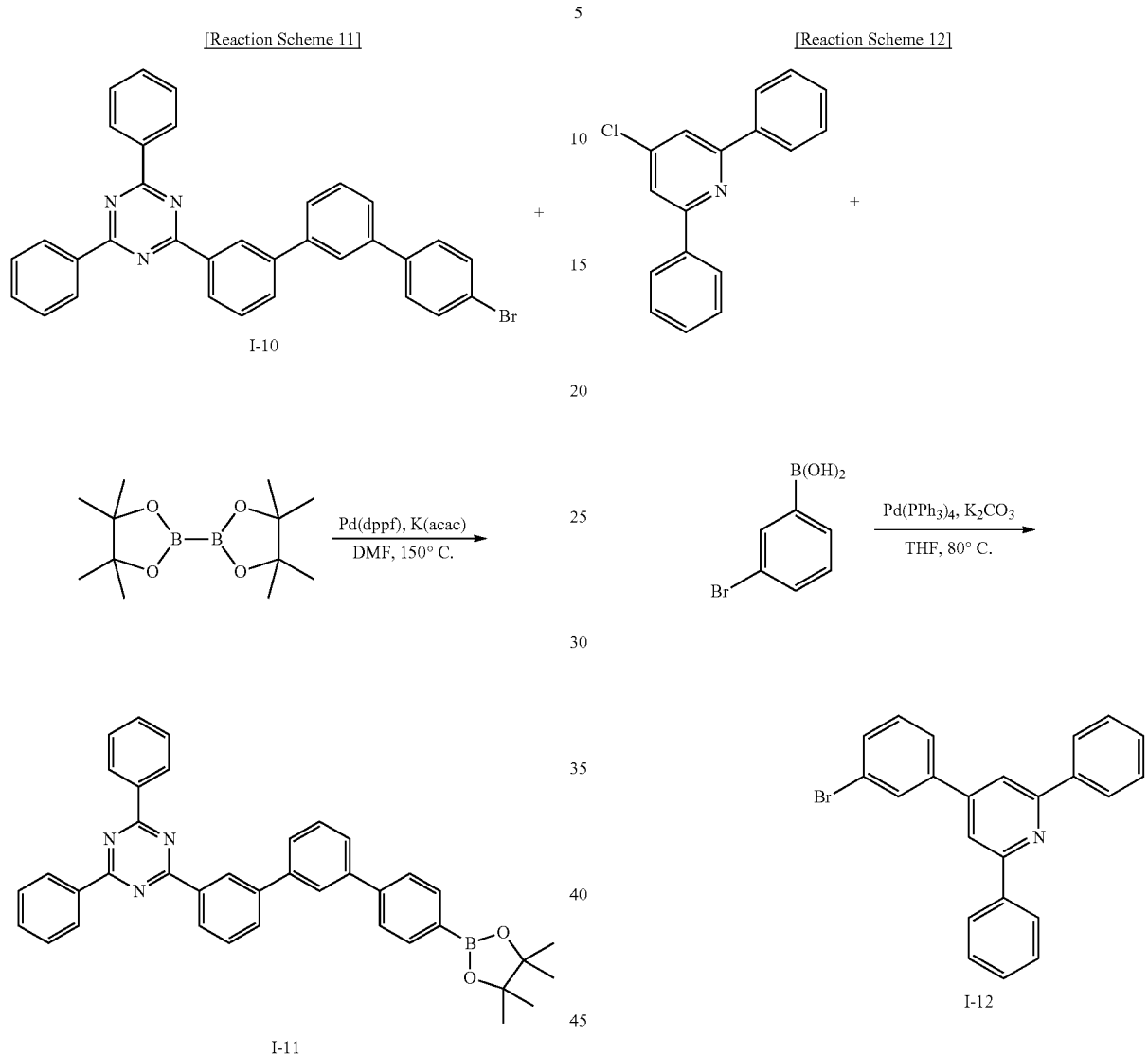

The compound I-10 (100 g, 185 mmol) was dissolved in 1 L of dimethylforamide (DMF) under a nitrogen atmosphere, bis(pinacolato)diboron (56 g, 222 mmol), (1,1-bis(diphenylphosphine)ferrocene)dichloropalladium (II) (1.5 g, 1.85 mmol) and potassium acetate (45 g, 595 mmol) were added thereto, and the mixture was heated and refluxed at 150° C. for 5 hours. When the reaction was terminated, water was added to the reaction solution, and the mixture was filtered and dried in a vacuum oven. The obtained residue was separated and purified through flash column chromatography to obtain the compound I-11 (95 g, 88%).

HRMS (70 eV, EI+): m/z calcd for $C_{39}H_{34}BN_3O_2$: 587.2744, found: 587

Elemental Analysis: C, 80%; H, 6%

The compound (4-chloro-2,6-diphenylpyridine) (50 g, 188 mmol) was dissolved in 1 L of THF under a nitrogen atmosphere, (3-bromophenyl)boronic acid (45 g, 225 mmol) and tetrakis(triphenylphosphine)palladium (2.2 g, 1.88 mmol) were added thereto, and the mixture was agitated. Then, potassium carbonate saturated in water (65 g, 470 mmol) was added thereto, and the obtained mixture was heated and refluxed at 80° C. for 12 hours. When the reaction was terminated, water was added to the reaction solution, the mixture was extracted with dichloromethane (DCM), and the extract was treated with anhydrous $MgSO_4$ to remove moisture therefrom, filtered, and concentrated under a reduced pressure. The obtained residue was separated and purified through flash column chromatography to obtain the compound I-12 (69 g, 95%).

HRMS (70 eV, EI+): m/z calcd for $C_{23}H_{16}BrN$: 385.0466, found: 385.

Elemental Analysis: C, 72%; H, 4%

Synthesis Example 13: Synthesis of Intermediate I-13

Synthesis Example 14: Synthesis of Intermediate I-14

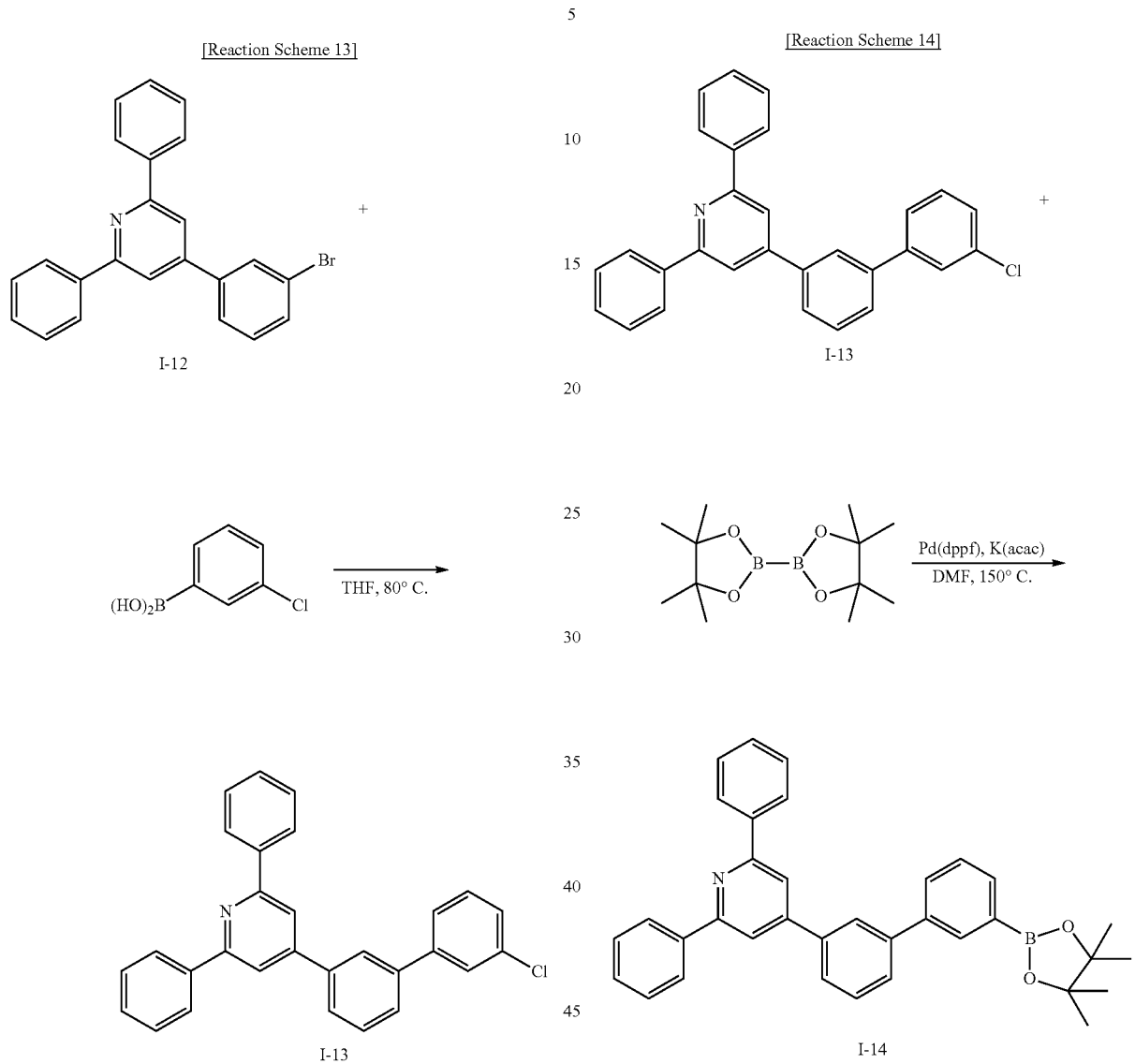

The compound I-12 (50 g, 129 mmol) was dissolved in 1 L of dioxane nitrogen, (3-chlorophenyl)boronic acid (24 g, 155 mmol) and tetrakis(triphenylphosphine)palladium (1.5 g, 1.3 mmol) were added thereto, and the mixture was agitated. Then, potassium carbonate saturated in water (45 g, 322 mmol) was added thereto, and the obtained mixture was heated and refluxed at 80° C. for 12 hours. When the reaction was terminated, water was added to the reaction solution, the mixture was extracted with dichloromethane (DCM), and the extract was treated with anhydrous $MgSO_4$ to remove moisture therefrom, filtered, and concentrated under a reduced pressure. The obtained residue was separated and purified through flash column chromatography to obtain the compound I-13 (50 g, 92%).

HRMS (70 eV, EI+): m/z calcd for C29H20ClN: 417.1284, found: 417.

Elemental Analysis: C, 83%; H, 5%

The compound I-13 (100 g, 239 mmol) was dissolved in 1 L of dimethylforamide (DMF) under a nitrogen atmosphere, bis(pinacolato)diboron (72.5 g, 287 mmol), (1,1-bis(diphenylphosphine)ferrocene)dichloropalladium (II) (2 g, 2.38 mmol) and potassium acetate (58 g, 595 mmol) were added thereto, and the mixture was heated and refluxed at 150° C. for 48 hours. When the reaction was terminated, water was added to the reaction solution, and the mixture was filtered and dried in a vacuum oven. The obtained residue was separated and purified through flash column chromatography to obtain the compound I-14 (107 g, 88%).

HRMS (70 eV, EI+): m/z calcd for C35H32BNO2: 509.2526, found: 509

Elemental Analysis: C, 83%; H, 6%

Synthesis Example 15: Synthesis of Intermediate I-15

[Reaction Scheme 15]

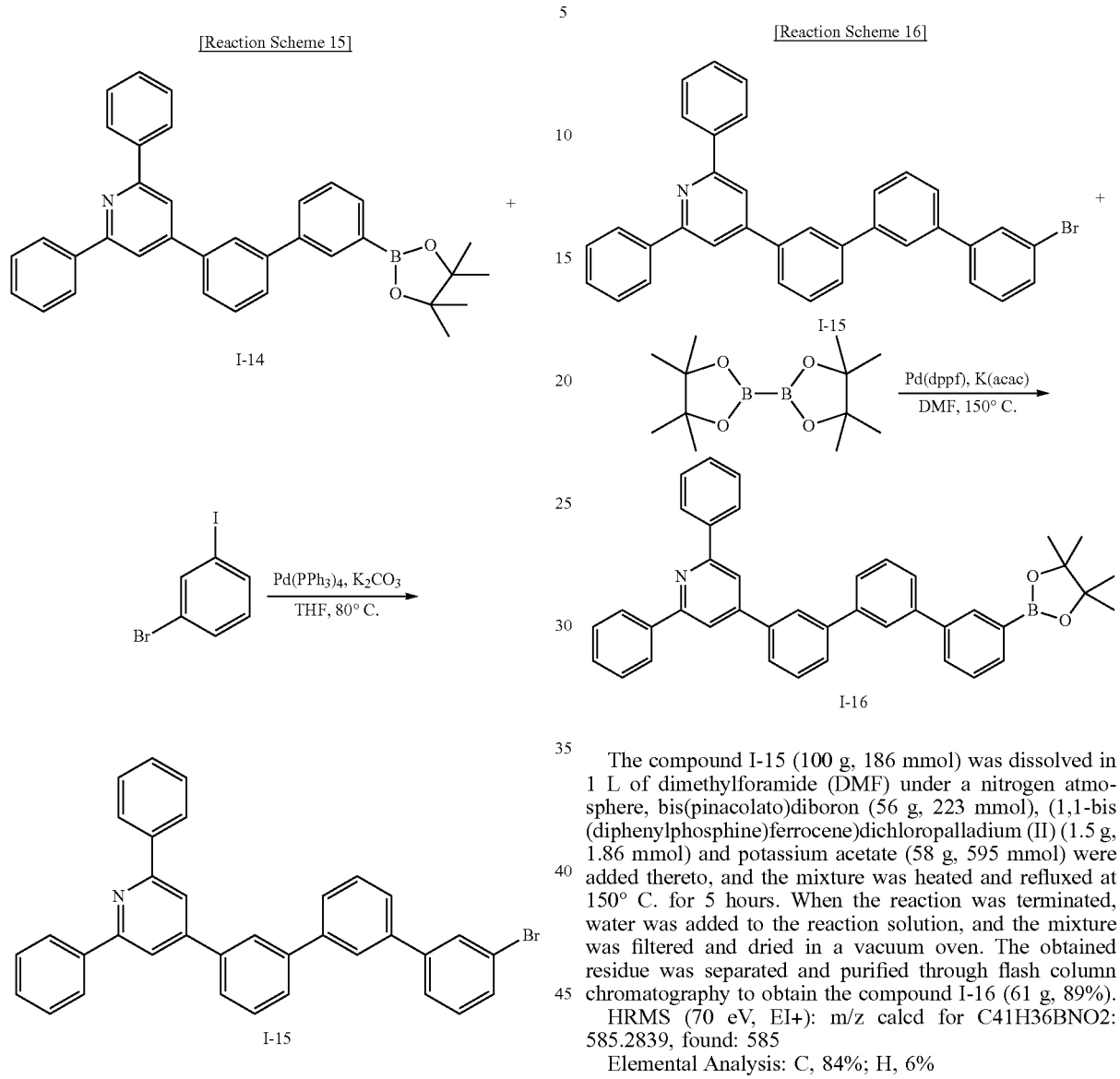

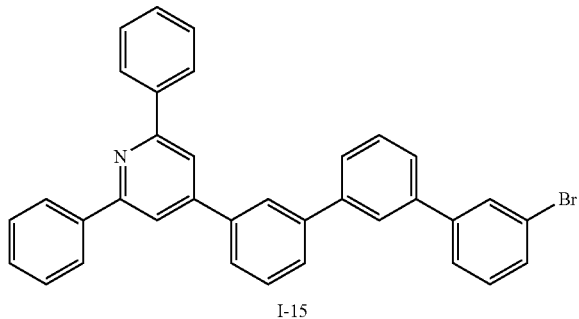

The compound I-14 (50 g, 98 mmol) was dissolved in 1 L of THF under a nitrogen atmosphere, 1-bromo-3-iodobenzene (33 g, 117 mmol) and tetrakis(triphenylphosphine)palladium (1 g, 0.98 mmol) were added thereto, and the mixture was agitated. Then, potassium carbonate saturated in water (34 g, 245 mmol) was added thereto, and the obtained mixture was heated and refluxed at 80° C. for 12 hours. When the reaction was terminated, water was added to the reaction solution, the mixture was extracted with dichloromethane (DCM), and the extract was treated with anhydrous MgSO₄ to remove moisture therefrom, filtered, and concentrated under a reduced pressure. The obtained residue was separated and purified through flash column chromatography to obtain the compound I-15 (50 g, 95%).

HRMS (70 eV, EI+): m/z calcd for C35H24BrN: 537.1092, found: 537.

Elemental Analysis: C, 78%; H, 4%

Synthesis Example 16: Synthesis of Intermediate I-16

[Reaction Scheme 16]

The compound I-15 (100 g, 186 mmol) was dissolved in 1 L of dimethylforamide (DMF) under a nitrogen atmosphere, bis(pinacolato)diboron (56 g, 223 mmol), (1,1-bis(diphenylphosphine)ferrocene)dichloropalladium (II) (1.5 g, 1.86 mmol) and potassium acetate (58 g, 595 mmol) were added thereto, and the mixture was heated and refluxed at 150° C. for 5 hours. When the reaction was terminated, water was added to the reaction solution, and the mixture was filtered and dried in a vacuum oven. The obtained residue was separated and purified through flash column chromatography to obtain the compound I-16 (61 g, 89%).

HRMS (70 eV, EI+): m/z calcd for C41H36BNO2: 585.2839, found: 585

Elemental Analysis: C, 84%; H, 6%

Synthesis Example 17: Synthesis of Intermediate I-17

[Reaction Scheme 17]

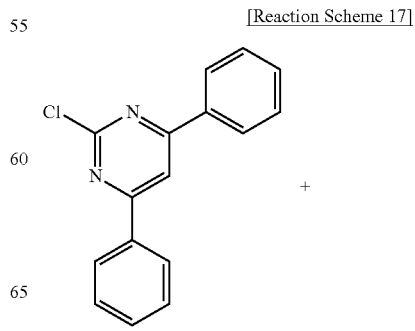

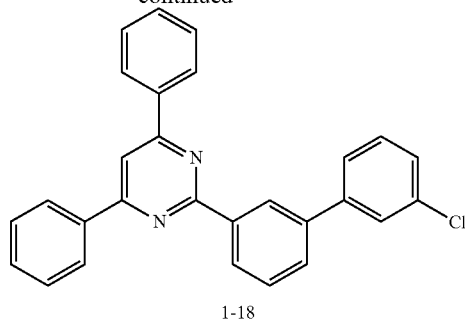

I-18

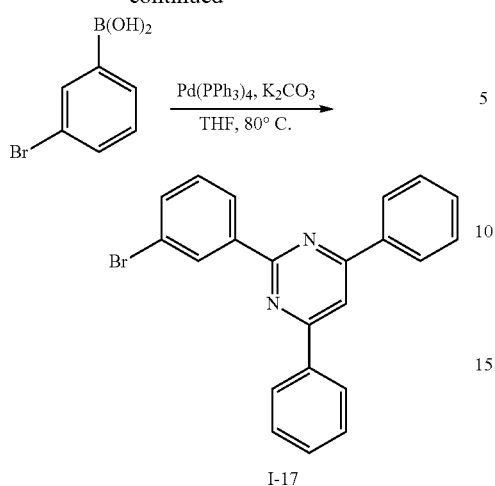

I-17

2-chloro-4,6-diphenylpyrimidine (50 g, 187 mmol) was dissolved in 1 L of THF under a nitrogen atmosphere, (3-bromophenyl)boronic acid (37 g, 155 mmol) and tetrakis(triphenylphosphine)palladium (2.1 g, 1.8 mmol) were added thereto, and the mixture was agitated. Then, potassium carbonate saturated in water (64 g, 467 mmol) was added thereto, and the obtained mixture was heated and refluxed at 80° C. for 12 hours. When the reaction was terminated, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain the compound I-17 (66 g, 92%).

HRMS (70 eV, EI+): m/z calcd for C22H15BrN2: 386.0419, found: 386.

Elemental Analysis: C, 68%; H, 4%

Synthesis Example 18: Synthesis of Intermediate I-18

[Reaction Scheme 18]

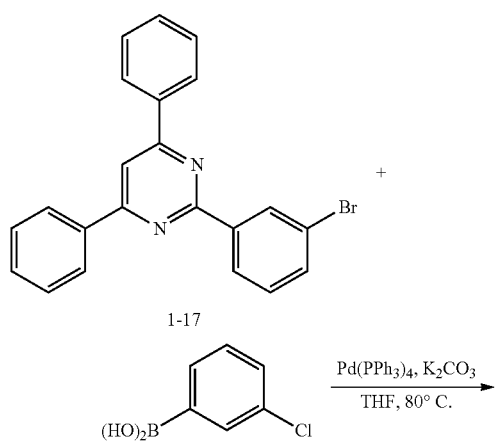

The compound I-17 (50 g, 129 mmol) was dissolved in 1 L of THF under a nitrogen atmosphere, (3-chlorophenyl)boronic acid (24 g, 155 mmol) and tetrakis(triphenylphosphine) palladium (1.5 g, 1.3 mmol) were added thereto, and the mixture was agitated. Then, potassium carbonate saturated in water (45 g, 322 mmol) was added thereto, and the obtained mixture was heated and refluxed at 80° C. for 12 hours. When the reaction was terminated, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain the compound I-18 (50 g, 92%).

HRMS (70 eV, EI+): m/z calcd for C28H19ClN2: 418.1237, found: 418.

Elemental Analysis: C, 80%; H, 4%

Synthesis Example 19: Synthesis of Intermediate I-19

[Reaction Scheme 19]

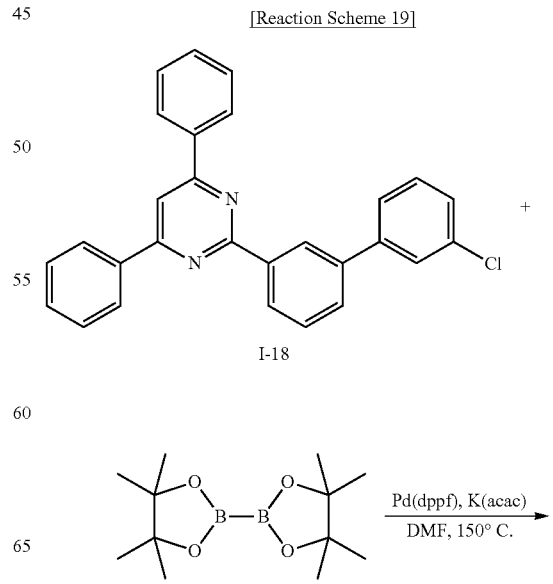

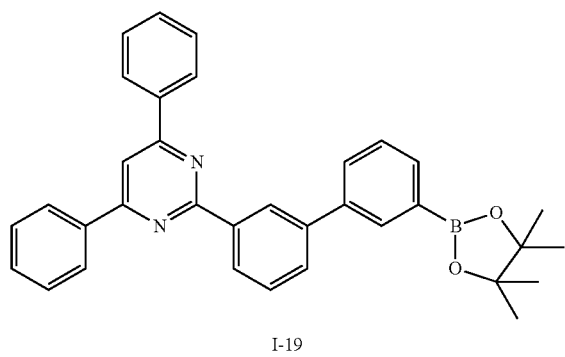

I-19

The compound I-18 (100 g, 239 mmol) was dissolved in 1 L of dimethylforamide (DMF) under a nitrogen atmosphere, bis(pinacolato)diboron (72.5 g, 287 mmol), (1,1-bis(diphenylphosphine)ferrocene)dichloropalladium (II) (2 g, 2.38 mmol) and potassium acetate (58 g, 595 mmol) were added thereto, and the mixture was heated and refluxed at 150° C. for 48 hours. When the reaction was terminated, water was added to the reaction solution, and the mixture was filtered and dried in a vacuum oven. The obtained residue was separated and purified through flash column chromatography to obtain the compound I-19 (105 g, 86%).

HRMS (70 eV, EI+): m/z calcd for C34H31BN2O2: 510.2479, found: 510

Elemental Analysis: C, 80%; H, 6%

Synthesis Example 20: Synthesis of Intermediate I-20

[Reaction Scheme 20]

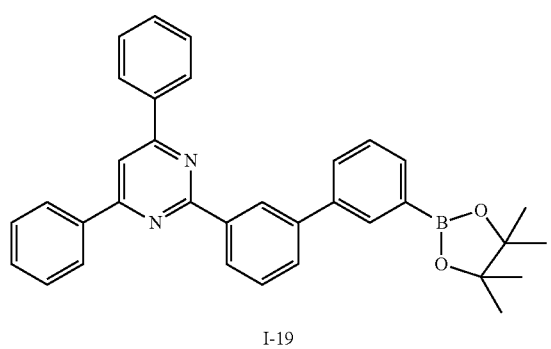

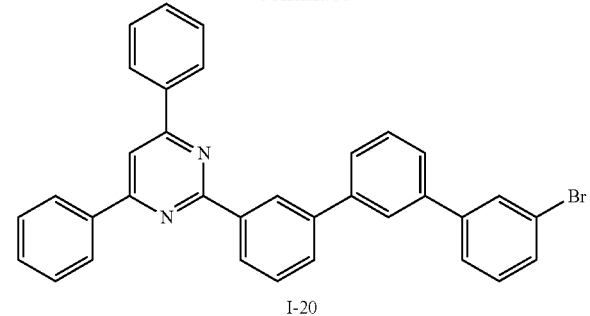

I-20

The compound I-19 (50 g, 98 mmol) was dissolved in 1 L of THF under a nitrogen atmosphere, 1-bromo-3-iodobenzene (33 g, 117 mmol) and tetrakis(triphenylphosphine)palladium (1 g, 0.98 mmol) were added thereto, and the mixture was agitated. Then, potassium carbonate saturated in water (34 g, 245 mmol) was added thereto, and the obtained mixture was heated and refluxed at 80° C. for 12 hours. When the reaction was terminated, water was added to the reaction solution, the mixture was extracted with dichloromethane (DCM), and the extract was treated with anhydrous MgSO4 to remove moisture therefrom, filtered, and concentrated under a reduced pressure. The obtained residue was separated and purified through flash column chromatography to obtain the compound I-20 (50 g, 95%).

HRMS (70 eV, EI+): m/z calcd for C34H23BrN2: 538.1045, found 538

Elemental Analysis: C, 76%; H, 4%

Synthesis Example 21: Synthesis of Intermediate I-21

[Reaction Scheme 21]

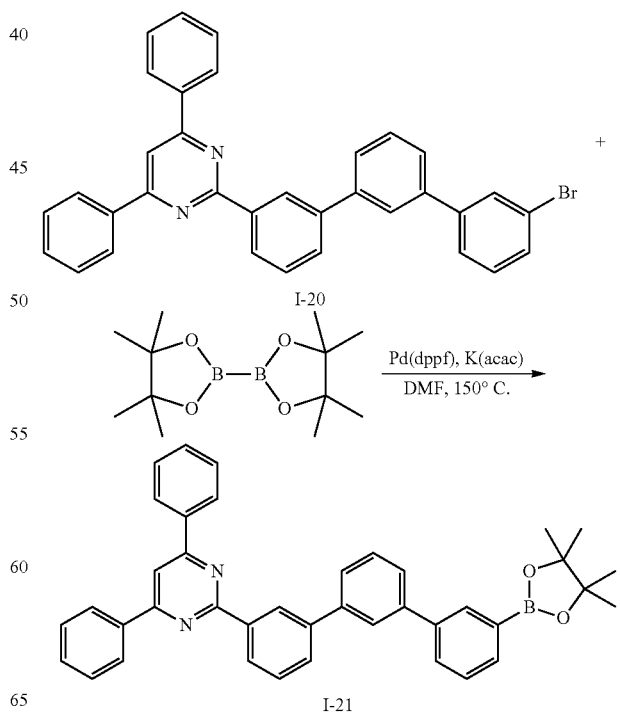

The compound I-20 (100 g, 185 mmol) was dissolved in 1 L of dimethylforamide (DMF) under a nitrogen atmosphere, bis(pinacolato)diboron (56 g, 222 mmol), (1,1-bis(diphenylphosphine)ferrocene)dichloropalladium (II) (1.5 g, 1.86 mmol) and potassium acetate (58 g, 595 mmol) were added thereto, and the mixture was heated and refluxed at 150° C. for 12 hours. When the reaction was terminated, water was added to the reaction solution, and the mixture was filtered and dried in a vacuum oven. The obtained residue was separated and purified through flash column chromatography to obtain the compound I-21 (61 g, 89%).

HRMS (70 eV, EI+): m/z calcd for C40H35BN2O2: 586.2792, found: 586

Elemental Analysis: C, 82%; H, 6%

Synthesis Example 22: Synthesis of Intermediate I-22

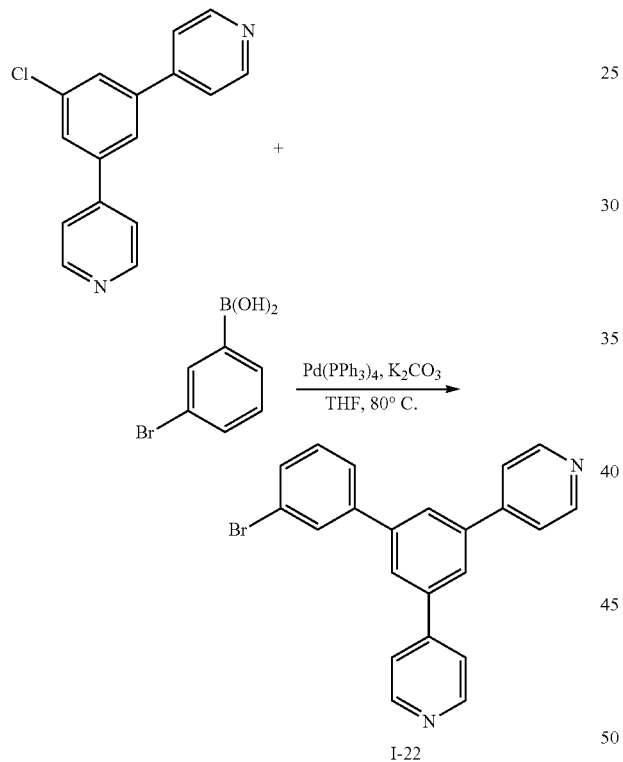

The compound 4,4'-(5-chloro-1,3-phenylene)dipyridine (50 g, 187 mmol) was dissolved in 1 L of THF under a nitrogen atmosphere, (3-bromophenyl)boronic acid (37 g, 155 mmol) and tetrakis(triphenylphosphine) palladium (2.1 g, 1.8 mmol) were added thereto, and the mixture was agitated. Then, potassium carbonate saturated in water (64 g, 467 mmol) was added thereto, and the obtained mixture was heated and refluxed at 80° C. for 12 hours. When the reaction was terminated, water was added to the reaction solution, the mixture was extracted with dichloromethane (DCM), and the extract was treated with anhydrous MgSO4 to remove moisture therefrom, filtered, and concentrated under a reduced pressure. The obtained residue was separated and purified through flash column chromatography to obtain the compound I-22 (66 g, 92%).

HRMS (70 eV, EI+): m/z calcd for C22H15BrN2: 386.0419, found: 386.

Elemental Analysis: C, 68%; H, 4%

Synthesis Example 23: Synthesis of Intermediate I-23

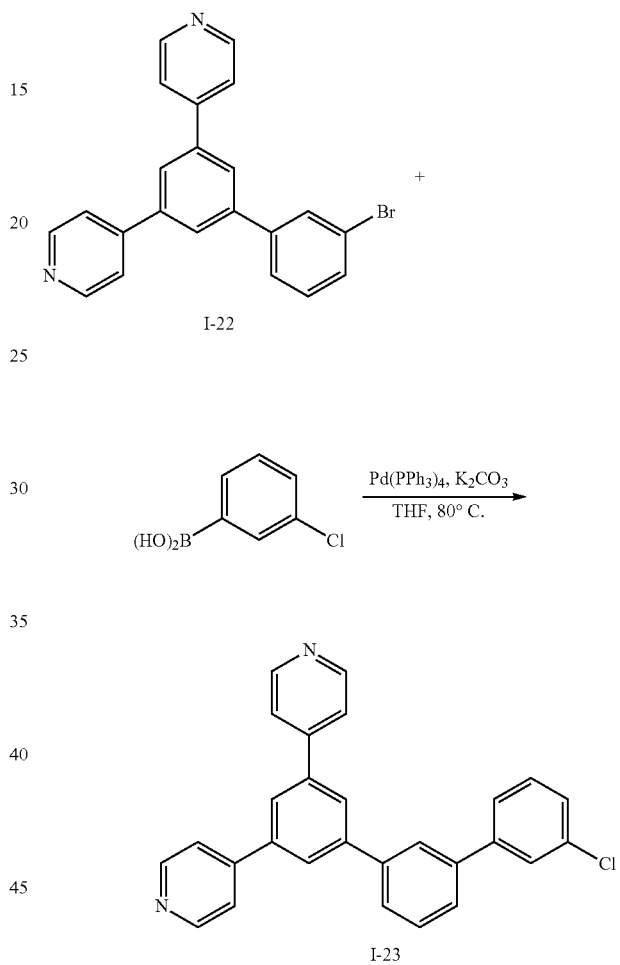

The compound I-22 (50 g, 129 mmol) was dissolved in 1 L of dioxane under a nitrogen atmosphere, (3-chlorophenyl)boronic acid (24 g, 155 mmol) and tetrakis(triphenylphosphine) palladium (1.5 g, 1.3 mmol) were added thereto, and the mixture was agitated. Then, potassium carbonate saturated in water (45 g, 322 mmol) was added thereto, and the obtained mixture was heated and refluxed at 80° C. for 12 hours. When the reaction was terminated, water was added to the reaction solution, the mixture was extracted with dichloromethane (DCM), and the extract was treated with anhydrous MgSO4 to remove moisture therefrom, filtered, and concentrated under a reduced pressure. The obtained residue was separated and purified through flash column chromatography to obtain the compound I-23 (50 g, 92%).

HRMS (70 eV, EI+): m/z calcd for C28H19ClN2: 418.1237, found: 418.

Elemental Analysis: C, 80%; H, 4%

Synthesis Example 24: Synthesis of Intermediate I-24

Synthesis Example 25: Synthesis of Intermediate I-25

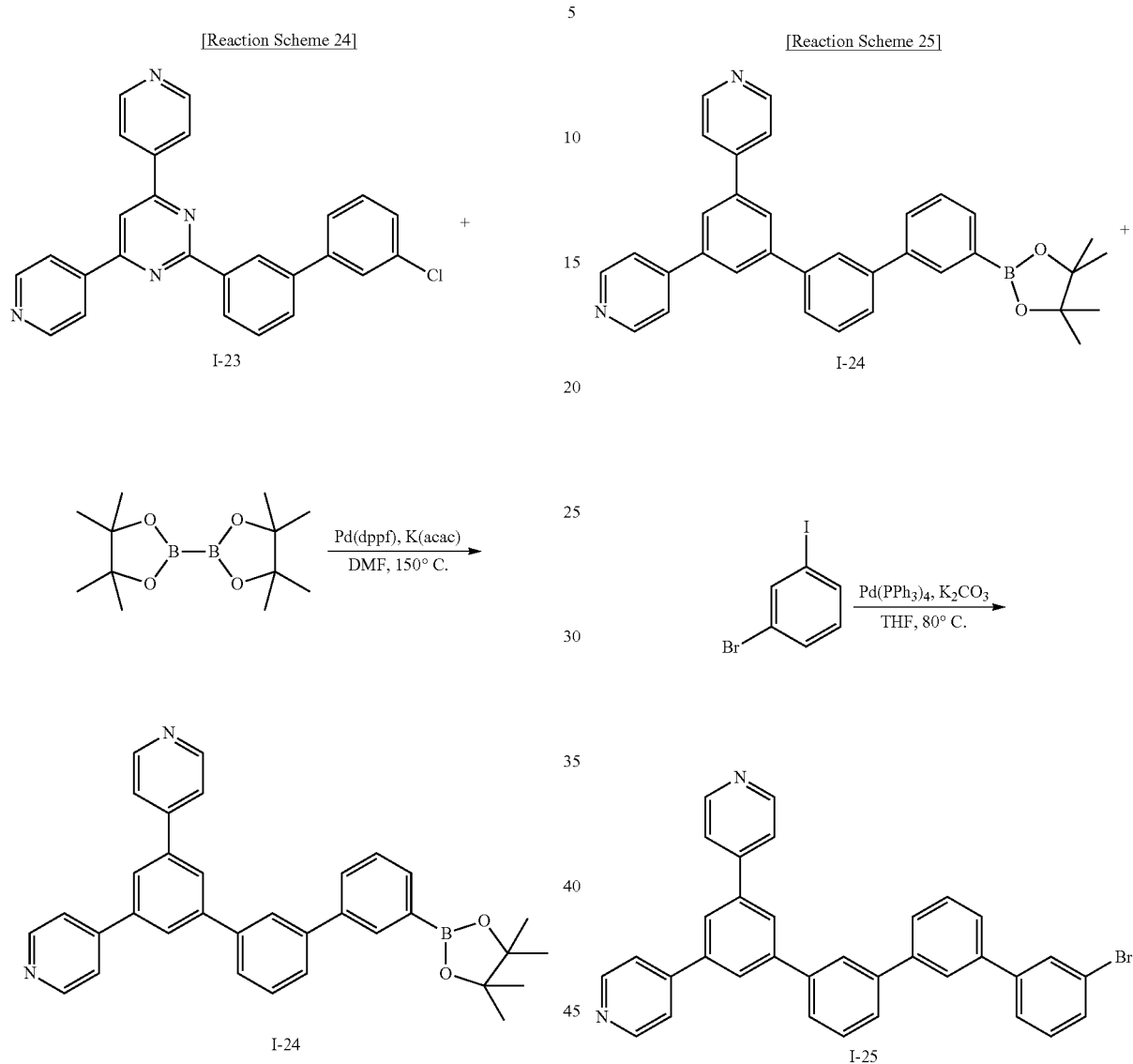

The compound I-23 (100 g, 239 mmol) was dissolved in 1 L of dimethylforamide (DMF) under a nitrogen atmosphere, bis(pinacolato)diboron (72.5 g, 287 mmol), (1,1-bis(diphenylphosphine)ferrocene)dichloropalladium (II) (2 g, 2.38 mmol) and potassium acetate (58 g, 595 mmol) were added thereto, and the mixture was heated and refluxed at 150° C. for 48 hours. When the reaction was terminated, water was added to the reaction solution, and the mixture was filtered and dried in a vacuum oven. The obtained residue was separated and purified through flash column chromatography to obtain the compound I-24 (105 g, 86%).

HRMS (70 eV, EI+): m/z calcd for $C_{34}H_{31}BN_2O_2$: 510.2479, found: 510

Elemental Analysis: C, 80%; H, 6%

The compound I-24 (50 g, 98 mmol) was dissolved in 1 L of THF under a nitrogen atmosphere, 1-bromo-3-iodobenzene (33 g, 117 mmol) and tetrakis(triphenylphosphine)palladium (1 g, 0.98 mmol) were added thereto, and the mixture was agitated. Then, potassium carbonate saturated in water (34 g, 245 mmol) was added thereto, and the obtained mixture was heated and refluxed at 80° C. for 12 hours. When the reaction was terminated, water was added to the reaction solution, the mixture was extracted with dichloromethane (DCM), and the extract was treated with anhydrous $MgSO_4$ to remove moisture therefrom, filtered, and concentrated under a reduced pressure. The obtained residue was separated and purified through flash column chromatography to obtain the compound I-25 (50 g, 96%).

HRMS (70 eV, EI+): m/z calcd for $C_{34}H_{23}BrN_2$: 538.1045, found 538

Elemental Analysis: C, 76%; H, 4%

Synthesis Example 26: Synthesis of Intermediate I-26

Synthesis Example 27: Synthesis of Intermediate I-27

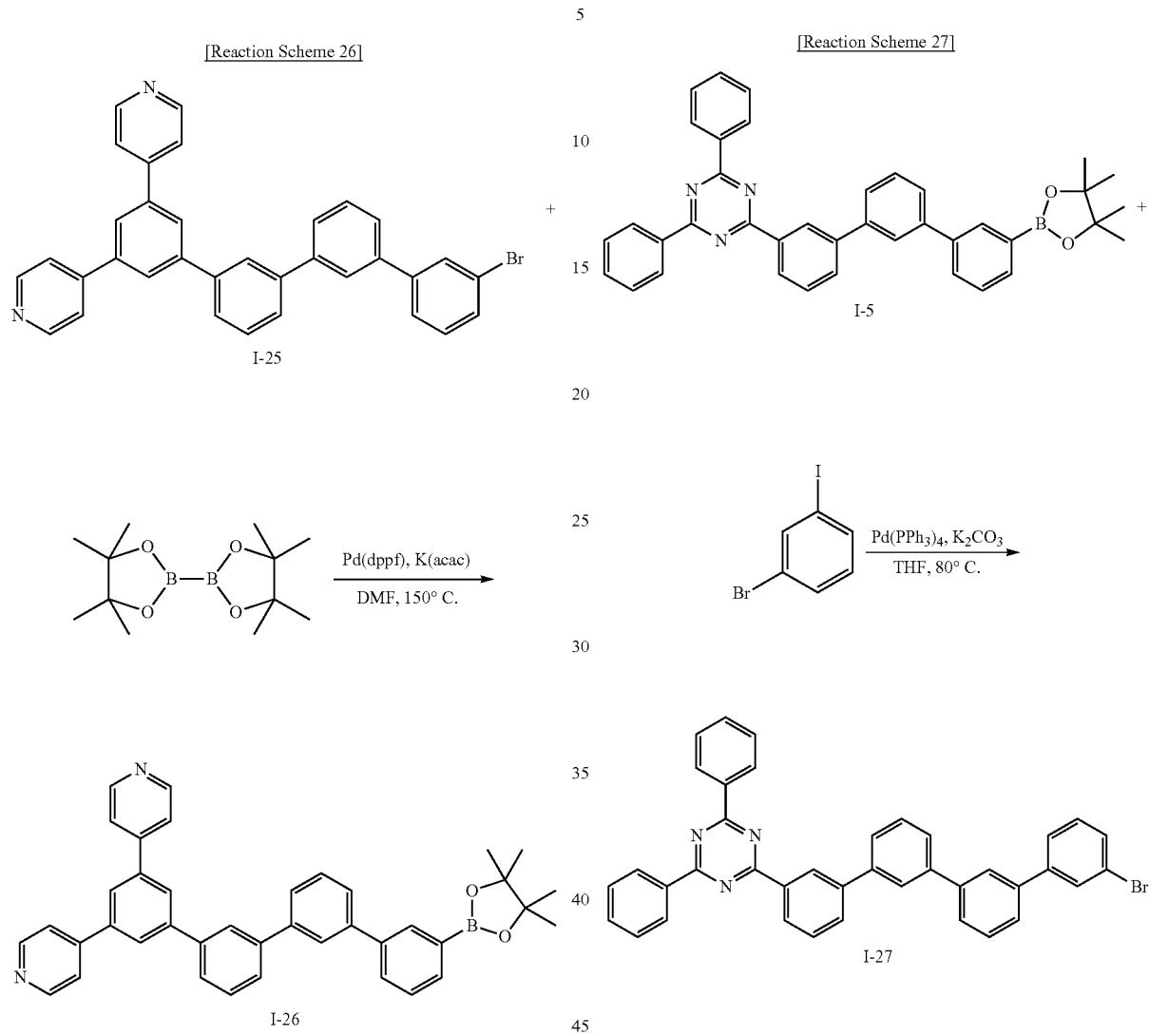

The compound I-25 (100 g, 185 mmol) was dissolved in 1 L of dimethylforamide (DMF) under a nitrogen atmosphere, bis(pinacolato)diboron (56 g, 222 mmol), (1,1-bis(diphenylphosphine)ferrocene)dichloropalladium (II) (1.5 g, 1.86 mmol) and potassium acetate (58 g, 595 mmol) were added thereto, and the mixture was heated and refluxed at 150° C. for 12 hours. When the reaction was terminated, water was added to the reaction solution, and the mixture was filtered and dried in a vacuum oven. The obtained residue was separated and purified through flash column chromatography to obtain the compound I-26 (92 g, 85%).

HRMS (70 eV, EI+): m/z calcd for C40H35BN2O2: 586.2792, found: 586

Elemental Analysis: C, 82%; H, 6%

The compound I-5 (50 g, 85 mmol) was dissolved in 1 L of THF under a nitrogen atmosphere, 1-bromo-3-iodobenzene (29 g, 102 mmol) and tetrakis(triphenylphosphine)palladium (1 g, 0.85 mmol) were added thereto, and the mixture was agitated. Then, potassium carbonate saturated in water (30 g, 212 mmol) was added thereto, and the obtained mixture was heated and refluxed at 80° C. for 12 hours.

When the reaction was terminated, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain the compound I-27 (50 g, 95%).

HRMS (70 eV, EI+): m/z calcd for C39H26BrN3: 615.1310, found 616

Elemental Analysis: C, 76%; H, 4%

Synthesis Example 28: Synthesis of Intermediate I-28

[Reaction Scheme 28]

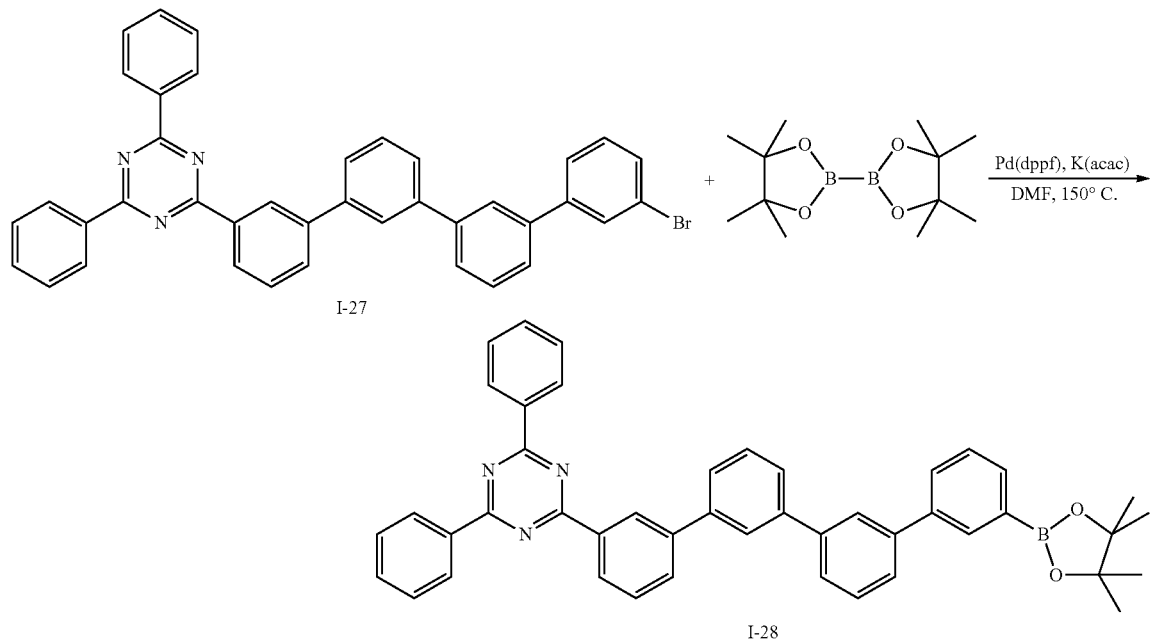

The compound I-27 (100 g, 162 mmol) was dissolved in 1 L of dimethylforamide (DMF) under a nitrogen atmosphere, bis(pinacolato)diboron (49 g, 194 mmol) and (1,1-bis(diphenylphosphine)ferrocene)dichloropalladium(II) (1.3 g, 1.62 mmol) and potassium acetate (40 g, 405 mmol) were added thereto, and the mixture was heated and refluxed at 150° C. for 12 hours. When the reaction was terminated, water was added to the reaction solution, and the mixture was filtered and dried in a vacuum oven. The obtained residue was separated and purified through flash column chromatography to obtain the compound I-28 (86 g, 80%).

HRMS (70 eV, EI+): m/z calcd for C45H38BN3O2: 663.3057, found: 663

Elemental Analysis: C, 81%; H, 6%

Synthesis Example 29: Synthesis of Intermediate I-29

[Reaction Scheme 29]

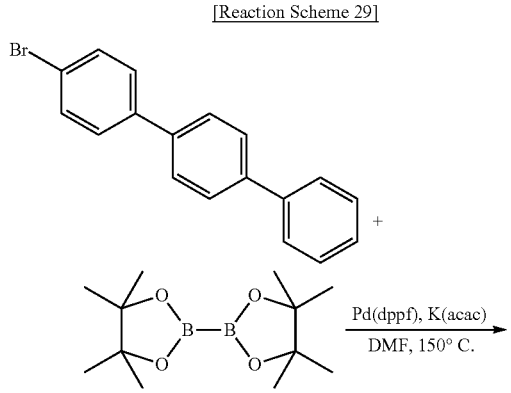

-continued

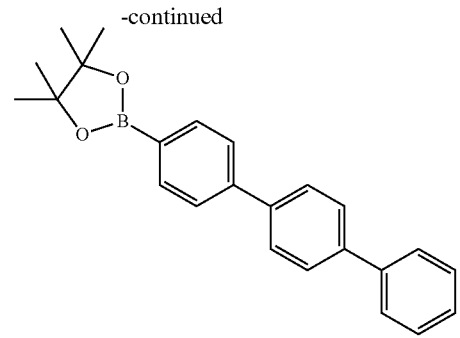

4-bromo-1,1':4',1''-terphenyl (50 g, 162 mmol) was dissolved in 1 L of dimethylforamide (DMF) under a nitrogen atmosphere, bis(pinacolato)diboron (49 g, 194 mmol), (1,1-bis(diphenylphosphine)ferrocene)dichloropalladium (II) (1.3 g, 1.62 mmol) and potassium acetate (40 g, 405 mmol) were added thereto, and the mixture was heated and refluxed at 150° C. for 12 hours. When the reaction was terminated, water was added to the reaction solution, and the mixture was filtered and dried in a vacuum oven. The obtained residue was separated and purified through flash column chromatography to obtain the compound I-29 (47 g, 82%).

HRMS (70 eV, EI+): m/z calcd for C24H25BO2: 356.1948, found: 356

Elemental Analysis: C, 81%; H, 7%

Synthesis Example 30: Synthesis of Intermediate I-30

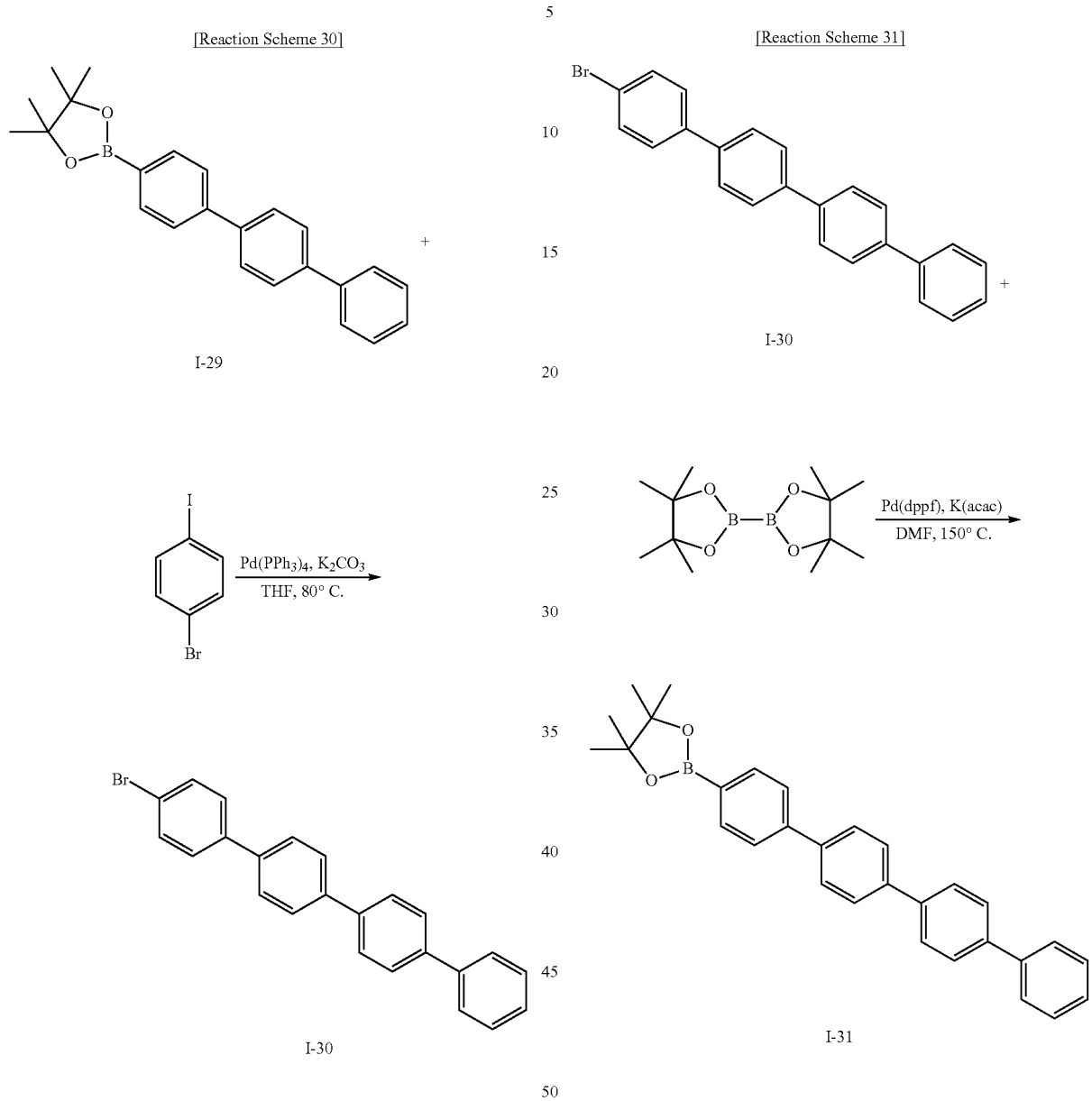

The compound I-29 (50 g, 140 mmol) was dissolved in 1 L of THF under a nitrogen atmosphere, 1-bromo-4-iodobenzene (47 g, 168 mmol) and tetrakis(triphenylphosphine) palladium (1.6 g, 1.4 mmol) were added thereto, and the mixture was agitated. Then, potassium carbonate saturated in water (48 g, 350 mmol) was added thereto, and the obtained mixture was heated and refluxed at 80° C. for 12 hours. When the reaction was terminated, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain the compound I-30 (44 g, 89%).

HRMS (70 eV, EI+): m/z calcd for C24H17Br: 384.0514, found 384 Elemental Analysis: C, 75%; H, 4%

Synthesis Example 31: Synthesis of Intermediate I-31

The compound I-30 (20 g, 52 mmol) was dissolved in 1 L of dimethylforamide (DMF) under a nitrogen atmosphere, bis(pinacolato)diboron (16 g, 62.5 mmol), (1,1'-bis(diphenylphosphine)ferrocene)dichloropalladium (II) (0.4 g, 0.52 mmol) and potassium acetate (13 g, 130 mmol) were added thereto, and the mixture was heated and refluxed at 150° C. for 5 hours. When the reaction was terminated, water was added to the reaction solution, and the mixture was filtered and dried in a vacuum oven. The obtained residue was separated and purified through flash column chromatography to obtain the compound I-31 (19 g, 85%).

HRMS (70 eV, EI+): m/z calcd for C30H29BO2: 432.2261, found: 432

Elemental Analysis: C, 83%; H, 7%

Synthesis Example 32: Synthesis of Intermediate I-32

Synthesis Example 33: Synthesis of Intermediate I-33

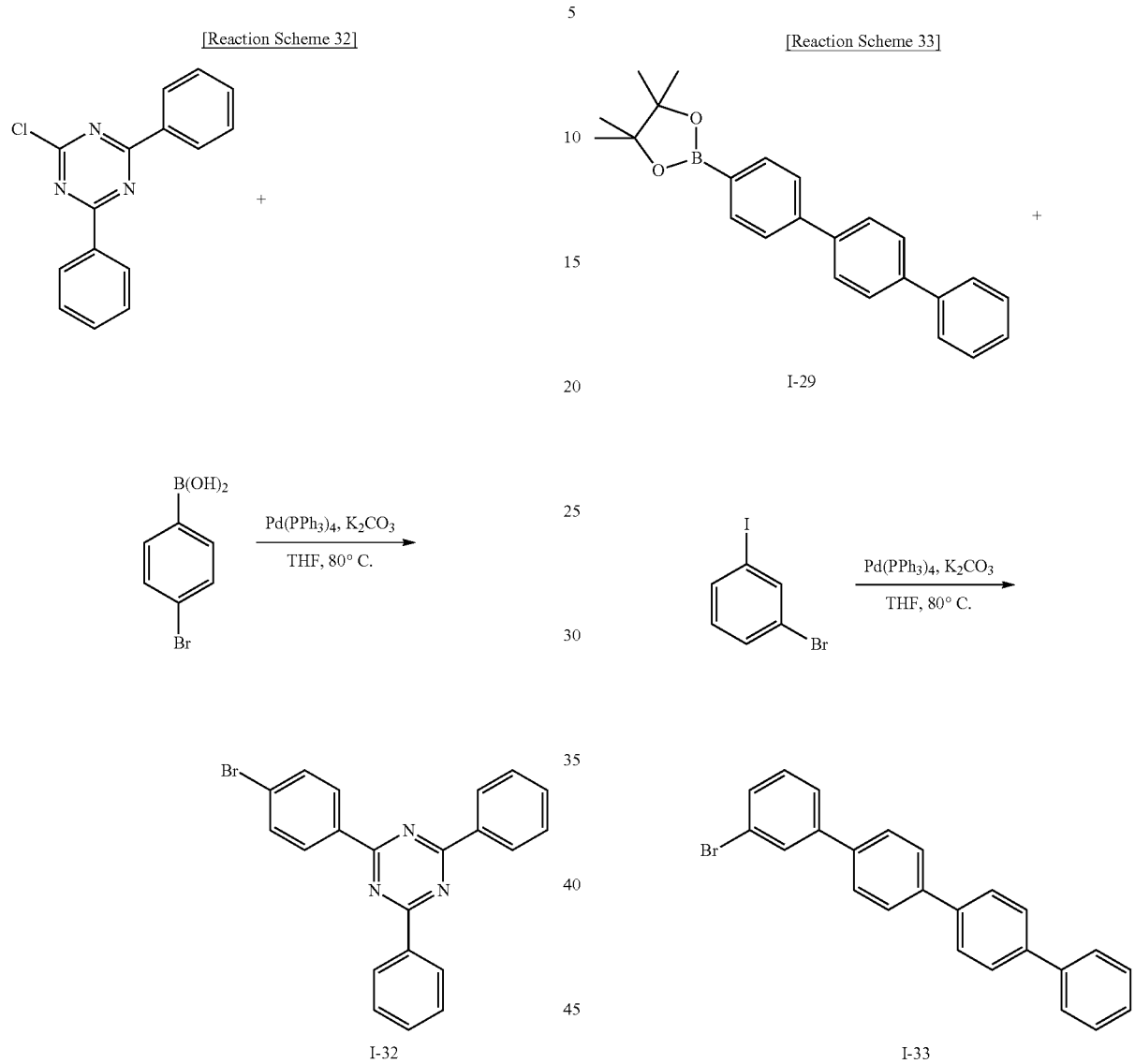

The compound (2-chloro-4,6-diphenyl-1,3,5-triazine) (50 g, 187 mmol) was dissolved in 1 L of THF under a nitrogen atmosphere, (4-bromophenyl)boronic acid (45 g, 224.12 mmol) and tetrakis(triphenylphosphine)palladium (2.1 g, 1.87 mmol) were added thereto, and the mixture was agitated. Then, potassium carbonate saturated in water (64 g, 467 mmol) was added thereto, and the mixture was heated and refluxed at 80° C. for 12 hours. When the reaction was terminated, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain the compound I-32 (70 g, 96%).

HRMS (70 eV, EI+): m/z calcd for C21H14BrN3: 387.0371, found: 387.

Elemental Analysis: C, 65%; H, 4%

The compound I-29 (50 g, 140 mmol) was dissolved in 1 L of THF under a nitrogen atmosphere, 1-bromo-3-iodobenzene (47 g, 168 mmol) and tetrakis(triphenylphosphine) palladium (1.6 g, 1.4 mmol) were added thereto, and the mixture was agitated. Then, the potassium carbonate saturated in water (48 g, 350 mmol) was added thereto, and the mixture was heated and refluxed at 80° C. for 12 hours. When the reaction was terminated, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain the compound I-33 (46 g, 90%).

HRMS (70 eV, EI+): m/z calcd for C24H17Br: 384.0514, found 384

Elemental Analysis: C, 75%; H, 4%

Synthesis Example 34: Synthesis of Intermediate I-34

[Reaction Scheme 34]

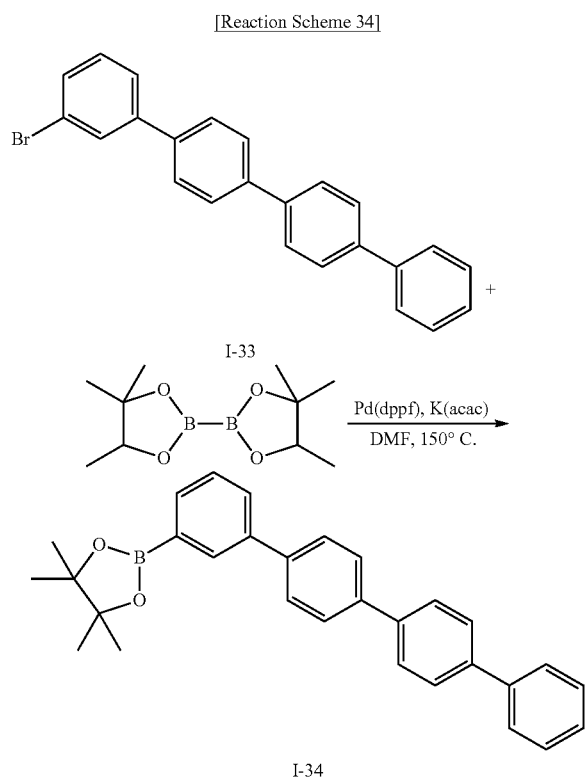

The compound I-33 (20 g, 52 mmol) was dissolved in 1 L of dimethylforamide (DMF) under a nitrogen atmosphere, bis(pinacolato)diboron (16 g, 62.5 mmol), (1,1'-bis(diphenylphosphine)ferrocene)dichloropalladium (II) (0.4 g, 0.52 mmol) and potassium acetate (13 g, 130 mmol) were added thereto, and the mixture was heated and refluxed at 150° C. for 5 hours. When the reaction was terminated, water was added to the reaction solution, and the mixture was filtered and dried in a vacuum oven. The obtained residue was separated and purified through flash column chromatography to obtain the compound I-34 (21 g, 83%).

HRMS (70 eV, EI+): m/z calcd for C30H29BO2: 432.2261, found: 432

Elemental Analysis: C, 83%; H, 7%

Synthesis Example 35: Synthesis of Intermediate I-35

[Reaction Scheme 35]

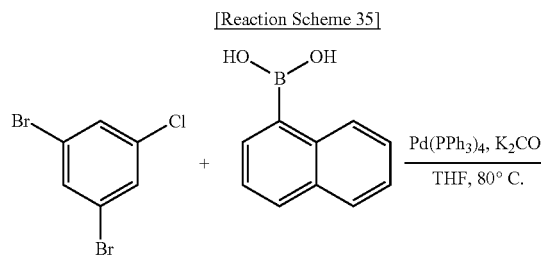

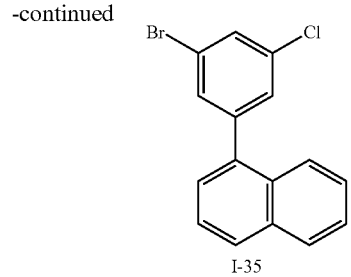

The compound of 1,3-dibromo-5-chlorobenzene (50 g, 185 mmol) was dissolved in 1 L of THF under a nitrogen atmosphere, naphthalen-1-ylboronic acid (32 g, 185 mmol) and tetrakis(triphenylphosphine)palladium (2 g, 1.8 mmol) were added thereto, and the mixture was agitated. Then, potassium carbonate saturated in water (64 g, 462 mmol) was added thereto, and the mixture was heated and refluxed at 80° C. for 12 hours. When the reaction was terminated, water was added to the reaction solution, the mixture was extracted with dichloromethane (DCM), and the extract was treated with anhydrous MgSO4 to remove moisture therefrom, filtered, and concentrated under a reduced pressure. The obtained residue was separated and purified through flash column chromatography to obtain the compound I-35 (32 g, 56%).

HRMS (70 eV, EI+): m/z calcd for C16H10BrCl: 315.9654, found 316

Elemental Analysis: C, 61%; H, 3%

Synthesis Example 36: Synthesis of Intermediate I-36

[Reaction Scheme 36]

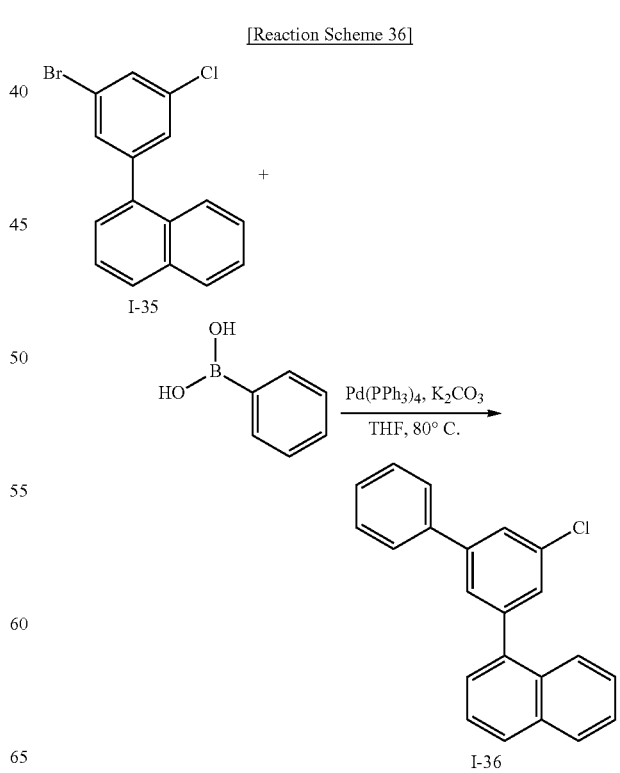

The compound I-35 (30 g, 95 mmol) was dissolved in 1 L of THF under a nitrogen atmosphere, phenylboronic acid (14 g, 114 mmol) and tetrakis(triphenylphosphine)palladium (1 g, 0.95 mmol) were added thereto, and the mixture was agitated. Then, potassium carbonate saturated in water (33 g, 237 mmol) was added thereto, and the obtained mixture was heated and refluxed at 80° C. for 12 hours. When the reaction was terminated, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain the compound I-36 (32 g, 75%).

HRMS (70 eV, EI+): m/z calcd for C22H15Cl: 314.0862, found 314

Elemental Analysis: C, 84%; H, 5%

Synthesis Example 37: Synthesis of Intermediate I-37

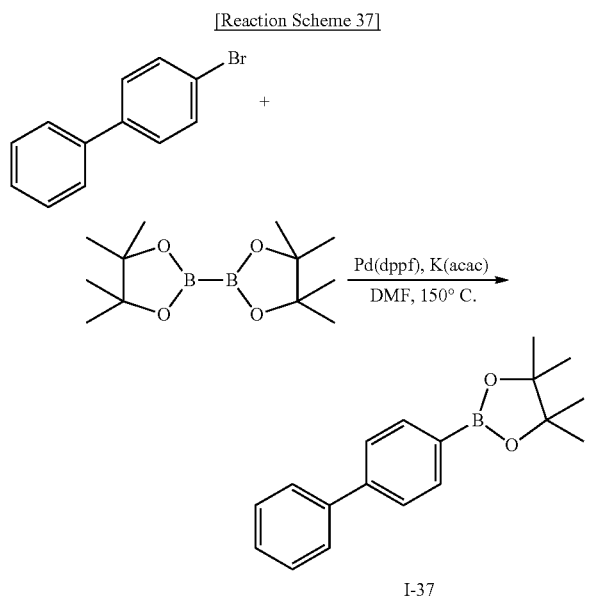

4-bromo-1,1'-biphenyl (20 g, 86 mmol) was dissolved in 1 L of dimethylforamide (DMF) under a nitrogen atmosphere, bis(pinacolato)diboron (26 g, 103 mmol), (1,1-bis(diphenylphosphine)ferrocene)dichloropalladium (II) (0.7 g, 0.86 mmol) and potassium acetate (21 g, 215 mmol) were added thereto, and the mixture was heated and refluxed at 150° C. for 5 hours. When the reaction was terminated, water was added to the reaction solution, and the mixture was filtered and dried in a vacuum oven. The obtained residue was separated and purified through flash column chromatography to obtain the compound I-37 (20 g, 85%).

HRMS (70 eV, EI+): m/z calcd for C18H21BO2: 280.1635, found: 280

Elemental Analysis: C, 77%; H, 8%

Synthesis Example 38: Synthesis of Intermediate I-38

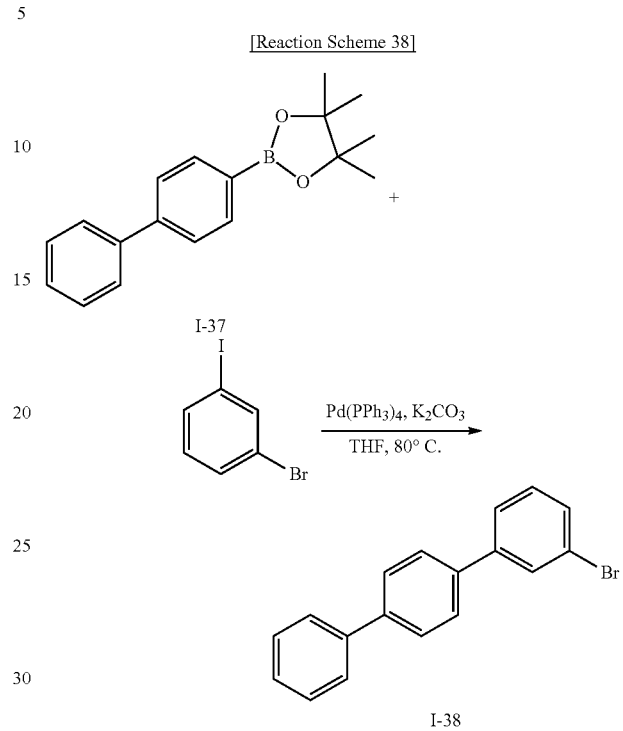

The compound I-38 (20 g, 71 mmol) was dissolved in 1 L of THF under a nitrogen atmosphere, 1-bromo-3-iodobenzene (24 g, 85 mmol) and tetrakis(triphenylphosphine)palladium (0.8 mg, 0.7 mmol) were added thereto, and the mixture was agitated. Then, potassium carbonate saturated in water (24.5 g, 177 mmol) was added thereto, and the mixture was heated and refluxed at 80° C. for 12 hours. When the reaction was terminated, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain the compound I-38 (30 g, 90%).

HRMS (70 eV, EI+): m/z calcd for C18H13Br: 309.1998, found 309 Elemental Analysis: C, 70%; H, 4%

Synthesis Example 39: Synthesis of Intermediate I-39

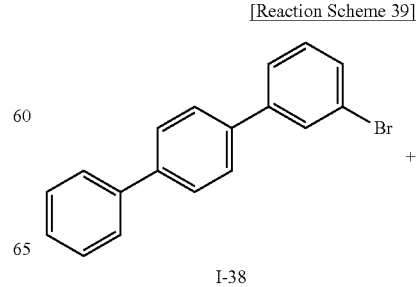

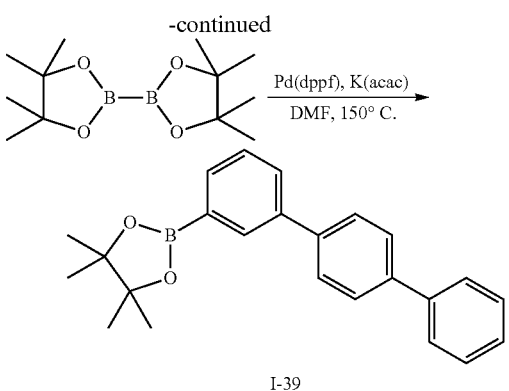

I-39

The compound I-38 (25 g, 81 mmol) was dissolved in 1 L of dimethylforamide (DMF) under a nitrogen atmosphere, bis(pinacolato)diboron (25 g, 97 mmol), (1,1-bis(diphenylphosphine)ferrocene)dichloropalladium (II) (0.7 g, 0.81 mmol) and potassium acetate (20 g, 203 mmol) were added thereto, and the mixture was heated and refluxed at 150° C. for 5 hours. When the reaction was terminated, water was added to the reaction solution, and the mixture was filtered and dried in a vacuum oven. The obtained residue was separated and purified through flash column chromatography to obtain the compound I-39 (27 g, 93%).

HRMS (70 eV, EI+): m/z calcd for C24H25BO2: 356.1948, found: 356

Elemental Analysis: C, 81%; H, 7%

Synthesis Example 40: Synthesis of Intermediate I-40

[Reaction Scheme 40]

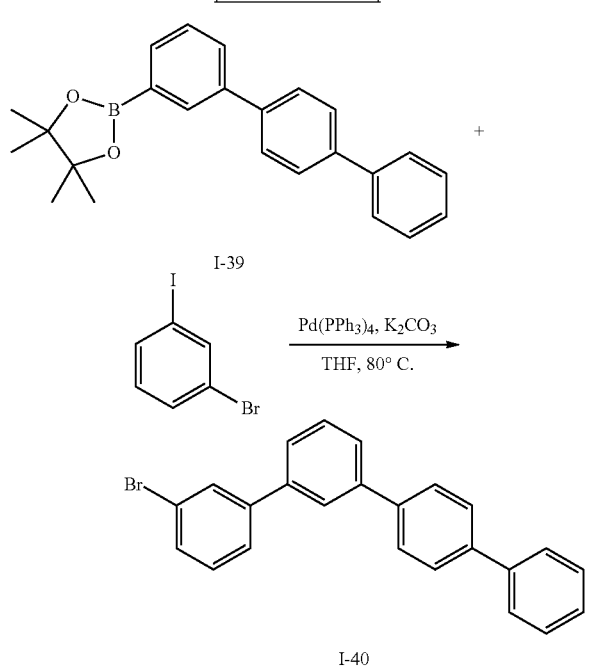

I-40

The compound I-39 (50 g, 140 mmol) was dissolved in 1 L of THF under a nitrogen atmosphere, 1-bromo-3-iodobenzene (47 g, 168 mmol) and tetrakis(triphenylphosphine) palladium (1.6 g, 1.4 mmol) were added thereto, and the mixture was agitated. Then, potassium carbonate saturated in water (48 g, 350 mmol) was added thereto, and the mixture was heated and refluxed at 80° C. for 12 hours. When the reaction was terminated, water was added to the reaction solution, the mixture was extracted with dichloromethane (DCM), and the extract was treated with anhydrous MgSO4 to remove moisture therefrom, filtered, and concentrated under a reduced pressure. The obtained residue was separated and purified through flash column chromatography to obtain the compound I-40 (44 g, 89%).

HRMS (70 eV, EI+): m/z calcd for C24H17Br: 384.0514, found 384 Elemental Analysis: C, 75%; H, 4%

Synthesis Example 41: Synthesis of Intermediate I-41

[Reaction Scheme 41]

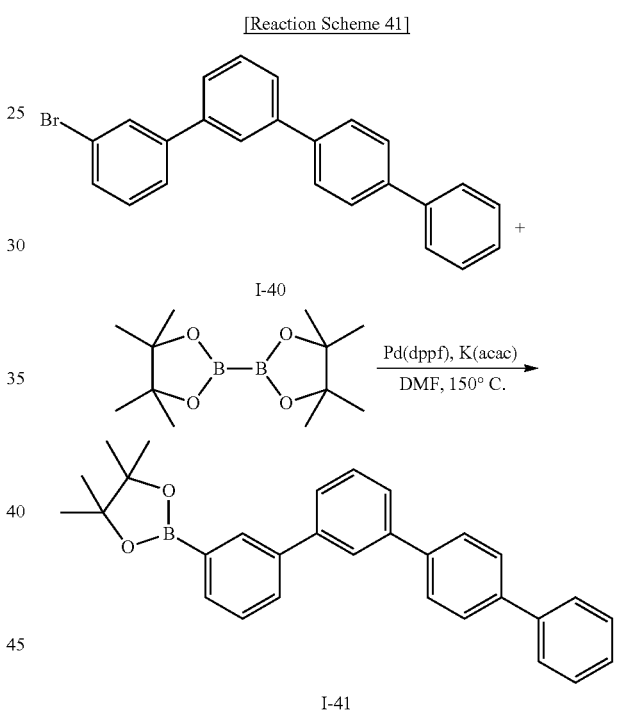

I-41

The compound I-40 (20 g, 52 mmol) was dissolved in 1 L of dimethylforamide (DMF) under a nitrogen atmosphere, bis(pinacolato)diboron (16 g, 62.5 mmol), (1,1-bis(diphenylphosphine)ferrocene)dichloropalladium (II) (0.4 g, 0.52 mmol) and potassium acetate (13 g, 130 mmol) were added thereto, and the mixture was heated and refluxed at 150° C. for 5 hours. When the reaction was terminated, water was added to the reaction solution, and the mixture was filtered and dried in a vacuum oven. The obtained residue was separated and purified through flash column chromatography to obtain the compound I-41 (19 g, 85%).

HRMS (70 eV, EI+): m/z calcd for C30H29BO2: 432.2261, found: 432

Elemental Analysis: C, 83%; H, 7%

Synthesis Example 42: Synthesis of Intermediate I-42

[Reaction Scheme 42]

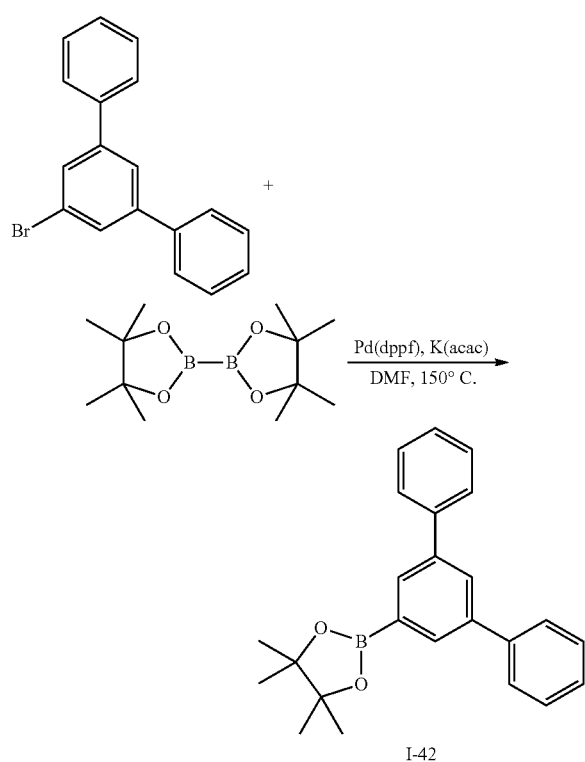

5'-bromo-1,1':3',1''-terphenyl (32.5 g, 105.10 mmol) was dissolved in 1 L of dimethylforamide (DMF) under a nitrogen atmosphere, bis(pinacolato)diboron (32 g, 126.13 mmol), (1,1'-bis(diphenylphosphine)ferrocene)dichloropalladium (II) (0.86 g, 1.05 mmol) and potassium acetate (25 g, 262.75 mmol) were added thereto, and the mixture was heated and refluxed at 150° C. for 5 hours. When the reaction was terminated, water was added to the reaction solution, and the mixture was filtered and dried in a vacuum oven. The obtained residue was separated and purified through flash column chromatography to obtain the compound I-42 (33 g, 88%).

HRMS (70 eV, EI+): m/z calcd for C24H25BO2: 356.1948, found: 356

Elemental Analysis: C, 81%; H, 7%

Synthesis Example 43: Synthesis of Intermediate I-43

[Reaction Scheme 43]

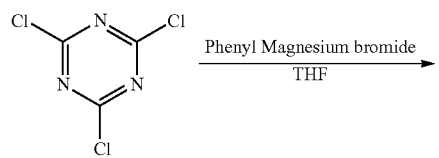

Phenyl Magnesium bromide / THF →

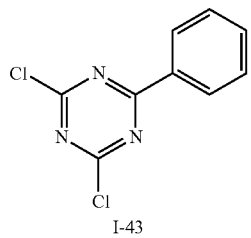

I-43

Cyanuric chloride (50 g, 271.13 mmol) was dissolved in 1 L of THF under a nitrogen atmosphere, and the solution was cooled down to −10° C. Then, 3.0 M phenyl magnesium bromide (90 ml, 271.13 mmol) was slowly added in a dropwise fashion, and the mixture was slowly heated up to room temperature. The heated mixture was agitated for 30 minutes. When the reaction was complete, the resultant was washed with a HCl solution, and a solvent was removed from an organic layer produced therein. The obtained residue was separated and purified through flash column chromatography to obtain the compound I-43 (33 g, 85%).

HRMS (70 eV, EI+): m/z calcd for C9H5Cl2N3: 224.9861, found: 225

Elemental Analysis: C, 48%; H, 2%

Synthesis Example 44: Synthesis of Intermediate I-44

[Reaction Scheme 44]

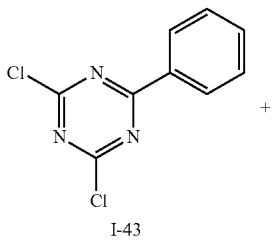

I-43

+

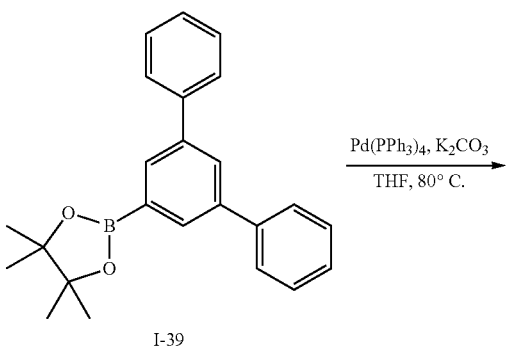

I-39

Pd(PPh3)4, K2CO3 / THF, 80° C.

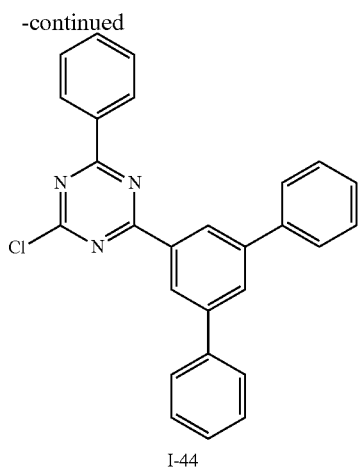

I-44

The compound I-39 (50 g, 140 mmol) was dissolved in 1 L of THF under a nitrogen atmosphere, the compound I-43 (31 g, 140 mmol) and tetrakis(triphenylphosphine) palladium (1.6 g, 1.4 mmol) were added thereto, and the mixture was agitated. Then, potassium carbonate saturated in water (48 g, 350 mmol) was added thereto, and the mixture was heated and refluxed at 80° C. for 12 hours. When the reaction was terminated, water was added to the reaction solution, the mixture was extracted with dichloromethane (DCM), and the extract was treated with anhydrous $MgSO_4$ to remove moisture therefrom, filtered, and concentrated under a reduced pressure. The obtained residue was separated and purified through flash column chromatography to obtain the compound I-44 (32 g, 70%).

HRMS (70 eV, EI+): m/z calcd forC27H18ClN3: 419.1189, found 419 Elemental Analysis: C, 77%; H, 4%

Synthesis Example 45: Synthesis of Intermediate I-45

[Reaction Scheme 45]

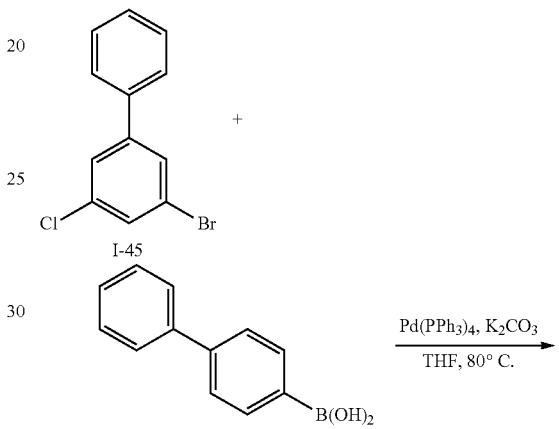

The compound of 1,3-dibromo-5-chlorobenzene (100 g, 370 mmol) was dissolved in 2 L of THF under a nitrogen atmosphere, phenylboronic acid (47.3 g, 388 mmol) and tetrakis(triphenylphosphine)palladium (1.5 g, 1.36 mmol) were added thereto, and the mixture was agitated. Then, potassium carbonate saturated in water (127 g, 925 mmol) was added thereto, and the mixture was heated and refluxed at 80° C. for 12 hours. When the reaction was terminated, water was added to the reaction solution, the mixture was extracted with dichloromethane (DCM), and the extract was treated with anhydrous $MgSO_4$ to remove moisture therefrom, filtered, and concentrated under a reduced pressure. The obtained residue was separated and purified through flash column chromatography to obtain the compound I-45 (49 g, 50%).

HRMS (70 eV, EI+): m/z calcd for C12H8BrCl: 265.9498, found 266 Elemental Analysis: C, 54%; H, 3%

Synthesis Example 46: Synthesis of Intermediate I-46

[Reaction Scheme 46]

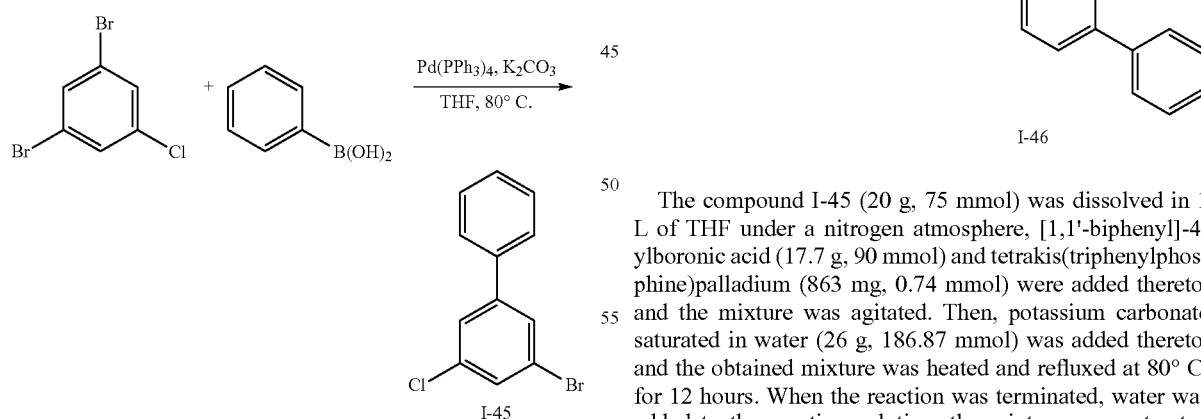

The compound I-45 (20 g, 75 mmol) was dissolved in 1 L of THF under a nitrogen atmosphere, [1,1'-biphenyl]-4-ylboronic acid (17.7 g, 90 mmol) and tetrakis(triphenylphosphine)palladium (863 mg, 0.74 mmol) were added thereto, and the mixture was agitated. Then, potassium carbonate saturated in water (26 g, 186.87 mmol) was added thereto, and the obtained mixture was heated and refluxed at 80° C. for 12 hours. When the reaction was terminated, water was added to the reaction solution, the mixture was extracted with dichloromethane (DCM), and the extract was treated with anhydrous $MgSO_4$ to remove moisture therefrom, filtered, and concentrated under a reduced pressure. The obtained residue was separated and purified through flash column chromatography to obtain the compound I-46 (21 g, 81%).

HRMS (70 eV, EI+): m/z calcd for C24H17Cl: 340.1019, found 340 Elemental Analysis: C, 85%; H, 5%

Synthesis Example 47: Synthesis of Intermediate I-47

[Reaction Scheme 47]

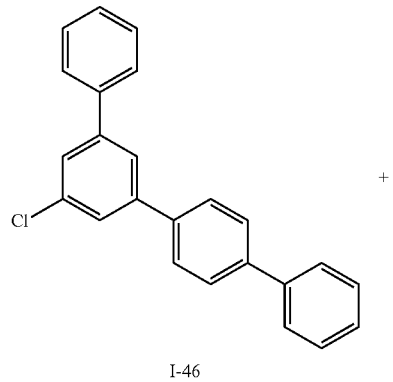

Synthesis Example 48: Synthesis of Intermediate I-48

[Reaction Scheme 48]

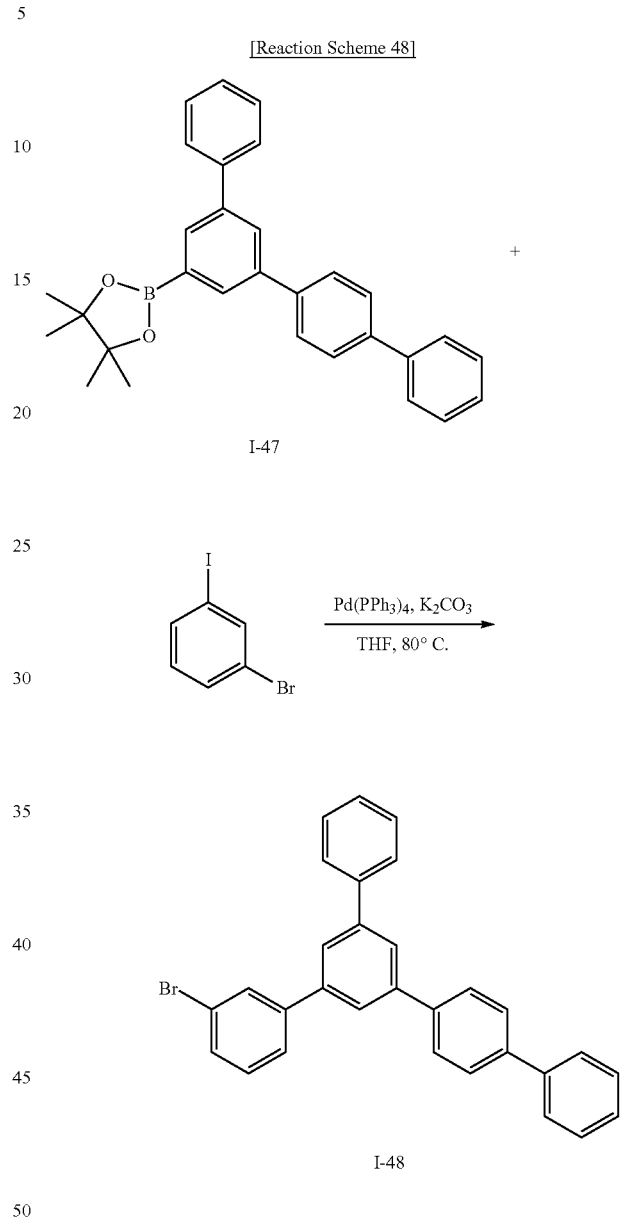

The compound I-46 (17.5 g, 51 mmol) was dissolved in 1 L of dimethylforamide (DMF) under a nitrogen atmosphere, bis(pinacolato)diboron (15.6 g, 61.6 mmol), (1,1'-bis(diphenylphosphine)ferrocene)dichloropalladium (II) (2.5 g, 3.06 mmol) and potassium acetate (15 g, 153 mmol) were added thereto, and the mixture was heated and refluxed at 150° C. for 5 hours. When the reaction was terminated, water was added to the reaction solution, and the mixture was filtered and dried in a vacuum oven. The obtained residue was separated and purified through flash column chromatography to obtain the compound I-47 (20 g, 90%).

HRMS (70 eV, EI+): m/z calcd for $C_{30}H_{29}BO_2$: 432.2261, found: 432

Elemental Analysis: C, 83%; H, 7%

The compound I-47 (31 g, 71 mmol) was dissolved in 1 L of THF under a nitrogen atmosphere, 1-bromo-3-iodobenzene (24 g, 85 mmol) and tetrakis(triphenylphosphine)palladium (0.8 mg, 0.7 mmol) were added thereto, and the mixture was agitated. Then, potassium carbonate saturated in water (24.5 g, 177 mmol) was added thereto, and the obtained mixture was heated and refluxed at 80° C. for 12 hours. When the reaction was terminated, water was added to the reaction solution, the mixture was extracted with dichloromethane (DCM), and the extract was treated with anhydrous $MgSO_4$ to remove moisture therefrom, filtered, and concentrated under a reduced pressure. The obtained residue was separated and purified through flash column chromatography to obtain the compound I-48 (29 g, 90%).

HRMS (70 eV, EI+): m/z calcd for $C_{30}H_{21}Br$: 460.0827, found 460 Elemental Analysis: C, 78%; H, 5%

Synthesis Example 49: Synthesis of Intermediate I-49

Synthesis Example 50: Synthesis of Intermediate I-50

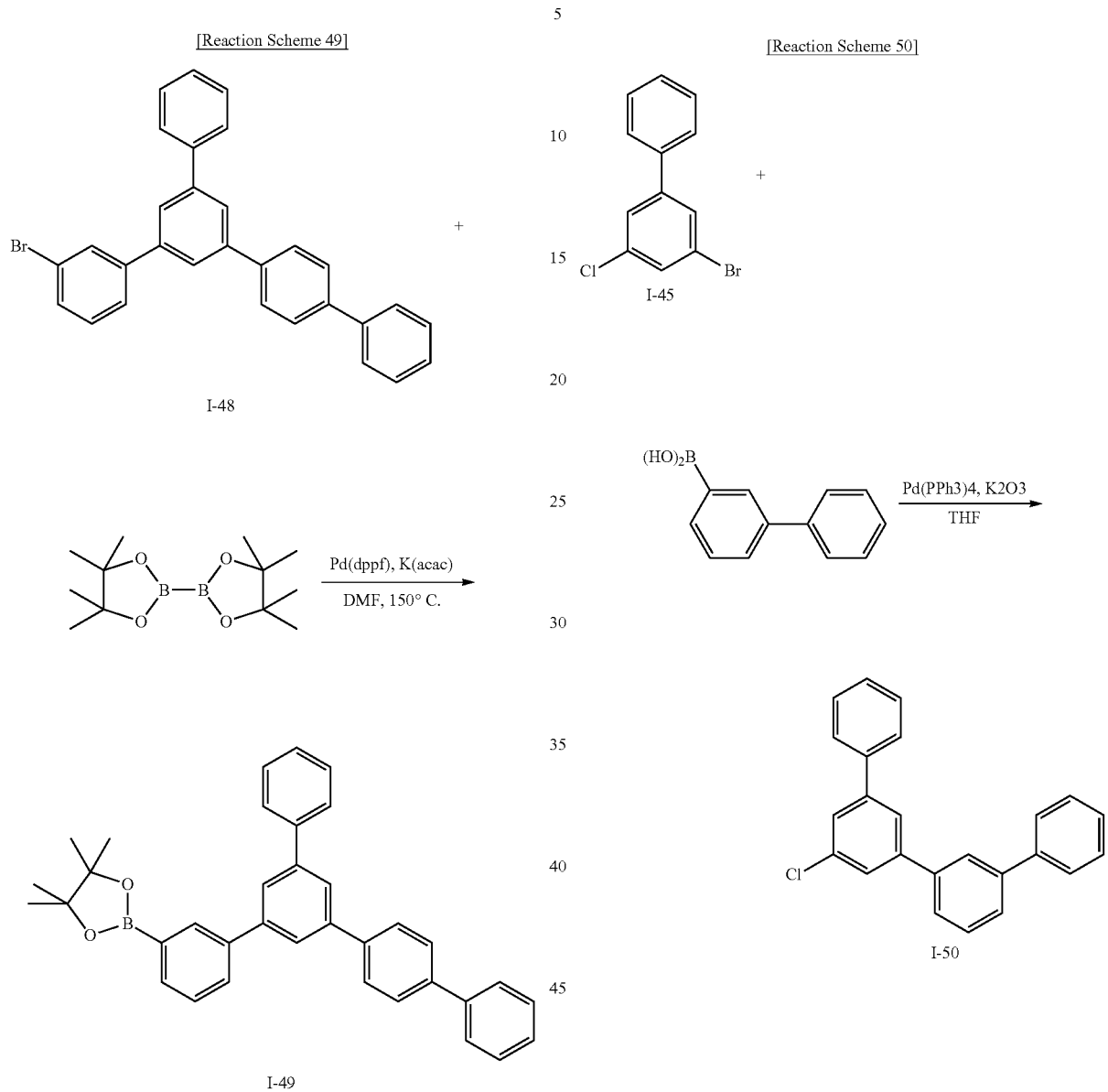

The compound I-48 (23.5 g, 51 mmol) was dissolved in 1 L of dimethylforamide (DMF) under a nitrogen atmosphere, bis(pinacolato)diboron (15.6 g, 61.6 mmol), (1,1-bis(diphenylphosphine)ferrocene)dichloropalladium (II) (2.5 g, 3.06 mmol) and potassium acetate (15 g, 153 mmol) were added thereto, and the mixture was heated and refluxed at 150° C. for 5 hours. When the reaction was terminated, water was added to the reaction solution, and the mixture was filtered and dried in a vacuum oven. The obtained residue was separated and purified through flash column chromatography to obtain the compound I-49 (23 g, 90%).

HRMS (70 eV, EI+): m/z calcd for C36H33BO2: 508.2574, found: 508

Elemental Analysis: C, 85%; H, 7%

The compound I-45 (22.43 g, 83.83 mmol) was dissolved in 500 mL of THF under a nitrogen atmosphere, 3-biphenyl boronic acid (23.3 g, 117.36 mmol) and tetrakis(triphenylphosphine)palladium (2.9 g, 2.5 mmol) were added thereto, and the mixture was agitated. Then, potassium carbonate saturated in water (46 g, 335.31 mmol) was added thereto, and the obtained mixture was heated and refluxed at 80° C. for 12 hours. When the reaction was terminated, water was added to the reaction solution, the mixture was extracted with dichloromethane (DCM), and the extract was treated with anhydrous MgSO4 to remove moisture therefrom, filtered, and concentrated under a reduced pressure. The obtained residue was separated and purified through flash column chromatography to obtain the compound I-50 (23 g, 81%).

HRMS (70 eV, EI+): m/z calcd for C24H17Cl: 340.1019, found 340 Elemental Analysis: C, 85%; H, 5%

Synthesis Example 51: Synthesis of Intermediate I-51

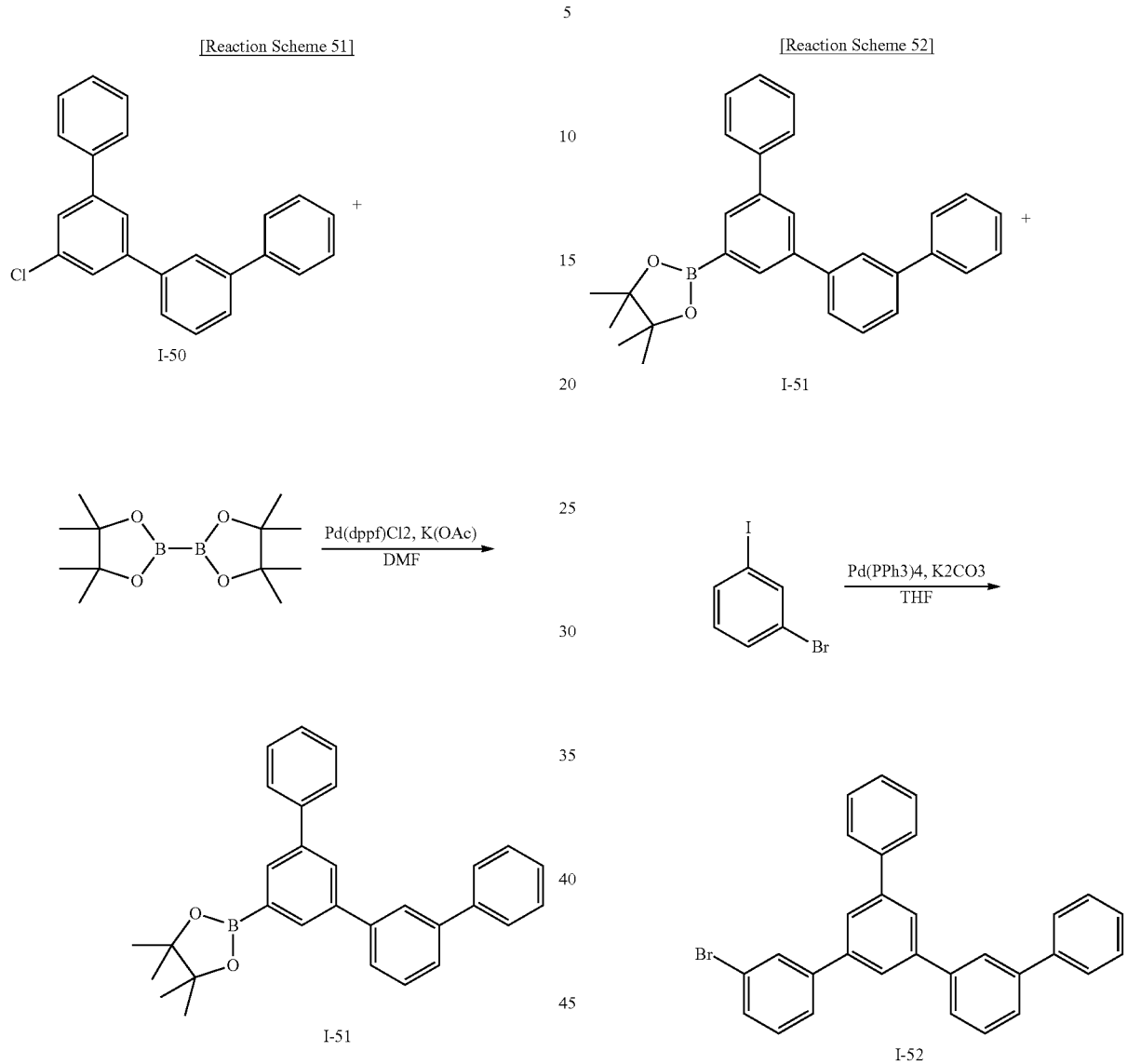

[Reaction Scheme 51]

The compound I-50 (17.7 g, 52 mmol) was dissolved in 1 L of dimethylforamide (DMF) under a nitrogen atmosphere, bis(pinacolato)diboron (19.8 g, 78 mmol), (1,1-bis(diphenylphosphine)ferrocene)dichloropalladium (II) (2.55 g, 3.12 mmol) and potassium acetate (15.3 g, 156 mmol) were added thereto, and the mixture was heated and refluxed at 150° C. for 5 hours. When the reaction was terminated, water was added to the reaction solution, and the mixture was filtered and dried in a vacuum oven. The obtained residue was separated and purified through flash column chromatography to obtain the compound I-51 (17 g, 76%).

HRMS (70 eV, EI+): m/z calcd for C30H29BO2: 432.2261, found: 432

Elemental Analysis: C, 83%; H, 7%

Synthesis Example 52: Synthesis of Intermediate I-52

[Reaction Scheme 52]

The compound I-51 (26.8 g, 62 mmol) was dissolved in 1 L of THF under a nitrogen atmosphere, 1-bromo-3-iodobenzene (24.5 g, 86.6 mmol) and tetrakis(triphenylphosphine)palladium (2.1 g, 1.86 mmol) were added thereto, and the mixture was agitated. Then, potassium carbonate saturated in water (34.2 g, 247.7 mmol) were added thereto, and the obtained mixture was heated and refluxed at 80° C. for 12 hours. When the reaction was terminated, water was added to the reaction solution, the mixture was extracted with dichloromethane (DCM), and the extract was treated with anhydrous MgSO4 to remove moisture therefrom, filtered, and concentrated under a reduced pressure. The obtained residue was separated and purified through flash column chromatography to obtain the compound I-52 (22 g, 77%).

HRMS (70 eV, EI+): m/z calcd for C30H21Br: 460.0827, found 460 Elemental Analysis: C, 78%; H, 5%

Synthesis Example 53: Synthesis of Intermediate I-53

[Reaction Scheme 53]

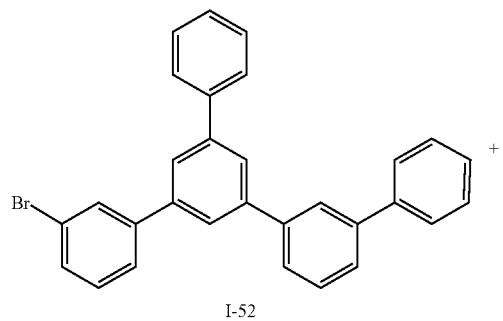

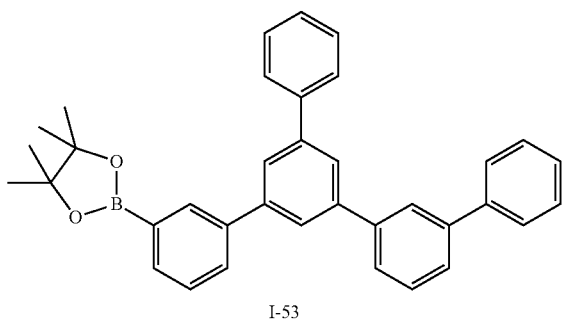

The compound I-52 (20.4 g, 44.25 mmol) was dissolved in 1 L of dimethylforamide (DMF) under a nitrogen atmosphere, bis(pinacolato)diboron (16.9 g, 66.4 mmol), (1,1'-bis(diphenylphosphine)ferrocene)dichloropalladium (II) (2.2 g, 2.66 mmol) and potassium acetate (13 g, 132.7 mmol) were added thereto, and the mixture was heated and refluxed at 150° C. for 5 hours. When the reaction was terminated, water was added to the reaction solution, and the mixture was filtered and dried in a vacuum oven. The obtained residue was separated and purified through flash column chromatography to obtain the compound I-53 (20 g, 89%).

HRMS (70 eV, EI+): m/z calcd for $C_{36}H_{33}BO_2$: 508.2574, found: 508

Elemental Analysis: C, 85%; H, 7%

Synthesis of Final Compound

Synthesis Example 54: Synthesis of Compound 1

[Reaction Scheme 54]

The compound I-5 (20 g, 34 mmol) was dissolved in 0.2 L of tetrahydrofuran (THF) under a nitrogen atmosphere, 3-bromo-1,1'-biphenyl (9.5 g, 40 mmol) and tetrakis(triphenylphosphine)palladium (0.39 g, 0.34 mmol) were added thereto, and the mixture was agitated. Then, potassium carbonate saturated in water (12 g, 85 mmol) was added thereto, and the obtained mixture was heated and refluxed at 80° C. for 20 hours. When the reaction was terminated, water was added to the reaction solution, the mixture was extracted with dichloromethane (DCM), and the extract was treated with anhydrous $MgSO_4$ to remove moisture therefrom, filtered, and concentrated under a reduced pressure. The obtained residue was separated and purified through flash column chromatography to obtain the compound 1 (24 g, 70%). The compound 1 had a molecular weight of 613.2518.

HRMS (70 eV, EI+): m/z calcd for $C_{45}H_{31}N_3$: 613.2518, found: 613 Elemental Analysis: C, 88%; H, 5%

Synthesis Example 55: Synthesis of Compound 2

[Reaction Scheme 55]

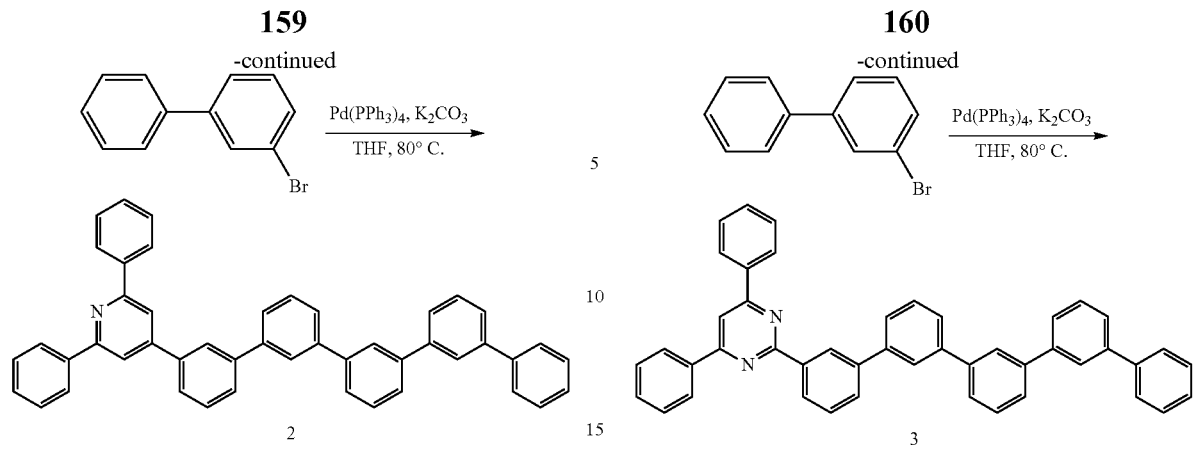

The compound I-16 (20 g, 34 mmol) was dissolved in 0.2 L of tetrahydrofuran (THF) under a nitrogen atmosphere, 3-bromo-1,1'-biphenyl (9.5 g, 40 mmol) and tetrakis(triphenylphosphine)palladium (0.39 g, 0.34 mmol) were added thereto, and the mixture was agitated. Then, potassium carbonate saturated in water (12 g, 85 mmol) was added thereto, and the obtained mixture was heated and refluxed at 80° C. for 20 hours. When the reaction was terminated, water was added to the reaction solution, the mixture was extracted with dichloromethane (DCM), and the extract was treated with anhydrous $MgSO_4$ to remove moisture therefrom, filtered, and concentrated under a reduced pressure. The obtained residue was separated and purified through flash column chromatography to obtain the compound 2 (15 g, 72%). The compound 2 had a molecular weight of 611.2613.

HRMS (70 eV, EI+): m/z calcd for $C_{47}H_{33}N$: 611.2613, found: 611

Elemental Analysis: C, 92%; H, 5%

Synthesis Example 56: Synthesis of Compound 3

[Reaction Scheme 56]

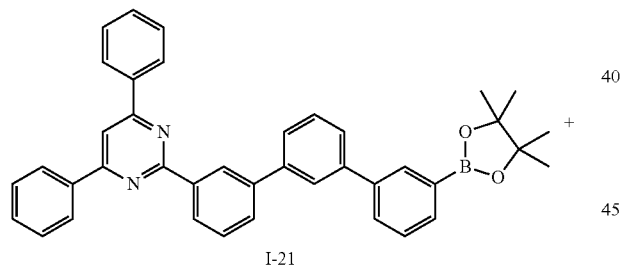

The compound I-21 (20 g, 34 mmol) was dissolved in 0.2 L of tetrahydrofuran (THF) under a nitrogen atmosphere, 3-bromo-1,1'-biphenyl (9.5 g, 40 mmol) and tetrakis(triphenylphosphine)palladium (0.39 g, 0.34 mmol) were added thereto, and the mixture was agitated. Then, potassium carbonate saturated in water (12 g, 85 mmol) was added thereto, and the obtained mixture was heated and refluxed at 80° C. for 20 hours. When the reaction was terminated, water was added to the reaction solution, the mixture was extracted with dichloromethane (DCM), and the extract was treated with anhydrous $MgSO_4$ to remove moisture therefrom, filtered, and concentrated under a reduced pressure. The obtained residue was separated and purified through flash column chromatography to obtain the compound 3 (16 g, 75%). The compound 3 had a molecular weight of 612.2565.

HRMS (70 eV, EI+): m/z calcd for $C_{46}H_{32}N_2$: 612.2565, found: 612

Elemental Analysis: C, 90%; H, 5%

Synthesis Example 57: Synthesis of Compound 10

[Reaction Scheme 57]

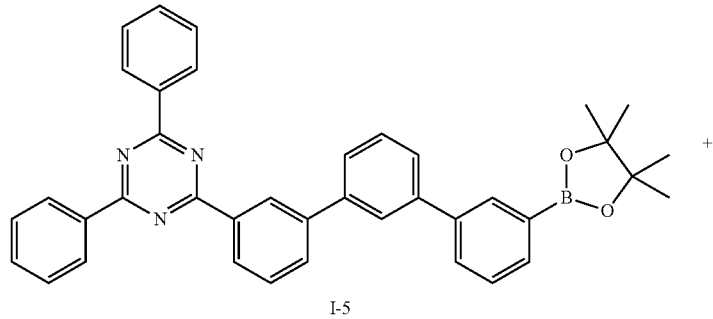

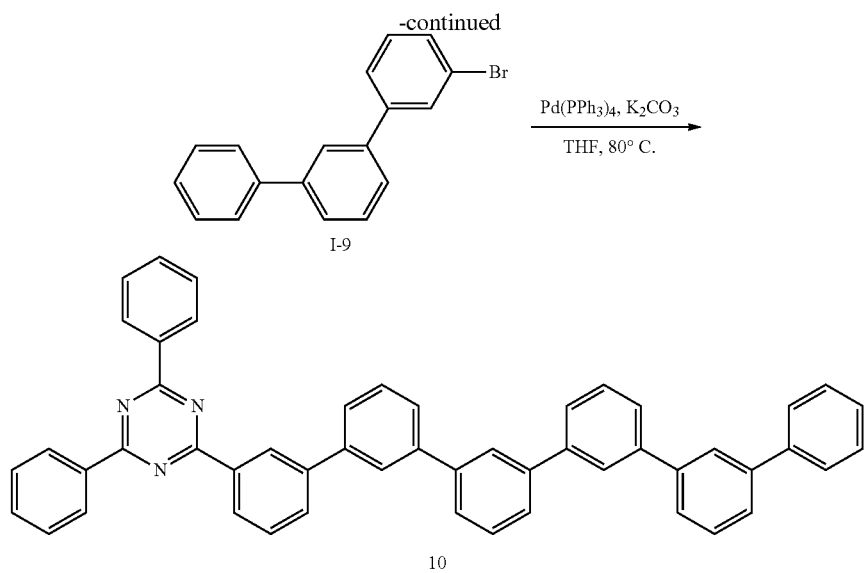

The compound I-5 (20 g, 34 mmol) was dissolved in 0.2 L of tetrahydrofuran (THF) under a nitrogen atmosphere, the compound I-9 (13 g, 41 mmol) and tetrakis(triphenylphosphine)palladium (0.39 g, 0.34 mmol) were added thereto, and the mixture was agitated. Then, potassium carbonate saturated in water (12 g, 85 mmol) was added thereto, and the obtained mixture was heated and refluxed at 80° C. for 20 hours. When the reaction was terminated, water was added to the reaction solution, the mixture was extracted with dichloromethane (DCM), and the extract was treated with anhydrous MgSO₄ to remove moisture therefrom, filtered, and concentrated under a reduced pressure. The obtained residue was separated and purified through flash column chromatography to obtain the compound 10 (19 g, 75%). The compound 10 had a molecular weight of 689.2831.

HRMS (70 eV, EI+): m/z calcd for C51H35N3: 689.2831, found: 689

Elemental Analysis: C, 89%; H, 5%

Synthesis Example 58: Synthesis of Compound 13

[Reaction Scheme 58]

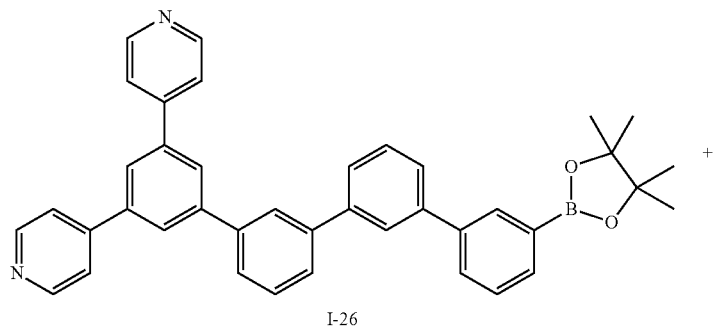

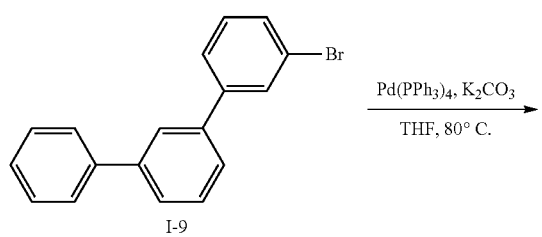

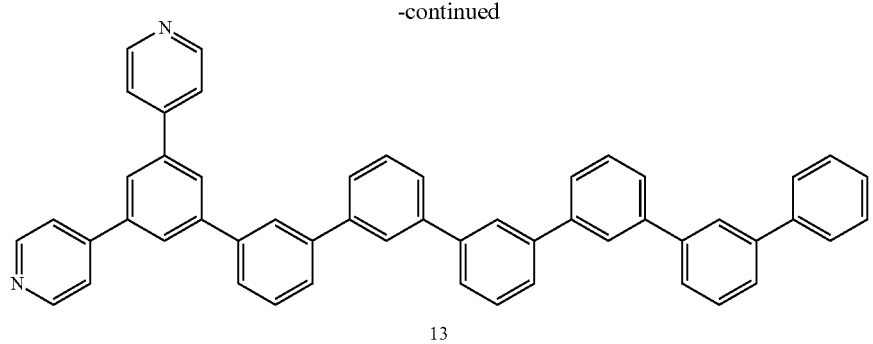

13

The compound I-26 (20 g, 34 mmol) was dissolved in 0.2 L of tetrahydrofuran (THF) under a nitrogen atmosphere, the compound I-9 (13 g, 41 mmol) and tetrakis(triphenylphosphine)palladium (0.39 g, 0.34 mmol) were added thereto, and the mixture was agitated. Then, potassium carbonate saturated in water (12 g, 85 mmol) was added thereto, and the obtained mixture was heated and refluxed at 80° C. for 20 hours. When the reaction was terminated, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain the compound 13 (17 g, 72%). The compound 13 had a molecular weight of 688.2878.

HRMS (70 eV, EI+): m/z calcd for C51H35N3: 688.2878 689.8437, found: 688

Elemental Analysis: C, 89%; H, 5%

Synthesis Example 59: Synthesis of Compound 19

[Reaction Scheme 59]

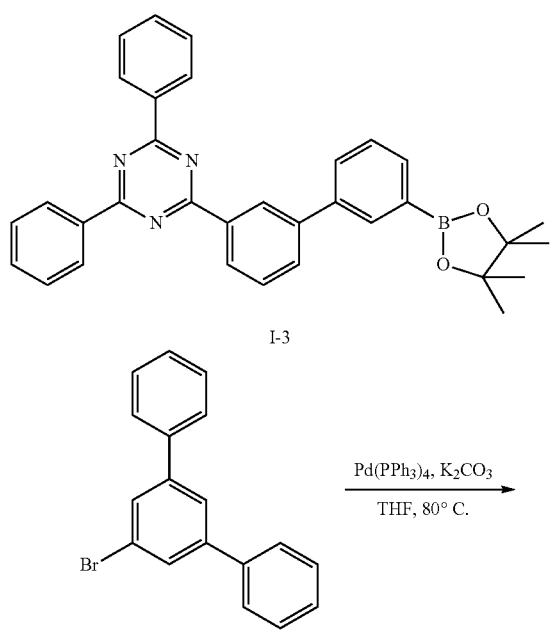

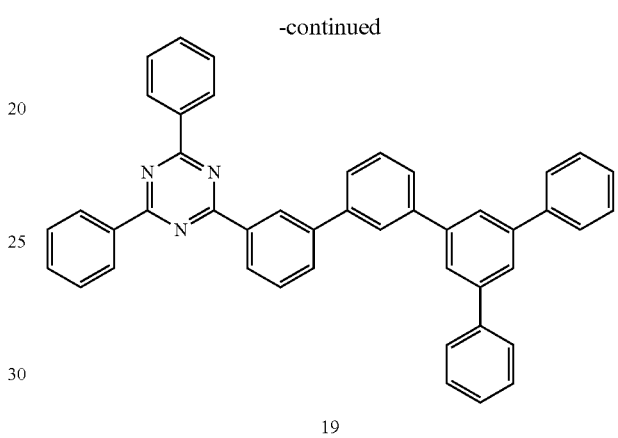

19

The compound I-3 (20 g, 39.1 mmol) was dissolved in 0.2 L of tetrahydrofuran (THF) under a nitrogen atmosphere, 5'-bromo-1,1':3',1''-terphenyl (14.5 g, 47 mmol) and tetrakis(triphenylphosphine)palladium (0.45 g, 0.39 mmol) were added thereto, and the mixture was agitated. Then, potassium carbonate saturated in water (9.7 g, 99 mmol) was added thereto, and the mixture was heated and refluxed at 80° C. for 20 hours. When the reaction was terminated, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain the compound 19 (20 g, 83%). The compound 19 had a molecular weight of 613.2518.

HRMS (70 eV, EI+): m/z calcd for C45H31N3: 613.2518, found: 613

Elemental Analysis: C, 88%; H, 5%

Synthesis Example 60: Synthesis of Compound 28

[Reaction Scheme 60]

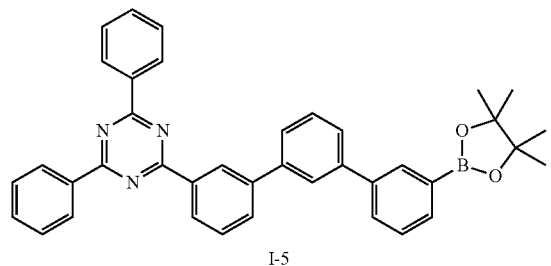

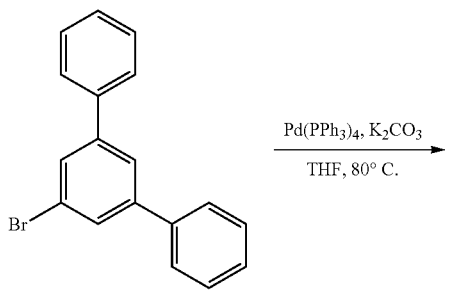

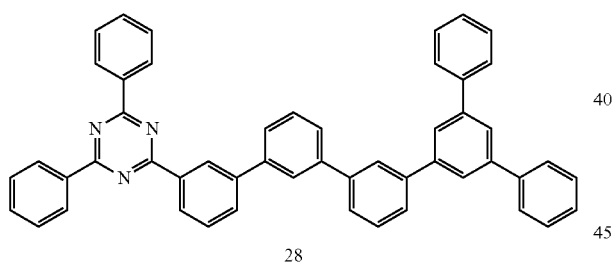

The compound 1-5 (20 g, 34 mmol) was dissolved in 0.2 L of tetrahydrofuran (THF) under a nitrogen atmosphere, 5'-bromo-1,1':3',1''-terphenyl (12.6 g, 40 mmol) and tetrakis(triphenylphosphine)palladium (0.40 g, 0.34 mmol) were added thereto, and the mixture was agitated. Then, potassium carbonate saturated in water (12 g, 85 mmol) was added thereto, and the obtained mixture was heated and refluxed at 80° C. for 20 hours. When the reaction was terminated, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain the compound 28 (19 g, 80%). The compound 28 had a molecular weight of 689.2831.

HRMS (70 eV, EI+): m/z calcd for C51H35N3: 689.2831, found: 689.

Elemental Analysis: C, 89%; H, 5%

Synthesis Example 61: Synthesis of Compound 37

[Reaction Scheme 61]

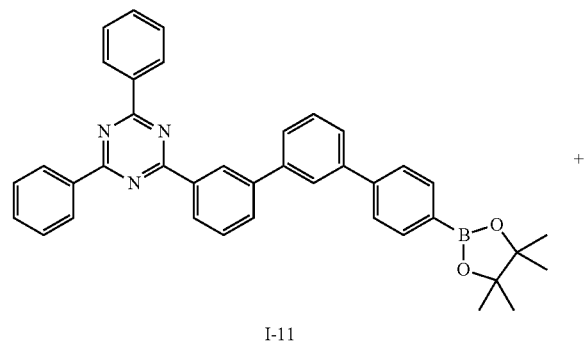

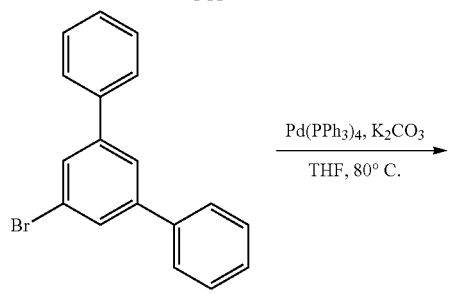

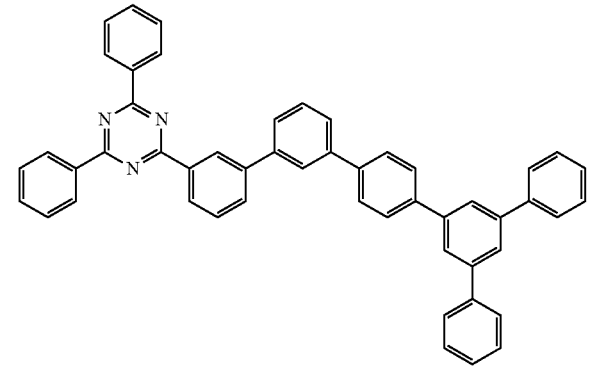

The compound 1-11 (20 g, 34 mmol) was dissolved in 0.2 L of tetrahydrofuran (THF) under a nitrogen atmosphere, 5'-bromo-1,1':3',1''-terphenyl (12.6 g, 40 mmol) and tetrakis(triphenylphosphine)palladium (0.40 g, 0.34 mmol) were added thereto, and the mixture was agitated. Then, potassium carbonate saturated in water (12 g, 85 mmol) was added thereto, and the mixture was heated and refluxed at 80° C. for 20 hours. When the reaction was terminated, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain the compound 37 (20 g, 85%). The compound 37 had a molecular weight of 689.2831.

HRMS (70 eV, EI+): m/z calcd for C51H35N3: 689.2831, found: 689.

Elemental Analysis: C, 89%; H, 5%

Synthesis Example 62: Synthesis of Compound 56

[Reaction Scheme 62]

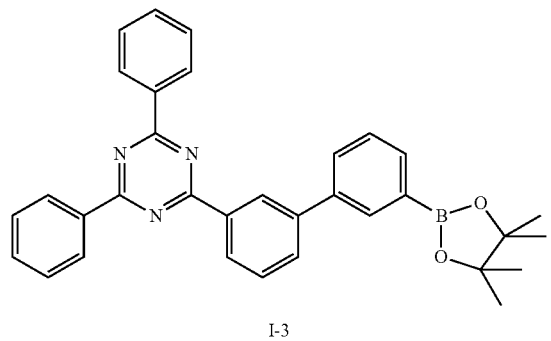

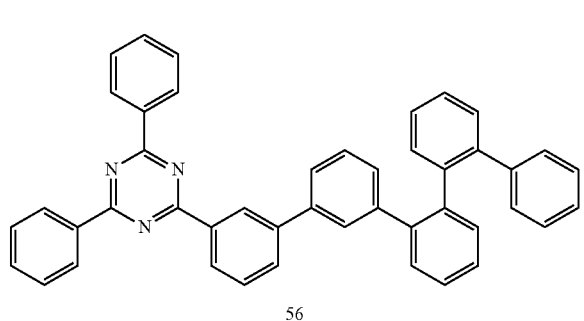

The compound I-3 (20 g, 39 mmol) was dissolved in 0.2 L of tetrahydrofuran (THF) under a nitrogen atmosphere, the compound I-7 (14.5 g, 47 mmol) and tetrakis(triphenylphosphine)palladium (0.45 g, 0.39 mmol) were added thereto, and the mixture was agitated. Then, potassium carbonate saturated in water (13.5 g, 97 mmol) was added thereto, and the mixture was heated and refluxed at 80° C. for 20 hours. When the reaction was terminated, water was added to the reaction solution, the mixture was extracted with dichloromethane (DCM), and the extract was treated with anhydrous $MgSO_4$ to remove moisture therefrom, filtered, and concentrated under a reduced pressure. The obtained residue was separated and purified through flash column chromatography to obtain the compound 56 (17 g, 70%). The compound 56 had a molecular weight of 613.2518.

HRMS (70 eV, EI+); m/z calcd for $C_{45}H_{31}N_3$ 613.2518, found: 613

Elemental Analysis: C, 88%; H, 5%

Synthesis Example 63: Synthesis of Compound 57

[Reaction Scheme 63]

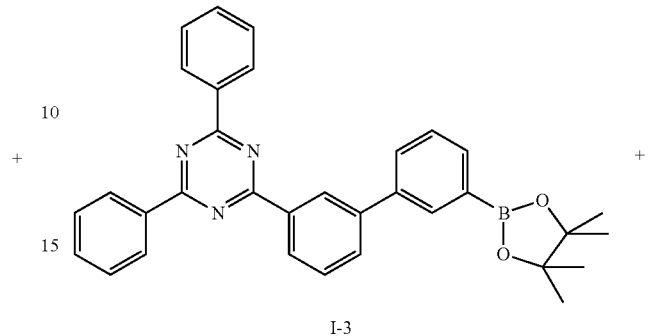

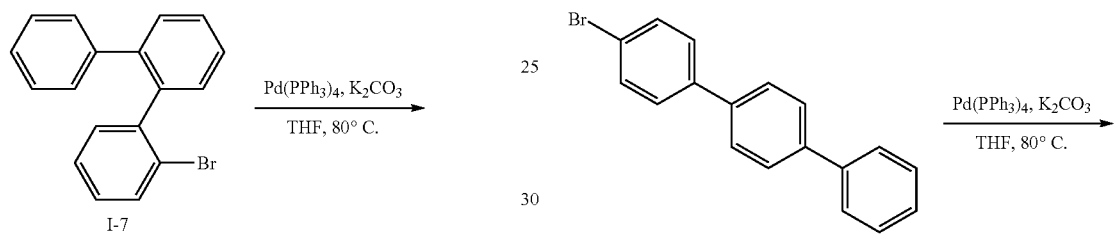

The compound I-3 (20 g, 39 mmol) was dissolved in 0.2 L of tetrahydrofuran (THF) under a nitrogen atmosphere, 4-bromo-1,1':4',1"-terphenyl (14.5 g, 47 mmol) and tetrakis(triphenylphosphine)palladium (0.45 g, 0.39 mmol) were added thereto, and the mixture was agitated. Then, potassium carbonate saturated in water (13.5 g, 97 mmol) was added thereto, and the obtained mixture was heated and refluxed at 80° C. for 20 hours. When the reaction was terminated, water was added to the reaction solution, the mixture was extracted with dichloromethane (DCM), and the extract was treated with anhydrous $MgSO_4$ to remove moisture therefrom, filtered, and concentrated under a reduced pressure. The obtained residue was separated and purified through flash column chromatography to obtain the compound 57 (19 g, 79%). The compound 57 had a molecular weight of 613.2518.

HRMS (70 eV, EI+): m/z calcd for $C_{45}H_{31}N_3$: 613.2518, found: 613

Elemental Analysis: C, 88%; H, 5%

Synthesis Example 64: Synthesis of Compound 74

[Reaction Scheme 64]

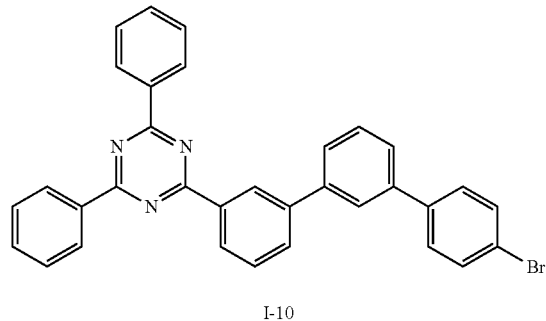

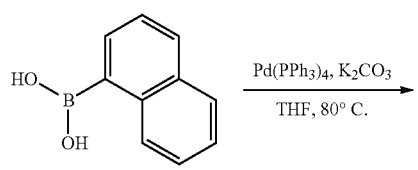

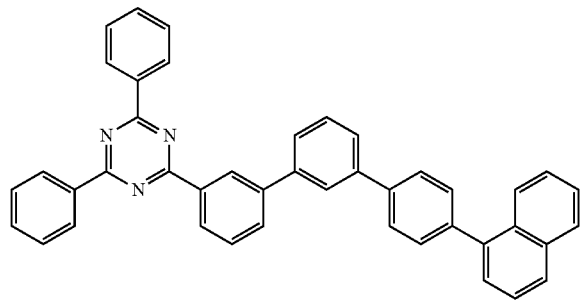

74

The compound I-10 (20 g, 37 mmol) was dissolved in 0.2 L of tetrahydrofuran (THF) under a nitrogen atmosphere, naphthalen-1-yl boronic acid (7.6 g, 44 mmol) and tetrakis(triphenylphosphine)palladium (0.43 g, 0.37 mmol) were added thereto, and the mixture was agitated. Then, potassium carbonate saturated in water (13 g, 92 mmol) was added thereto, and the obtained mixture was heated and refluxed at 80° C. for 20 hours. When the reaction was terminated, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain the compound 74 (15 g, 72%). The compound 74 had a molecular weight of 587.2361.

HRMS (70 eV, EI+): m/z calcd for C$_{43}$H$_{29}$N$_3$: 587.2361, found: 587

Elemental Analysis: C, 88%; H, 5%

Synthesis Example 65: Synthesis of Compound 68

[Reaction Scheme 65]

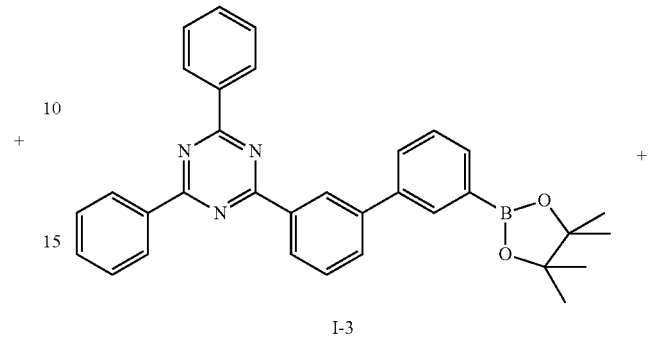

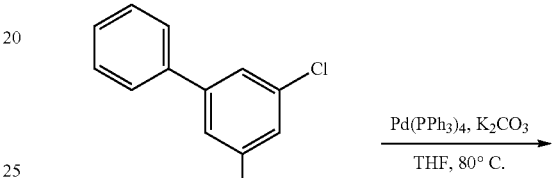

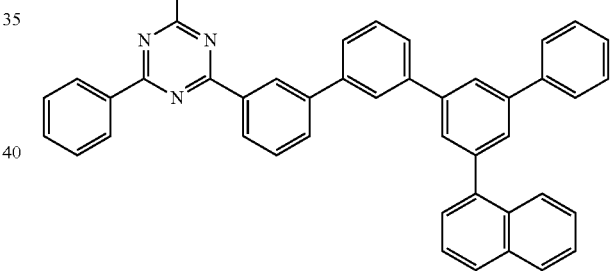

68

The compound I-3 (20 g, 39 mmol) was dissolved in 0.2 L of tetrahydrofuran (THF) under a nitrogen atmosphere, the compound I-36 (15 g, 44 mmol) and tetrakis(triphenylphosphine)palladium (0.45 g, 0.39 mmol) were added thereto, and the mixture was agitated. Then, potassium carbonate saturated in water (13 g, 97 mmol) was added thereto, and the mixture was heated and refluxed at 80° C. for 20 hours. When the reaction was terminated, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain the compound 68 (18 g, 70%). The compound 68 had a molecular weight of 663.2674.

HRMS (70 eV, EI+): m/z calcd for C$_{49}$H$_{33}$N$_3$: 663.2674, found: 663

Elemental Analysis: C, 89%; H, 5%

Synthesis Example 66: Synthesis of Compound 105

[Reaction Scheme 66]

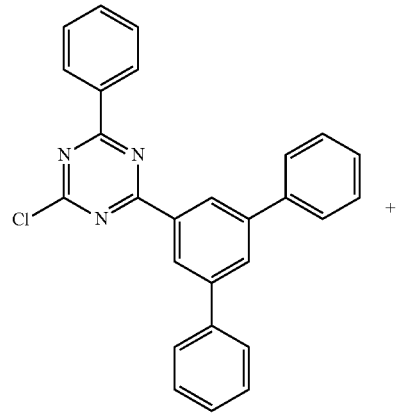

I-44

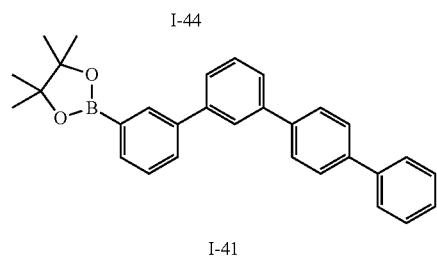

I-41

Pd(PPh$_3$)$_4$, K$_2$CO$_3$
THF, 80° C.

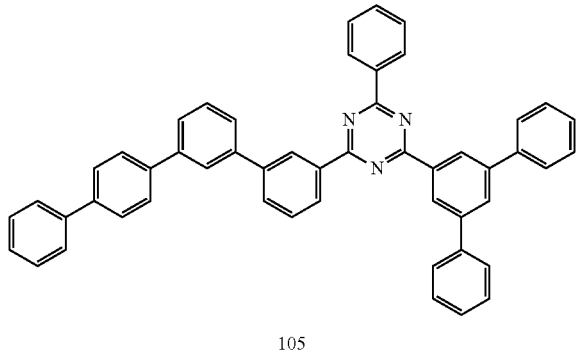

105

The compound I-44 (32 g, 76 mmol) was dissolved in 1 L of THF under a nitrogen atmosphere, the compound I-41 (33 g, 76 mmol) and tetrakis(triphenylphosphine)palladium (0.88 g, 0.76 mmol) were added thereto, and the mixture was agitated. Then, potassium carbonate saturated in water (26 g, 190 mmol) was added thereto, and the mixture was heated and refluxed at 80° C. for 12 hours. When the reaction was terminated, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain the compound 105 (32 g, 80%). The compound 105 had a molecular weight of 689.2831.

HRMS (70 eV, EI+): m/z calcd for C51H35N3: 689.2831, found 689 Elemental Analysis: C, 89%; H, 5%

Synthesis Example 67: Synthesis of Compound 135

[Reaction Scheme 67]

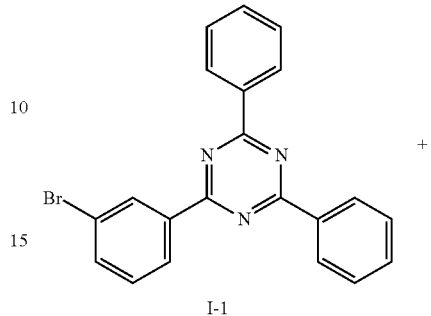

I-1

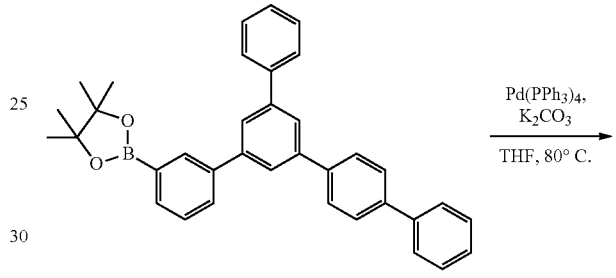

I-49

Pd(PPh$_3$)$_4$, K$_2$CO$_3$
THF, 80° C.

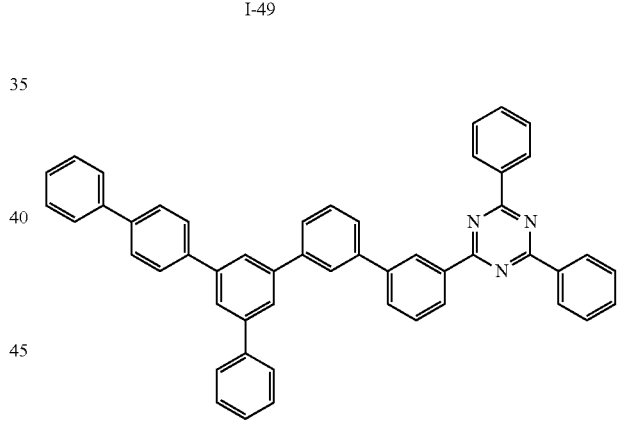

135

The compound I-1 (11 g, 23.8 mmol) was dissolved in 1 L of THF under a nitrogen atmosphere, the compound I-49 (14.5 g, 28.6 mmol) and tetrakis(triphenylphosphine)palladium (0.265 g, 0.23 mmol) were added thereto, and the mixture was agitated. Then, potassium carbonate saturated in water (8.2 g, 59.5 mmol) was added thereto, and the mixture was heated and refluxed at 80° C. for 12 hours. When the reaction was terminated, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain the compound 135 (13 g, 80%).

HRMS (70 eV, EI+): m/z calcd for C51H35N3: 689.2831, found 689 Elemental Analysis: C, 89%; H, 5%

Synthesis Example 68: Synthesis of Compound 112

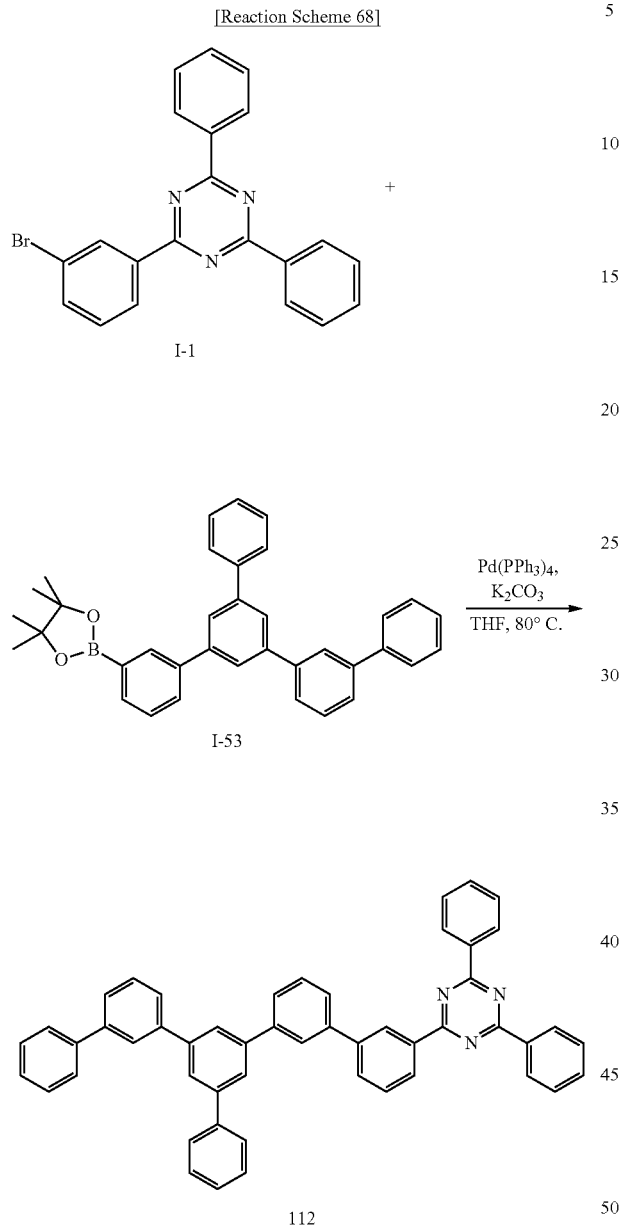

[Reaction Scheme 68]

I-1

I-53

112

The compound I-1 (12 g, 31.6 mmol) was dissolved in 500 mL of THF under a nitrogen atmosphere, the compound I-53 (17.3 g, 34.2 mmol) and tetrakis(triphenylphosphine)palladium (1.07 g, 0.93 mmol) were added thereto, and the mixture was agitated. Then, potassium carbonate saturated in water (13 g, 93.2 mmol) was added thereto, and the obtained mixture was heated and refluxed at 80° C. for 12 hours. When the reaction was terminated, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain the compound 112 (16 g, 75%).

HRMS (70 eV, EI+): m/z calcd for C51H35N3: 689.2831, found 689 Elemental Analysis: C, 89%; H, 5%

Comparative Synthesis Example 69: Synthesis of HOST 1

[Reaction Scheme 69]

I-3

HOST 1

The compound I-3 (20 g, 39 mmol) was dissolved in 0.2 L of tetrahydrofuran (THF) under a nitrogen atmosphere, 3-bromo-1,1'-biphenyl (11 g, 47 mmol) and tetrakis(triphenylphosphine)palladium (0.45 g, 0.39 mmol) were added thereto, and the mixture was agitated. Then, potassium carbonate saturated in water (13.5 g, 97 mmol) was added thereto, and the obtained mixture was heated and refluxed at 80° C. for 20 hours. When the reaction was terminated, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain the HOST 1 (16 g, 78%). The HOST 1 had a molecular weight of 537.2205.

HRMS (70 eV, EI+): m/z calcd for C39H27N3: 537.2205, found: 537

Elemental Analysis: C, 87%; H, 5%

Comparative Synthesis Example 70: Synthesis of HOST 2

[Reaction Scheme 70]

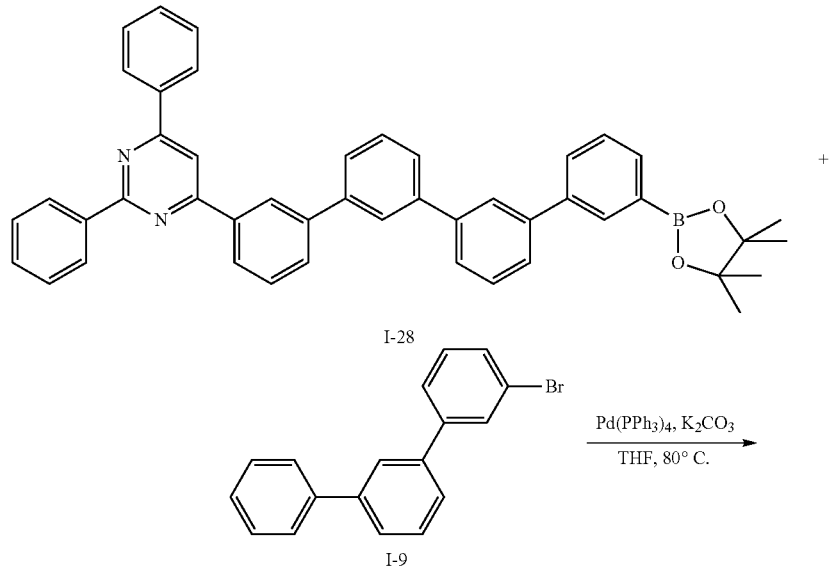

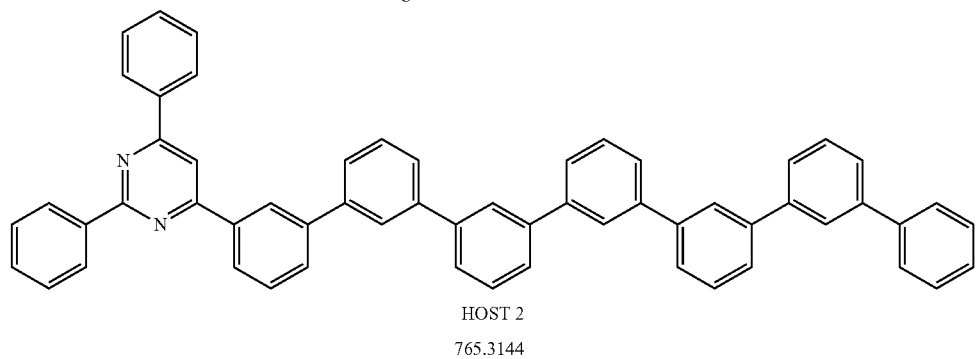

HOST 2
765.3144

The compound I-28 (20 g, 30 mmol) was dissolved in 0.2 L of tetrahydrofuran (THF) under a nitrogen atmosphere, the compound I-9 (11 g, 36 mmol) and tetrakis(triphenylphosphine)palladium (0.35 g, 0.30 mmol) were added thereto, and the mixture was agitated. Then, potassium carbonate saturated in water (10 g, 75 mmol) was added thereto, and the obtained mixture was heated and refluxed at 80° C. for 20 hours. When the reaction was terminated, water was added to the reaction solution, the mixture was extracted with dichloromethane (DCM), and the extract was treated with anhydrous $MgSO_4$ to remove moisture therefrom, filtered, and concentrated under a reduced pressure. The obtained residue was separated and purified through flash column chromatography to obtain the HOST 2 (14.5 g, 70%). The HOST 2 had a molecular weight of 765.3144.

HRMS (70 eV, EI+): m/z calcd for $C_{51}H_{35}N_3$: 765.3144, found: 765

Elemental Analysis: C, 89%; H, 5%

Comparative Synthesis Example 71: Synthesis of HOST 3

[Reaction Scheme 71]

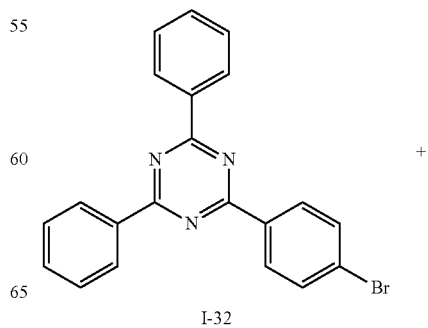

I-32

-continued

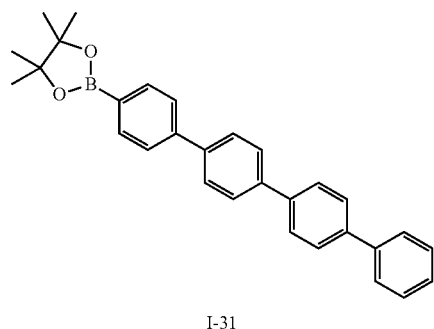

I-31

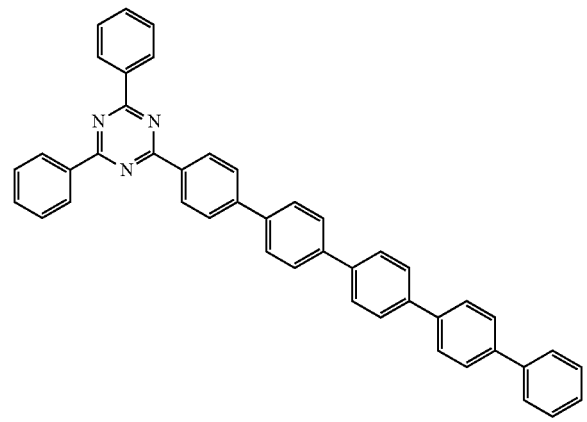

HOST 3

The compound I-32 (20 g, 51 mmol) was dissolved in 0.2 L of tetrahydrofuran (THF) under a nitrogen atmosphere, the compound I-31 (26.5 g, 61.2 mmol) and tetrakis(triphenylphosphine)palladium (0.6 g, 0.51 mmol) were added thereto, and the mixture was agitated. Then, the potassium carbonate saturated in water (17.5 g, 127 mmol) was added thereto, and the obtained mixture was heated and refluxed at 80° C. for 20 hours. When the reaction was terminated, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain the HOST 3 (24 g, 76%). The HOST 3 had a molecular weight of 613.2518.

HRMS (70 eV, EI+): m/z calcd for C45H31N3: 613.2518, found: 613.

Elemental Analysis: C, 88%; H, 5%

Comparative Synthesis Example 72: Synthesis of HOST 4

[Reaction Scheme 72]

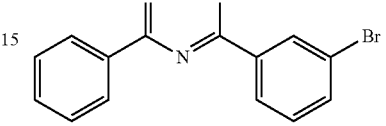

I-1

I-31

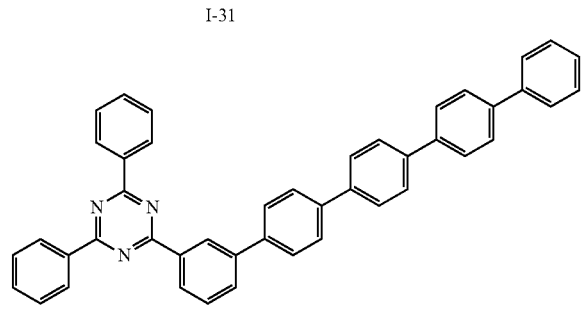

HOST 4

The compound I-1 (20 g, 51 mmol) was dissolved in 0.2 L of tetrahydrofuran (THF) under a nitrogen atmosphere, the compound I-31 (26.5 g, 61.2 mmol) and tetrakis(triphenylphosphine)palladium (0.6 g, 0.51 mmol) were added thereto, and the mixture was agitated. Then, potassium carbonate saturated in water (17.5 g, 127 mmol) was added thereto, and the obtained mixture was heated and refluxed at 80° C. for 20 hours. When the reaction was terminated, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain the HOST 4 (23 g, 75%). The HOST 4 had a molecular weight of 613.2518.

HRMS (70 eV, EI+): m/z calcd for C45H31N3: 613.2518, found: 613.

Elemental Analysis: C, 88%; H, 5%

Comparative Synthesis Example 73: Synthesis of HOST 5

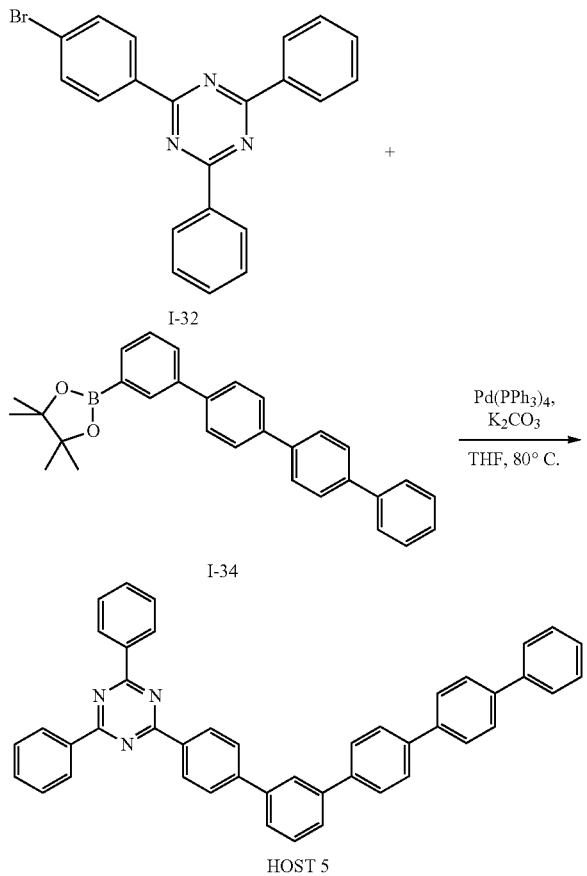

The compound I-32 (20 g, 51 mmol) was dissolved in 0.2 L of tetrahydrofuran (THF) under a nitrogen atmosphere, the compound I-34 (26.5 g, 61.2 mmol) and tetrakis(triphenylphosphine)palladium (0.6 g, 0.51 mmol) were added thereto, and the mixture was agitated. Then, potassium carbonate saturated in water (17.5 g, 127 mmol) was added thereto, and the obtained mixture was heated and refluxed at 80° C. for 20 hours. When the reaction was terminated, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain the HOST5 (22.5 g, 75%). The HOST 5 had a molecular weight of 613.2518.

HRMS (70 eV, EI+): m/z calcd for C45H31N3: 613.2518, found: 613.

Elemental Analysis: C, 88%; H, 5%

Manufacture of Organic Light Emitting Diode

Example 1

An organic light emitting diode was manufactured by using the compound 1 of Synthesis Example 54 as a host and Ir(PPy)$_3$ as a dopant.

As for an anode, 1000 Å-thick ITO was used, and as for a cathode, 1000 Å-thick aluminum (Al) was used. Specifically, illustrating a method of manufacturing the organic light emitting diode, the anode is manufactured by cutting an ITO glass substrate having 15 Ω/cm$^2$ of sheet resistance into a size of 50 mm×50 mm×0.7 mm, ultrasonic wave-cleaning them in acetone, isopropylalcohol, and pure water for 15 minutes respectively, and UV ozone cleaning them for 30 minutes.

On the substrate, an 800 Å-thick hole transport layer (HTL) was formed by depositing N4,N4'-di(naphthalen-1-yl)-N4,N4'-diphenylbiphenyl-4,4'-diamine (NPB) under a vacuum degree 650×10−7 Pa at a deposition rate of 0.1 to 0.3 nm/s. Subsequently, A 300 Å-thick emission layer was formed by using the compound 1 of Synthesis Example 54 under the same vacuum deposition condition, and herein, a phosphorescent dopant of Ir(PPy)$_3$ was simultaneously deposited. Herein, the phosphorescent dopant was deposited to be 7 wt % based on 100 wt % of the total weight of the emission layer by adjusting the deposition rate.

On the emission layer, a 50 Å-thick hole blocking layer was formed by depositing bis(2-methyl-8-quinolinolate)-4-(phenylphenolato)aluminium (BAlq) under the same vacuum deposition condition. Subsequently, a 200 Å-thick electron transport layer (ETL) was formed by depositing Alq3 under the same vacuum deposition condition. On the electron transport layer (ETL), a cathode is formed by sequentially depositing LiF and Al, manufacturing an organic photoelectric device.

The organic photoelectric device has a structure of ITO/NPB (80 nm)/EML (compound 1 (93 wt %)+Ir(PPy)$_3$ (7 wt %), 30 nm)/Balq (5 nm)/Alq3 (20 nm)/LiF (1 nm)/Al (100 nm).

Example 2

An organic light emitting diode was manufactured according to the same method as Example 1 except for using the compound 2 of Synthesis Example 55 instead of the compound 1 of Synthesis Example 54.

Example 3

An organic light emitting diode was manufactured according to the same method as Example 1 except for using the compound 3 of Synthesis Example 56 instead of the compound 1 of Synthesis Example 54.

Example 4

An organic light emitting diode was manufactured according to the same method as Example 1 except for using the compound 10 of Synthesis Example 57 instead of the compound 1 of Synthesis Example 54.

Example 5

An organic light emitting diode was manufactured according to the same method as Example 1 except for using the compound 13 of Synthesis Example 58 instead of the compound 1 of Synthesis Example 54.

Example 6

An organic light emitting diode was manufactured according to the same method as Example 1 except for using the compound 19 of Synthesis Example 59 instead of the compound 1 of Synthesis Example 54.

Example 7

An organic light emitting diode was manufactured according to the same method as Example 1 except for using the compound 28 of Synthesis Example 60 instead of the compound 1 of Synthesis Example 54.

Example 8

An organic light emitting diode was manufactured according to the same method as Example 1 except for using the compound 37 of Synthesis Example 61 instead of the compound 1 of Synthesis Example 54.

Example 9

An organic light emitting diode was manufactured according to the same method as Example 1 except for using the compound 56 of Synthesis Example 62 instead of the compound 1 of Synthesis Example 54.

Example 10

An organic light emitting diode was manufactured according to the same method as Example 1 except for using the compound 57 of Synthesis Example 63 instead of the compound 1 of Synthesis Example 54.

Example 11

An organic light emitting diode was manufactured according to the same method as Example 1 except for using the compound 74 of Synthesis Example 64 instead of the compound 1 of Synthesis Example 54.

Example 12

An organic light emitting diode was manufactured according to the same method as Example 1 except for using the compound 68 of Synthesis Example 65 instead of the compound 1 of Synthesis Example 54.

Example 13

An organic light emitting diode was manufactured according to the same method as Example 1 except for using the compound 105 of Synthesis Example 66 instead of the compound 1 of Synthesis Example 54.

Example 14

An organic light emitting diode was manufactured according to the same method as Example 1 except for using the compound 135 of Synthesis Example 67 instead of the compound 1 of Synthesis Example 54.

Comparative Example 1

An organic light emitting diode was manufactured according to the same method as Example 1 except for using CBP having the following structure instead of the compound 1 of Synthesis Example 54.

Reference Example 1

An organic light emitting diode was manufactured according to the same method as Example 1 except for using the compound HOST1 of Comparative Synthesis Example 69 instead of the compound 1 of Synthesis Example 54.

Reference Example 2

An organic light emitting diode was manufactured according to the same method as Example 1 except for using the compound HOST2 of Comparative Synthesis Example 70 instead of the compound 1 of Synthesis Example 54.

Reference Example 3

An organic light emitting diode was manufactured according to the same method as Example 1 except for using the compound HOST3 of Comparative Synthesis Example 71 instead of the compound 1 of Synthesis Example 54.

Reference Example 4

An organic light emitting diode was manufactured according to the same method as Example 1 except for using the compound HOST4 of Comparative Synthesis Example 72 instead of the compound 1 of Synthesis Example 54.

Reference Example 5

An organic light emitting diode was manufactured according to the same method as Example 1 except for using the compound HOST5 of Comparative Synthesis Example 73 instead of the compound 1 of Synthesis Example 54.

The structures of NPB, BAlq, CBP and Ir(PPy)$_3$ used to manufacture the organic light emitting diodes are as follows.

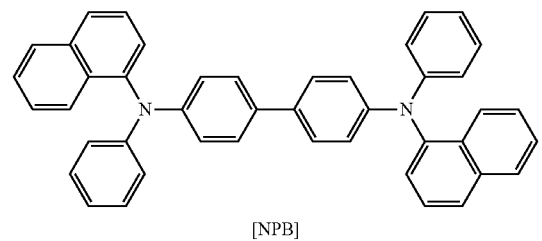

[NPB]

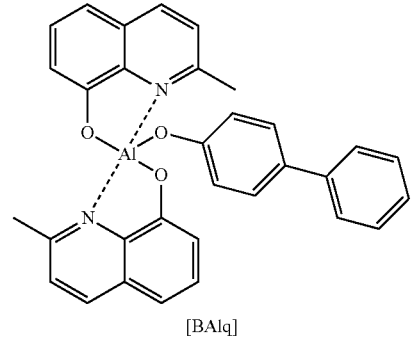

[BAlq]

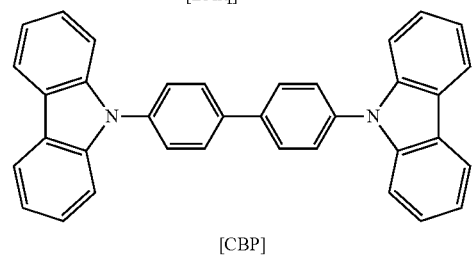

[CBP]

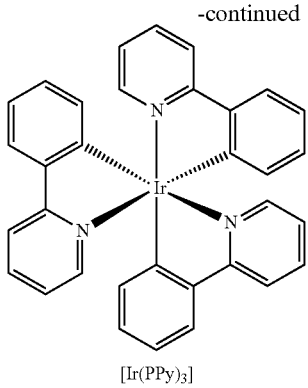

[Ir(PPy)₃]

Evaluation

Current density and luminance changes depending on a voltage and luminous efficiency of each organic light emitting diode according to Example 1 to 14, Comparative Example 1 and Reference Example 1 to 5 were measured.

The measurements were specifically performed in the following method, and the results were provided in the following Table 1.

(1) Measurement of Current Density Change Depending on Voltage Change

Current values flowing in the unit device of the manufactured organic light emitting diodes were measured for, while increasing the voltage from 0V to 10V using a current-voltage meter (Keithley 2400), and the measured current values were divided by an area to provide the results.

(2) Measurement of Luminance Change Depending on Voltage Change

Luminance of the manufactured organic light emitting diodes was measured for luminance, while increasing the voltage from 0 V to 10 V using a luminance meter (Minolta Cs-1000A).

(3) Measurement of Luminous Efficiency

Current efficiency (cd/A) at the same current density (10 mA/cm2) were calculated by using the luminance, current density, and voltages (V) from the items (1) and (2).

(4) Measurement of Life-Span

Life-span was obtained by measuring time taken until current efficiency (cd/A) decreased down to 90% while luminance (cd/m$^2$) was maintained at 5000 cd/m$^2$.

TABLE 1

| Nos. | Compounds | Driving voltage (V) | Color (EL color) | Efficiency (cd/A) | 90% life-span (h) (@5000 cd/m$^2$) |
|---|---|---|---|---|---|
| Example 1 | Compound 1 | 4.6 | Green | 81.7 | 2,460 |
| Example 2 | Compound 2 | 4.8 | Green | 95.1 | 1,300 |
| Example 3 | Compound 3 | 4.7 | Green | 88.9 | 1,930 |
| Example 4 | Compound 10 | 4.3 | Green | 78.0 | 2,770 |
| Example 5 | Compound 13 | 4.2 | Green | 73.3 | 900 |
| Example 6 | Compound 19 | 4.5 | Green | 72.6 | 930 |
| Example 7 | Compound 28 | 4.5 | Green | 80.9 | 2,320 |
| Example 8 | Compound 37 | 4.3 | Green | 88.2 | 2,120 |
| Example 9 | Compound 56 | 4.4 | Green | 91.1 | 2,000 |
| Example 10 | Compound 57 | 4.2 | Green | 94.4 | 1,990 |
| Example 11 | Compound 74 | 4.3 | Green | 75.7 | 950 |
| Example 12 | Compound 68 | 4.5 | Green | 77.3 | 1,000 |
| Example 13 | Compound 105 | 4.5 | Green | 82.1 | 2,150 |
| Example 14 | Compound 135 | 4.6 | Green | 80.5 | 2,500 |
| Comparative Example 1 | CBP | 4.8 | Green | 31.4 | 40 |
| Reference Example 1 | HOST1 | 4.5 | Green | 96.3 | 250 |
| Reference Example 2 | HOST2 | 5.1 | Green | 69.5 | 80 |
| Reference Example 3 | HOST3 | 3.9 | Green | 99.7 | 210 |
| Reference Example 4 | HOST4 | 4.1 | Green | 97.1 | 420 |
| Reference Example 5 | HOST5 | 4.1 | Green | 96.5 | 390 |

Analysis

The deposition temperature, glass transition temperature (Tg) and purity at a high temperature of the compound 1 according to Synthesis Example 54, the compound 74 according to Synthesis Example 64, and the HOST1 and the HOST2 according to Comparative Synthesis Examples 69 and 70 were measured.

The measurements were specifically performed in the following method, and the results were provided in the following Table 2.

(1) Deposition Temperature (° C.)

A deposition temperature indicates a temperature at which a host of an emission layer was deposited during manufacture of the organic light emitting diode according to Example 1 and specifically, a 1 Å-thick emission layer per 1 second (sec) (A/sec) was deposited.

(2) Glass Transition Temperature (Tg)

An energy input difference was measured as a function of a temperature by changing temperatures of a sample and a reference with a DSC1 equipment made by Metter teledo Inc.

(3) Purity at Room Temperature (%)

HPLC made by Waters (Model No.: Alliance e2695-4 gradient pump) and PDA (Model No.: 2994) made by Waters were used. As for a column pipe, Symmetry C18 (3.9×150 mm, 5 μm) was used.

(4) Purity at High Temperature (%)

One g of sample was taken from a compound and charged with a glass vessel with nitrogen, and the glass vessel was closed and sealed. The glass vessel was stored in a 200° C. oven for 200 hours, and the purity of the compound sample at a high temperature was measured in the same method as purity at room temperature.

TABLE 2

| Nos. | Deposition temperature (° C.) | Tg (° C.) | Purity at room temperature (%) | Purity at high temperature (%) |
|---|---|---|---|---|
| Compound 1 | 199.8 | 73.8 | 100 | 99.91 |
| Compound 74 | 198.2 | 93.5 | 100 | 99.95 |
| HOST 1 | 181.3 | 56.0 | 100 | 99.93 |
| HOST 2 | 221.0 | 95.1 | 100 | 99.12 |

Referring to Table 1, the organic light emitting diodes according to Examples 1 to 14 had equivalent or excellent driving voltage and efficiency and also, showed remarkably improved life-span characteristics compared with the ones according to Comparative Example 1 and Reference Examples 1 to 5.

Specifically, the organic light emitting diodes using a compound consecutively including a linear meta bond according to Examples 1, 4 and 7 showed the highest life-span. The reason is that a phenyl group playing a role of hole characteristics at the terminal end and a triazine structure playing a role of electron characteristics were favorably localized and expected to minimize an interference effect each other. For example, when a para and/or ortho bond was added to the compound, a driving voltage or a life-span was decreased.

Herein, two phenylene groups bound to a moiety having electron characteristics through a meta bond had an large influence on life-span of an organic light emitting diode. The organic light emitting diodes according to Reference Examples 3, 4 and 5 used a compound having no two phenylene groups bound to a moiety having electron characteristics through a meta bond unlike the organic light emitting diodes according to Examples 1 to 14 and showed remarkably deteriorated life-span characteristics compared with the organic light emitting diodes according to Examples 1 to 14. The organic light emitting diode according to Reference Example 1 (HOST 1) used a compound including two phenylene groups bound to a moiety having electron characteristics through a meta bond, but the phenyl group at the terminal end played a role of weak hole characteristics and showed an interference effect with the moiety having electron characteristics. Accordingly, life-span of the organic light emitting diode was deteriorated. In addition, since the compound used in the organic light emitting diode according to Reference Example 1 had a low glass transition temperature (Tg) as shown in Table 2, a layer was not only well formed during a deposition process but a life-span was also largely deteriorated by a temperature during a subsequent process such as, for example, an encapsulation process.

As for the compound 74, a naphthyl group was substituted for a phenyl group at the terminal end compared with the HOST1. The naphthyl group is a strong electron-withdrawing group and thus, may well collect weak hole characteristic groups toward the naphthyl group and bring about an effective localization, remarkably improving a life-span compared with the HOST1. In addition, the compound 74 had greater than or equal to 40° C. higher glass transition temperature (Tg) than the HOST1 and was stable in the subsequent process of an encapsulation process due to an effect of improving glass transition temperature (Tg) of the naphthyl group.

Reference Example 2 (HOST 2) used a compound having a molecular weight of greater than or equal to 760, showed deteriorated purity at a high temperature and thus, was broken during a deposition process and deteriorated life-span characteristics.

Synthesis Example 1 of Second Host Compound:
Synthesis of Compound B-1

[Reaction Scheme 74]

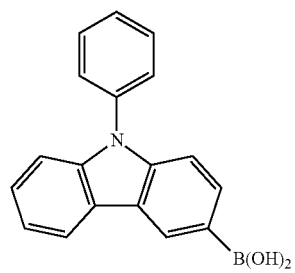

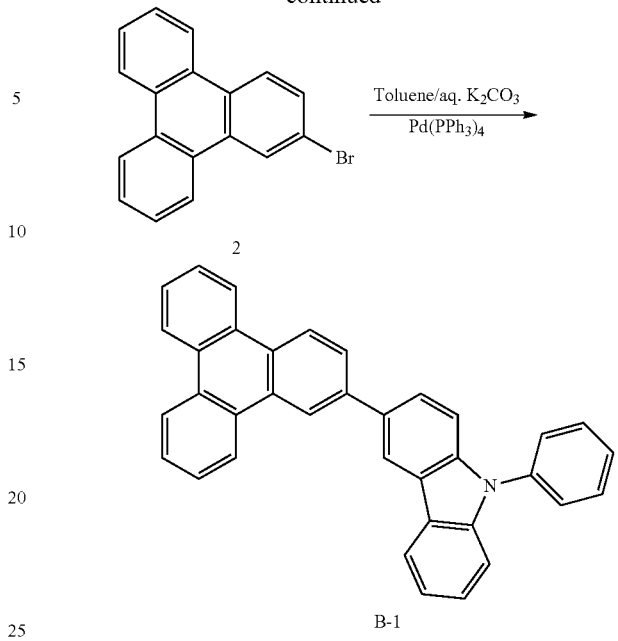

The compound of phenylcarbazolyl boronic acid (10 g, 34.83 mmol) was dissolved in 0.2 L of toluene under a nitrogen atmosphere, 2-bromotriphenylene (11.77 g, 38.31 mmol) and tetrakis(triphenylphosphine)palladium (0.80 g, 0.7 mmmol) were added thereto, and the mixture was agitated. Then, potassium carbonate saturated in water (14.44 g, 104.49 mmol) was added thereto, and the resultant was heated and refluxed at 120° C. for 12 hours. When the reaction was terminated, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain the compound B-1 (14.4 g, 88%).

HRMS (70 eV, EI+): m/z calcd for C36H23N: 469.18, found: 469

Elemental Analysis: C, 92%; H, 5%

Synthesis Example 2 of Second Host Compound:
Synthesis of Compound B-10

[Reaction Scheme 75]

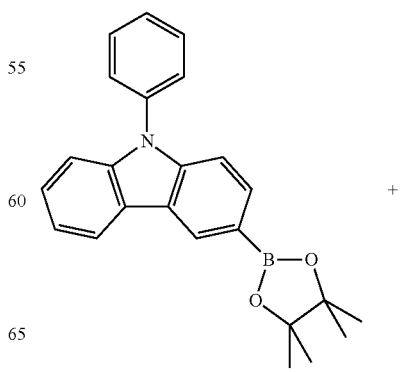

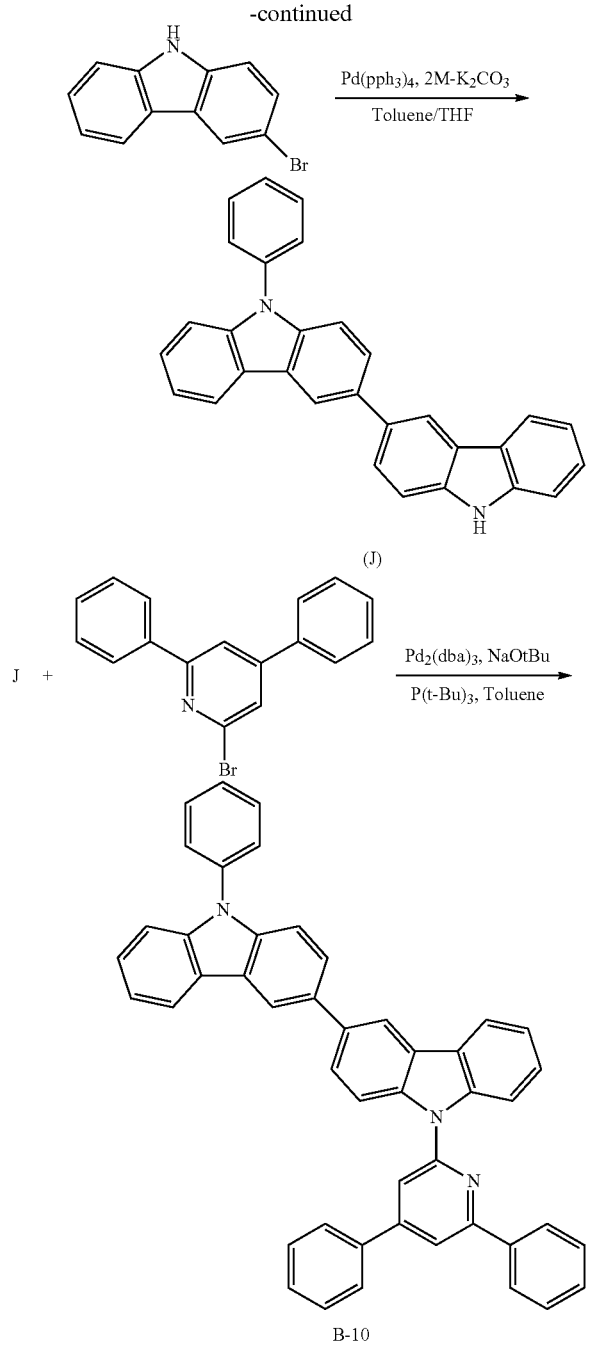

(J)

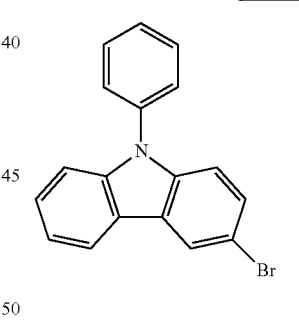

B-10 extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain the compound J (22.6 g, 68%).

HRMS (70 eV, EI+): m/z calcd for C30H20N2: 408.16, found: 408

Elemental Analysis: C, 88%; H, 5%

Second Step: Synthesis of Compound B-10

The compound J (22.42 g, 54.88 mmol) was dissolved in 0.2 L of toluene under a nitrogen atmosphere, 2-bromo-4,6-diphenylpyridine (20.43 g, 65.85 mmol), NaOtBu (7.92 g, 82.32 mmol), tris(dibenzylideneacetone)dipalladium (0, 1.65 g, 1.65 mmol), tri-tert-butylphosphine (1.78 g, 4.39 mmol) was added thereto, and the resultant was heated and refluxed at 120° C. for 12 hours. When the reaction was terminated, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain the compound B-10 (28.10 g, 80%).

HRMS (70 eV, EI+): m/z calcd for C47H31N3: 637.25, found: 637

Elemental Analysis: C, 89%; H, 5%

Synthesis Example 3 of Second Host Compound: Synthesis of Compound B-31

[Reaction Scheme 76]

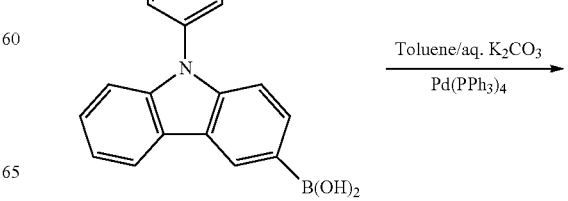

First Step: Synthesis of Compound J

The compound of 9-phenyl-3-(4,4,5,5-tetramethyl-1,3,2-dioxaborolan-2-yl)-9H-carbazole (26.96 g, 81.4 mmol) was dissolved in 0.2 L of toluene/THF under a nitrogen atmosphere, 3-bromo-9H-carbazole (23.96 g, 97.36 mmol) and tetrakis(triphenylphosphine)palladium (0.90 g, 0.8 mmmol) were added thereto, and the mixture was agitated. Then, potassium carbonate saturated in water (28 g, 203.49 mmol) was added thereto, and the resultant was heated and refluxed at 120° C. for 12 hours. When the reaction was terminated, water was added to the reaction solution, the mixture was

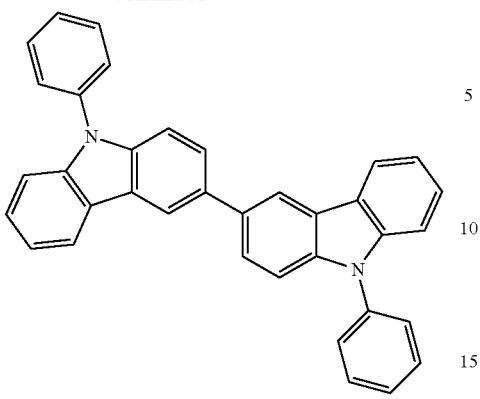

B-31

The compound of phenylcarbazolyl bromide (9.97 g, 30.95 mmol) was dissolved in 0.2 L of toluene under a nitrogen atmosphere, phenylcarbazolylboronic acid (9.78 g, 34.05 mmol) and tetrakis(triphenylphosphine)palladium (1.07 g, 0.93 mmmol) were added thereto, and the mixture was agitated. Then, potassium carbonate saturated in water (12.83 g, 92.86 mmol) was added and the resultant was heated and refluxed at 120° C. for 12 hours. When the reaction was terminated, water was added to the reaction solution, the mixture was extracted with dichloromethane (DCM), and the extract was treated with anhydrous MgSO₄ to remove moisture therefrom, filtered, and concentrated under a reduced pressure. The obtained residue was separated and purified through flash column chromatography to obtain the compound B-31 (13.8 g, 92%).

HRMS (70 eV, EI+): m/z calcd for C36H24N2: 484.19, found: 484

Elemental Analysis: C, 89%; H, 5%

Synthesis Example 4 of Second Host Compound: Synthesis of Compound B-34

[Reaction Scheme 77]

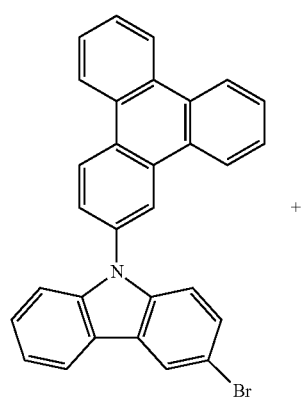

+

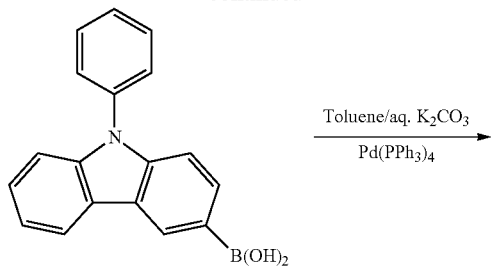

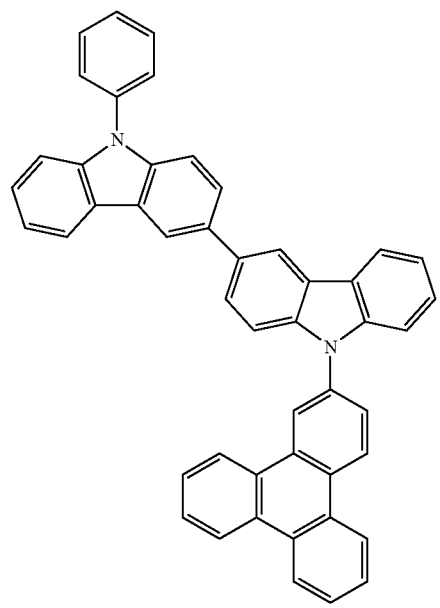

B-34

The compound of triphenylcarbazolyl bromide (14.62 g, 30.95 mmol) was dissolved in 0.2 L of toluene under a nitrogen atmosphere, phenylcarbazolylboronic acid (9.78 g, 34.05 mmol) and tetrakis(triphenylphosphine)palladium (1.07 g, 0.93 mmmol) were added thereto, and the mixture was agitated. Then, potassium carbonate saturated in water (12.83 g, 92.86 mmol) was added and the resultant was heated and refluxed at 120° C. for 12 hours. When the reaction was terminated, water was added to the reaction solution, the mixture was extracted with dichloromethane (DCM), and the extract was treated with anhydrous MgSO₄ to remove moisture therefrom, filtered, and concentrated under a reduced pressure. The obtained residue was separated and purified through flash column chromatography to obtain the compound B-34 (16.7 g, 85%).

HRMS (70 eV, EI+): m/z calcd for C47H29N2: 621.23, found: 621

Elemental Analysis: C, 91%; H, 5%

Synthesis Example 5 of Second Host Compound: Synthesis of Compound B-43

[Reaction Scheme 78]

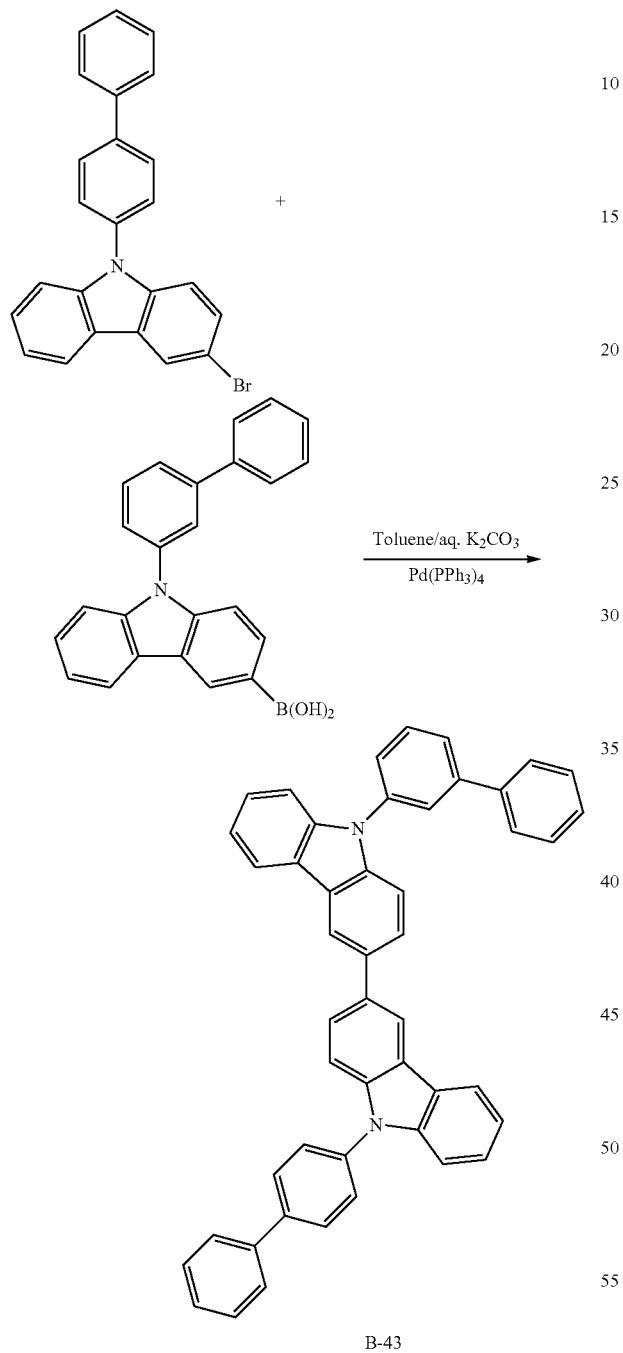

B-43

The compound of biphenylcarbazolyl bromide (12.33 g, 30.95 mmol) was dissolved in 0.2 L of toluene under a nitrogen atmosphere, biphenylcarbazolylboronic acid (12.37 g, 34.05 mmol) and tetrakis(triphenylphosphine)palladium (1.07 g, 0.93 mmmol) were added thereto, and the mixture was agitated. Then, potassium carbonate saturated in water (12.83 g, 92.86 mmol) was added and the resultant was heated and refluxed at 120° C. for 12 hours. When the reaction was terminated, water was added to the reaction solution, the mixture was extracted with dichloromethane (DCM), and the extract was treated with anhydrous $MgSO_4$ to remove moisture therefrom, filtered, and concentrated under a reduced pressure. The obtained residue was separated and purified through flash column chromatography to obtain the compound B-43 (18.7 g, 92%).

HRMS (70 eV, EI+): m/z calcd for C48H32N2: 636.26, found: 636

Elemental Analysis: C, 91%; H, 5%

Synthesis Example 6 of Second Host Compound: Synthesis of Compound B-114

[Reaction Scheme 79]

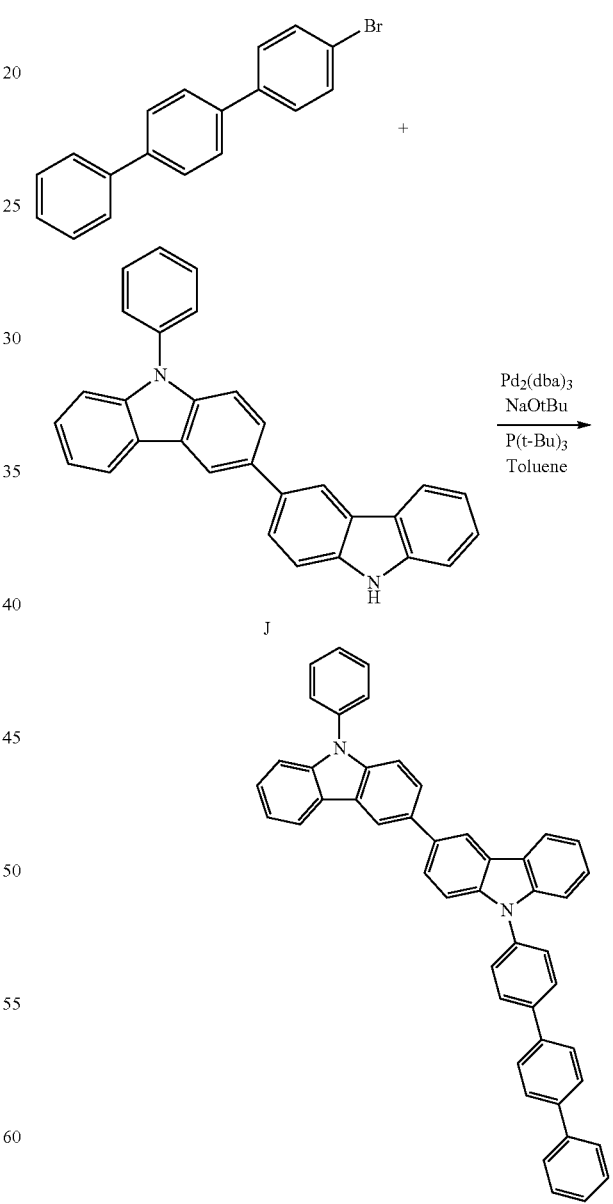

B-114

4-bromo-1,1':4',1''-terphenyl (15 g, 48.5 mmol) was dissolved in 0.2 L of toluene under a nitrogen atmosphere, the compound J (20 g, 48.5 mmol), NaOtBu (6 g, 58.2 mmol), tris(dibenzylideneacetone)dipalladium (0) (0.439 g, 0.48 mmol), and tri-tert-butylphosphine (0.388 g, 1.92 mmol) was added thereto, and the resultant was heated and refluxed at 120° C. for 12 hours. When the reaction was terminated, water was added to the reaction solution, the mixture was extracted with dichloromethane (DCM), and the extract was treated with anhydrous MgSO$_4$ to remove moisture therefrom, filtered, and concentrated under a reduced pressure. The obtained residue was separated and purified through flash column chromatography to obtain the compound B-114 (25 g, 80%).

HRMS (70 eV, EI+): m/z calcd for C48H32N2: 636.2565, found: 636

Elemental Analysis: C, 95%; H, 5%

Synthesis Example 7 of Second Host Compound: Synthesis of Compound E-1

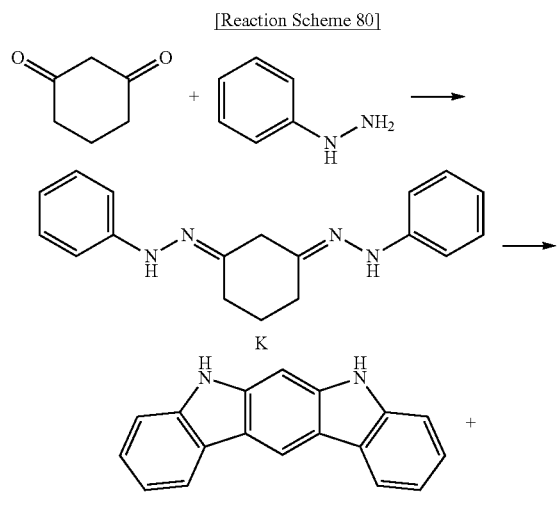

First Step: Synthesis of Compound K

Phenylhydrazine hydrochloride was dissolved in distilled water, and the solution was added to a 2 M NaOH aqueous solution. Then, a solid crystallized therein was filtered to obtain phenylhydrazine. The compound of cyclohexane-1,3-dione (30 g, 267.5 mmol) was dissolved in 1000 ml of ethanol under a nitrogen atmosphere, phenylhydrazine was slowly added thereto, and the mixture was reacted for 20 minutes. When the reaction was terminated, ice water was added thereto. Then, a solid produced therein was washed with ethanol and filtered. The obtained solid was dried under a reduced pressure to obtain a compound K (46.2 g, 38%).

HRMS (70 eV, EI+): m/z calcd for C18H20N4: 292.3782, found: 292

Elemental Analysis: C, 74%; H, 7%

Second step: Synthesis of Compound L

The compound K (46.2 g, 102.6 mmol) was slowly added to 140 ml of a mixed solution of acetic acid and sulfuric acid in a ratio of 1:4 under a nitrogen atmosphere at 0° C. The mixture was agitated for 5 minutes and heated up to 50° C. fast and then, up to 110° C. slowly. After 20 minutes, the resultant was cooled down to room temperature and agitated for 12 hours. Then, ethanol was added thereto, and a solid produced therein was filtered under a reduced pressure and neutralized. The solid was dried under reduced pressure to obtain the compound L (21.7 g, 51%).

HRMS (70 eV, EI+): m/z calcd for C18H12N2: 256.3013, found: 256

Elemental Analysis: C, 84%; H, 5%

Third Step: Synthesis of Compound E-1

The compound L (10 g, 39.0 mmol), iodobenzene (10.4 ml, 93.6 mmol), 18-crown-6 (4.2 g, 15.6 mmol), copper (3 g, 46.8 mmol), and potassium carbonate (48.6 g, 351 mmol) was mixed under a nitrogen atmosphere, and the resultant was heated and refluxed at 180° C. for 20 hours. When the reaction was terminated, water was added to the reaction solution, the mixture was extracted with ethyl acetate (e.a), the extract was treated with anhydrous MgSO$_4$ to remove moisture therefrom, filtered, and concentrated under a reduced pressure. The obtained residue was separated and purified through flash column chromatography to obtain the compound E-1 (6.7 g, 17.3%).

HRMS (70 eV, EI+): m/z calcd for C30H20N2: 408.4932, found: 408

Elemental Analysis: C, 88%; H, 5%

Synthesis Example 8 of Second Host Compound: Synthesis of Compound B-116

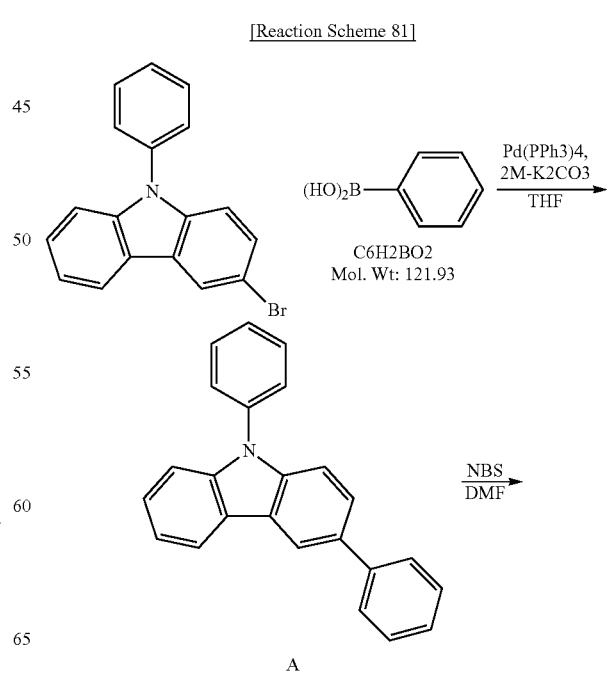

-continued

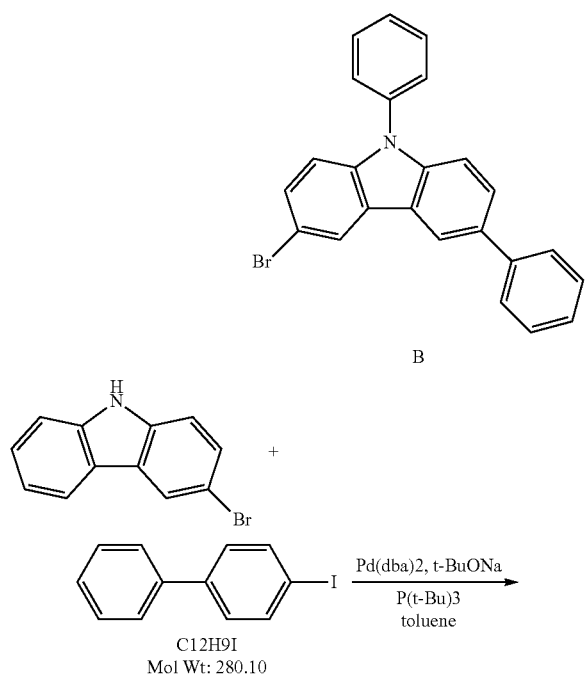

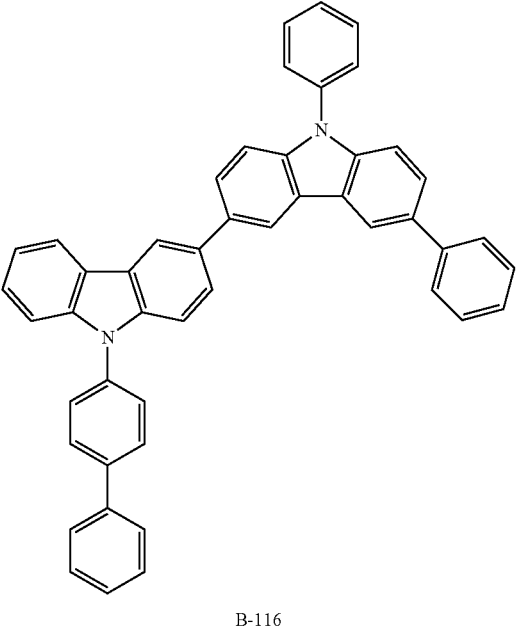

B-116

First Step: Synthesis of Compound A

A compound A (32 g, 75%) was synthesizes according to the same method as Synthesis Example 3 of synthesizing the second host compound except for using 3-bromo-N-phenyl carbazole (43.2 g, 134.2 mmol) and phenylboronic acid (18 g, 147.6 mmol).

Second Step: Synthesis of Compound B

A compound B (35 g, 82%) was obtained by dissolving 34.4 g (107.6 mmol) of the compound 1 in 500 mL of dichloromethane, adding 19.2 g (107.6 mmol) of N-bromo-succinimide thereto, and agitating the mixture at room temperature for 8 hours.

Third Step: Synthesis of Compound C

A compound C (15 g, 53%) was obtained according to the same method as Synthesis Example 6 of synthesizing the second host compound except for using 17.65 g (71.74 mmol) of 3-bromocarbazole and 22 g (78.91 mmol) of 4-Iodobiphenyl.

Fourth Step: Synthesis of Compound D

A compound D (20 g, 89%) was obtained according to the same method as Synthesis Example 5 except for using the compound C (20.1 g, 50.5 mmol) and bis(pinacolato)diboron (19.2 g, 75.8 mmol).

Fifth Step: Synthesis of Compound B-116

A compound B-116 (18 g, 84%) was obtained according to the same method of synthesizing the second host compound as Synthesis Example 3 except for using the compound B (13 g, 33.1 mmol) and the compound D (16.2 g, 36.4 mmol).

HRMS (70 eV, EI+): m/z calcd for $C_{48}H_{32}N_2$: 636.2565, found: 636

Elemental Analysis: C, 90%; H, 5%

Synthesis Example 9 of Second Host Compound: Synthesis of Compound B-118

[Reaction Scheme 82]

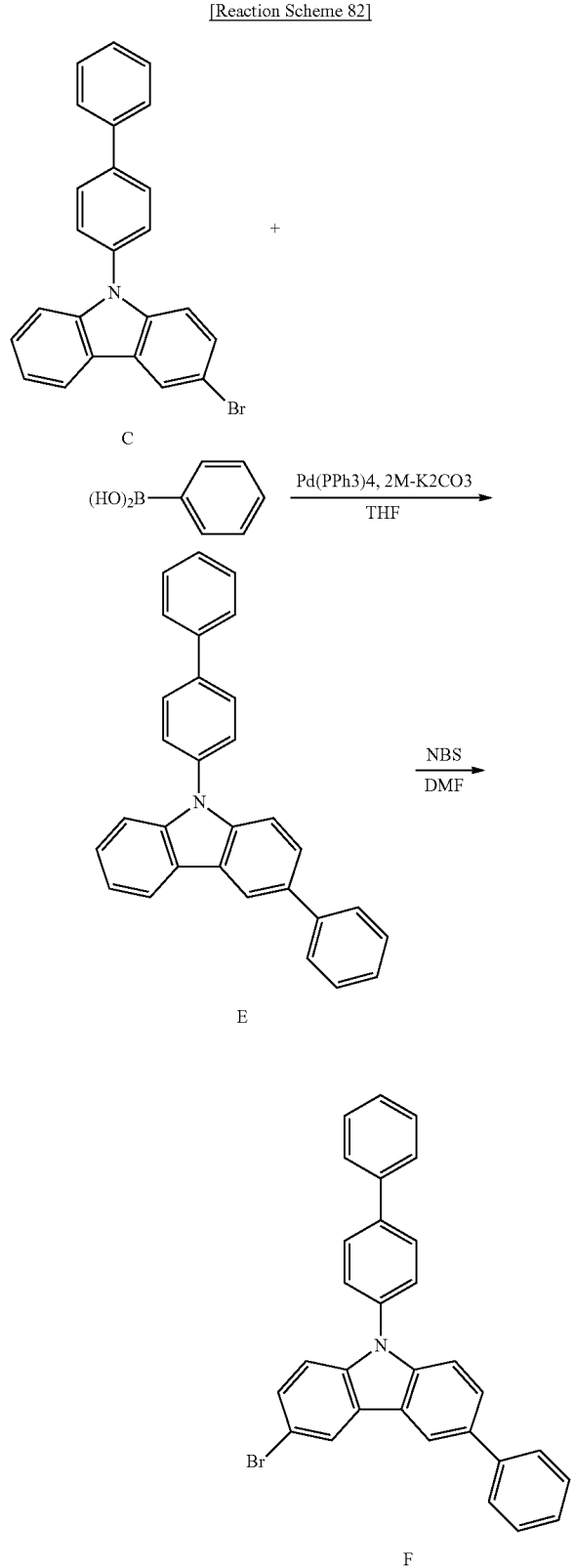

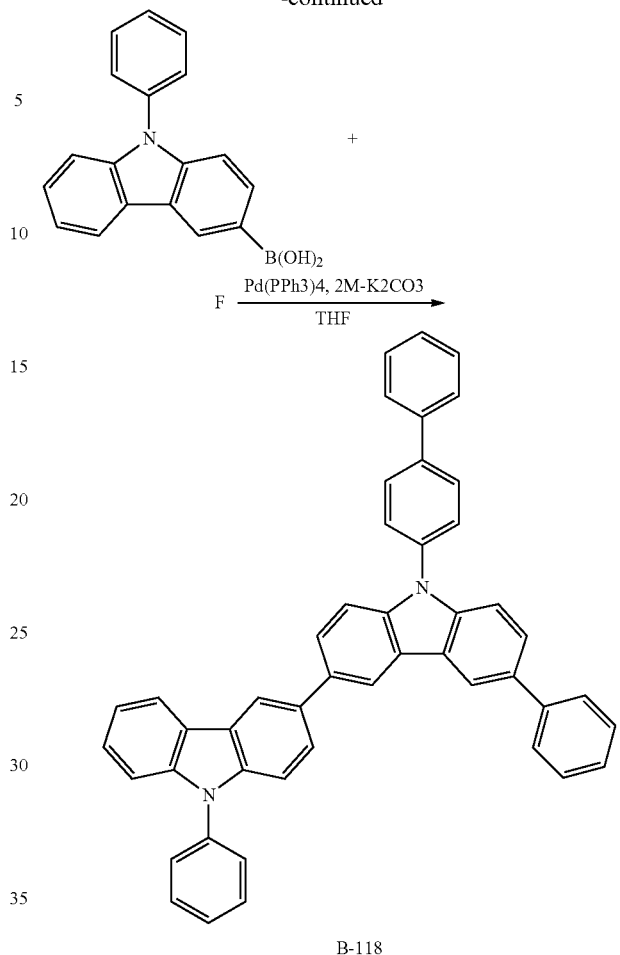

B-118

First Step: Synthesis of Compound E

A compound E (33 g, 77%) was obtained according to the same method of synthesizing the second host compound as Synthesis Example 3 except for using the compound C (43.2 g, 108.4 mmol) and phenylboronic acid (14.5 g, 119 mmol).

Second Step: Synthesis of Compound F

A compound F (29 g, 81%) was obtained according to the same method of synthesizing the second host compound as Synthesis Example 8 except for using the compound E (29.8 g, 75.28 mmol) and N-bromosuccinimide (14 g, 75.28 mmol).

Third Step: Synthesis of Compound B-118

A compound B-118 (17 g, 79%) was obtained according to the same method of synthesizing the second host compound as Synthesis Example 3 except for using N-phenyl-carbazoe-3-yl-boronic acid (9.7 g, 33.65 mmol) and the compound F (16 g, 33.65 mmol).

HRMS (70 eV, EI+): m/z calcd for $C_{48}H_{32}N_2$: 636.2565, found: 636

Elemental Analysis: C, 90%; H, 5%

Manufacture of Organic Light Emitting Diode I

Example 15

ITO (indium tin oxide) was deposited to be 1500 Å thick on a glass substrate, and the deposited glass was ultrasonic wave-washed with a distilled water. After washing with distilled water, the washed glass substrate was ultrasonic wave-washed with a solvent such as isopropyl alcohol, acetone, methanol, and the like was moved to a plasma cleaner to clean the substrate by using oxygen plasma for 10 minutes and moved to a vacuum depositor. This ITO transparent electrode was used as an anode, the compound A is vacuum-deposited on the ITO substrate to form a 700 Å-thick hole injection layer, the compound B is deposited in a 50 Å thickness, the compound C is deposited in a 1020 Å thickness on the injection layer to form a hole transport layer. The compound 1 of Synthesis Example 54 and the compound B-10 of Synthesis Example 2 as a second host compound were simultaneously used as a host on the hole transport layer (HTL), and 10 wt % of tris(2-phenylpyridine) iridium (III) [Ir(ppy)$_3$] was doped by vacuum deposition to form a 400 Å-thick emission layer. Herein, the compound 1 and the compound B-10 were used in a ratio of 4:1.

Subsequently, On the emission layer, the compound D and Liq were simultaneously vacuum-deposited in a ratio of 1:1 to form a 300 Å-thick electron transport layer, and 15 Å Liq and 1200 Å Al were sequentially vacuum-deposited on the electron transport layer to form a cathode, manufacturing an organic light emitting diode.

The organic light emitting diode has a structure including five-layered organic thin layers, and specifically the following structure.

ITO/compound A (700 Å)/compound B (50 Å)/compound C (1020 Å)/EML [compound 1: B-10:Ir(ppy)$_3$=X:X:10%] (400 Å)/compound D:Liq (300 Å)/Liq (15 Å)/Al (1200 Å). (X=weight ratio)

Compound A: N4,N4'-diphenyl-N4,N4'-bis(9-phenyl-9H-carbazol-3-yl)biphenyl-4,4'-diamine,
Compound B: 1,4,5,8,9,11-hexaazatriphenylene-hexacarbonitrile (HAT-CN),
Compound C: N-(biphenyl-4-yl)-9,9-dimethyl-N-(4-(9-phenyl-9H-carbazol-3-yl)phenyl)-9H-fluoren-2-amine
Compound D: 8-(4-(4,6-di(naphthalen-2-yl)-1,3,5-triazin-2-yl)phenyl)quinoline Example 16

An organic light emitting diode was manufactured according to the same method as Example 15 except for using the compound 1 and compound B-10 in a ratio of 1:1.

Example 17

An organic light emitting diode was manufactured according to the same method as Example 15 except for using the compound 1 and compound B-10 in a ratio of 1:4.

Example 18

An organic light emitting diode was manufactured according to the same method as Example 15 except for using the compound B-31 of Synthesis Example 3 of the second host compound, instead of the compound B-10.

Example 19

An organic light emitting diode was manufactured according to the same method as Example 18 except for using the compound 1 and compound B-31 in a ratio of 1:1.

Example 20

An organic light emitting diode was manufactured according to the same method as Example 15 except for using the compound B-1 of Synthesis Example 1 of the second host compound, instead of the compound B-10.

Example 21

An organic light emitting diode was manufactured according to the same method as Example 20 except for using the compound 1 and compound B-1 in a ratio of 1:1.

Example 22

An organic light emitting diode was manufactured according to the same method as Example 20 except for using the compound 1 and compound B-1 in a ratio of 1:4.

Example 23

An organic light emitting diode was manufactured according to the same method as Example 15 except for using the compound B-34 of Synthesis Example 4 of the second host compound, instead of the compound B-10.

Example 24

An organic light emitting diode was manufactured according to the same method as Example 23 except for using the compound 1 and compound B-34 in a ratio of 1:1.

Example 25

An organic light emitting diode was manufactured according to the same method as Example 15 except for using the compound B-43 of Synthesis Example 5 of the second host compound in a ratio of 1:1, instead of the compound B-10.

Example 26

An organic light emitting diode was manufactured according to the same method as Example 15 except for using the compound 135 of Synthesis Example 63 of the second host compound instead of the compound 1 and the compound B-114 of Synthesis Example 6 of the second host compound instead of the compound in a ratio of 7:3.

Example 27

An organic light emitting diode was manufactured according to the same method as Example 26 except for using the compound 135 and compound B-114 in a ratio of 1:1.

Example 28

An organic light emitting diode was manufactured according to the same method as Example 26 except for using the compound 135 and compound B-114 in a ratio of 3:7.

Reference Example 6

An organic light emitting diode was manufactured according to the same method as Example 15 except for using the compound 1 at alone as a single host instead of two kinds of host including the compound 1 and the compound B-10.

Comparative Example 2

An organic light emitting diode was manufactured according to the same method as Example 15 except for using CBP at alone as a single host instead of two kinds of host including the compound 1 and the compound B-10.

Comparative Example 3

An organic light emitting diode was manufactured according to the same method as Example 15 except for using the compound B-10 at alone as a single host instead of two kinds of host including the compound 1 and the compound B-10.

Comparative Example 4

An organic light emitting diode was manufactured according to the same method as Example 19 except for using the compound B-31 at alone as a single host instead of two kinds of host including the compound 1 and the compound B-31.

Comparative Example 5

An organic light emitting diode was manufactured according to the same method as Example 20 except for using the compound B-1 at alone as a single host instead of two kinds of host including the compound 1 and the compound B-1.

Comparative Example 6

An organic light emitting diode was manufactured according to the same method as Example 23 except for using the compound B-34 at alone as a single host instead of two kinds of host including the compound 1 and the compound B-34.

Comparative Example 7

An organic light emitting diode was manufactured according to the same method as Example 25 except for using the compound B-43 at alone as a single host instead of two kinds of host including the compound 1 and the compound B-43.

Evaluation 1

Luminous efficiency and life-span characteristics of each organic light emitting diode according to Examples 15 to 28, Reference Example 6 and Comparative Examples 2 to 7 were measured.

The measurements were specifically performed in the following method, and the results were provided in the following Table 3.

(1) Measurement of Current Density Change Depending on Voltage Change

Current values flowing in the unit device of the manufactured organic light emitting diodes were measured for, while increasing the voltage from 0V to 10V using a current-voltage meter (Keithley 2400), and the measured current values were divided by an area to provide the results.

(2) Measurement of Luminance Change Depending on Voltage Change

Luminance of the manufactured organic light emitting diodes was measured for luminance, while increasing the voltage from 0 V to 10 V using a luminance meter (Minolta Cs-1000A).

(3) Measurement of Luminous Efficiency

Current efficiency (cd/A) at the same current density (10 mA/cm2) were calculated by using the luminance, current density, and voltages (V) from the items (1) and (2).

(4) Measurement of Life-Span

Life-span was obtained by measuring time taken until current efficiency (cd/A) decreased down to 97% while luminance ($cd/m^2$) was maintained at 6000 $cd/m^2$.

TABLE 3

| | First host | Second host | First host:Second host | Luminous efficiency (cd/A) | Life-span T97 (h) |
|---|---|---|---|---|---|
| Example 15 | Compound 1 | B-10 | 4:1 | 43.2 | 570 |
| Example 16 | Compound 1 | B-10 | 1:1 | 50.1 | 650 |
| Example 17 | Compound 1 | B-10 | 1:4 | 47.1 | 410 |
| Example 18 | Compound 1 | B-31 | 4:1 | 51.3 | 480 |
| Example 19 | Compound 1 | B-31 | 1:1 | 55.8 | 330 |
| Example 20 | Compound 1 | B-1 | 4:1 | 43.1 | 650 |
| Example 21 | Compound 1 | B-1 | 1:1 | 48.0 | 650 |
| Example 22 | Compound 1 | B-1 | 1:4 | 48.9 | 460 |
| Example 23 | Compound 1 | B-34 | 4:1 | 44.2 | 980 |
| Example 24 | Compound 1 | B-34 | 1:1 | 49.6 | 1,140 |
| Example 25 | Compound 1 | B-43 | 1:1 | 47.9 | 1,300 |
| Example 26 | Compound 135 | B-114 | 7:3 | 48.1 | 1,240 |
| Example 27 | Compound 135 | B-114 | 1:1 | 48.3 | 1,250 |
| Example 28 | Compound 135 | B-114 | 3:7 | 50.7 | 1,290 |
| Reference Example 6 | Compound 1 | | — | 33.5 | 550 |
| Comparative Example 2 | CBP | | — | 19.3 | 0.5 |
| Comparative Example 3 | B-10 | | — | 37.5 | 10 |
| Comparative Example 4 | B-31 | | — | 2.5 | — |
| Comparative Example 5 | B-1 | | — | 16.5 | 10 |
| Comparative Example 6 | B-34 | | — | 18.3 | 10 |
| Comparative Example 7 | B-43 | | — | 2.8 | 10 |

Referring to 3, the organic light emitting diodes according to Examples 15 to 28 showed remarkably improved characteristics of luminous efficiency and life-span characteristics compared with the organic light emitting diodes according to Reference Example 6 and Comparative Examples 2 to 7.

Manufacture of Organic Light Emitting Diode II

Example 29

ITO (indium tin oxide) was deposited to be 1500 Å thick on a glass substrate, and the deposited glass was ultrasonic wave-washed with a distilled water. After washing with distilled water, the washed glass substrate was ultrasonic wave-washed with a solvent such as isopropyl alcohol, acetone, methanol, and the like was moved to a plasma cleaner to clean the substrate by using oxygen plasma for 10 minutes and moved to a vacuum depositor. This ITO transparent electrode was used as an anode, the compound P is vacuum-deposited on the ITO substrate to form a 700 Å-thick hole injection layer (HIL), the compound Q is deposited in a 50 Å thickness, the compound R is deposited in a 1020 Å thickness on the injection layer to form a hole transport layer (HTL). BH113 and BD370 (manufactured by SFC) as a blue fluorescent light emitting host and a dopant in a dopant concentration of 5 wt % were vacuum-deposited thereon to form a 200 Å-thick emission layer The compound 28 and the compound B-116 were vacuum-deposited in a ratio of 50:50 (wt/wt) on the emission layer to form a 50 Å-thick electron transport auxiliary layer. The compound S and Liq were simultaneously vacuum-deposited in a ratio of 1:1 ratio on the electron transport auxiliary layer to form a 300 Å-thick electron transport layer, and 15 Å Liq and 1200 Å Al were sequentially vacuum-deposited on the electron transport layer to form a cathode, manufacturing an organic light emitting diode. The organic light emitting diode has a structure including five-layered organic thin layers, and specifically the following structure: ITO/compound P (700 Å)/compound Q (50 Å)/compound R (1020 Å)/EML[BH113: BD370=95:5 wt %] (200 Å)/compound 28: Synthesis of Compound B-116=1:1 50 (Å)/compound S: Liq (300 Å)/Liq (15 Å)/Al (1200 Å).

Compound P: N4,N4'-diphenyl-N4,N4'-bis(9-phenyl-9H-carbazol-3-yl)biphenyl-4,4-diamine Compound Q: 1,4,5,8,9,11-hexaazatriphenylene-hexacarbonitrile (HAT-CN), Compound R: N-(biphenyl-4-yl)-9,9-dimethyl-N-(4-(9-phenyl-9H-carbazol-3-yl)phenyl)-9H-fluoren-2-amine Compound S: 8-(4-(4,6-di(naphthalen-2-yl)-1,3,5-triazin-2-yl)phenyl)quinoline

Example 30

An organic light emitting diode was manufactured according to the same method as Example 29 except for using the compound 28 and compound B-118 in a ratio of 30:70.

Example 31

An organic light emitting diode was manufactured according to the same method as Example 29 except for using the compound 28 and compound B-118 in a ratio of 50:50.

Example 32

An organic light emitting diode was manufactured according to the same method as Example 29 except for using the compound 135 and compound B-114 in a ratio of 50:50.

Comparative Example 8

An organic light emitting diode was manufactured according to the same method as Example 29 except for not using the electron transport auxiliary layer.

Evaluation 2

Current density and luminance changes depending on a voltage and luminous efficiency of each organic light emitting diode according to Examples 29 to 32 and Comparative Example 8 were measured.

The measurements were specifically performed in the following method, and the results were provided in the following Table 4.

(1) Measurement of Current Density Change Depending on Voltage Change

Current values flowing in the unit device of the manufactured organic light emitting diodes were measured for, while increasing the voltage from 0V to 10V using a current-voltage meter (Keithley 2400), and the measured current values were divided by an area to provide the results.

(2) Measurement of Luminance Change Depending on Voltage Change

Luminance of the manufactured organic light emitting diodes was measured for luminance, while increasing the voltage from 0 V to 10 V using a luminance meter (Minolta Cs-1000A).

(3) Measurement of Luminous Efficiency

Current efficiency (cd/A) at the same current density (10 mA/cm2) were calculated by using the luminance, current density, and voltages (V) from the items (1) and (2).

(5) Measurement of Life-Span

T97 life-spans of the devices according to Example 1 and Comparative Example 1 were measured using a Polaronix life-span measurement system, by light-emitting the devices at initial luminance (cd/m$^2$) of 750 cd/m$^2$ and measuring the time when the luminance became 97%.

TABLE 4

| Devices | Electron transport auxiliary layer (weight ratio) | Luminous efficiency (cd/A) | Color coordinate (x, y) | T97 life-span (h)@750 nit |
|---|---|---|---|---|
| Example 29 | compound 28:compound B-116 (50:50) | 7.2 | (0.134, 0.150) | 46 |
| Example 30 | compound 28:compound B-118 (30:70) | 6.5 | (0.133, 0.151) | 58 |
| Example 31 | compound112:compound B-118 (50:50) | 6.9 | (0.133, 0.152) | 56 |
| Example 32 | Compound 135:compound B-114 (50:50) | 6.2 | (0.134, 0.151) | 53 |
| Comparative Example 8 | None | 5.8 | (0.135, 0.147) | 25 |

Referring to Table 4, the organic light emitting diodes according to Examples 29 to 32 showed remarkably improved luminous efficiency and life-span characteristics compared with the organic light emitting diode according to Comparative Example 8.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

DESCRIPTION OF SYMBOLS

100, 200: organic light emitting diode

105: organic layer

110: cathode

120: anode

130: emission layer

140: hole auxiliary layer

The invention claimed is:

1. An organic optoelectronic device, comprising
an anode and a cathode facing each other, and
at least one organic layer between the anode and the cathode,
wherein the organic layer comprises a first organic compound represented by one of the following Chemical Formula 5a, 5b, 5c, 5d, or 5g and having a molecular weight of greater than or equal to 538 and less than 750:

[Chemical Formula 5a]

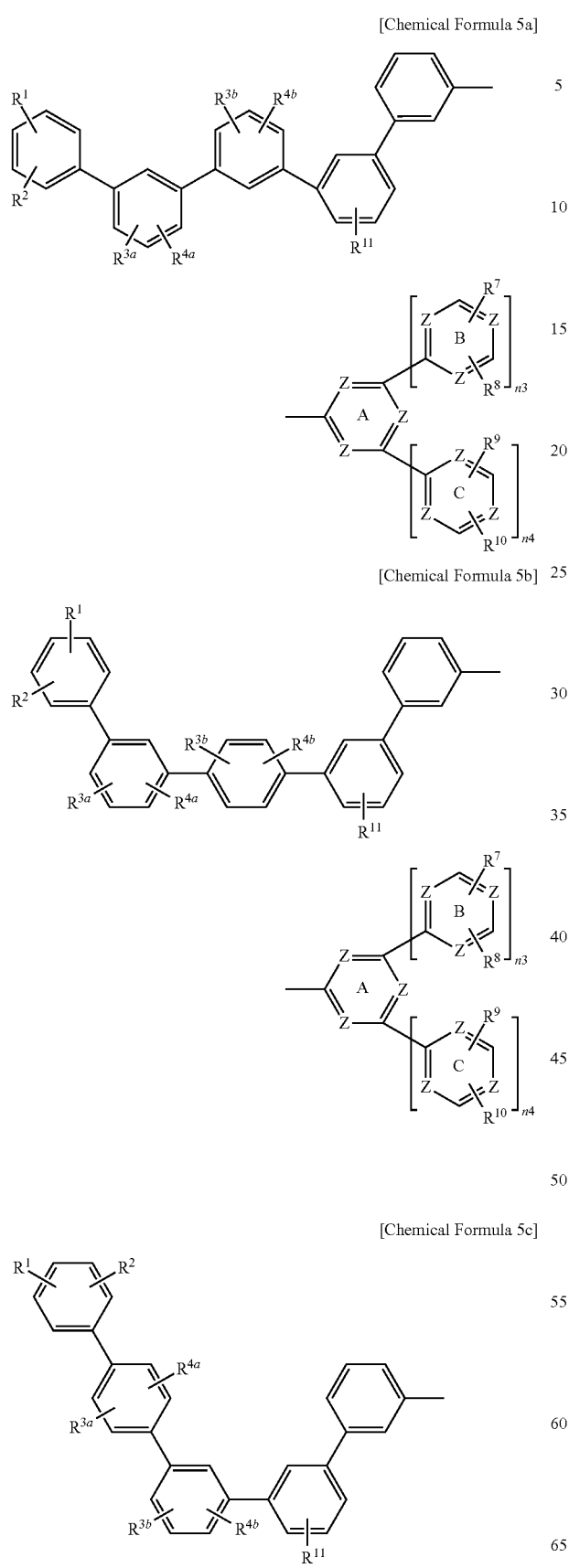

[Chemical Formula 5b]

[Chemical Formula 5c]

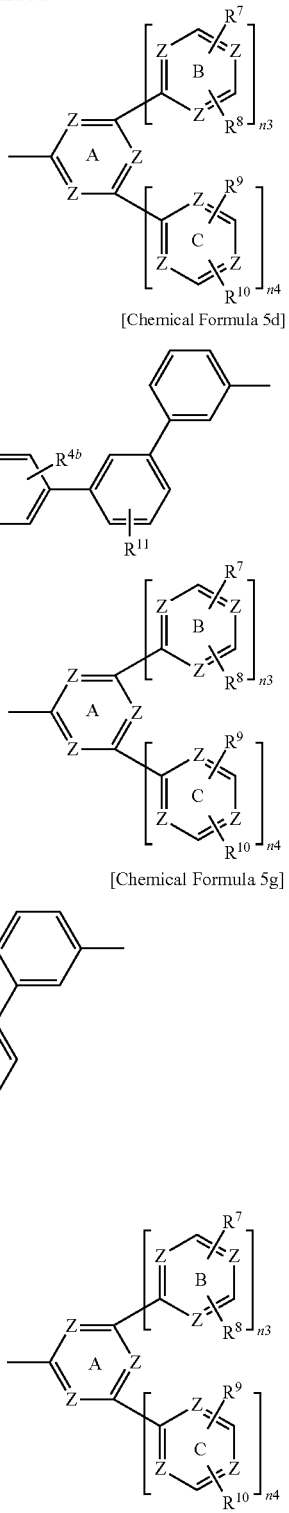

[Chemical Formula 5d]

[Chemical Formula 5g]

wherein, in Chemical Formula 5a, 5b, 5c, 5d, and 5g,
each Z in ring A is N, and each Z in rings B and C is CH,
$R^1$ and $R^2$ are each independently hydrogen or a phenyl group,
$R^{3a}$ and $R^{4a}$ are each independently hydrogen or a phenyl group,
$R^{3b}$ and $R^{4b}$ are each independently hydrogen or a phenyl group,
$R^7$ and $R^8$ are each independently hydrogen, $R^9$ and $R^{10}$ are each independently hydrogen, $R^{11}$ is hydrogen or a phenyl group and n3 and n4 are each 1.
2. The organic optoelectronic device of claim 1, wherein the first organic compound is one of compounds listed in the following Group 1:
[Group 1]
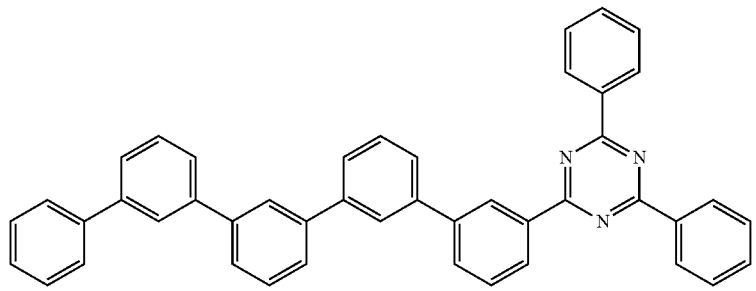
1
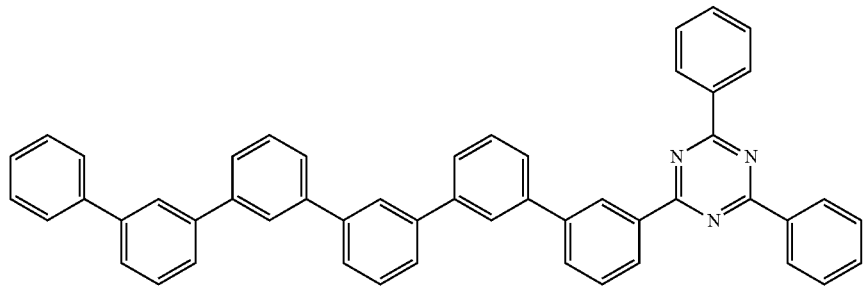
10
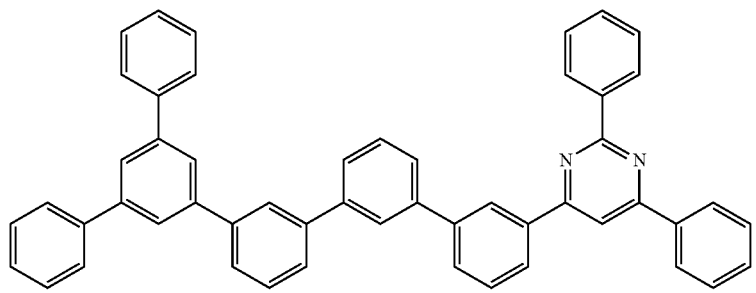
28
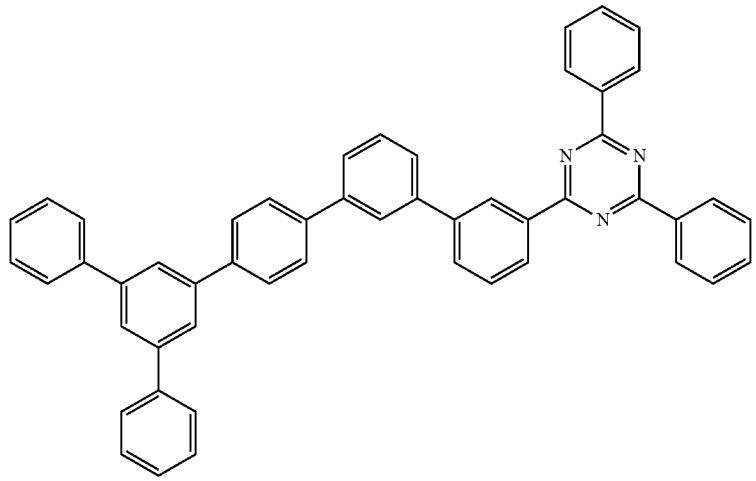
37

-continued
46
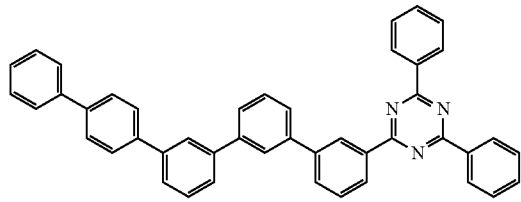
55
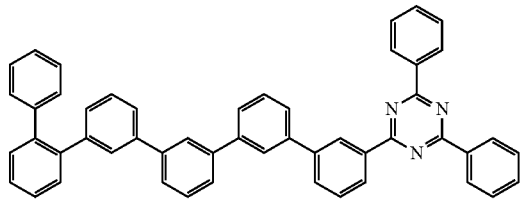
56
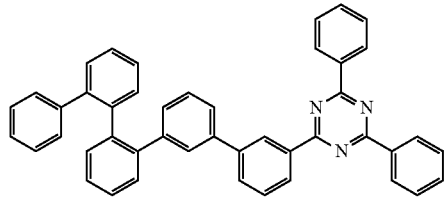
57
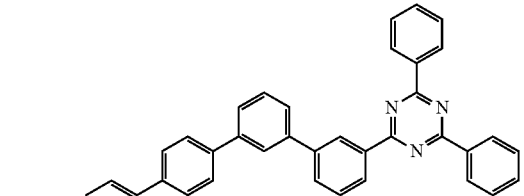
85
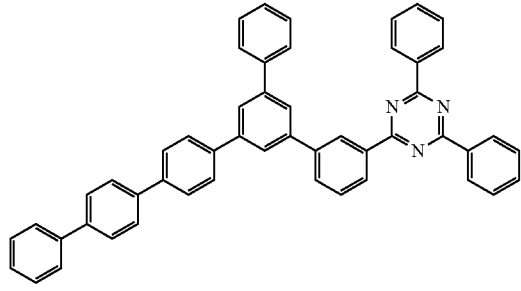
99
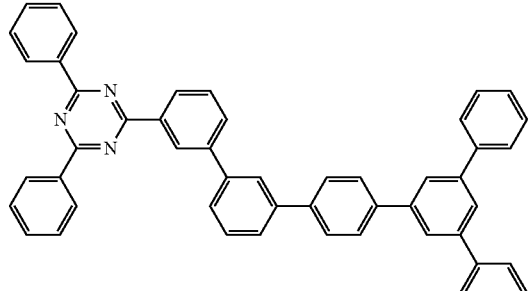
102
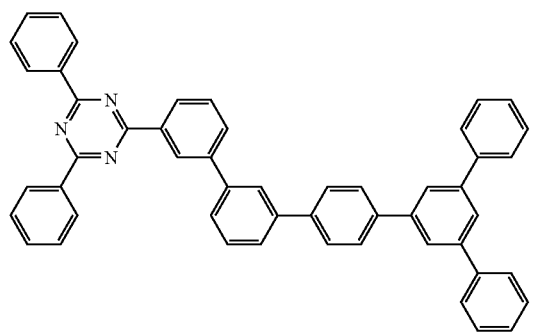
112
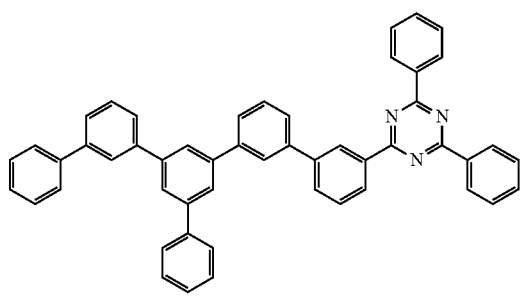
116
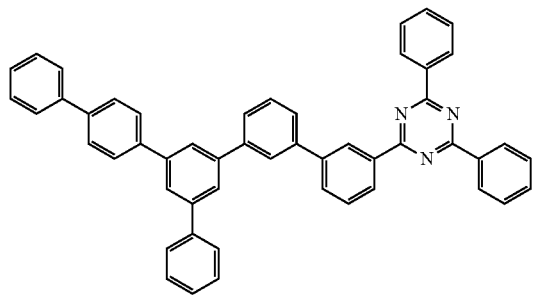
135
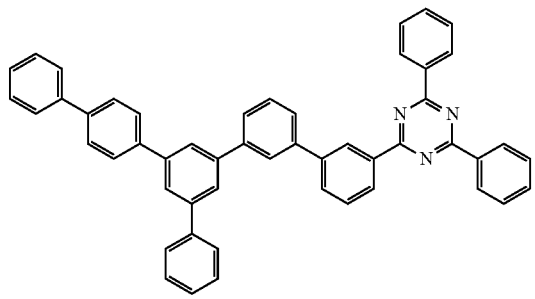

-continued

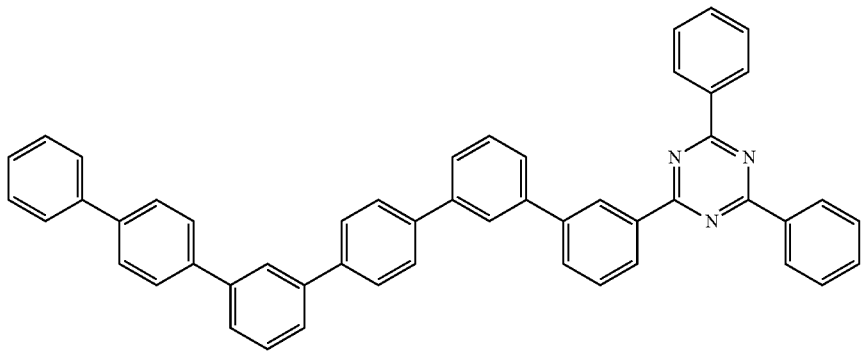

136

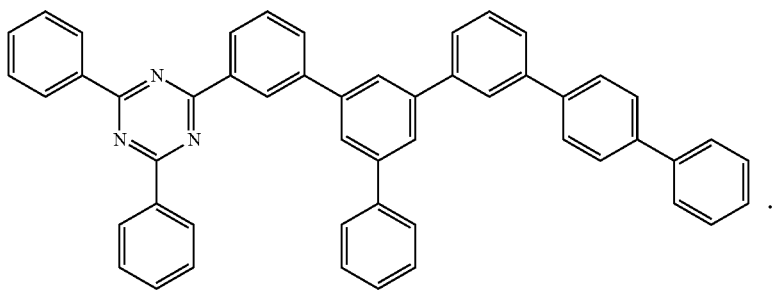

137

3. The organic optoelectronic device of claim 1, wherein the organic layer comprises an emission layer, and
the emission layer comprises the first organic compound.

4. A display device comprising the organic optoelectronic device of claim 1.

5. The organic optoelectronic device of claim 1, wherein the organic layer farther comprises at least one second organic compound having a carbazole moiety.

6. The organic optoelectronic device of claim 5, wherein the second organic compound includes at least one of a compound represented by the following Chemical Formula 8 and a compound consisting of a combination of a moiety represented by the following Chemical Formula 9 and a moiety represented by the following Chemical Formula 10:

[Chemical Formula 8]

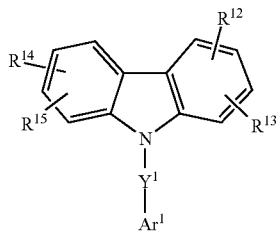

wherein, in Chemical Formula 8,
$Y^1$ is a single bond, a substituted or unsubstituted C1 to C20 alkylene group, a substituted or unsubstituted C2 to C20 alkenylene group, a substituted or unsubstituted C6 to C30 arylene group, a substituted or unsubstituted C2 to C30 heteroarylene group, or a combination thereof,
$Ar^1$ is a substituted or unsubstituted C6 to C30 aryl group, a substituted or unsubstituted C2 to C30 heteroaryl group, or a combination thereof, $R^{12}$ to $R^{15}$ are each independently hydrogen, deuterium, a substituted or unsubstituted C1 to C20 alkyl group, a substituted or unsubstituted C6 to C50 aryl group, a substituted or unsubstituted C2 to C50 heteroaryl group, or a combination thereof, and
at least one of $R^{12}$ to $R^{15}$ and $Ar^1$ includes a substituted or unsubstituted triphenylene group or a substituted or unsubstituted carbazole group,

[Chemical Formula 9]

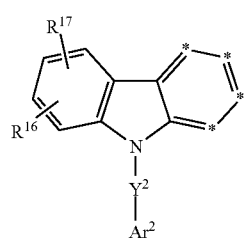

[Chemical Formula 10]

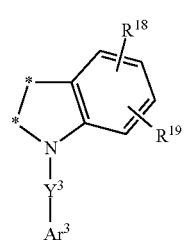

wherein, in Chemical Formulae 9 and 10,
$Y^2$ and $Y^3$ are each independently a single bond, a substituted or unsubstituted C1 to C20 alkylene group, a substituted or unsubstituted C2 to C20 alkenylene group, a substituted or unsubstituted C6 to C30 arylene group, a substituted or unsubstituted C2 to C30 heteroarylene group, or a combination thereof, Ar² and Ar³ are each independently substituted or unsubstituted C6 to C30 aryl group, a substituted or unsubstituted C2 to C30 heteroaryl group, or a combination thereof, $R^{16}$ to $R^{19}$ are each independently hydrogen, deuterium, a substituted or unsubstituted C1 to C20 alkyl group, a substituted or unsubstituted C6 to C50 aryl group, a substituted or unsubstituted C2 to C50 heteroaryl group, or a combination thereof, the adjacent two *'s of the Chemical Formula 9 are bound to two *'s of the Chemical Formula 10 to form a fused ring, and * that does not form the fused ring in the Chemical Formula 9 is each independently $CR^b$, and $R^b$ is hydrogen, deuterium, a substituted or unsubstituted C1 to C10 alkyl group, a substituted or unsubstituted C6 to C12 aryl group, a substituted or unsubstituted C3 to C12 heteroaryl group, or a combination thereof.

7. The organic optoelectronic device of claim 6, wherein the second organic compound represented by the Chemical Formula 8 is represented by at least one of the following Chemical Formulae 8-I to 8-III:

[Chemical Formula 8-I]

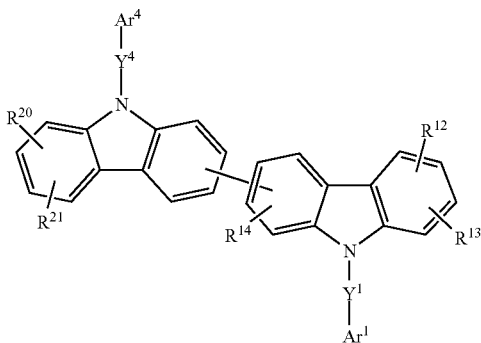

[Chemical Formula 8-II]

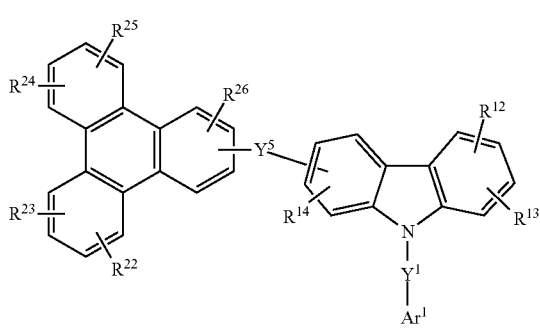

[Chemical Formula 8-III]

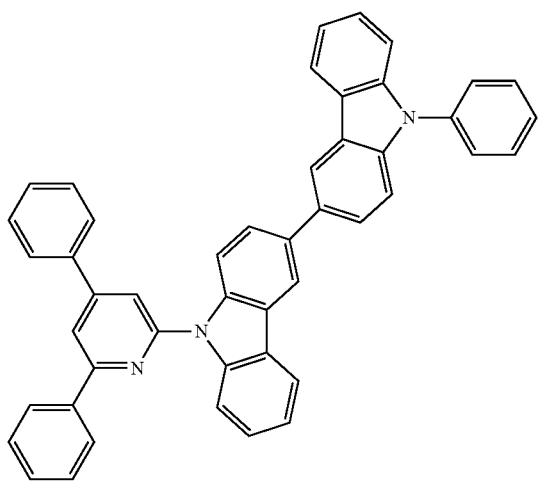

wherein, in Chemical Formulae 8-I to 8-III, $Y^1$, $Y^4$ and $Y^5$ are each independently a single bond, a substituted or unsubstituted C1 to C20 alkylene group, a substituted or unsubstituted C2 to C20 alkenylene group, a substituted or unsubstituted C6 to C30 arylene group, a substituted or unsubstituted C2 to C30 heteroarylene group, or a combination thereof, $Ar^1$ and $Ar^4$ are each independently substituted or unsubstituted C6 to C30 aryl group, a substituted or unsubstituted C2 to C30 heteroaryl group, or a combination thereof, and $R^{12}$ to $R^{15}$ and $R^{20}$ to $R^{31}$ are independently hydrogen, deuterium, a substituted or unsubstituted C1 to C20 alkyl group, a substituted or unsubstituted C6 to C50 aryl group, a substituted or unsubstituted C2 to C50 heteroaryl group, or a combination thereof.

8. The organic optoelectronic device of claim 6, wherein the second organic compound represented by the Chemical Formula 8 is one of compounds listed in Group 2:

[Group 2]

B-10

B-11
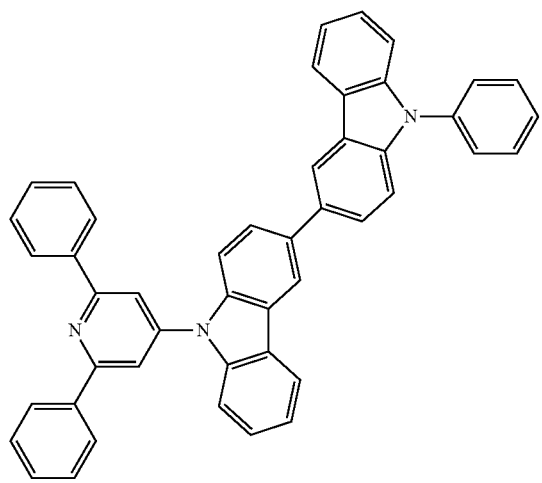
B-12
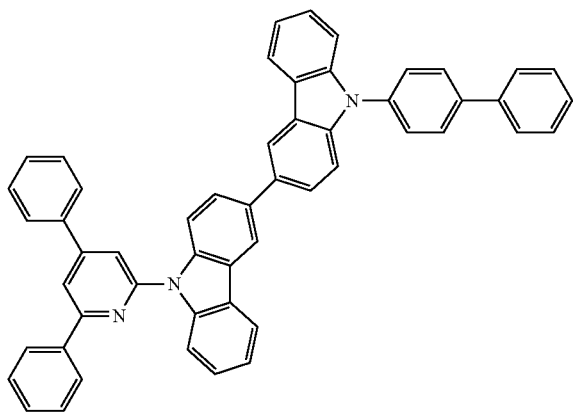
B-13
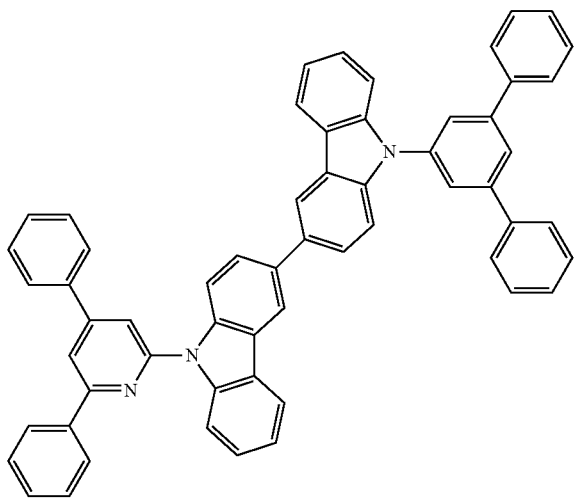
B-14
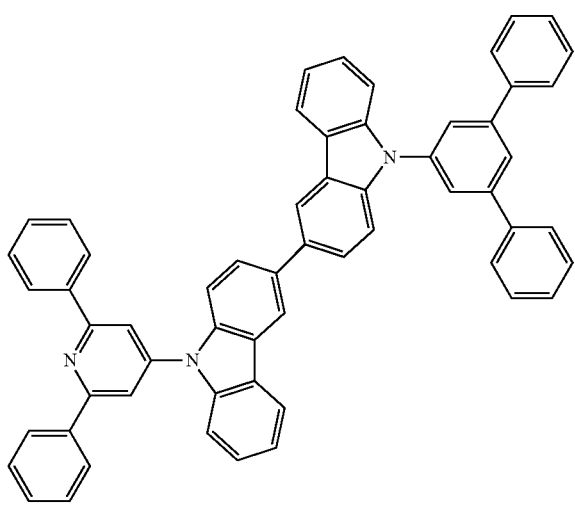
B-15
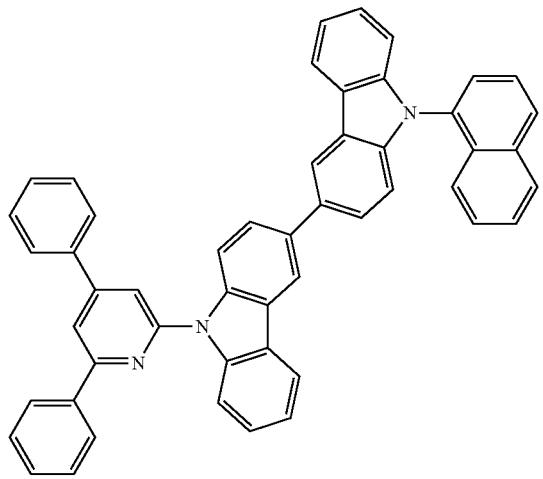
B-16
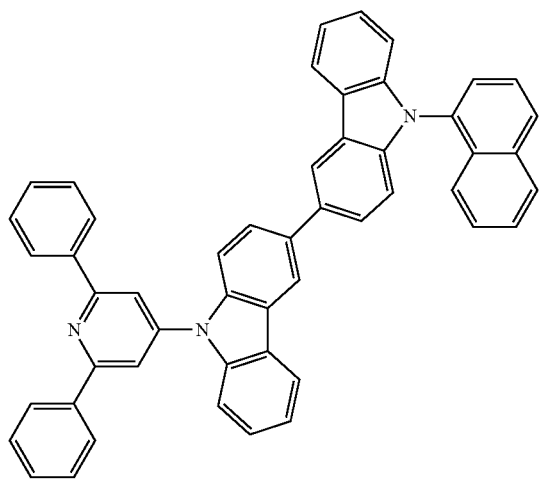

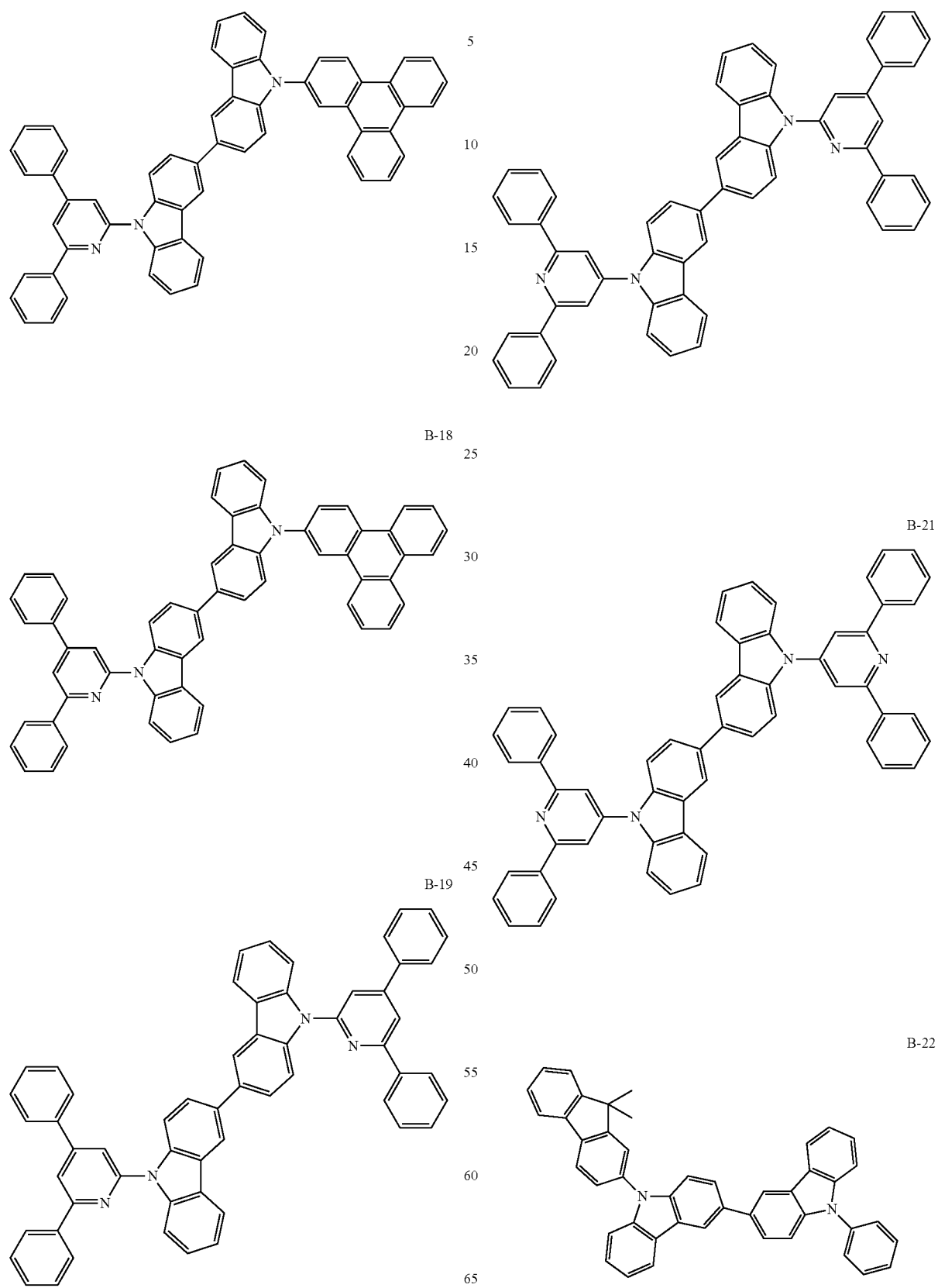

B-23
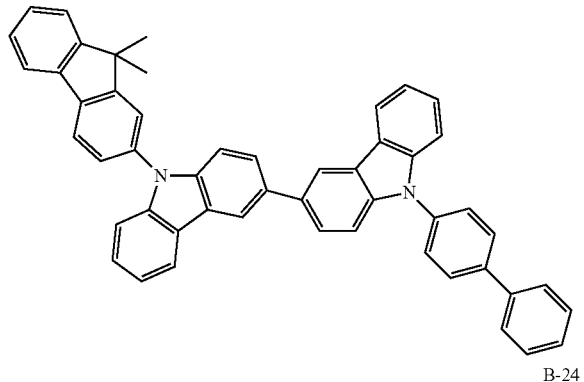
B-24
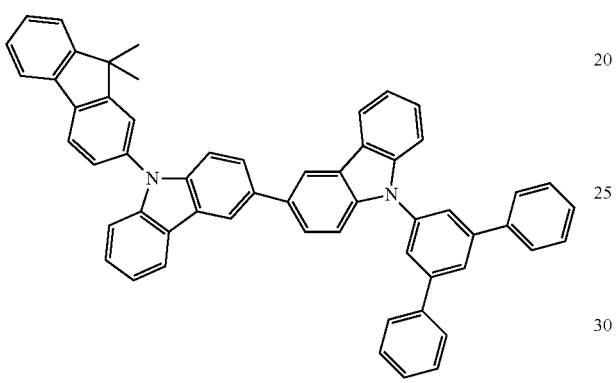
B-25
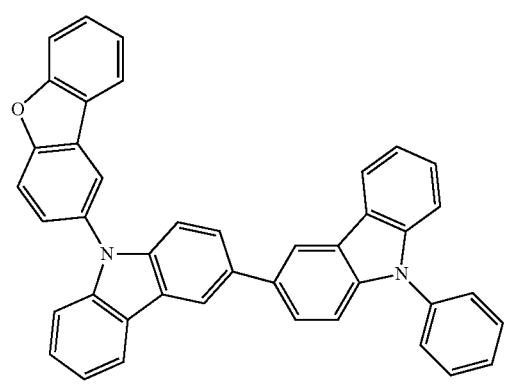
B-26
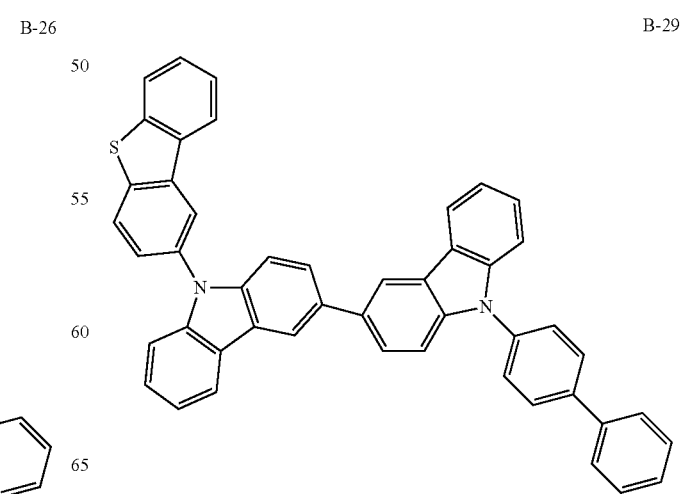
B-27
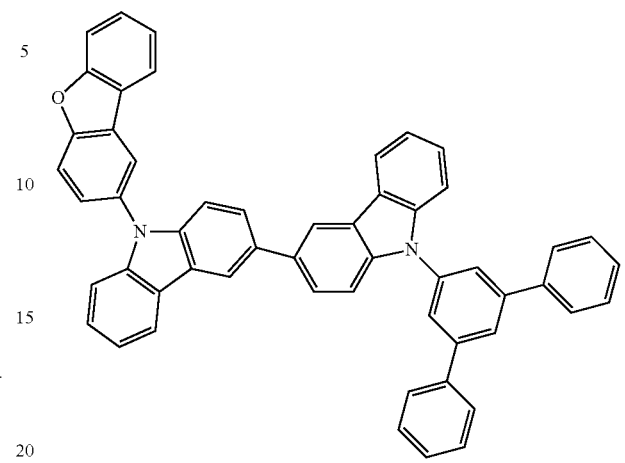
B-28
B-29

-continued
B-30
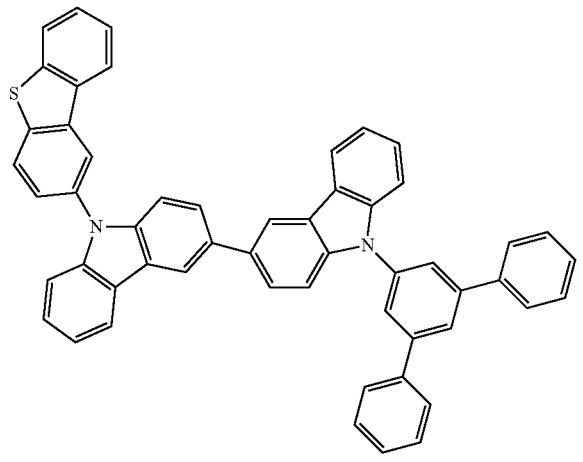
B-33
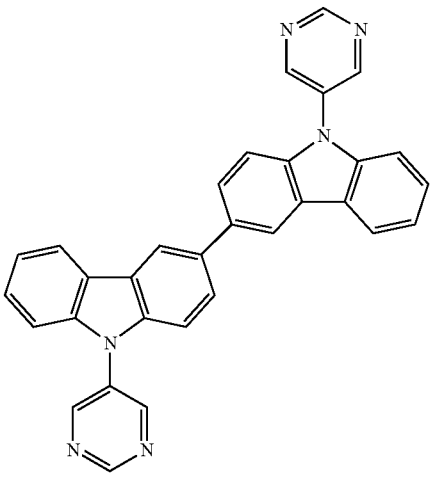
B-31
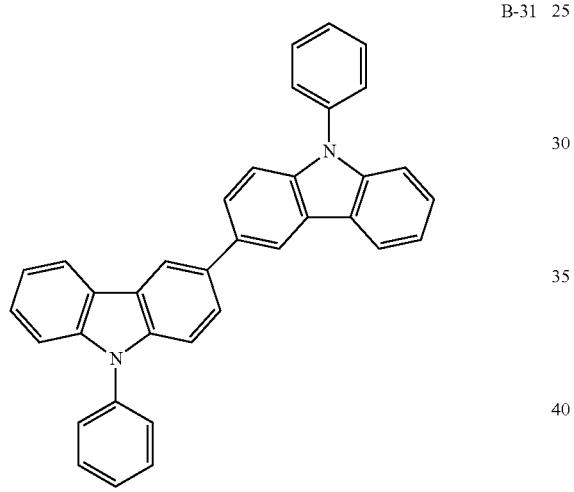
B-32
B-34
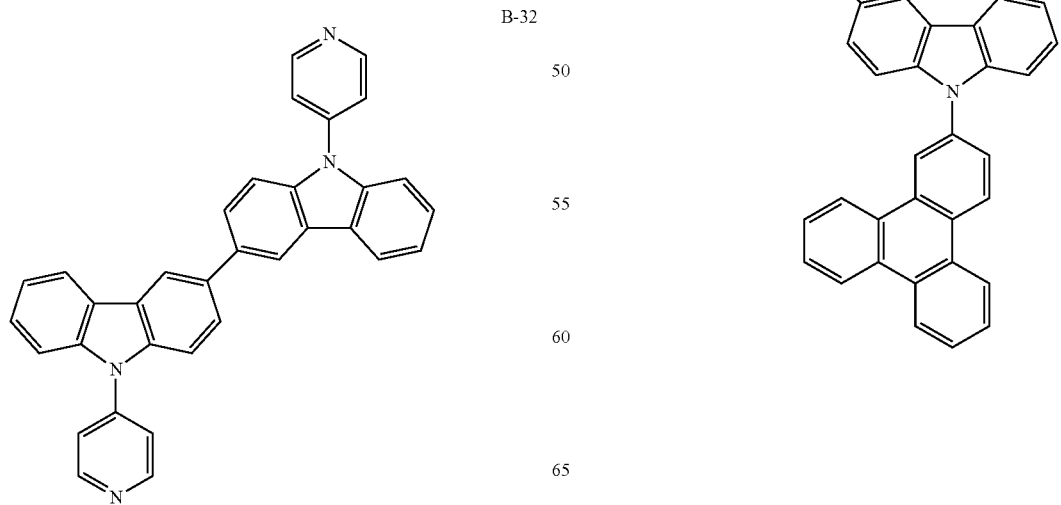

-continued
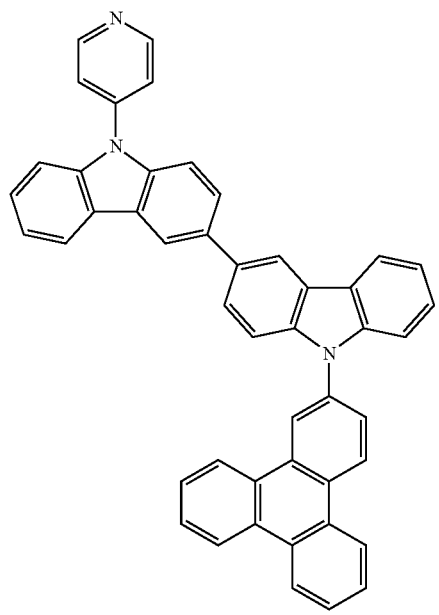
B-35
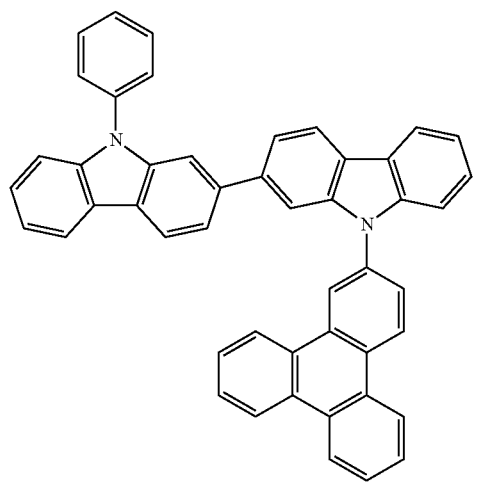
B-37
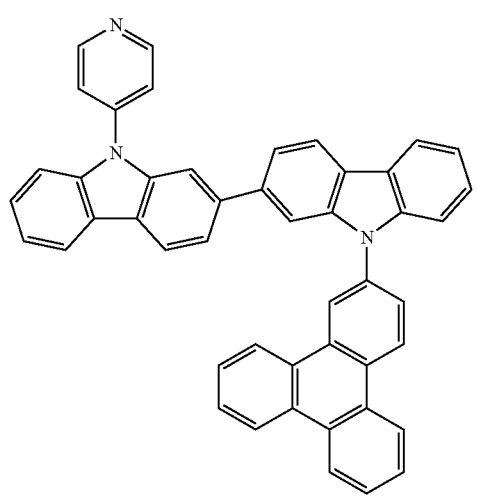
B-38
-continued
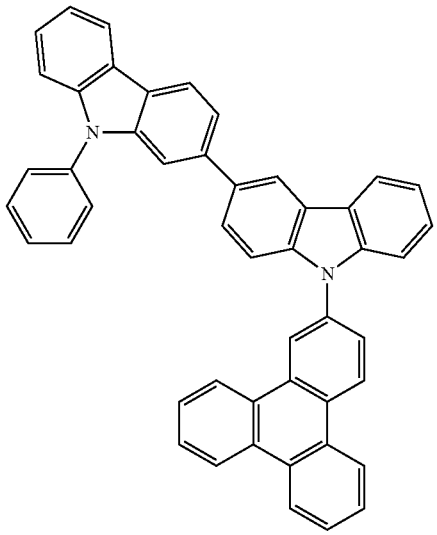
B-40
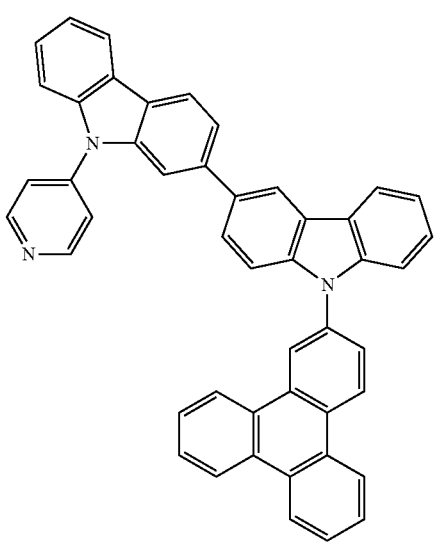
B-41

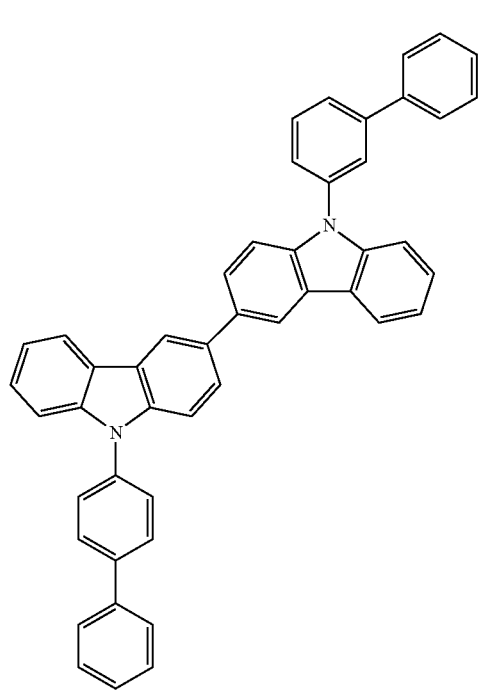
B-43
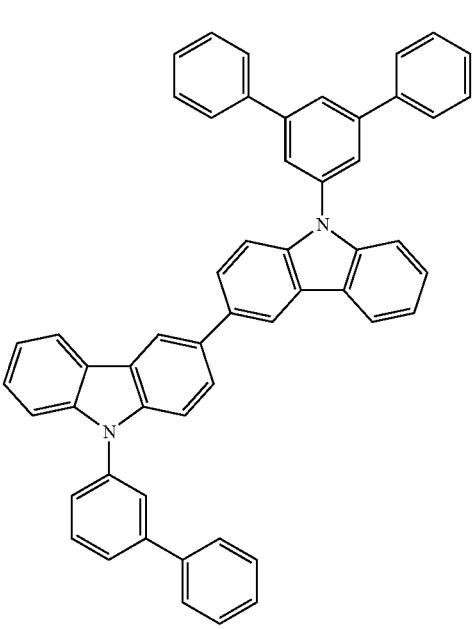
B-45
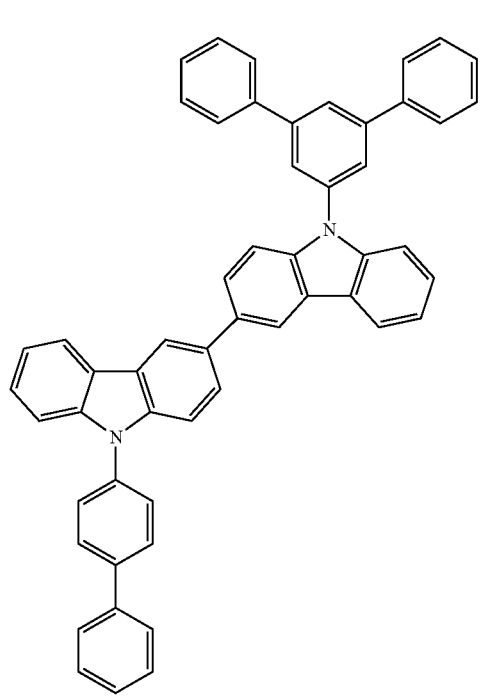
B-44
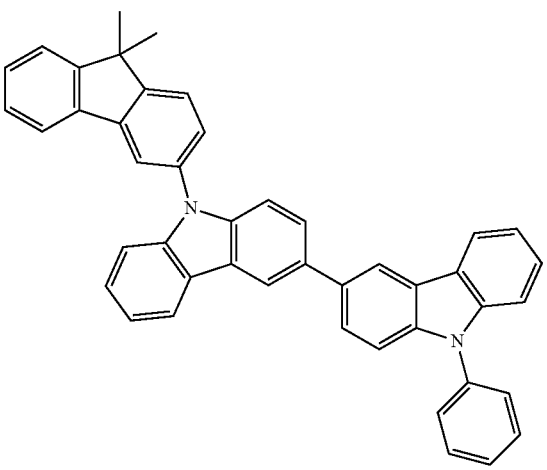
B-46

-continued
B47
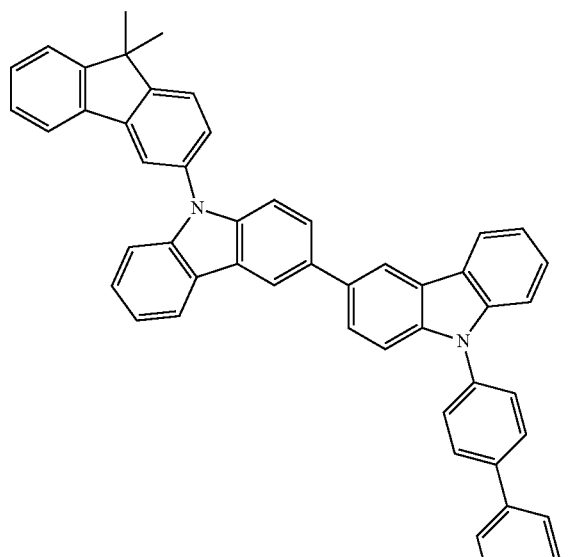
B-48
B-49
-continued
B-50
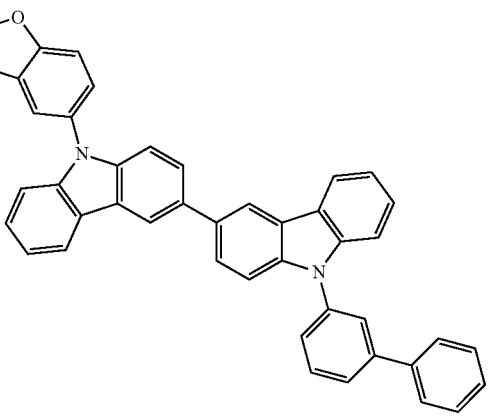
B-51
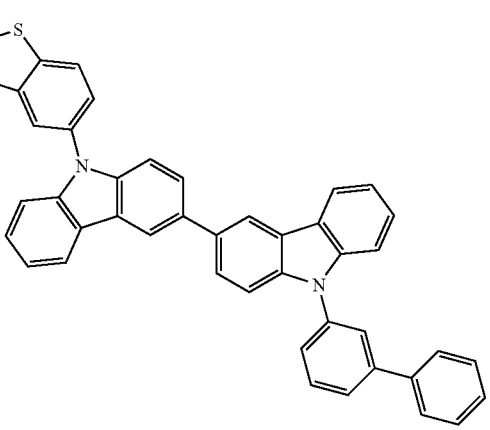
B-52
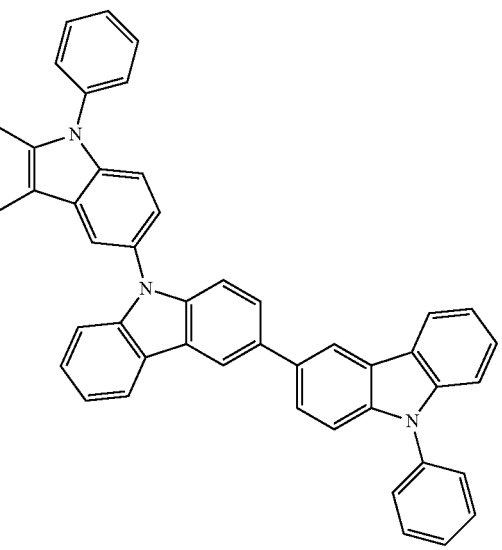

-continued
B-53
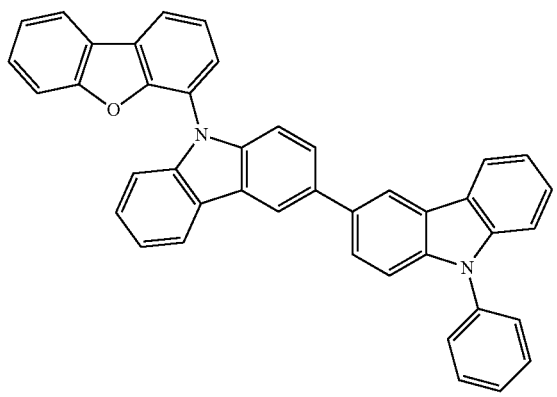
B-54
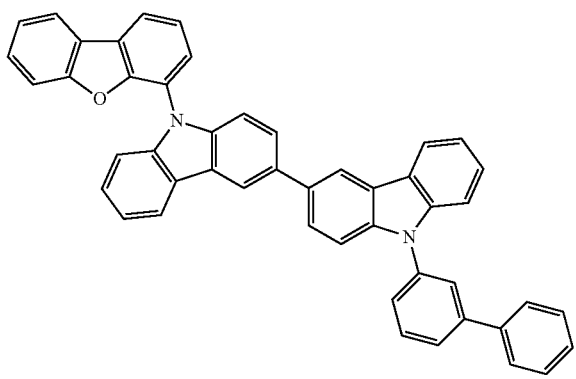
B-55
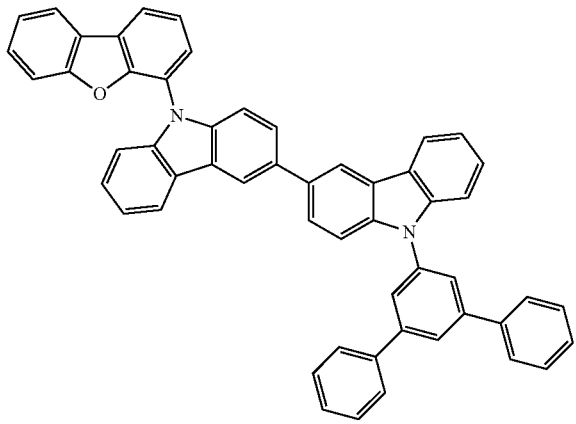
-continued
B-56
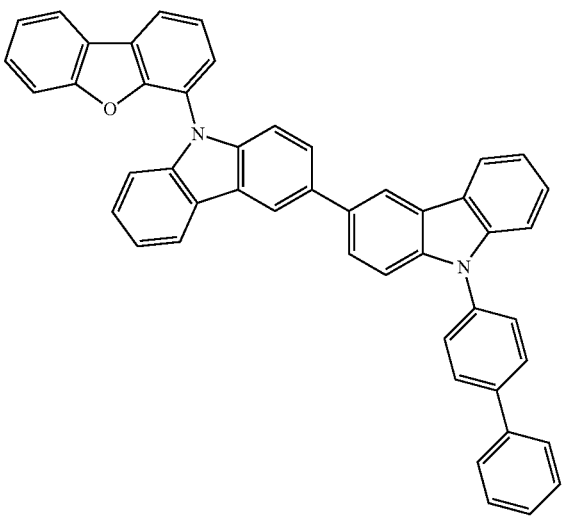
B-57
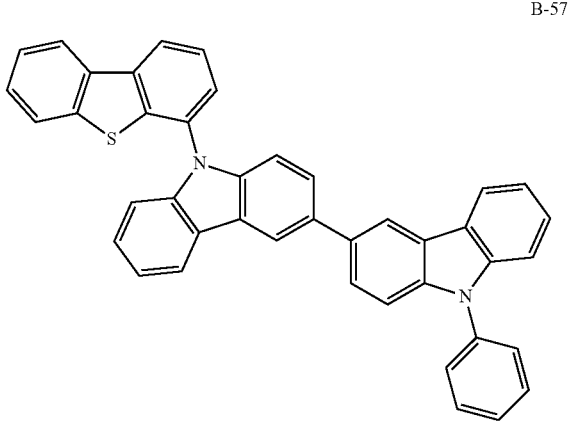
B-58
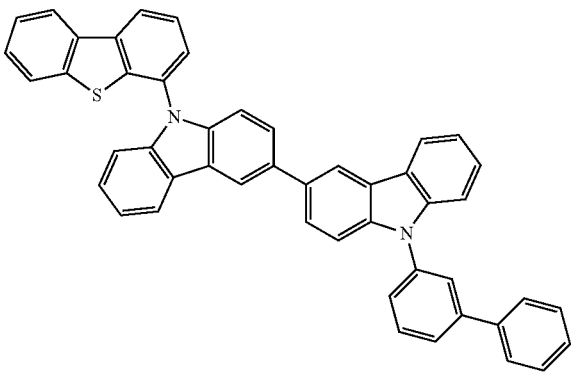

B-59
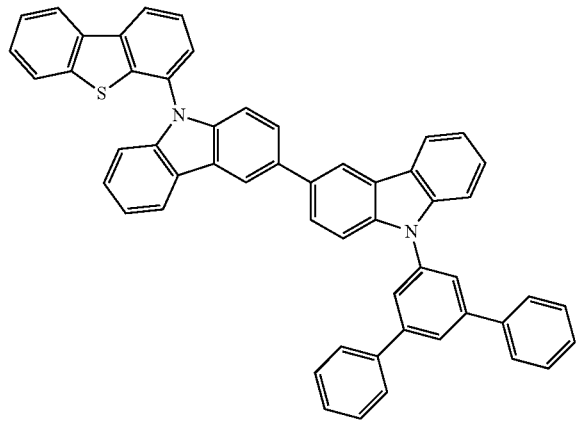
B-60
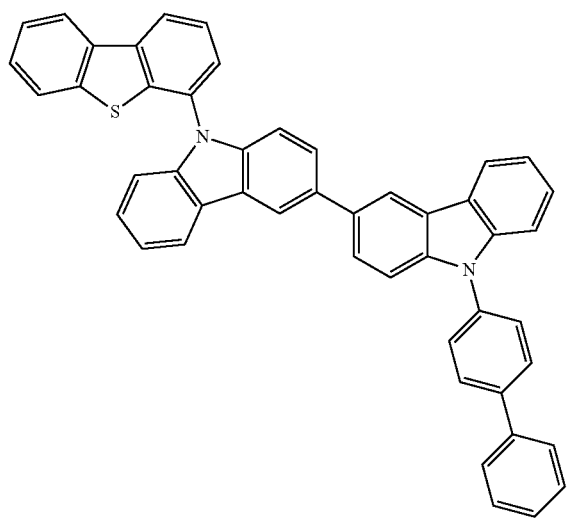
B-62
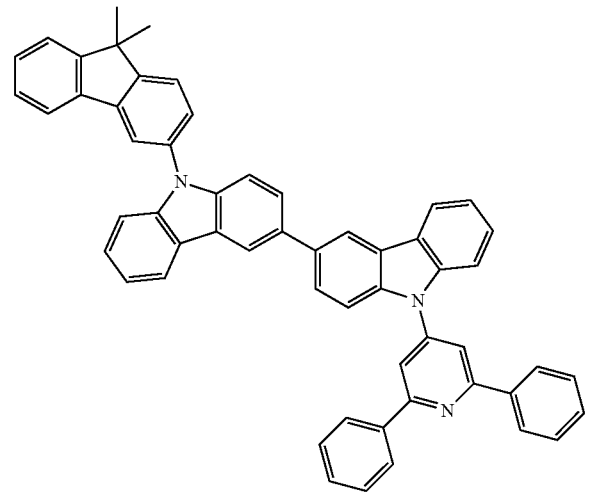
B-63
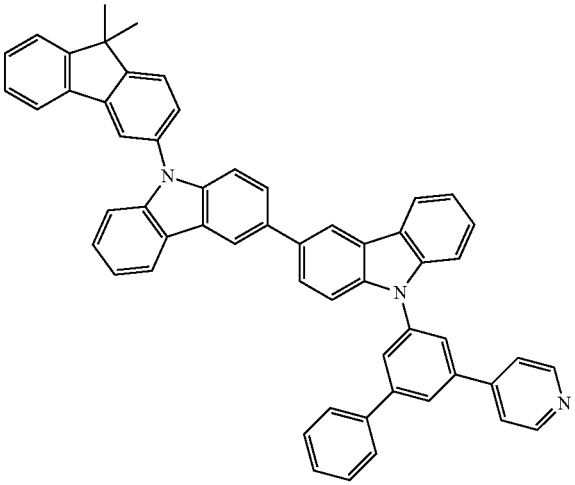
B-61
B-64
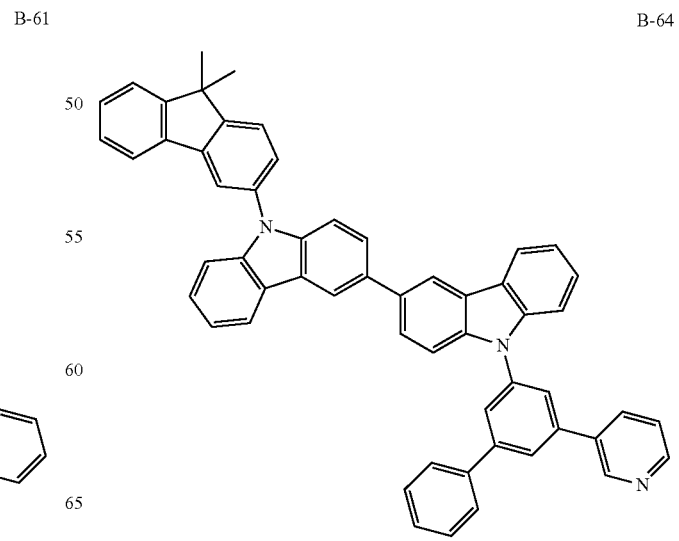

B-65
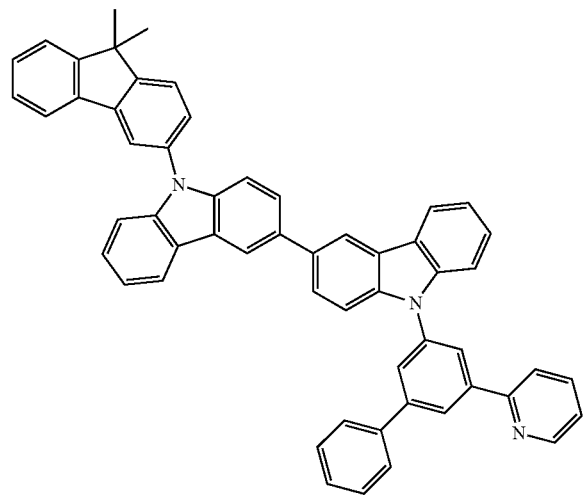
B-68
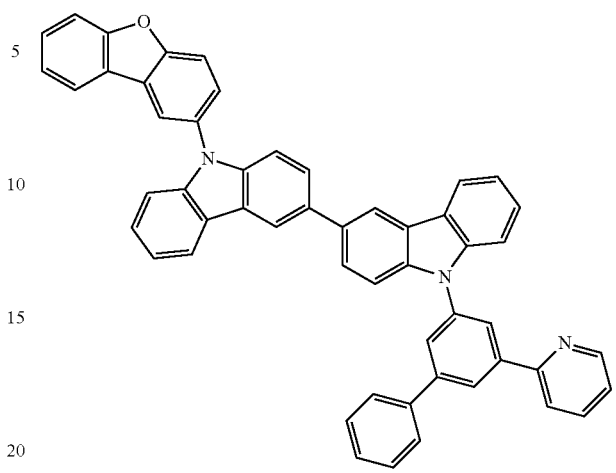
B-66
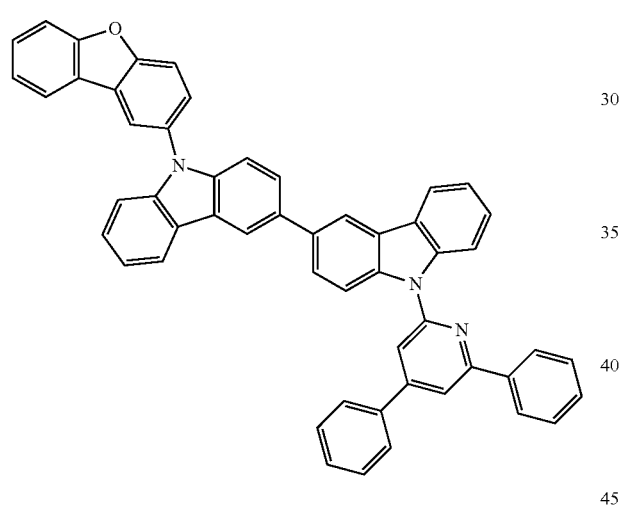
B-69
B-67
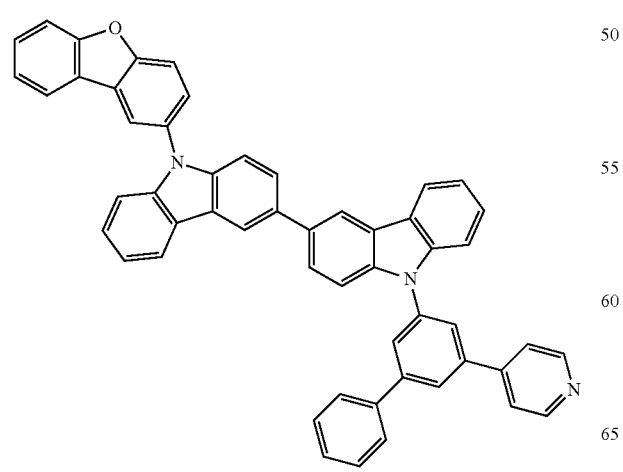
B-70
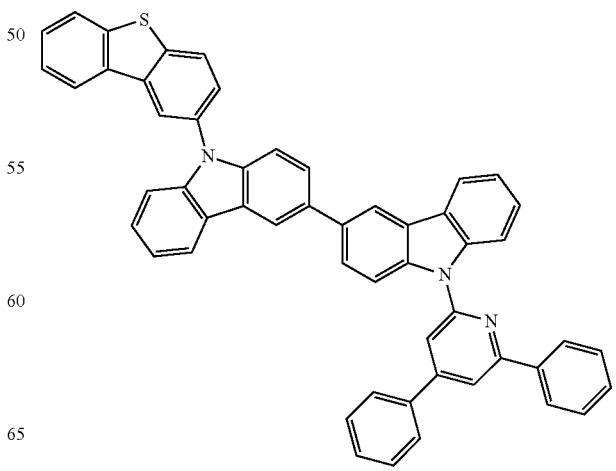

B-71
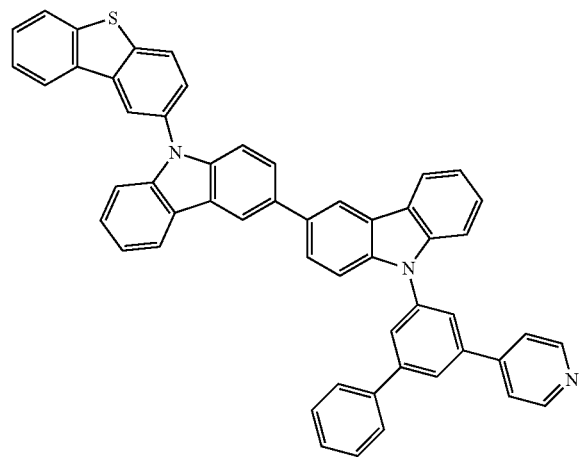
B-72
B-73
B-74
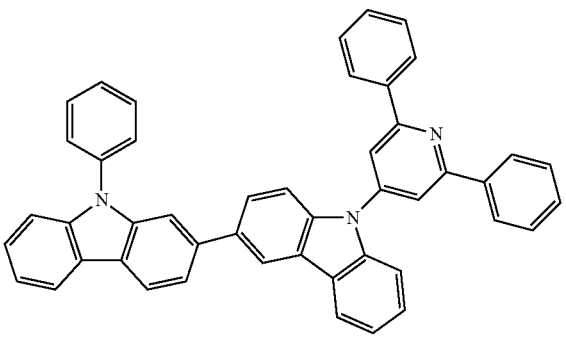
B-75
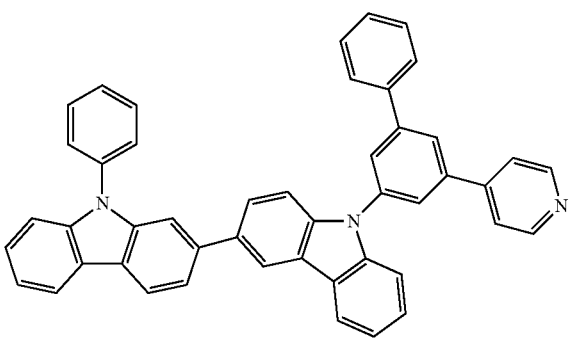
B-76
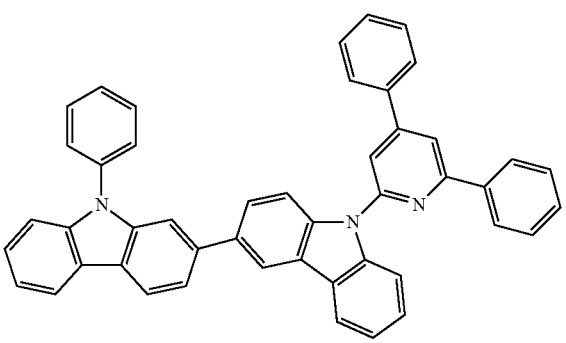
B-77
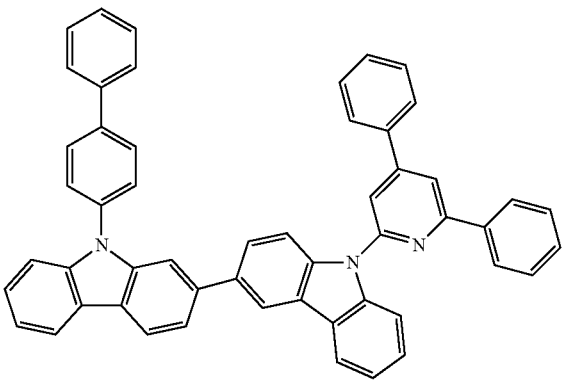

B-78
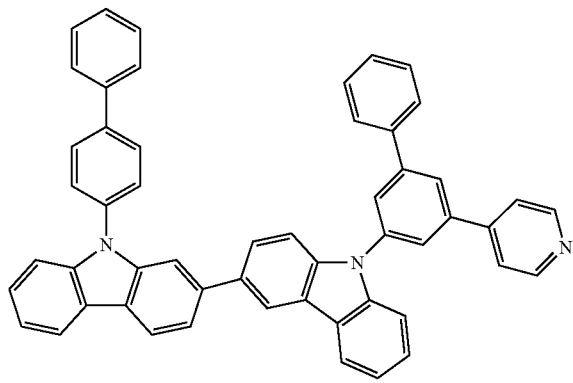
B-79
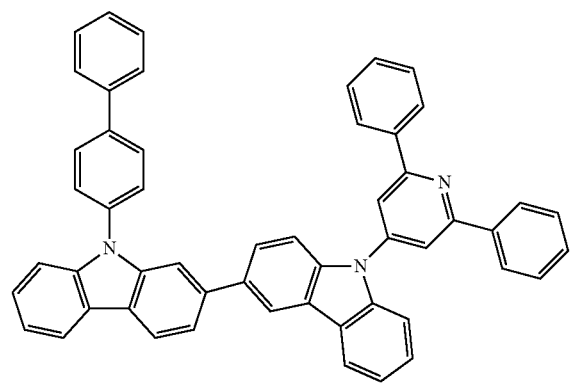
B-80
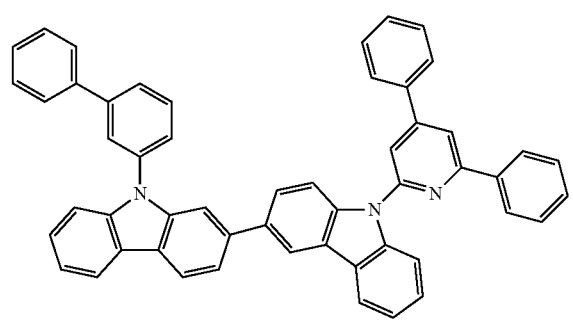
B-81
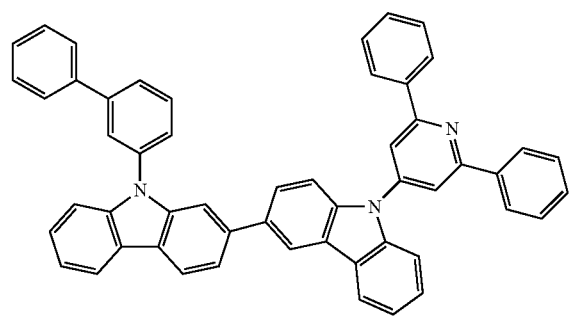
B-82
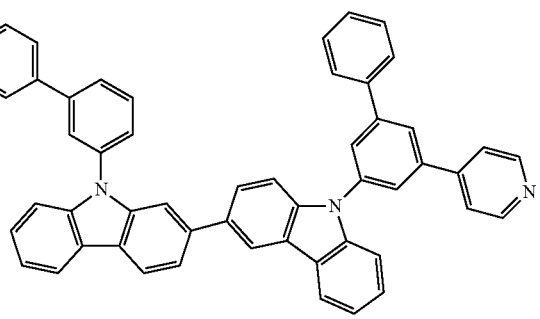
B-83
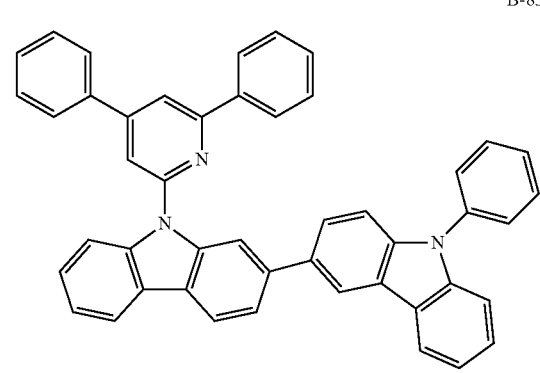
B-84
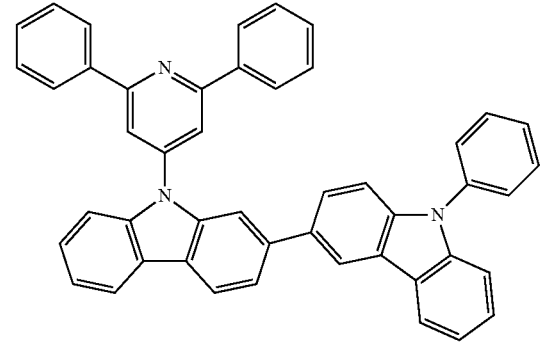
B-85
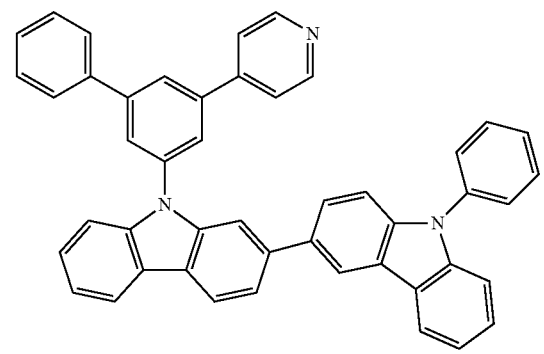

B-86
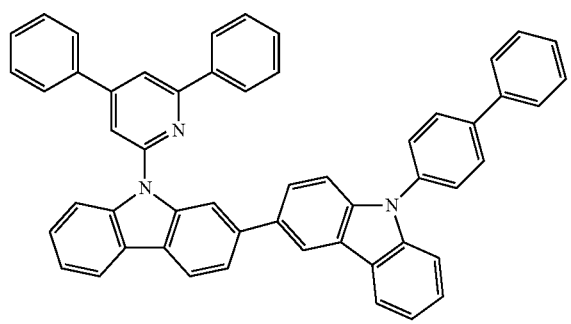
B-87
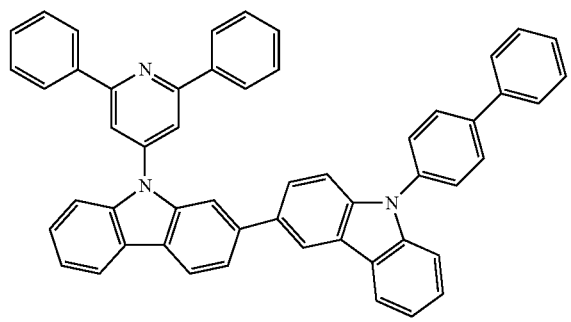
B-88
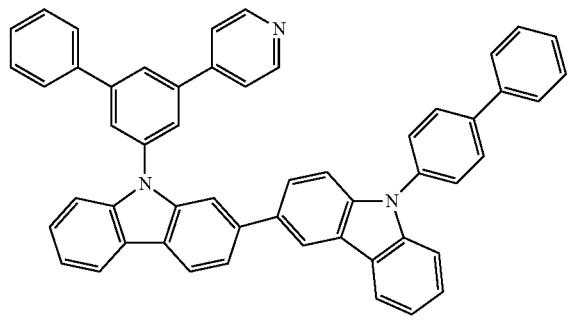
B-89
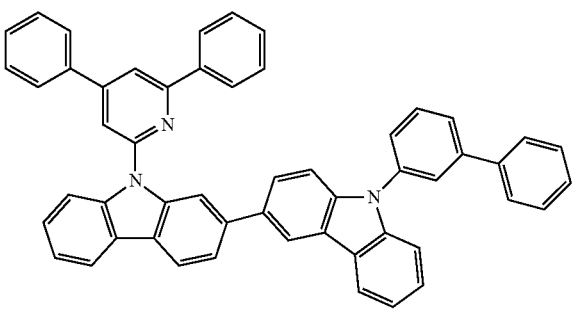
B-90
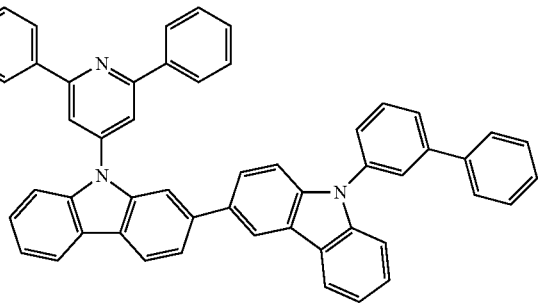
B-91
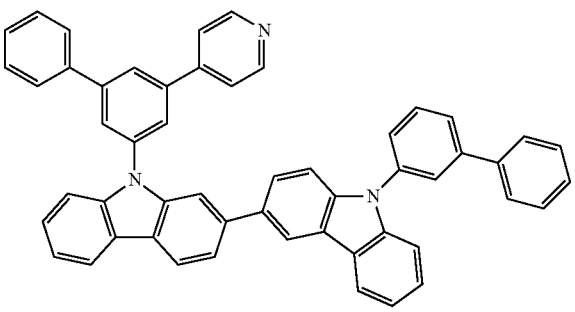
B-92
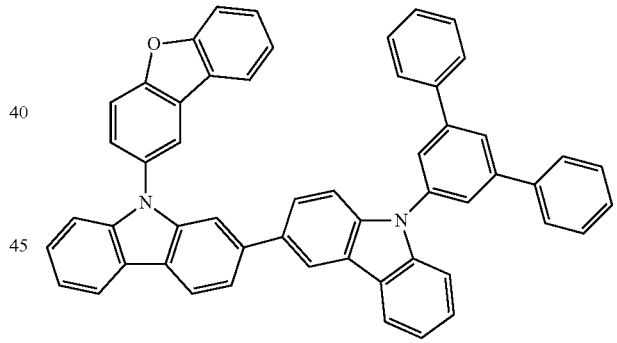
B-93
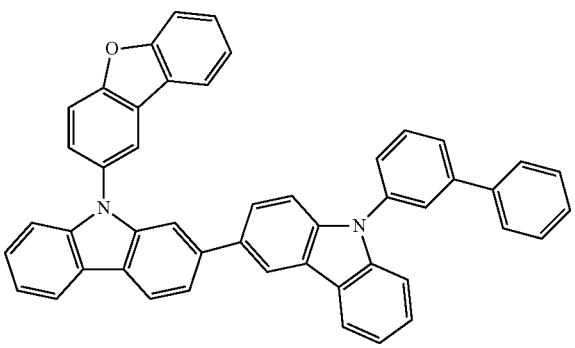

B-94
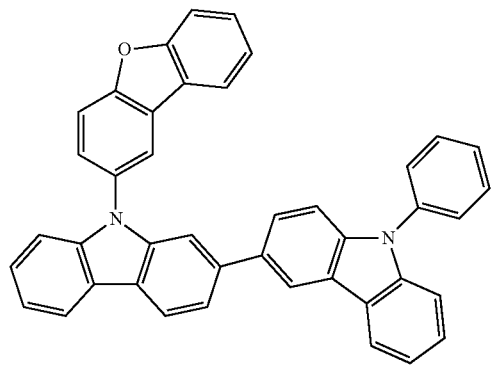
B-95
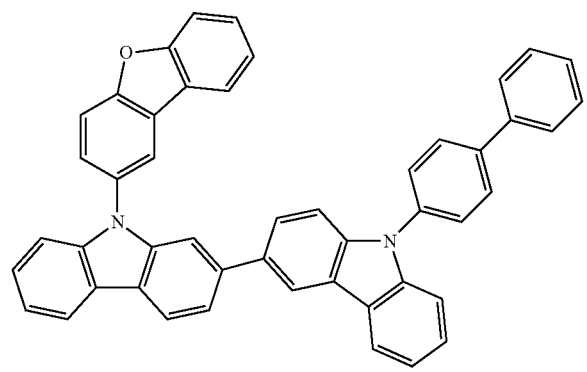
B-96
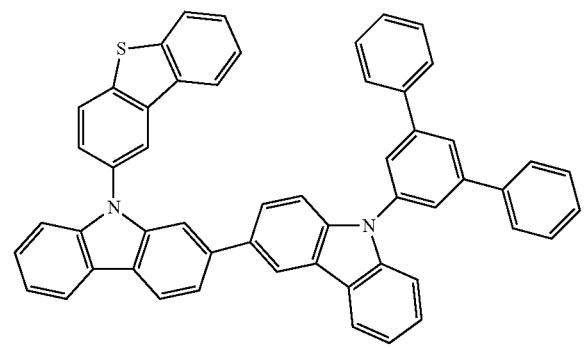
B-97
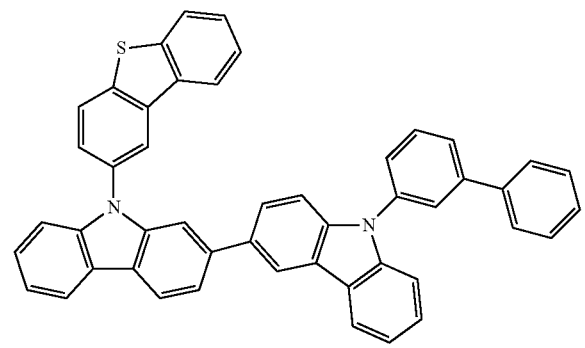
B-98
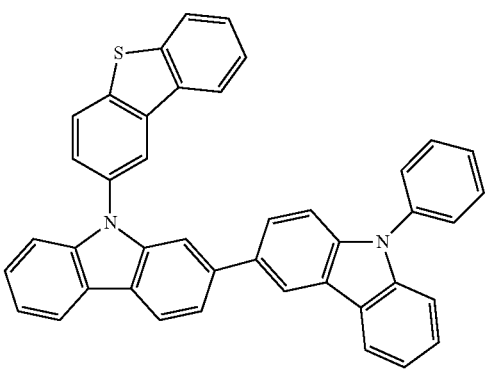
B-99
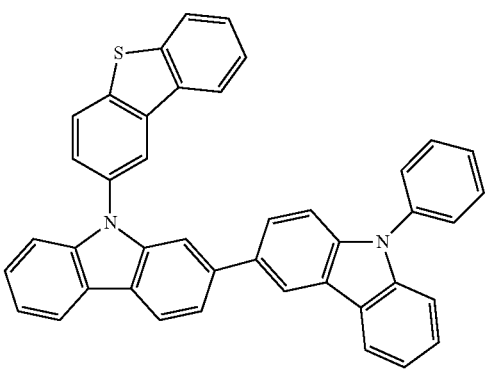
B-100
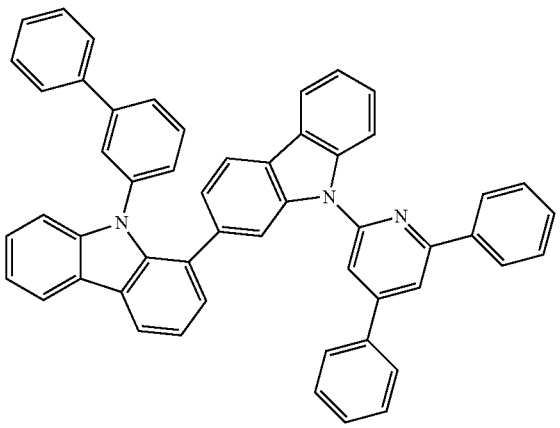
B-101
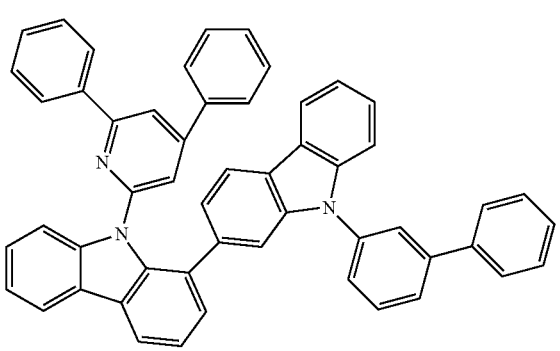

B-102
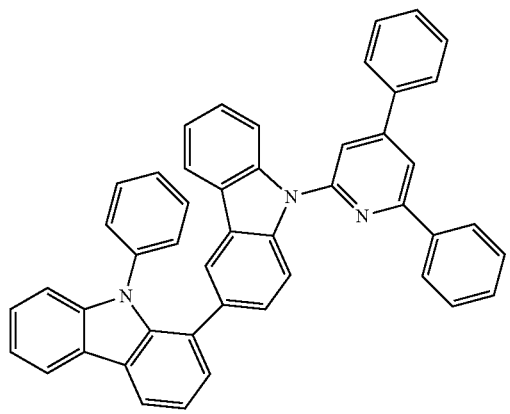
B-103
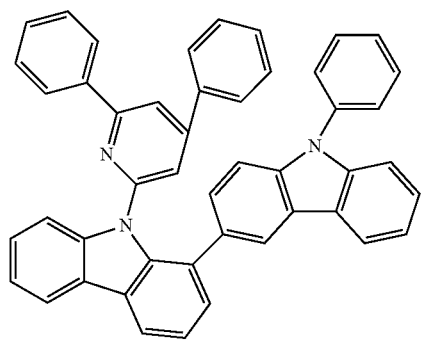
B-104
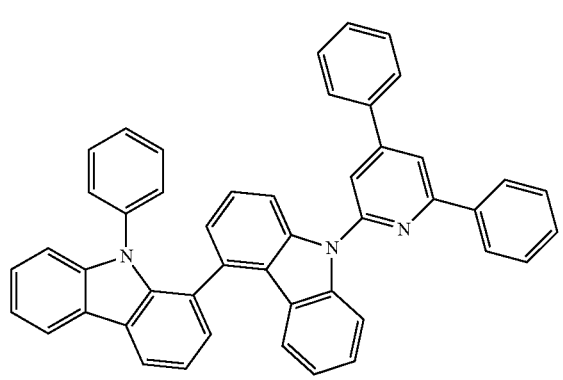
B-105
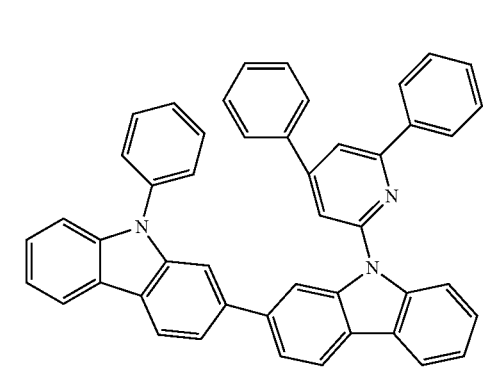
B-106
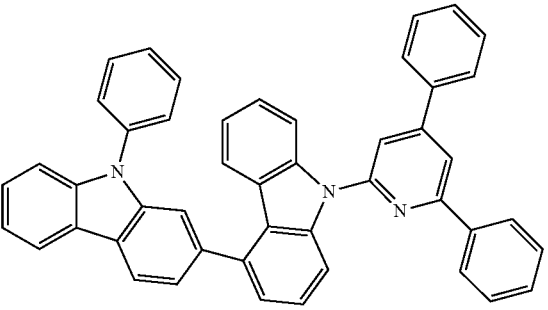
B-107
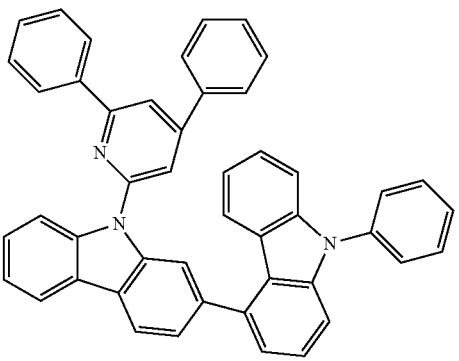
B-108
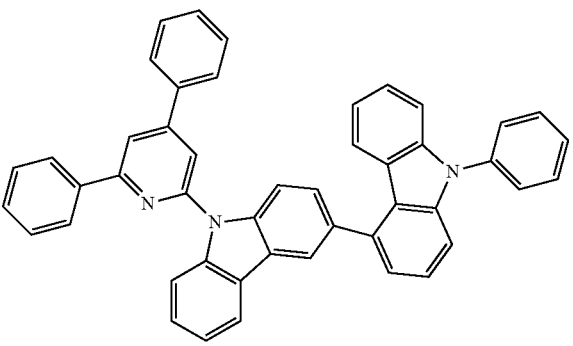
B-109
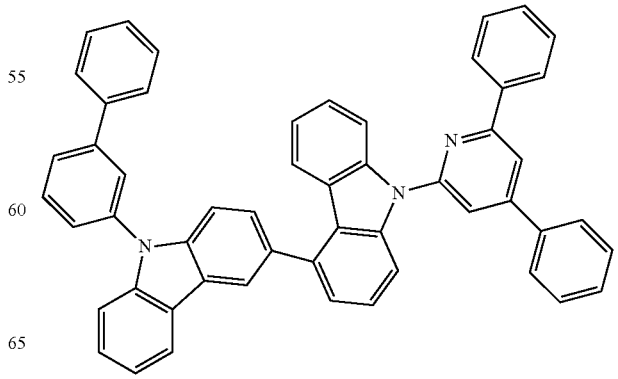

B-110
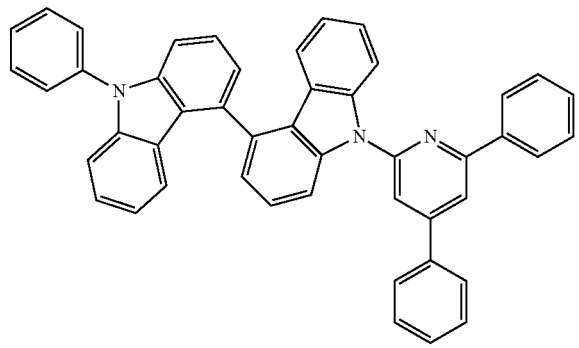
B-112
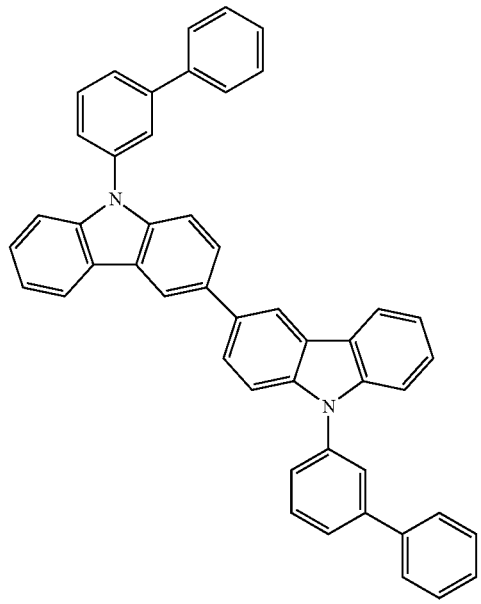
B-111
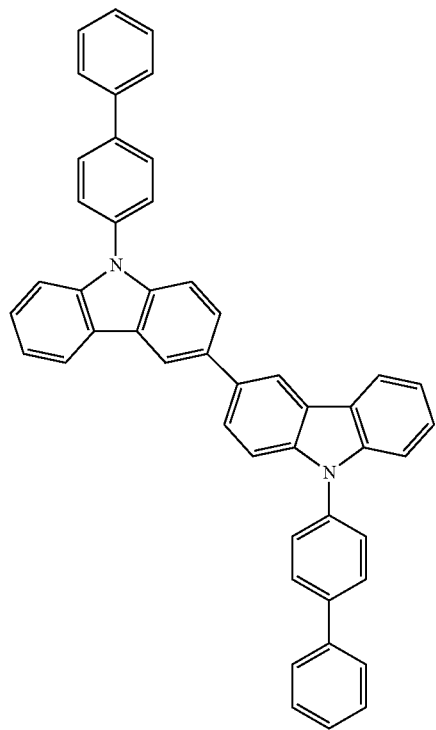
B-113
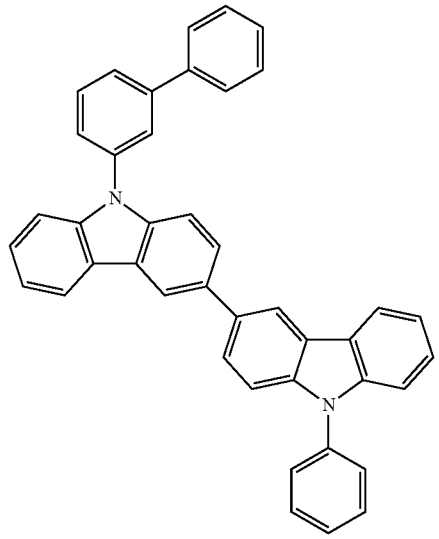

B-114
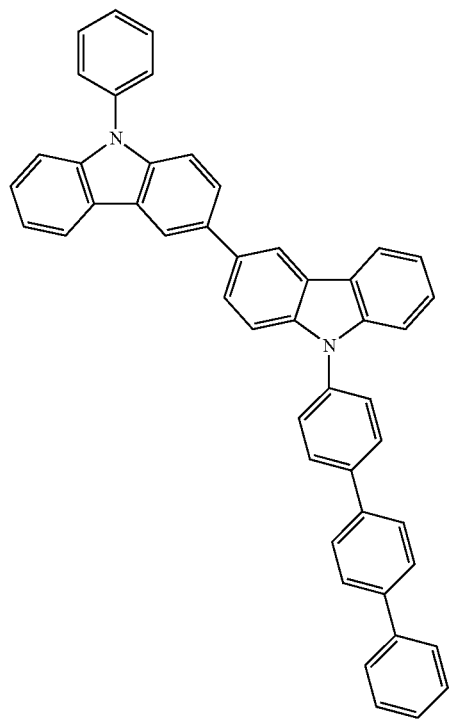
B-116
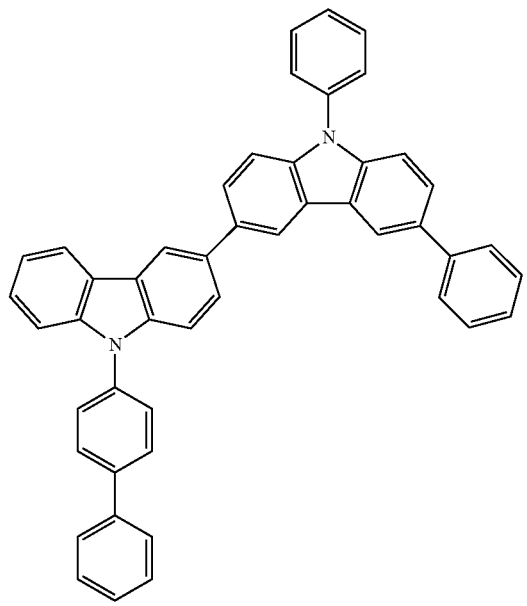
B-115
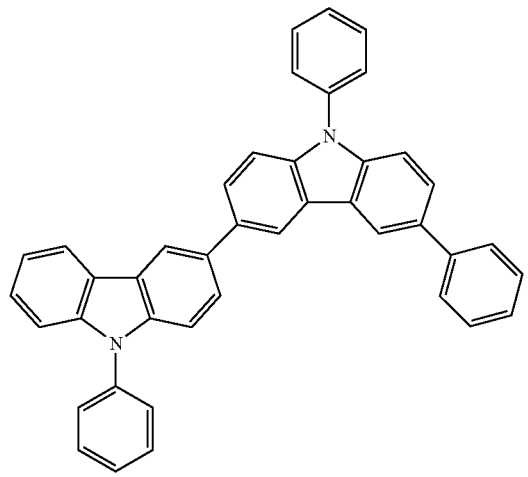
B-117
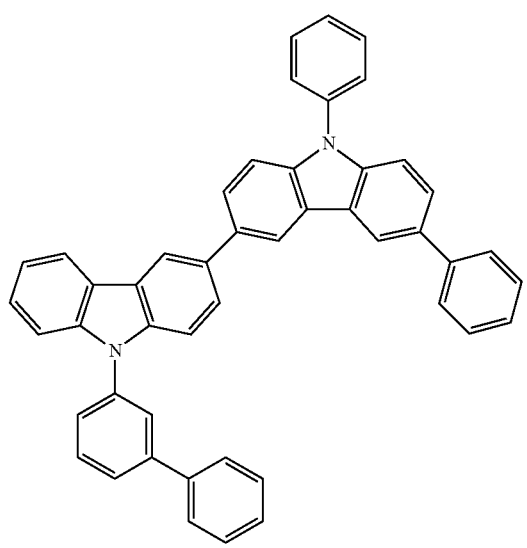

B-118
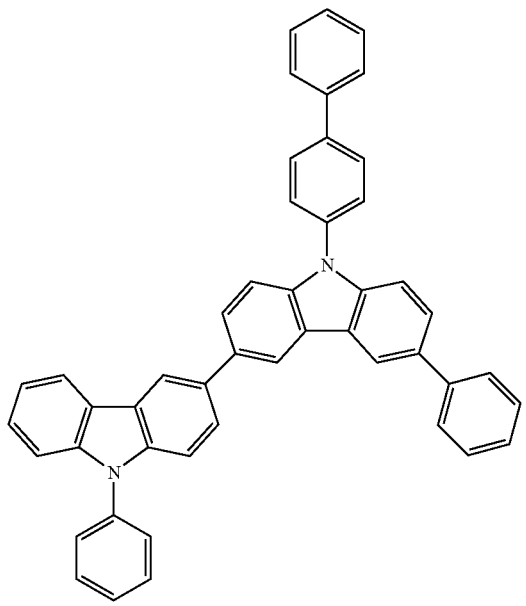
B-119
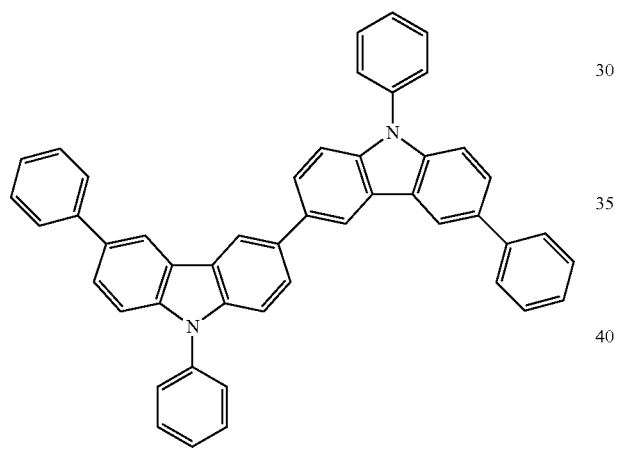
B-120
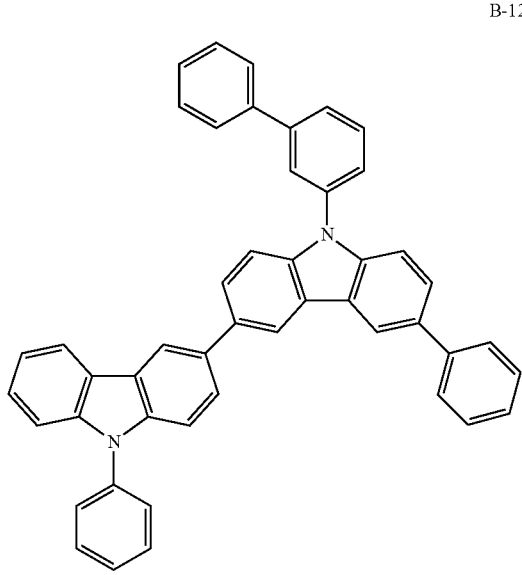
B-121
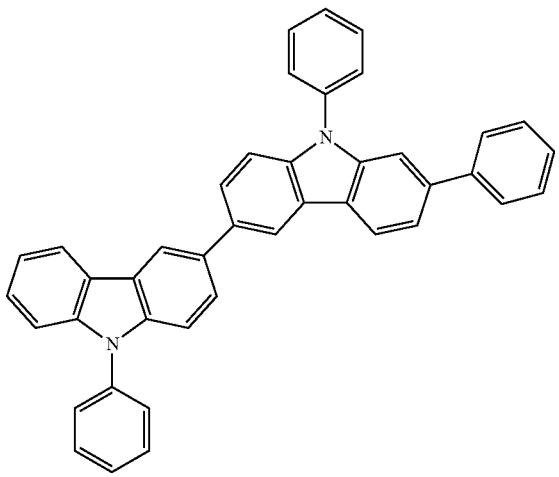
B-122
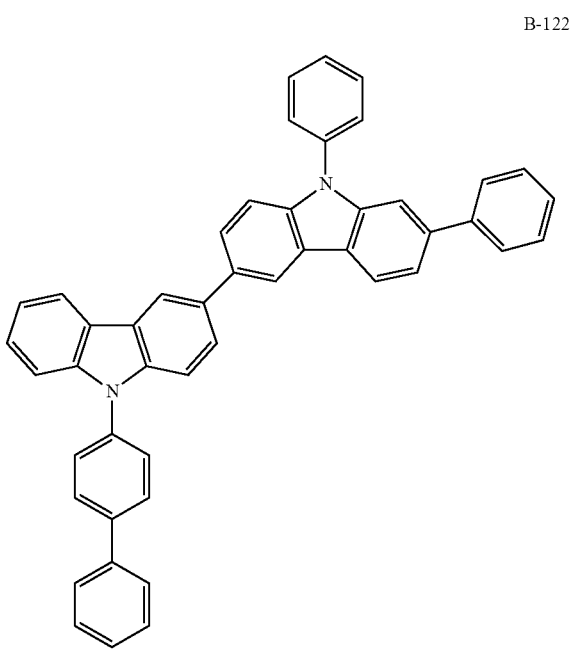

-continued
B-123
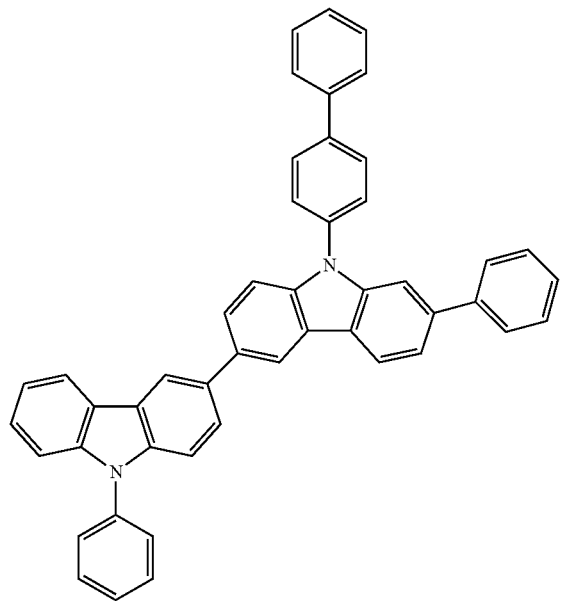
B-124
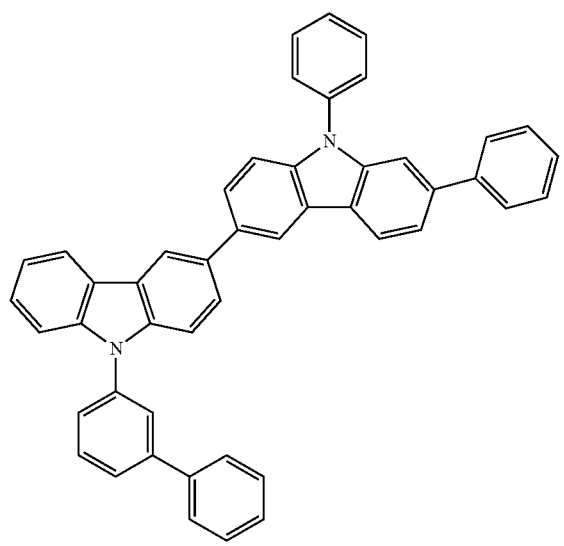
B-125
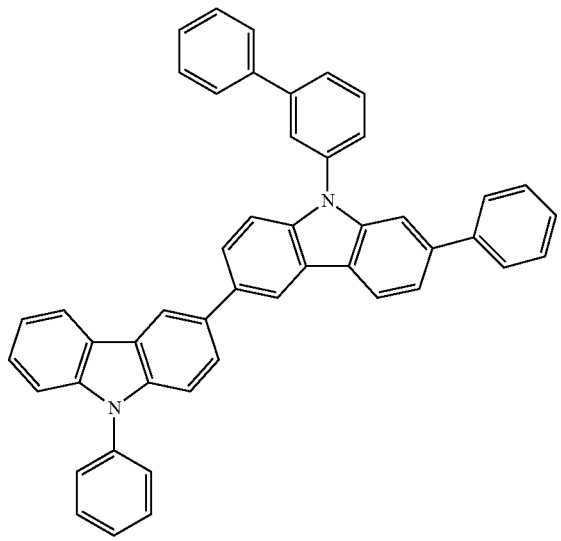
C-10
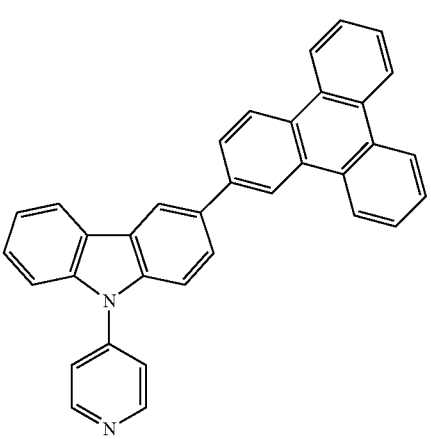
C-11

C-12
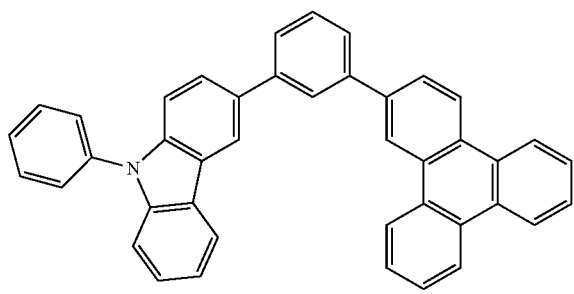
C-13
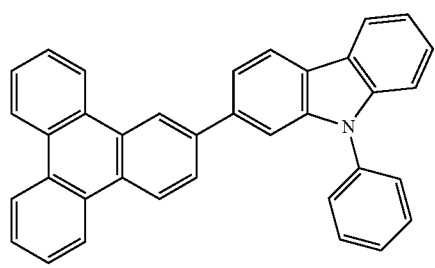
C-14
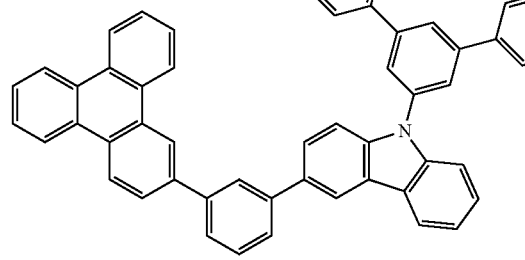
C-15
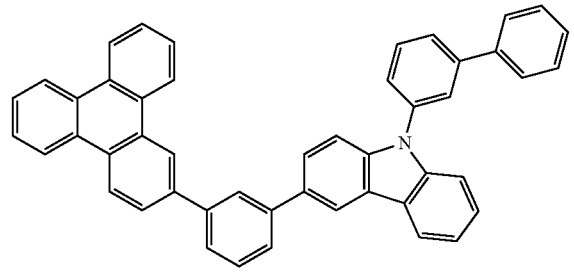
C-16
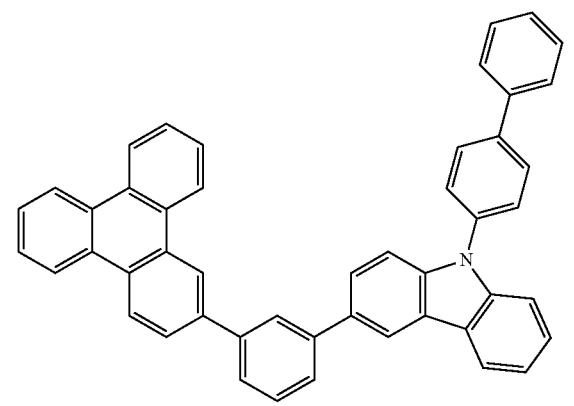
C-17
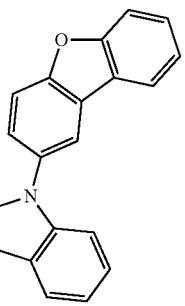
C-18
C-19
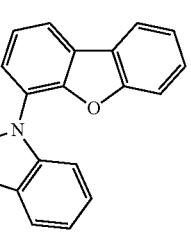
C-20
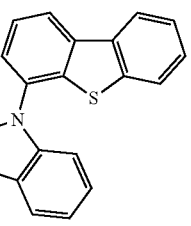

C-21
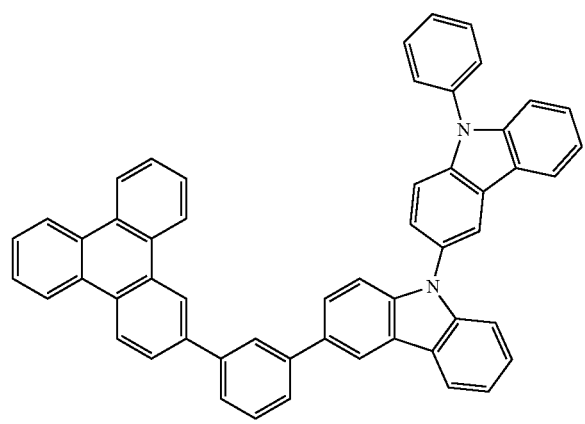
C-22
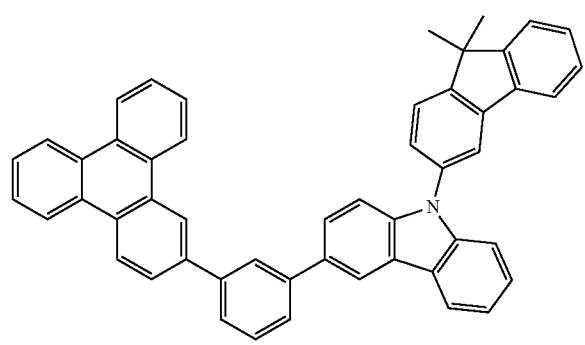
C-23
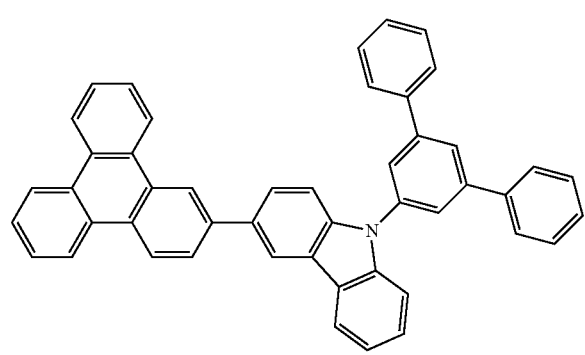
C-24
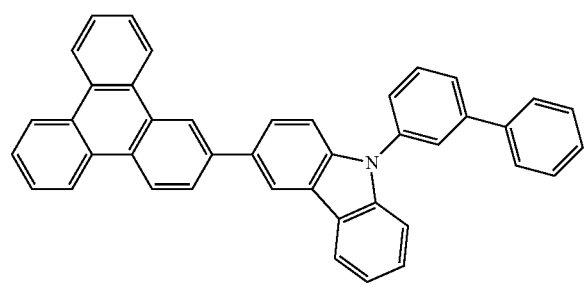
C-25
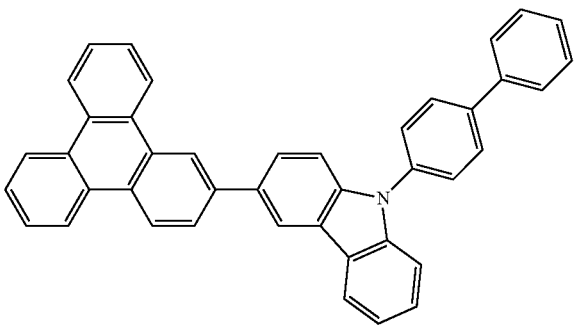
C-26
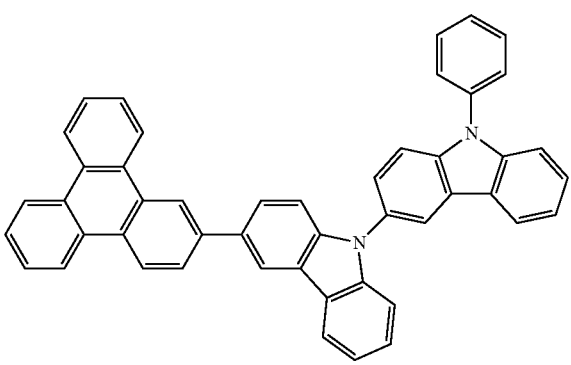
C-27
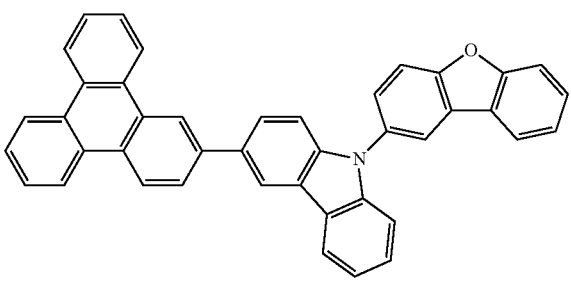
C-28
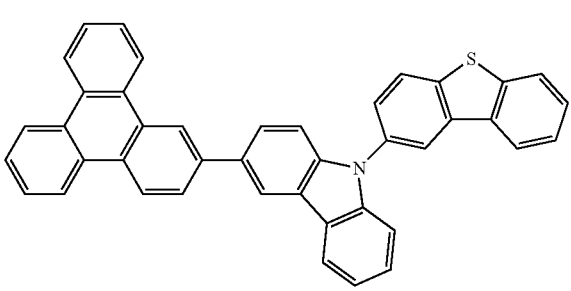
C-29
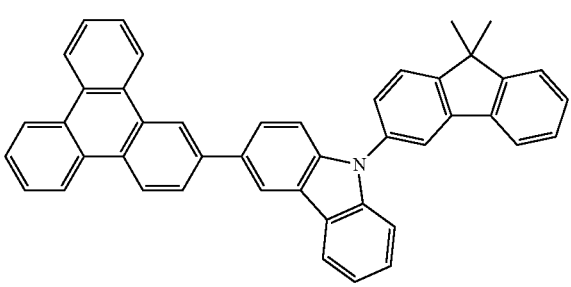

C-30
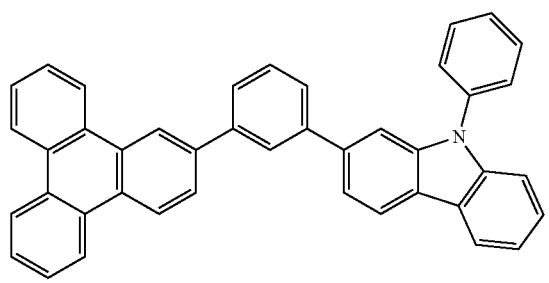
C-31
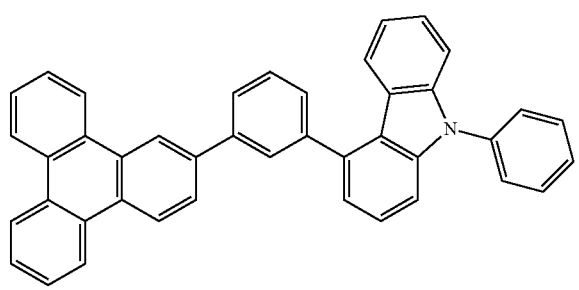
C-32
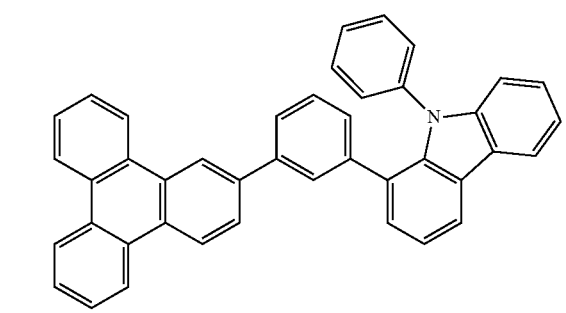
C-33
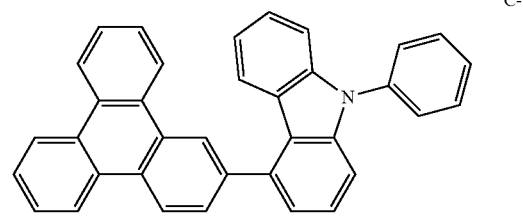
D-10
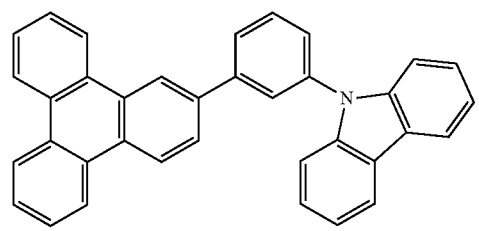
D-11
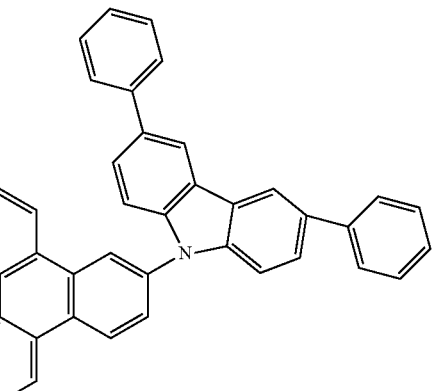
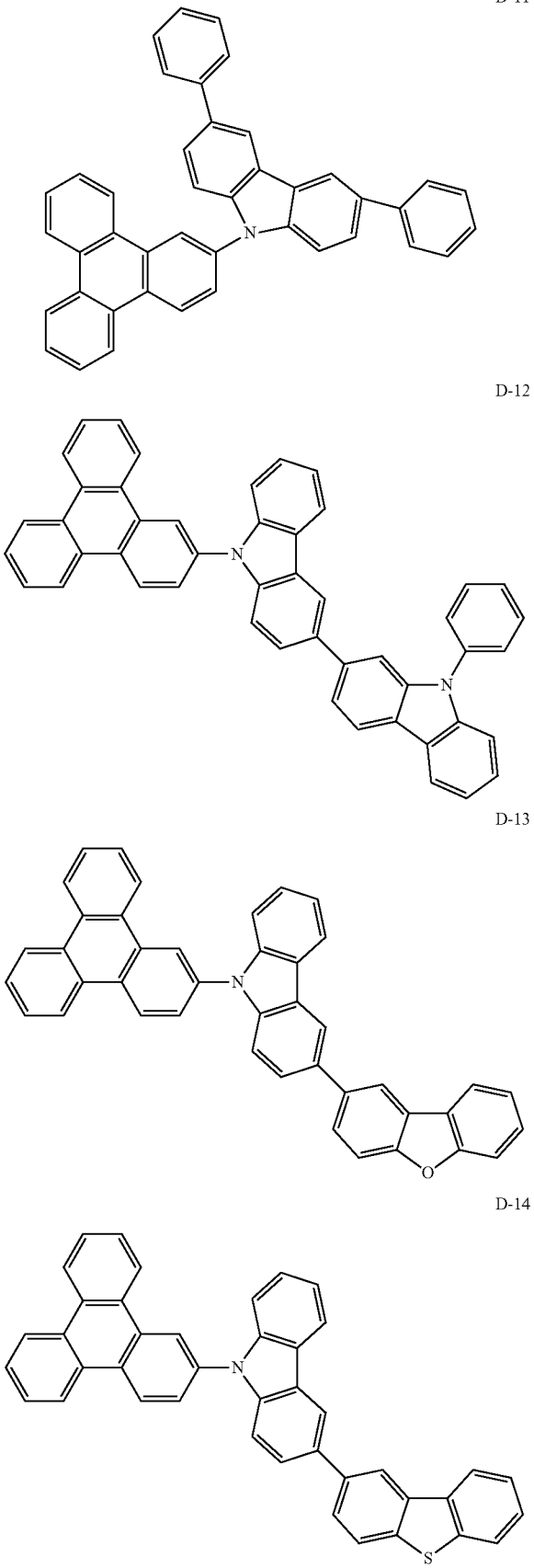

D-15
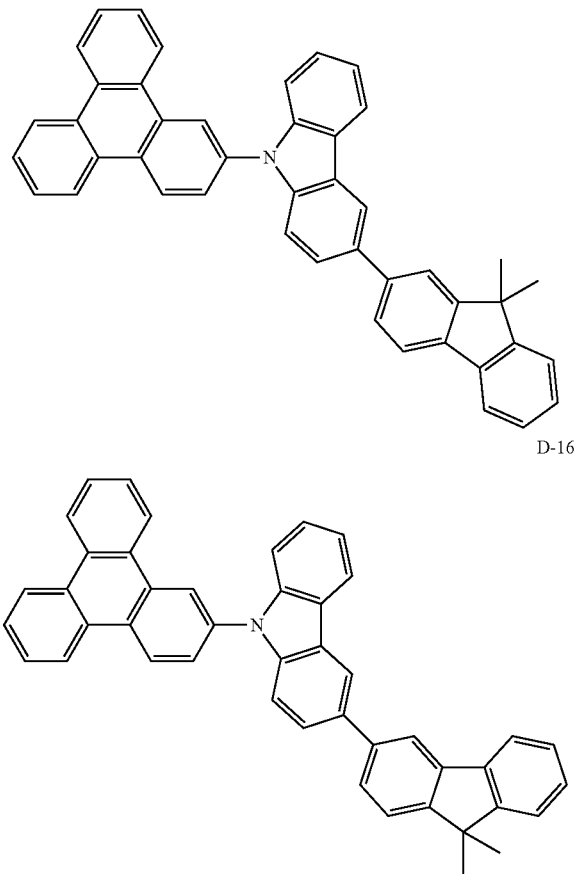
D-16
D-17
D-18
D-19
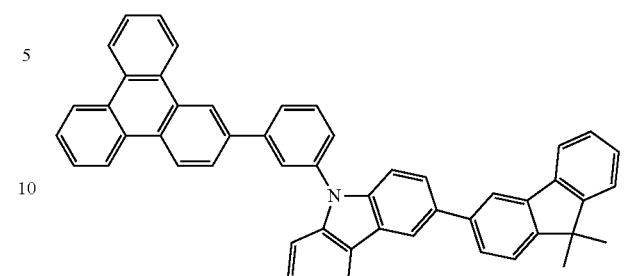
D-20
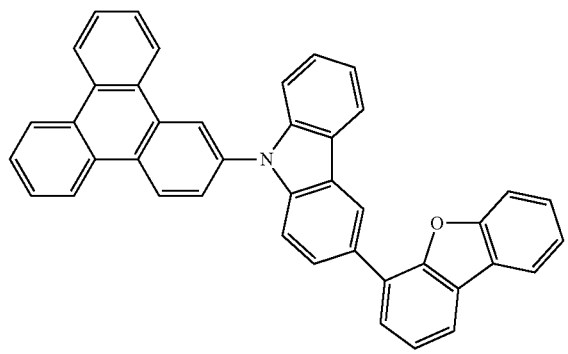
D-21
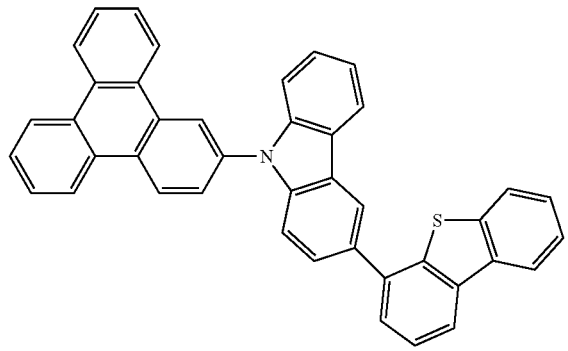
D-22
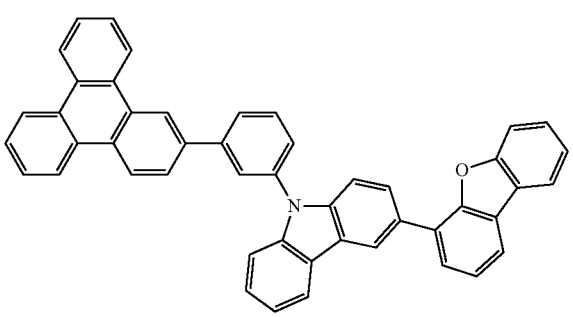

D-23
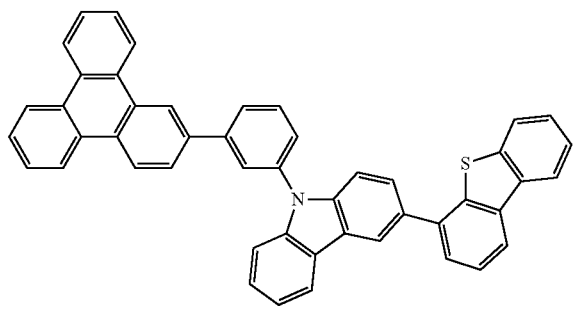
D-24
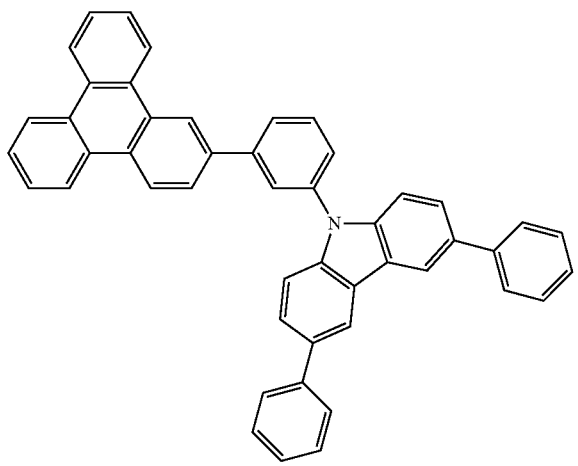
D-25
D-26
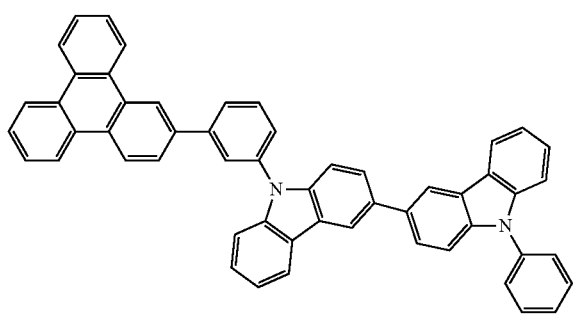
D-27
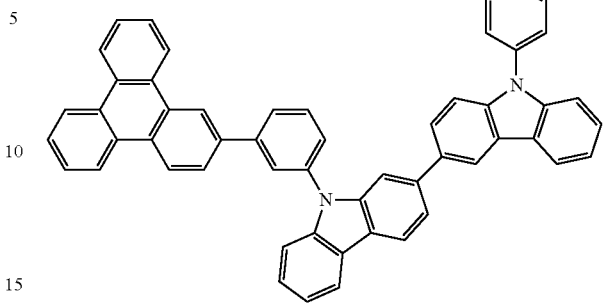
D-28
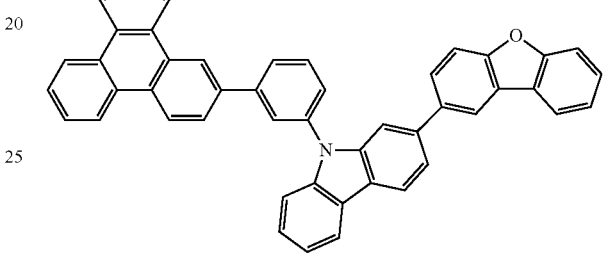
D-29
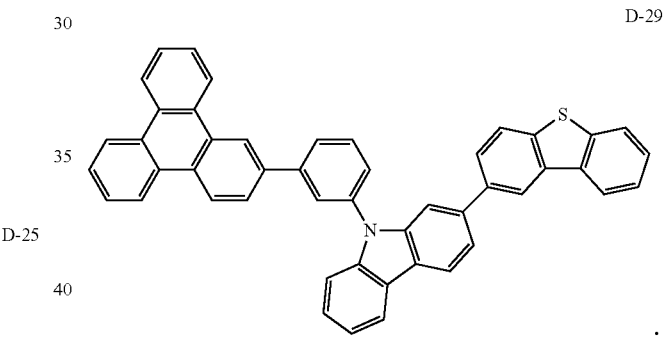
9. The organic optoelectronic device of claim 5, wherein the second organic compound consisting of the combination of the moiety represented by the Chemical Formula 9 and the moiety represented by the Chemical Formula 10 is one of compounds listed in the following Group 3:
[Group 3]
E-1
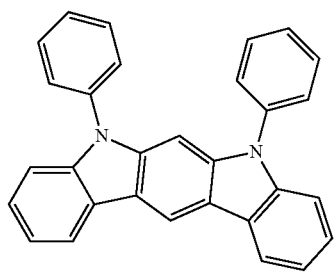

E-2
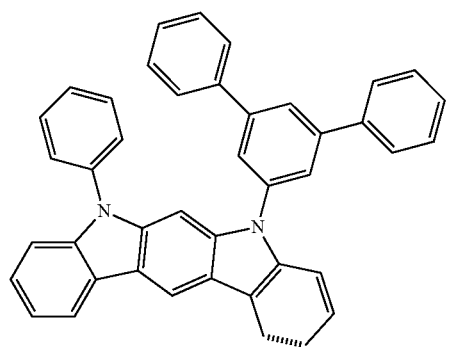
E-3
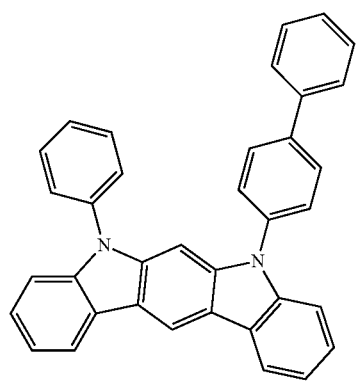
E-4
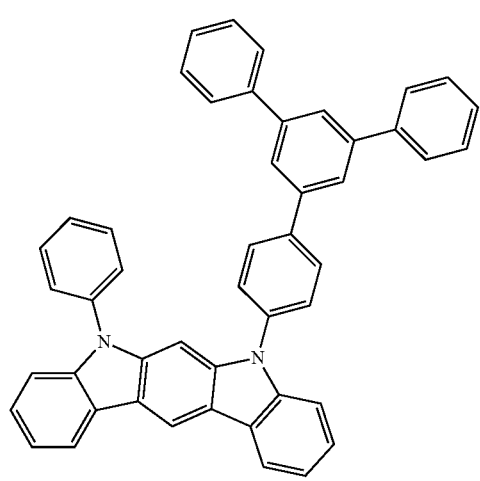
E-5
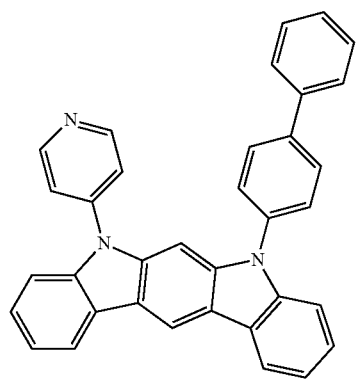
E-6
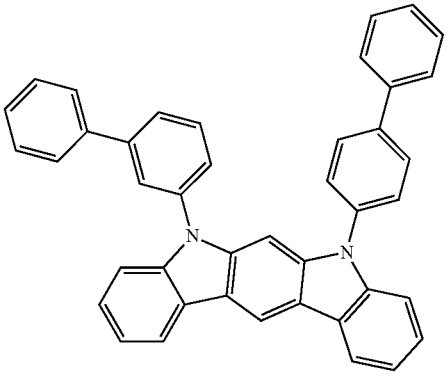
E-7
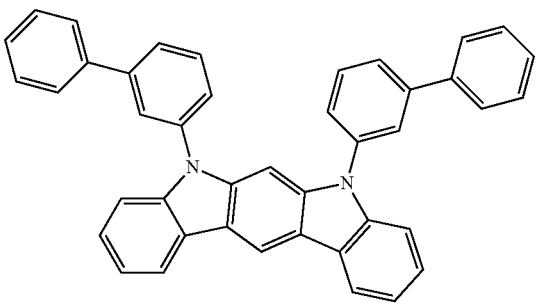
E-8
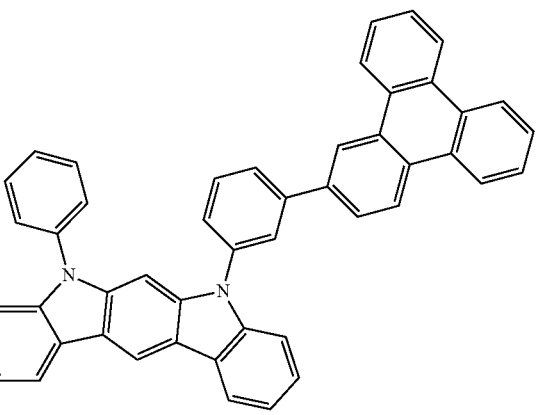
E-9
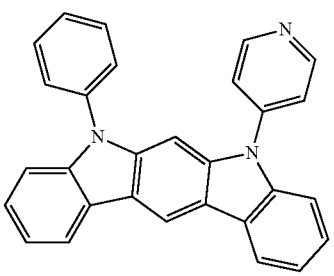

-continued
E-10
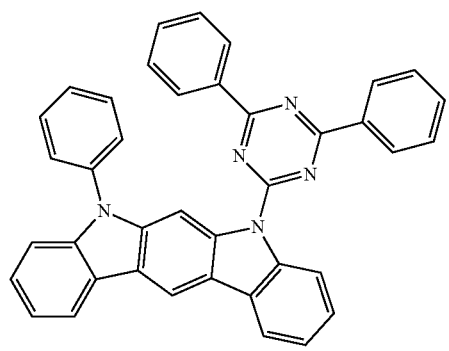
E-11
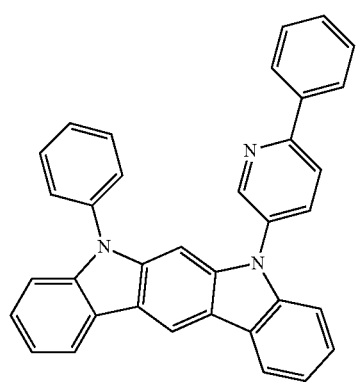
E-12
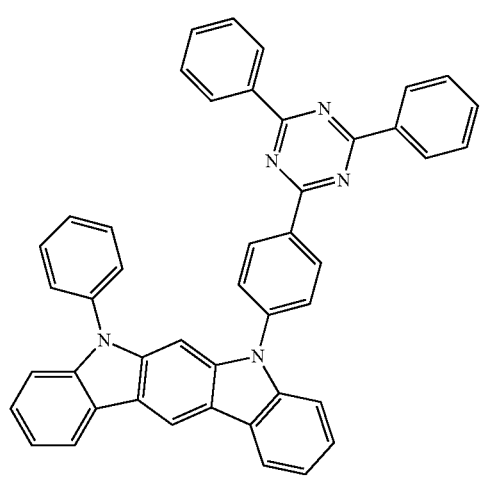
E-13
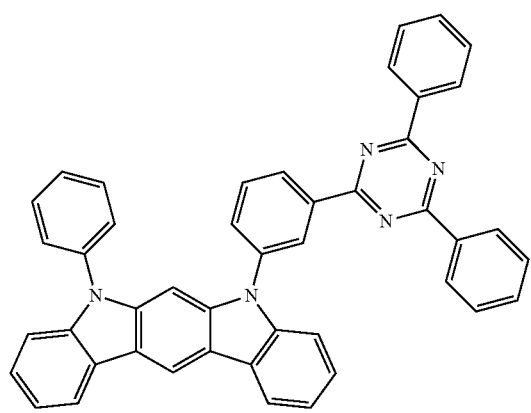
-continued
E-14
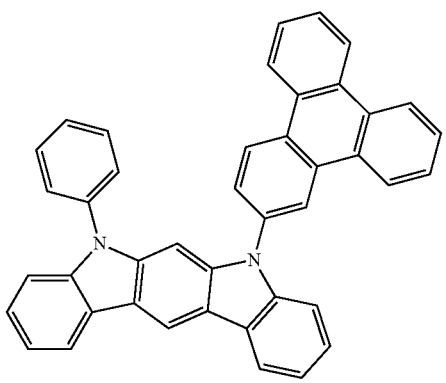
E-15
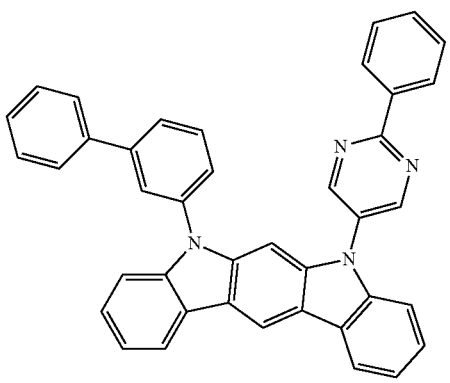
E-16
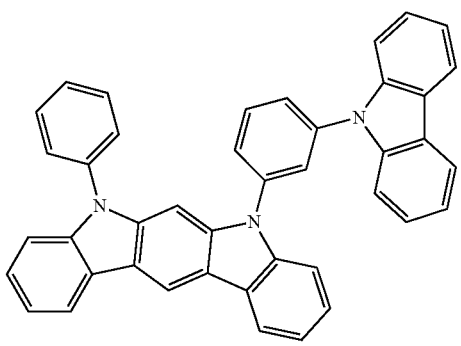
E-17
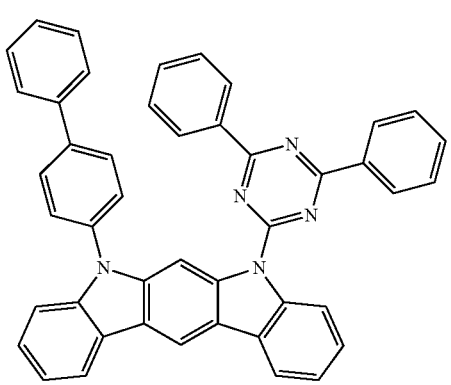

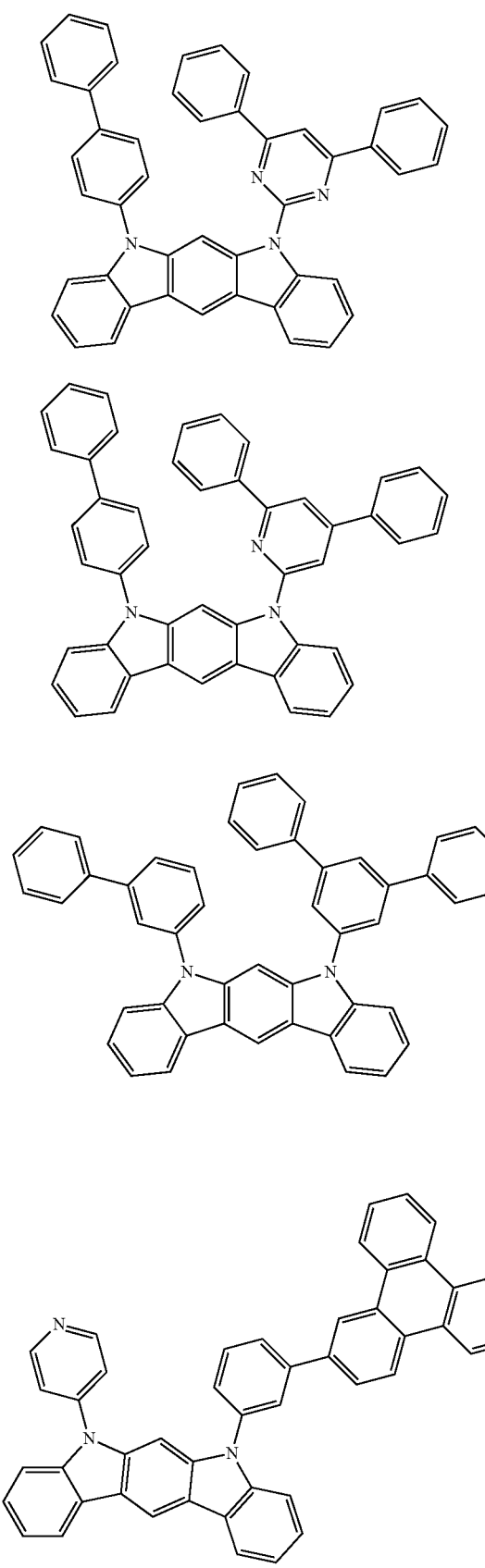
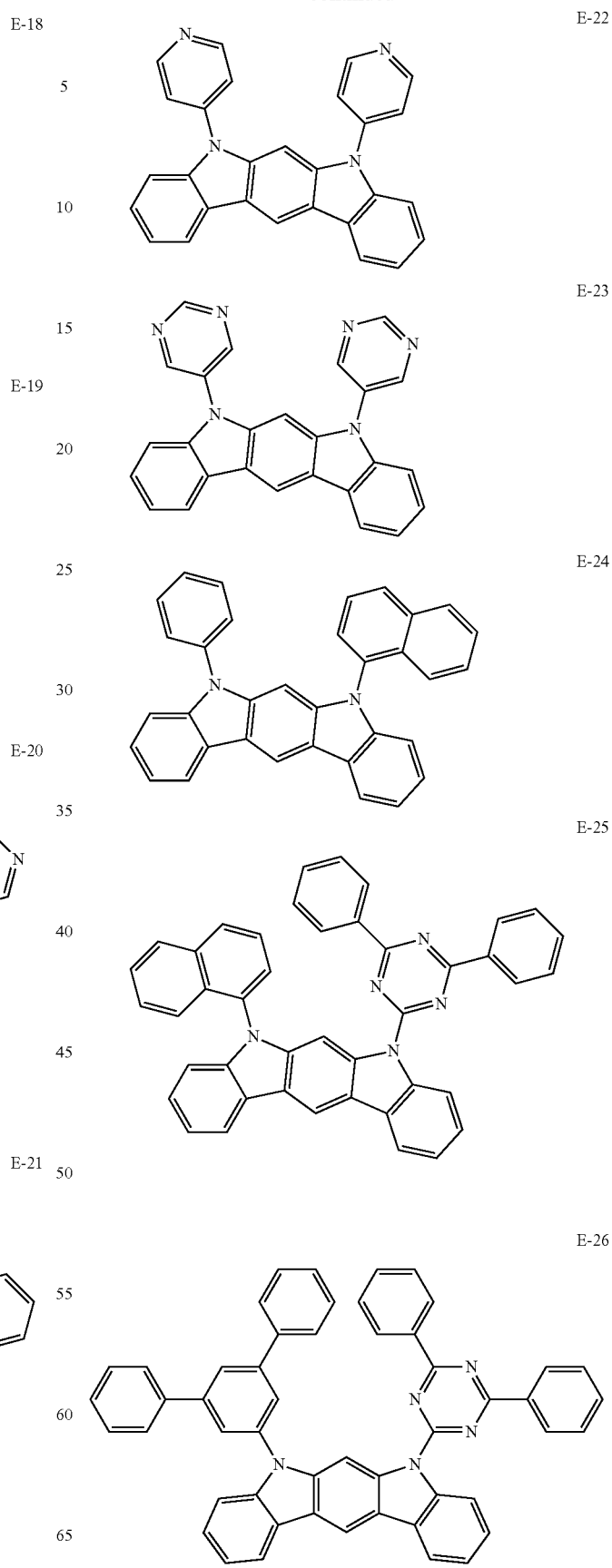

E-27
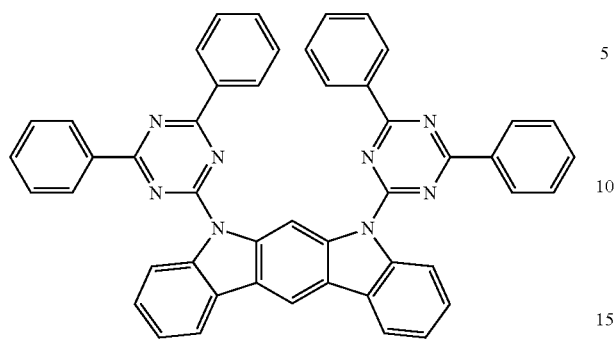
E-28
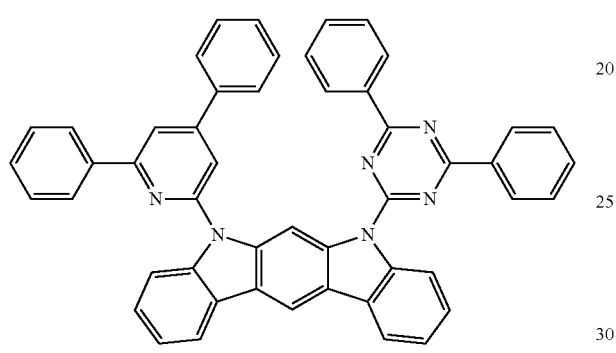
E-29
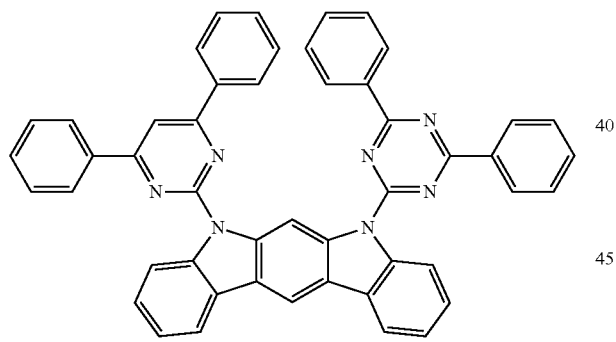
E-30
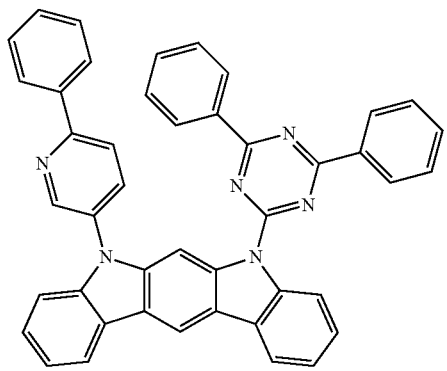
E-31
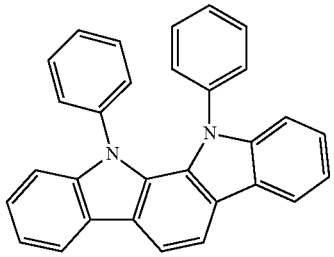
E-32
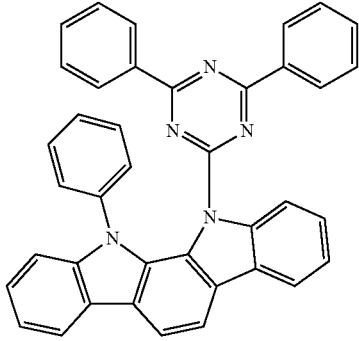
E-33
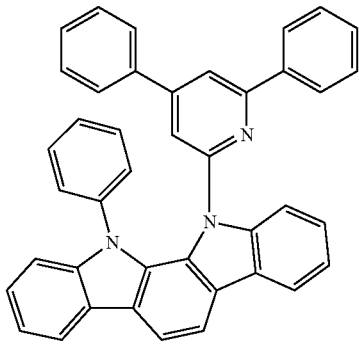
E-34
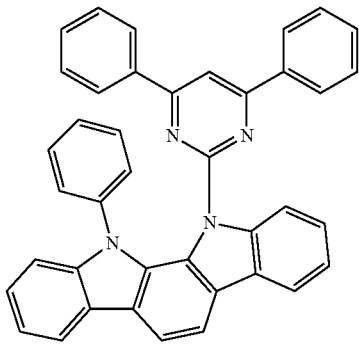

E-35 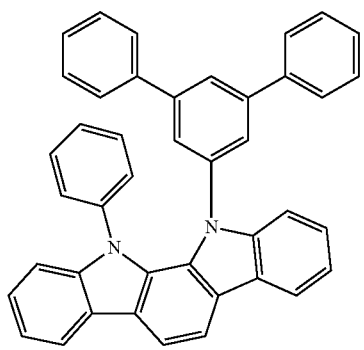
E-36 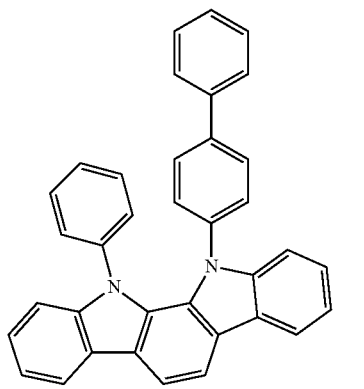
E-37 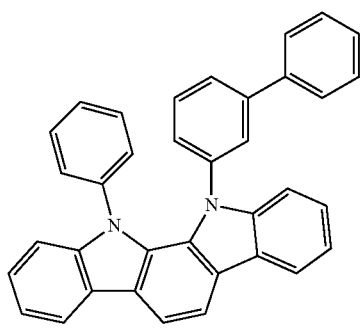
E-38 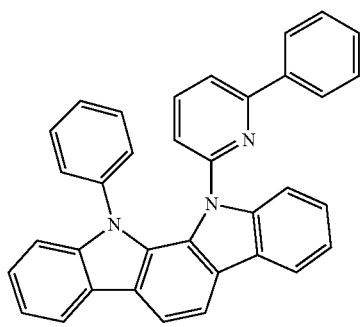
E-39 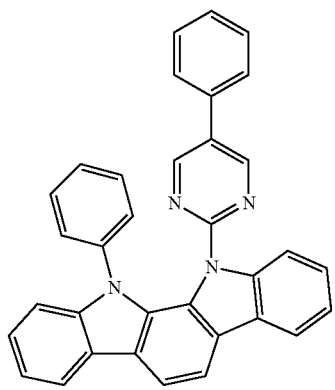
E-40 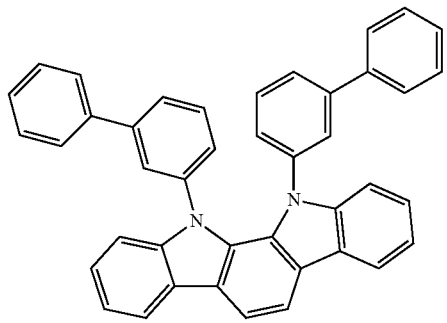
E-41 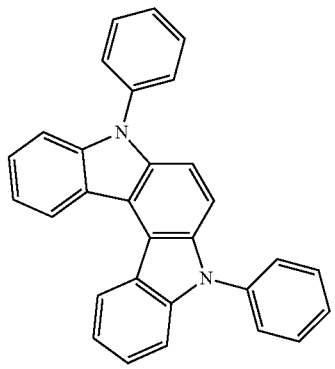
E-42 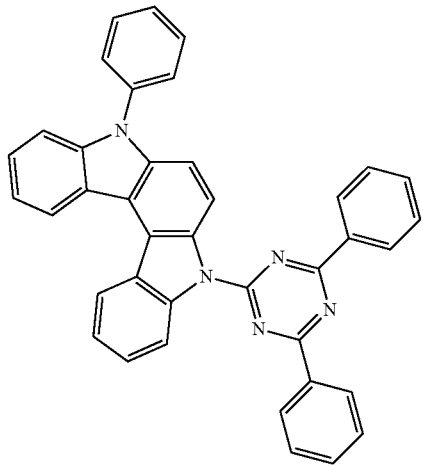

E-43
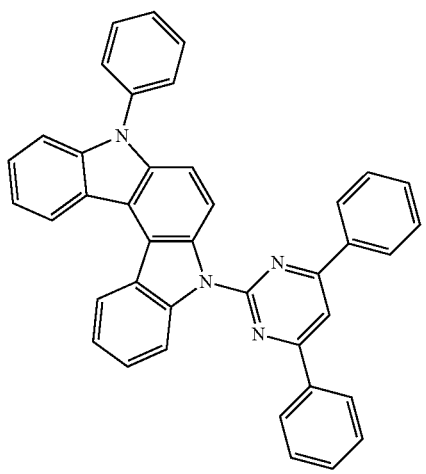
E-44
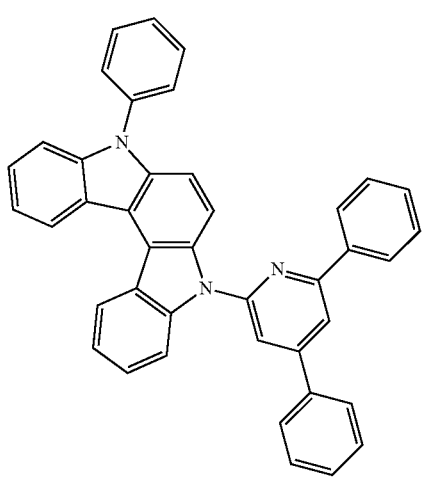
E-45
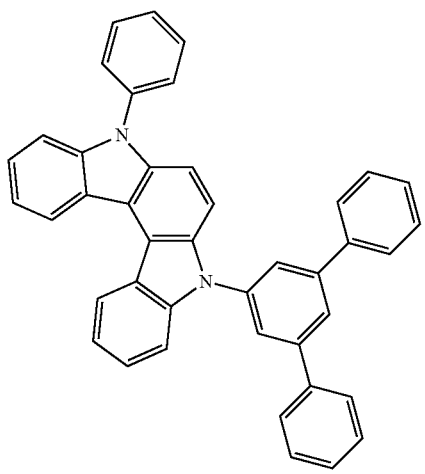
E-46
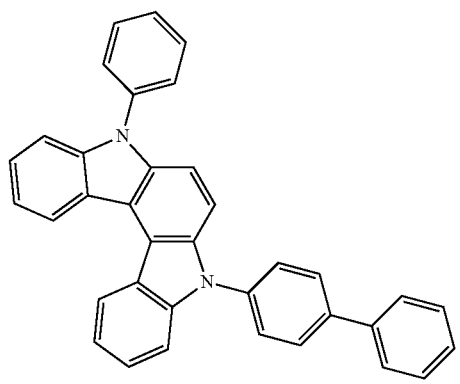
E-47
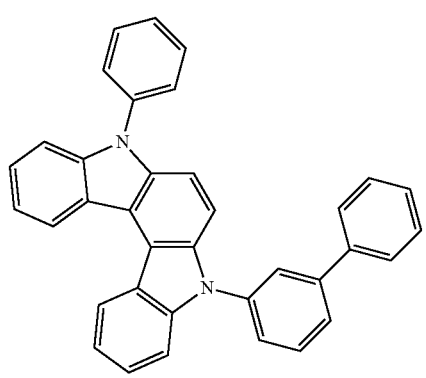
E-48
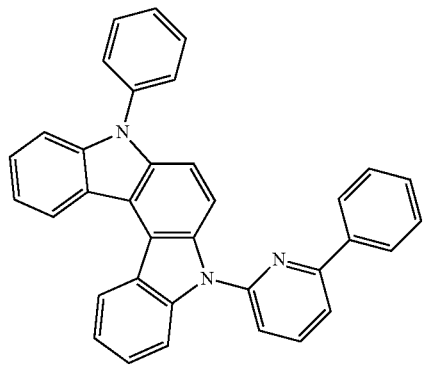
E-49
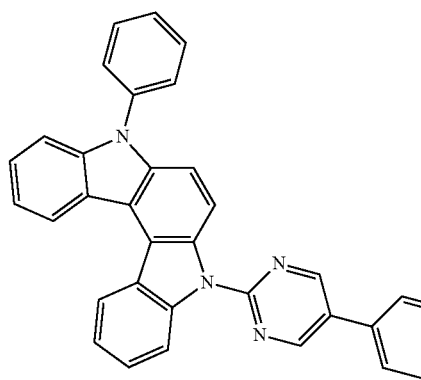

E-50
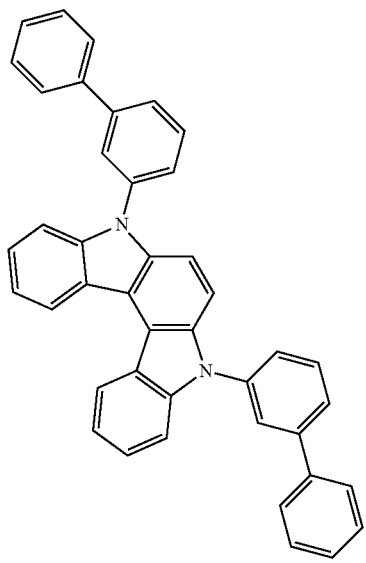
E-51
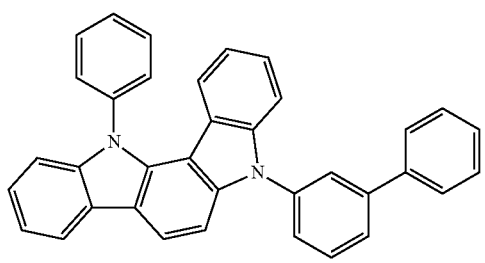
E-52
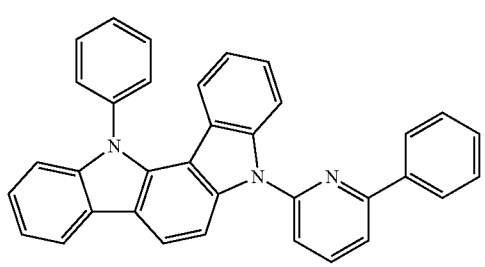
E-53
E-54
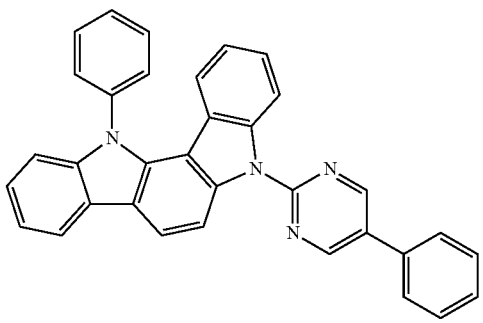
E-55
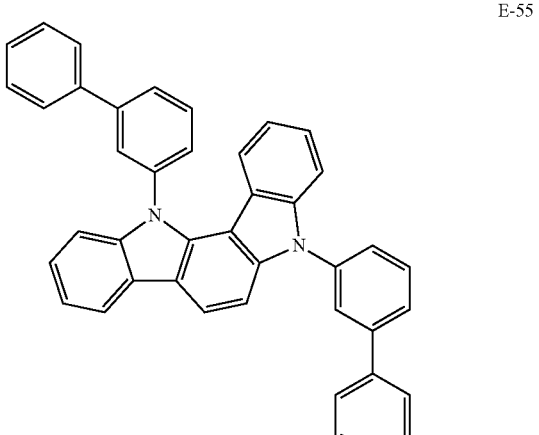
E-56
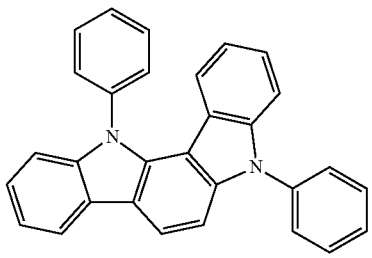
E-57
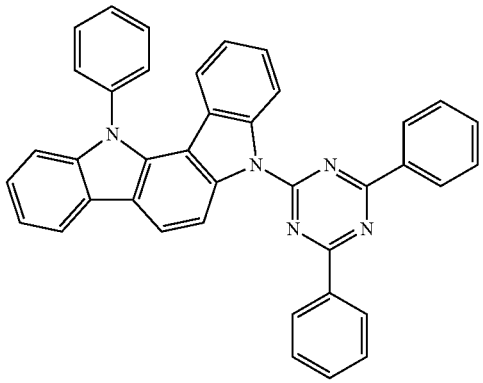

-continued
E-58
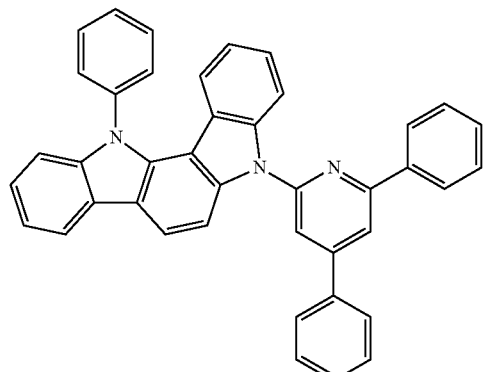
E-59
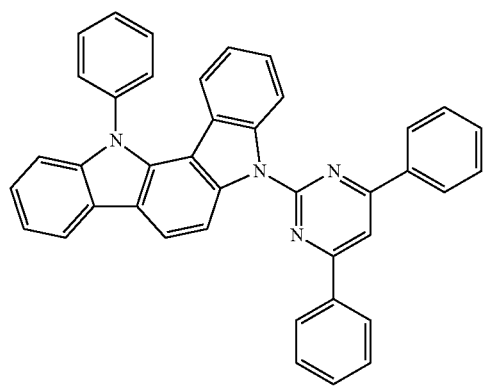
E-60
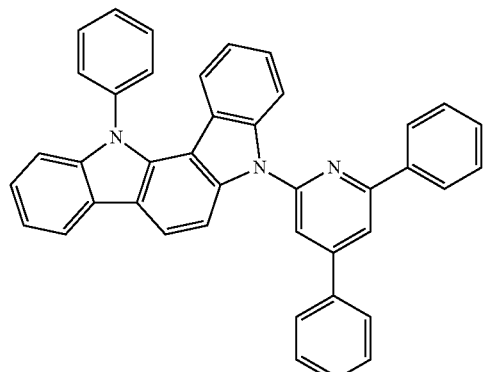
-continued
E-61
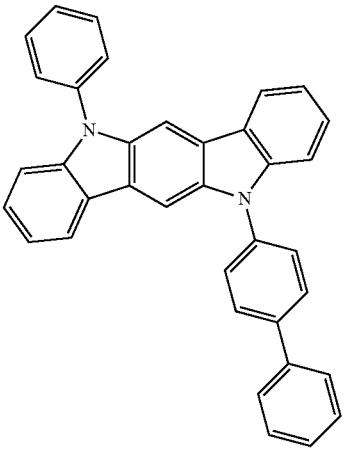
E-62
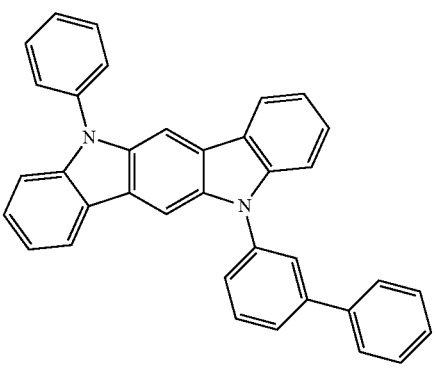
E-63
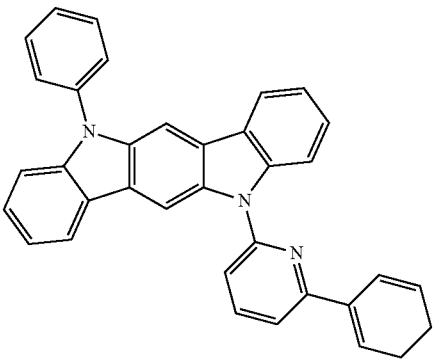
E-64
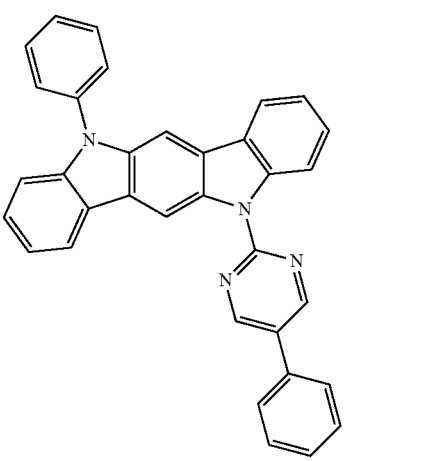

-continued
E-65
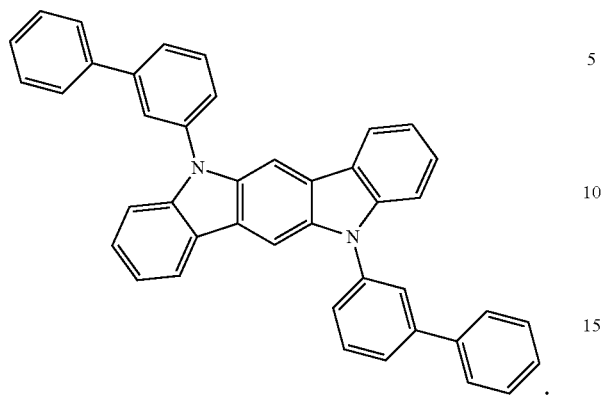
10. The organic optoelectronic device of claim 5, wherein the first organic compound and the second organic compound are included in a weight ratio of about 1:10 to 10:1.
11. The organic optoelectronic device of claim 5, wherein the organic layer further comprises a phosphorescent dopant.
* * * * *